United States Patent
Al-awar et al.

(10) Patent No.: US 11,242,351 B2
(45) Date of Patent: Feb. 8, 2022

(54) TRICYCLIC INHIBITORS OF THE BCL6 BTB DOMAIN PROTEIN-PROTEIN INTERACTION AND USES THEREOF

(71) Applicant: Ontario Institute for Cancer Research (OICR), Toronto (CA)

(72) Inventors: Rima Al-awar, Toronto (CA); Methvin Isaac, Brampton (CA); Anh My Chau, Toronto (CA); Ahmed Mamai, Mississauga (CA); Iain Watson, Toronto (CA); Gennady Poda, Toronto (CA); Pandiaraju Subramanian, Oakville (CA); Brian Wilson, Mississauga (CA); David Uehling, Toronto (CA)

(73) Assignee: ONTARIO INSTITUTE FOR CANCER RESEARCH (OICR), Toronto (CA)

(*) Notice: Subject to any disclaimer, the term of this patent is extended or adjusted under 35 U.S.C. 154(b) by 34 days.

(21) Appl. No.: 16/955,975

(22) PCT Filed: Dec. 21, 2018

(86) PCT No.: PCT/CA2018/051643
§ 371 (c)(1),
(2) Date: Jun. 19, 2020

(87) PCT Pub. No.: WO2019/119145
PCT Pub. Date: Jun. 27, 2019

(65) Prior Publication Data
US 2021/0053978 A1 Feb. 25, 2021

Related U.S. Application Data

(60) Provisional application No. 62/608,869, filed on Dec. 21, 2017.

(51) Int. Cl.
| | | |
|---|---|---|
| C07D 487/04 | (2006.01) | |
| A61K 31/519 | (2006.01) | |
| C07D 487/14 | (2006.01) | |
| A61P 35/04 | (2006.01) | |
| C07D 471/14 | (2006.01) | |
| C07D 498/14 | (2006.01) | |
| C07D 519/00 | (2006.01) | |

(52) U.S. Cl.
CPC ............ *C07D 487/14* (2013.01); *A61P 35/04* (2018.01); *C07D 471/14* (2013.01); *C07D 498/14* (2013.01); *C07D 519/00* (2013.01)

(58) Field of Classification Search
CPC .. C07D 487/04; C07D 498/14; A61K 31/519; A61K 31/5383; A61P 35/00
USPC ........................ 544/250, 101; 514/257, 229.8
See application file for complete search history.

(56) References Cited

FOREIGN PATENT DOCUMENTS

WO    WO 2019/153080 A1 *  8/2019  ............ C07D 487/04

OTHER PUBLICATIONS

Written Opinion and International Search Report of corresponding International Application No. PCT/CA2018/051643 dated Mar. 21, 2019, 11 pages.
Kamada et al., "Discovery of a B-Cell Lymphoma 6 Protein-Protein Interaction Inhibitor by a Biophysics-Driven Fragment-Based Approach", J. Med. Chem., 2017, 60(10), pp. 4358-4368 (published online on May 4, 2017).
McCoull et al., "Discovery of Pyrazolo [1,5-a]pyrimidine B-Cell Lymphoma 6 (BCL6) Binders and Optimization to High Affinity Macrocyclic Inhibitors", J. Med. Chem., 2017, 60(10), pp. 4386-4402 (published online May 9, 2017).
Kerres et al. "Chemically Induced Degradation of the Oncogenic Transcription Factor BCL6" Cell Reports 2017, 20, 2860-2875.
Polo et al. "Specific peptide interference reveals BCL6 transcriptional and oncogenic mechanisms in B-cell lymphoma cells", Nat Med, 2004. 10(12): 1329-35.
Duy et al. "BCL6 enables Ph acute lymphoblastic leukemia cells to survive BCR-ABL1 kinase inhibition" Nature, 2011, 473(7347):384-8.

* cited by examiner

*Primary Examiner* — Charanjit Aulakh
(74) *Attorney, Agent, or Firm* — Bereskin & Parr LLP/S.E.N.C.R.L, s.r.l.; Patricia Folkins

(57) ABSTRACT

The present application relates to compounds of Formula (I) or pharmaceutically acceptable salts, solvates and/or prodrugs thereof, to compositions comprising these compounds or pharmaceutically acceptable salts, solvates and/or prodrugs thereof, and various uses in the treatment of diseases, disorders or conditions that are treatable by inhibiting interactions with BCL6 BTB, such as cancer.

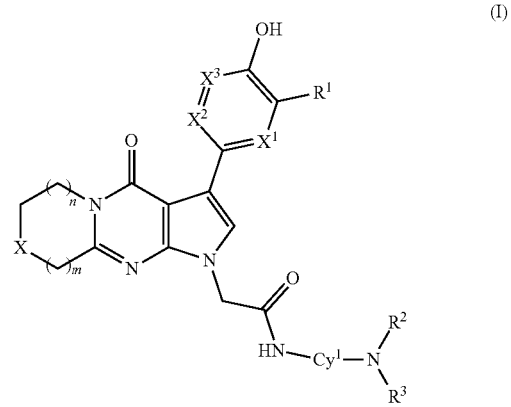

14 Claims, No Drawings
Specification includes a Sequence Listing.

US 11,242,351 B2

TRICYCLIC INHIBITORS OF THE BCL6 BTB DOMAIN PROTEIN-PROTEIN INTERACTION AND USES THEREOF

CROSS-REFERENCE TO RELATED APPLICATIONS

This application is a National Stage of International Application No. PCT/CA2018/051643 filed on Dec. 21, 2018 which claims the benefit of priority from U.S. Provisional Patent Application Ser. No. 62/608,869, filed on Dec. 21, 2017, the contents of both of which are incorporated herein by reference in their entirety.

INCORPORATION OF SEQUENCE LISTING

A computer readable form of the Sequence Listing "25308-P54697US01_SequenceListing.txt" (4,096 bytes), submitted via EFS-WEB and created on Oct. 2, 2020, is herein incorporated by reference.

FIELD

The present application relates to novel tricyclic compounds, to processes for their preparation, to compositions comprising them, and to their use in therapy. More particularly, it relates to tricyclic compounds useful in the treatment of diseases, disorders or conditions treatable by inhibiting or blocking the interaction of BCL6 BTB domain with its binding partners.

BACKGROUND

BCL6 (B Cell Lymphoma 6) is a member of the BTB/POZ (bric-á-brac, tramtrack, broad complex/pox virus zinc finger) family of transcription factors. The BCL6 gene was initially cloned by several groups in 1993 from a translocation occurring on chromosome 3q27 in diffuse large B-cell lymphoma (DLBCL) [*Histol Histopathol* 2004, 19:637-650]. Targeted disruption of the BCL6 gene revealed that BCL6 during normal B-cell development is a master regulator of antibody affinity maturation in germinal centers (GCs) [*Nat Rev Immunol* 2008, 8:22-33]. BCL6 is almost universally expressed in GC-derived B-cell lymphomas, including diffuse large B-cell lymphoma (DLBCL) and follicular lymphomas (FLs), regardless of translocations.

In normal lymphoid biology, BCL6 is required for naïve B cells to form GCs which are cellular compartments dedicated to the affinity maturation of antibodies. The GC is the site of two key molecular processes unique to B-cells: somatic hypermutation (SHM) and class switching recombination (CSR) [*Trends Biochem Sci* 2003, 28: 305-312]. Upon antigen-induced B-cell activation, B-cells proliferate and differentiate into either centroblasts or plasma cells [*Annu Rev Immunol* 1994 12: 117-139]. The centroblasts go through the dark zone of the GC where they rapidly proliferate, differentiate and revise their antigen receptors via SHM and CSR [*Cell* 1991 67: 1121-9; *Nature* 1991 354: 389-92; *Cell* 1981 27: 573-581]. SHM modulates the affinity of the antibodies to a specific antigen and, while not wishing to be limited by theory, it is believed that the mistargeting of SHM can result in the translocation of oncogenes.

BCL6 is a transcriptional repressor that reduces mRNA expression of its target genes by regulating survival and differentiation via distinct corepressor complexes [*Proc Natl Acad Sci USA*, 2007. 104(9): 3207-12; *Blood* 2007. 110(6): 2067-74; *Biochem Biophys Res Commun*, 2003. 300(2): 391-6]. BCL6 has six zinc fingers at its carboxyl terminus mediating sequence-specific DNA binding to regulatory sequences [*Nat Immunol*, 2007. 8(7): p. 705-14]. BCL6 binds to DNA as a homo-dimer and recruits, through its N-terminal domain, class I and II histone deacetylase complexes (HDACs) either directly or through corepressor molecules such as SMRT, NCOR1 and BCOR.

Different subsets of target genes appear to be repressed depending on which corepressors are engaged by BCL6 through the BTB domain [*Blood* 2007. 110(6): 2067-74]. The corepressors that bind to the BTB appear to be involved in the regulation of transcription associated with early stages of the GC process. Genome-wide studies indicate that BCL6 may, for example, target as many as 500 genes [*Blood* 2007. 110(6): 2067-74] mainly involved in cell cycle, gene transcription, DNA damage sensing, protein ubiquitylation and chromatin structure modification.

Direct BCL6 repressed target genes include ataxia telangectasia and Rad3 related (ATR), CHK1 checkpoint homolog (*S. pombe*) (CHEK1), tumor protein p53 (TP53) and cyclin dependent kinase inhibitor 1A or p21 (CDKN1A) [*Nat Immunol*, 2007. 8(7): 705-14]. These genes belong to survival pathways involved in DNA damage sensing and checkpoint activation. They are primarily regulated through the SMRT and NCOR corepressors. Both of these corepressors contain a highly conserved 17-residue BCL6 binding domain (BBD) that interacts with the homodimeric BTB domain [*Mol Cell*, 2003. 12(6): 11561-64] forming a promoter-localized protein complex. This complex represses the transcription of target genes such as ATR, TP53 and CDKN1A which in turn attenuates the DNA damage response and promote cell survival.

In addition to its role in survival, BCL6 also regulates differentiation through a specific BCL6 corepressor complex that represses B-lymphocyte-induced maturation protein1 or PRDM1 (BLIMP1), a transcription factor that promotes plasmacytic differentiation [*Cell*, 2004. 119(1): 75-86]. Maturation of GC B cells toward memory B-cells and plasma cells usually requires the down-regulation of BCL6. Such down-regulation of BCL6 function can occur via antigen-induced B cell receptor (BCR) mediated activation that subsequently leads to rapid BCL6 proteasomal degradation [*Genes Dev*, 1998. 12(13): 1953-61]. Alternatively, T-cell-mediated stimulation through the CD40 pathway leads to NF-κB driven induction of interferon regulatory factor 4 (IRF4), a regulator of plasma-cell development [*Science*, 1997. 275(5299): 540-3]. IRF4 leads to the transcriptional repression of BCL6 and to the transactivation of BLIMP1, which drives the regulatory program associated with plasmacytic differentiation and immunoglobulin (Ig) secretion [*Cell*. 1994; 77:297-306].

BCL6 has also been shown to play a role in the regulation of genes involved in the B-T cell interaction by regulating the expression levels of CD80 and CD274 (alias B7-H1, PDL1) [*J Exp Med*. 2003, 198(2):211-2; *Proc Natl Acad Sci USA*. 2009, 106(27):11294-9]. CD80 is expressed on B cells, and its interaction with CD28 is involved in T-cell activation, GC formation, and immunoglobulin class switching [*J Immunol*. 1997, 159(11):5336-44]. The B-T cell interaction is a step toward successful B-cell activation. Another gene for B-cell activation that is regulated by BCL6 is CD69. CD69 (a type II transmembrane glycoprotein) is an early activation marker in lymphocytes and is also a signal transmitter in inflammatory processes [*Life Sci*. 2012, 90(17-18):657-65]. The global BCL6-mediated repression of target genes such as CD69 and CD80 prevent premature activation of B cells during proliferative expansion. A number of other signaling pathways are modulated by BCL6 transcriptional repression. These include multiple interferon-types (e.g. interferon regulatory factor 7 or IRF7) and interleukin receptors as well as STAT (signal transducers and activators of transcription) family members including STAT1, STAT2 and STAT3 [*Adv Immunol.* 2010; 105:193-210; *Blood.* 2010, 115(5):975-84; *Blood* 2008, 111(3):1515-23]. Toll-like-receptor (TLR) signaling is also modulated by BCL6 via regulation of receptor expression (e.g. TLR7) as well as transduction of Toll-derived signals. The TLR pathway has also been shown to play a major role in the development and differentiation of memory B cells [Nature. 2005, 438(7066): 364-8; Adv Exp Med Biol. 2005; 560:11-8; *J Exp Med.* 2007, 204(13):3095-101].

Role of BCL6 in Cancers

The mechanisms that mediate the remodeling of antigen receptors in the GCs involve potentially mutagenic DNA double-strand breaks and suppression of the apoptotic machinery by BCL6. Failure to reactivate apoptosis upon exit from the GC has been established as a mechanism involved in lymphomagenesis, and has been specifically linked to diffuse large B cell lymphoma (DLBCL); an aggressive GC-derived malignancy that accounts for approximately 35% of all non-Hodgkin lymphoma (NHL) cases.

DLBCL is a heterogeneous disease with two major subtypes: the GC B cell-like (GCB) subtype characterized by an expression signature similar to normal GC B cells, and the activated B cell-like (ABC) subtype with gene expression pattern like in vitro BCR stimulation, which has a poorer prognosis [*Nature.* 2000. 403(6769): 503-11]. The most common genetic alterations in DLBCL affect the BCL6 promoter region and involve mutations in the 5' noncoding region and chromosomal translocations. Further experimental evidence that overexpression is sufficient for lymphomagenesis was provided by the production of transgenic mice in which BCL6 was driven by the immunoglobulin heavy chain (IgH) Iµ promoter [*Cancer. Cell.* 2005. 7(5): 445-55]. These mice developed a disease histologically similar to human DLBCL.

Gene rearrangements at 3q27 have been reported in 30-40% of DLBCL with a higher percentage being observed in the ABC subtype [*Oncogene.* 2001. 20(40): 5580-94]. These translocations place an intact BCL6 coding domain under the influence of heterologous promoter regions derived from a variety of alternative partner chromosomes (>20) including the immunoglobulin heavy and light chain genes resulting in deregulated expression of the normal BCL6 protein [*EMBO J.* 1995. 14(24): 6209-17]. In addition, while not wishing to be limited by theory, BCL6 may contribute to lymphomagenesis when its downregulation, which usually occurs after affinity maturation, is disrupted. One proposed mechanism for BCL6 downregulation disruption is the loss of IRF4 binding sites in the BCL6 gene. IRF4 expression is induced by sustained CD40 stimulation of the NF-κB pathway in germinal center cells. IRF4 usually binds to exon 1 and intron 1 of the BCL6 gene and represses BCL6 expression, but chromosome translocations or point mutations introduced during SHM (which commonly target the 5' non-coding promoter region of BCL6) may prevent this repressive effect [*Cancer. Cell.* 2007. 12(3): 280-92]. BCL6 promoter binding and gene repression has also been shown to vary between normal and malignant cells. BCL6 dependency has no correlation to the cell of origin (COO) classification system as dependency occurs in both ABC and GCB cell lines.

Studies have integrated genomic analysis and functional screens to provide a rationale for targeted therapies within defined populations of BCL6 driven DLBCL. Personalizing treatments by identifying patients with oncogenic dependencies via genotyping and specifically targeting the responsible drivers such as BCL6 may be useful for the treatment of DLBCL [*Clin. Cancer. Res,* 2012. 18(17): 4538-48].

Overexpression of BCL6 has been identified as a resistance mechanism arising during the targeted treatment of BCR-ABL1-positive leukemia and suggests a potential therapeutic opportunity to overcome this resistance. The BCR-ABL1 fusion gene is found in nearly all chronic myeloid leukemia (CMLs) and in about 25% of ALLs; the resulting oncogenic protein can be targeted by tyrosine kinase inhibitors (TKIs) such as imatinib, but the acute cellular response reveals protective feedback signaling leading to resistance. BCL6 expression appears to directly influence the response to imatinib as the authors found that modulation of BCL6 levels had the expected effects on the sensitivity of ALL cells to imatinib. A small molecule BCL6 BTB inhibitor that may have utility in, for example, TKI-resistant Ph+ ALL patients, since TKI-resistance develops in most cases of Ph+ ALL [*Nature,* 2011. 473(7343): 384-388].

CML is induced by the oncogenic BCR-ABL1 tyrosine kinase and can be treated with TKIs. However, if CML patients do not receive life-long TKI treatment, leukemia will eventually recur. Such resistance can be attributed to the failure of TKI treatment to eradicate leukemia-initiating cells (LICs). Recent studies demonstrated that forkhead box O (FoxO) transcription factors are critical for maintenance of CML-initiating cells. The BCL6 protooncogene was identified as a downstream effector of FoxO in self-renewal signaling of CML-initiating cells. BCL6 represses Arf and p53 in CML cells and is involved in colony formation and initiation of leukemia [*Curr Opin Immunol,* 2011. 13(2): 134-40]. Inhibition of BCL6 in human CML cells compromises colony formation and leukemia initiation in transplant recipients and selectively eradicates $CD34^+$ $CD38^-$ LICs in patient-derived CML samples. Pharmacological inhibition of BCL6 may therefore eradicate LICs in CML, potentially limiting the duration of TKI treatment in CML patients, and/or substantially decrease the risk of blast crisis transformation.

X-ray crystallographic studies have shown that the BCL6 BTB domain forms a tight homodimer, and in solution the BCL6 BTB domain also appears to exist exclusively as a dimer, exhibiting a very low dissociation constant [*Mol Cell,* 2003. 12(6): 1551-64]. The BCL6 BTB domain interacts in a mutually exclusive manner with three corepressors: SMRT, NCOR1 and BCOR. Mutations that change the surface of the BCL6 lateral groove (without affecting the overall structure of the domain) no longer bind to the corepressor BBDs, and these mutations abrogate BCL6 BTB domain repressor activity. The above structural features suggest that the BCL6 BTB domain is druggable. Hence, agents that bind to the BCL6 BTB domain and compete for corepressor binding can reverse the repression activities of BCL6. Selective targeting of the BCL6 BTB domain could minimize toxicity compared to complete abrogation of BCL6 function. However, the length and complexity of the interface between the BBD and the BCL6 BTB binding groove are potential barriers toward developing effective small molecule inhibitors. Molecules such as BBD peptides, which contain many polar and charged amino acids, interact with an extended surface of the BCL6 BTB dimer, mostly through hydrogen bonds and multiple van der Waals contacts. Molecules large enough to fully occupy the lateral groove would be unlikely to readily penetrate cells as demonstrated by the peptide BPI, with potency in the micromolar range and a short half-life in vivo [*Nat Med*, 2004. 10(12): 1329-35]. Three articles have reported the identification of chemical ligands for the BTB domain of BCL6 (*J. Med. Chem.* 2017, 60, 4358-4368; *J. Med. Chem.* 2017, 60, 4386-4402; *Cell Reports* 2017, 20, 2860-2875).

Considering the challenges generally associated with targeting protein-protein interactions, and the current need that exists to treat BCL6 dependent tumor types such as DLBCL, complementary approaches, namely virtual screening, focused library screening, and focused structure activity relationship studies, were used to identify compounds of Formula I, which inhibit the BCL6 BTB protein-protein interaction.

SUMMARY

Considering the challenges generally associated with targeting protein-protein interactions, and the current need that exists to treat BCL6 dependent tumor types such as DLBCL, complementary approaches, namely virtual screening, focused library screening and focused structure activity relationship studies, were used to identify compounds of the application, which inhibit or block the interaction of the BCL6 BTB domain with its binding partners, such as the SMRT, NCOR2 and BCOR corepressors.

Accordingly, the present application includes a compound of Formula I, or a pharmaceutically acceptable salt, solvate and/or prodrug thereof:

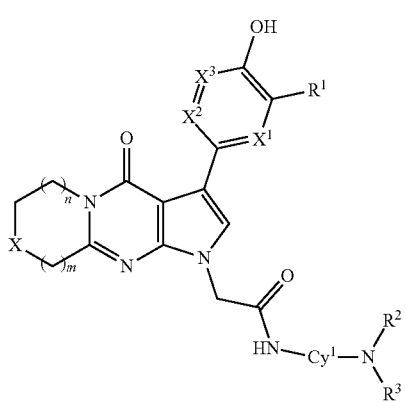

(I)

wherein

X is selected from $CR^4R^5$, O, S, S(O), $SO_2$ and $NR^4$;

$X^1$, $X^2$ and $X^3$ are independently selected from $CR^6$ and N, or $X^2$ and $X^3$ are linked to form, together with the carbon atoms to which they are attached, a 3-8-membered heterocycloalkyl or heteroaromatic ring, both of which optionally contain one to two additional heteroatoms selected from O, S, S(O), $SO_2$ and $NR^7$;

$Cy^1$ is selected from phenyl and $C_{5-6}$heteroaryl, both of which are unsubstituted or substituted with one to three substituents selected from halo, $C_{1-6}$alkyl and $OC_{1-6}$alkyl;

$R^1$ is selected from $C(O)NR^8R^9$, $C(O)OR^8$, CN and

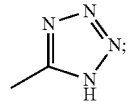

$R^2$ and $R^3$ are independently selected from H, $C_{1-10}$alkyl and $C_{1-6}$alkylene-O—$C_{1-6}$alkyl, or $R^2$ and $R^3$ are linked to form, together with the nitrogen atom to which they are attached, a 3-10-membered heterocycloalkyl or heteroaromatic ring, both of which optionally contain one to two additional heteroatoms selected from O, S, S(O), $SO_2$, NH and $NR^{10}$, and both of which are unsubstituted or substituted with one to four substituents selected from $R^{11}$;

$R^4$ and $R^5$ are independently selected from H and $C_{1-6}$alkyl;

$R^6$ is selected from H, OH, $OC_{1-6}$alkyl, $C_{1-6}$alkyl and halo;

$R^7$ is selected from H and $C_{1-6}$alkyl;

$R^8$ and $R^9$ are independently selected from H and $C_{1-6}$alkyl;

$R^{10}$ is selected from $C_{1-10}$alkyl, $ZC_{3-10}$cycloalkyl, $ZC_{3-10}$heterocycloalkyl, $ZC_{6-10}$aryl and $ZC_{5-10}$heteroaryl, each of which is unsubstituted or substituted with one to three substituents selected from $C_{1-6}$alkyl, $OC_{1-6}$alkyl, OH and halo;

$R^{11}$ is selected from $C_{1-10}$alkyl, $OC_{1-6}$alkyl, OH, $C_{1-6}$alkylene-O—$C_{1-6}$alkyl, $C_{1-10}$alkylene-OH $C_{1-10}$alkylene $(OH)_2$ and halo;

Z is selected from a direct bond and $C_{1-6}$alkylene;

n and m are independently selected from 0, 1, 2 and 3; and all alkyl and alkylene groups are optionally fluoro-substituted.

The present application also includes a composition comprising one or more compounds of the application and a carrier. In an embodiment, the composition is a pharmaceutical composition comprising one or more compounds of the application and a pharmaceutically acceptable carrier.

The compounds of the application have been shown to have the potential to inhibit or block BCL6 BTB protein-protein interaction with its binding partners, in particular SMRT/NCOR and BCOR. Therefore the compounds of the application are useful for treating diseases, disorders or conditions that are treatable by inhibiting interactions with BCL6 BTB. Accordingly, the present application also includes a method of treating a disease, disorder or condition that is treatable by inhibiting interactions with BCL6 BTB, comprising administering a therapeutically effective amount of one or more compounds of the application to a subject in need thereof.

In some embodiments, the compounds of the application are used as medicaments. Accordingly, the application also includes a compound of the application for use as a medicament.

The present application also includes a use of one or more compounds of the application for treatment of a disease, disorder or condition that is treatable by inhibiting interactions with BCL6 BTB as well as a use of one or more compounds of the application for the preparation of a medicament for treatment of a disease, disorder or condition that is treatable by inhibiting interactions with BCL6 BTB. The application further includes one or more compounds of the application for use in treating a disease, disorder or condition that is treatable by inhibiting interactions with BCL6 BTB.

In some embodiments, the disease, disorder or condition that is treatable by inhibiting interactions with BCL6 BTB, is a neoplastic disorder. In an embodiment, the treatment comprises administration or use of an amount of one or compounds of the application that is effective to ameliorate at least one symptom of the neoplastic disorder, for example, reduced cell proliferation or reduced tumor mass in a subject in need of such treatment.

In some embodiments, the disease, disorder or condition that is treatable by inhibiting interactions with BCL6 BTB, is cancer. In some embodiments, the cancer is selected from hematologic cancers, breast cancers, ovarian cancers, and glioblastomas. In some embodiments, the cancer is non-Hodgkin's lymphoma. In some embodiments the cancer is a B-cell lymphoma, such as diffuse large B-cell lymphoma (DLBCL) or follicular lymphomas.

In an embodiment, the disease, disorder or condition that is treatable by inhibiting interactions with BCL6 BTB, is a disease, disorder or condition associated with an uncontrolled and/or abnormal cellular activity affected directly or indirectly by the interaction of protein binding partners with the BCL6 BTB binding domain. In another embodiment, the uncontrolled and/or abnormal cellular activity that is affected directly or indirectly by the interaction of protein binding partners with the BCL6 BTB binding domain is proliferative activity in a cell.

The application also includes a method of inhibiting proliferative activity in a cell, comprising administering an effective amount of one or more compounds of the application to the cell.

In a further embodiment the disease, disorder or condition that is treatable by inhibiting interactions with BCL6 BTB, is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors therapies, immunotherapy, hormonal therapy and anti-angiogenic therapies.

The application additionally provides a process for the preparation of compounds of the application. General and specific processes are discussed in more detail and set forth in the Examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps.

As used herein, the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds. In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

Unless otherwise indicated, the definitions and embodiments described in this and other sections are intended to be applicable to all embodiments and aspects of the application herein described for which they are suitable as would be understood by a person skilled in the art.

Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program: ACD/ChemSketch, Version 5.09/September 2001, Advanced Chemistry Development, Inc., Toronto, Canada.

The term "compound of the application" or "compound of the present application" and the like as used herein refers to a compound of Formula I, and pharmaceutically acceptable salts, solvates and/or prodrugs thereof.

The term "composition of the application" or "composition of the present application" and the like as used herein refers to a composition comprising one or more compounds the application and at least one additional ingredient.

The term "suitable" as used herein means that the selection of the particular compound or conditions would depend on the specific synthetic manipulation to be performed, and the identity of the species to be transformed, but the selection would be well within the skill of a person trained in the art. All method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form are included within the scope of the present application.

The compounds of the present application may further exist in varying polymorphic forms and it is contemplated that any polymorphs which form are included within the scope of the present application.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "cell" as used herein refers to a single cell or a plurality of cells and includes a cell either in a cell culture or in a subject.

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. Either the mono- or di-acid salts can be formed, and such salts can exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful so that an ester functionality, if any, elsewhere in a compound is not hydrolyzed. The selection criteria for the appropriate salt will be known to one skilled in the art.

Prodrugs of the compounds of the present application may be, for example, conventional esters formed with available hydroxy, thiol, amino or carboxyl groups. Some common esters which have been utilized as prodrugs are phenyl esters, aliphatic ($C_1$-$C_{24}$) esters, acyloxymethyl esters, carbamates and amino acid esters.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "inert organic solvent" as used herein refers to a solvent that is generally considered as non-reactive with the functional groups that are present in the compounds to be combined together in any given reaction so that it does not interfere with or inhibit the desired synthetic transformation. Organic solvents are typically non-polar and dissolve compounds that are non soluble in aqueous solutions.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-6}$alkyl means an alkyl group having 1, 2, 3, 4, 5 or 6 carbon atoms. All alkyl groups are optionally fluorosubstituted unless otherwise stated.

The term "alkylene" as used herein, whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{1-6}$alkylene means an alkylene group having 1, 2, 3, 4, 5 or 6 carbon atoms. All alkylene groups are optionally fluorosubstituted unless otherwise stated.

The term "cycloalkyl," as used herein, whether it is used alone or as part of another group, means a saturated carbocyclic group containing one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to carbocyclic groups containing at least one aromatic ring. In an embodiment of the application, the aryl group contains from 6, 9 or 10 carbon atoms, such as phenyl, indanyl or naphthyl.

The term "heterocycloalkyl" as used herein, whether it is used alone or as part of another group, refers to cyclic groups containing at least one non-aromatic ring in which one or more of the atoms are a heteroatom selected from O, S and N. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as defined above.

The term "heteroaryl" as used herein refers to cyclic groups containing at least one aromatic ring and at least one a heteroatom selected from O, S and N. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above.

All cyclic groups, including aryl and cyclo a groups, contain one or more than one ring (i.e. are polycyclic). When a cyclic group contains more than one ring, the rings may be fused, bridged, spirofused or linked by a bond.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "halo" as used herein refers to a halogen atom and includes fluoro, chloro, bromo and iodo.

The term "atm" as used herein refers to atmosphere.

The term "MS" as used herein refers to mass spectrometry.

The term "aq." As used herein refers to aqueous.

The term "DCM" as used herein refers to dichloromethane.

The term "DIPEA" as used herein refers to N,N-diisopropyl ethylamine.

The term "DMF" as used herein refers to dimethylformamide.

The term "THF" as used herein refers to tetrahydrofuran.

The term "DMSO" as used herein refers to dimethylsulfoxide.

The term "EtOAc" as used herein refers to ethyl acetate.

The term "MeOH" as used herein refers to methanol.

The term "MeCN" or "ACN" as used herein refers to acetonitrile.

The term "HCl" as used herein refers to hydrochloric acid.

The term "TFA" as used herein refers to trifluoroacetic acid.

The term "CV" as used herein refers to column volume.

The term "Hex" as used herein refers to hexanes.

The term "PBS" as used herein refers to phosphate-based buffer.

The term "HBTU" as used herein refers to

The term "HATU" as used herein refers to

The term "RT" as used herein refers to room temperature.

The term "DIAD" as used herein refers to diisopropyl azodicarboxylate.

The term "TPP" as used herein refers to triphenylphosphine.

The term "TLC" as used herein refers to thin-layer chromatography.

The term "MOM-Cl" as used herein refers to methoxymethyl chloride.

The term "EDC-HCl" as used herein refers to N'-ethylcarbodiimide hydrochloride.

The term "TMEDA" as used herein refers to tetramethylethylenediamine.

The term "PyBOP" as used herein refers to benzotriazol-1-yl-oxytripyrrolidinophosphonium hexafluorophosphate.

The term "TEA" as used herein refers to triethylamine.

The term "mCPBA" as used herein refers to meta-chloroperoxybenzoic acid.

The term "TMSCl" as used herein refers to trimethylsilylchloride.

The term "NBS" as used herein refers to N-bromosuccinimide.

The term "DBAD" as used herein refers to di-tert-butyl azodicarboxylate.

The term "DPPA" as used herein refers to diphenylphosphoryl azide.

The term "NMP" as used herein refers to N-methyl-2-pyrrolidone.

The term "DiPA" as used herein refers to diisopropyl amine.

The term "NCS" as used herein refers to N-chloro succinimide.

The term "PMDTA" as used herein refers to N,N,N',N",N"-pentamethyldiethylenetriamine.

The term "DIMAP" as used herein refers to 4-Dimethylaminopyridine.

The term "optionally substituted" refers to groups, structures, or molecules that are either unsubstituted or are substituted with one or more substituents.

The term "fluorosubstituted" refers to the substitution of one or more, including all, hydrogens in a referenced group with fluorine.

The symbol "∿" is used herein to represent the point of attachment of a group to the remainder of a molecule or chemical formula.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, in some embodiments, the compounds of the application may be administered at least once a week. In some embodiments, the compounds may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required. For example, the compounds are administered to the subject in an amount and for duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition treatable by inhibition of interactions with BCL6 BTB, or manifesting a symptom associated with a disease, disorder or condition treatable by inhibition of BCL6 BTB protein-protein interaction.

As used herein, the term "effective amount" or "therapeutically effective amount" means an amount of a compound, or one or more compounds, of the application that is effective, at dosages and for periods of time necessary to achieve the desired result. For example in the context of treating a disease, disorder or condition treatable by inhibition of interactions with BCL6 BTB, an effective amount is an amount that, for example, inhibits interactions with BCL6 BTB, compared to the inhibition without administration of the one or more compounds. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art. The effective amount is one that following treatment therewith manifests as an improvement in or reduction of any disease symptom. When the disease is cancer, amounts that are effective can cause a reduction in the number, growth rate, size and/or distribution of tumours.

The expression "inhibiting interactions with BCL6 BTB" as used herein refers to inhibiting, blocking and/or disrupting an interaction between a therapeutically relevant binding partner, such as a corepressor protein, with the BCL6 BTB binding domain in a cell, in particular a B-cell. The inhibiting, blocking and/or disrupting causes a therapeutic effect in the cell.

By "inhibiting, blocking and/or disrupting" it is meant any detectable inhibition, block and/or disruption in the presence of a compound compared to otherwise the same conditions, except for in the absence in the compound.

The term "BCL6 BTB" as used herein refers to the bric-á-brac, tramtrack, broad (BTB) domain of B-cell lymphoma 6 (BLC6) which comprises the amino acid sequence disclosed in *Mol. Cell* 2008, 29: 384-391.

The term "SMRT" as used herein refers to a corepressor protein that interacts with BCL6 BTB and this interaction results in the reduction of mRNA expression of target genes. SMRT (Gene ID: 9612) comprises the amino acid sequence disclosed in *Proc Natl Acad Sci* 1999, 96: 2639-2644 and *Proc Natl Acad Sci,* 1999 96: 3519-3524.

The term "NCOR" as used herein refers to a corepressor protein that interacts with BCL6 BTB and this interaction results in the reduction of mRNA expression of target genes. NCOR (Gene ID: 9611) comprises the amino acid sequence disclosed in *Proc Natl Acad Sci* 1999, 96: 2639-2644 and *Proc Natl Acad Sci,* 1999 96: 3519-3524.

The term "BCOR" as used herein as used herein refers to a corepressor protein that interacts with BCL6 BTB and this interaction results in the reduction of mRNA expression of target genes. BCOR (Gene ID: 54880) comprises the amino acid sequence disclosed in *Genes Dev.* 2000, 14, 1810-1823.

The term "administered" as used herein means administration of a therapeutically effective amount of a compound, or one or more compounds, or a composition of the application to a cell either in cell culture or in a subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer).

II. Compounds and Compositions

The present application includes a compound of Formula I, or a pharmaceutically acceptable salt, solvate and/or prodrug thereof:

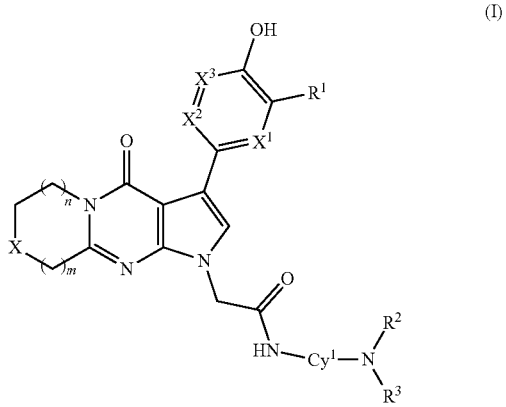

(I)

wherein
X is selected from $CR^4R^5$, O, S, S(O), $SO_2$ and $NR^4$;
$X^1$, $X^2$ and $X^3$ are independently selected from $CR^6$ and N, or
$X^2$ and $X^3$ are linked to form, together with the carbon atoms to which they are attached, a 3-8-membered heterocycloalkyl or heteroaromatic ring, both of which optionally contain one to two additional heteroatoms selected from O, S, S(O), $SO_2$ and $NR^7$;
$Cy^1$ is selected from phenyl and $C_{5-6}$heteroaryl, both of which are unsubstituted or substituted with one to three substituents selected from halo, $C_{1-6}$alkyl and $OC_{1-6}$alkyl;
$R^1$ is selected from $C(O)NR^8R^9$, $C(O)OR^8$, CN and

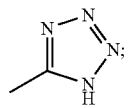

$R^2$ and $R^3$ are independently selected from H, $C_{1-10}$alkyl and $C_{1-6}$alkylene-O—$C_{1-6}$alkyl, or
$R^2$ and $R^3$ are linked to form, together with the nitrogen atom to which they are attached, a 3-10-membered heterocycloalkyl or heteroaromatic ring, both of which optionally contain one to two additional heteroatoms selected from O, S, S(O), $SO_2$, NH and $NR^{10}$, and both of which are unsubstituted or substituted with one to four substituents selected from $R^{11}$;
$R^4$ and $R^5$ are independently selected from H and $C_{1-6}$alkyl;
$R^6$ is selected from H, OH, $OC_{1-6}$alkyl, $C_{1-6}$alkyl and halo;
$R^7$ is selected from H and $C_{1-6}$alkyl;
$R^8$ and $R^9$ are independently selected from H and $C_{1-6}$alkyl;
$R^{10}$ is selected from $C_{1-10}$alkyl, $ZC_{3-10}$cycloalkyl, $ZC_{3-10}$heterocycloalkyl, $ZC_{6-10}$aryl and $ZC_{5-10}$heteroaryl, each of which is unsubstituted or substituted with one to three substituents selected from $C_{1-6}$alkyl, $OC_{1-6}$alkyl, OH and halo;
$R^{11}$ is selected from $C_{1-10}$alkyl, $OC_{1-6}$alkyl, OH, $C_{1-6}$alkylene-O—$C_{1-6}$alkyl, $C_{1-10}$alkylene-OH $C_{1-10}$alkylene $(OH)_2$ and halo;
Z is selected from a direct bond and $C_{1-6}$alkylene;
n and m are independently selected from 0, 1, 2 and 3; and
all alkyl and alkylene groups are optionally fluoro-substituted.

In some embodiments, X is selected from $CR^4R^5$, O and $NR^4$, wherein $R^4$ and $R^5$ are independently selected from H and $C_{1-4}$alkyl. In some embodiments, X is selected from $CR^4R^5$, O and $NR^4$, wherein $R^4$ and $R^5$ are independently selected from H and $CH_3$. In some embodiments, X is selected from $CH_2$, $CHCH_3$, $C(CH_3)_2$ and O.

In some embodiments, $X^1$, $X^2$ and $X^3$ are independently selected from $CR^6$ and N, wherein $R^6$ is selected from H, OH, $C_{1-4}$alkyl, $OC_{1-4}$alkyl, F and Cl. In some embodiments, $X^1$, $X^2$ and $X^3$ are independently selected from CH, CF, CCl, $CCH_3$, $COCH_3$ and N. In some embodiments, $X^1$ is CH and $X^2$ and $X^3$ are independently selected from CH, CF, CCl and $COCH_3$.

In some embodiments, $X^2$ and $X^3$ are linked to form, together with the carbon atoms to which they are attached, a 4-6-membered heterocycloalkyl ring which optionally contains one or two additional heteroatoms selected from O, S, S(O), $SO_2$ and $NR^7$, wherein $R^7$ is selected from H and $C_{1-4}$alkyl. In some embodiments, $X^2$ and $X^3$ are linked to form, together with the carbon atoms to which they are attached, a 5-6-membered heterocycloalkyl ring which optionally contain one or two additional heteroatom selected from O and $NR^7$, wherein $R^7$ is selected from H and $CH_3$. In some embodiments, $X^2$ and $X^3$ are linked to form, together with the carbon atoms to which they are attached, a 5-membered heterocycloalkyl ring which optionally contains one additional heteroatom selected from O and $NR^7$, wherein $R^7$ is selected from H and $CH_3$.

In some embodiments, $Cy^1$ is selected from phenyl and $C_6$heteroaryl, both of which are unsubstituted or substituted with one to three substituents selected from Cl, F, $C_{1-4}$alkyl and $OC_{1-4}$alkyl. In some embodiments, $Cy^1$ is selected from phenyl and pyridyl, both of which are unsubstituted or substituted with one to two substituents selected from Cl, F, $CH_3$ and $OCH_3$.

In some embodiments, $R^1$ is selected from $C(O)NR^8R^9$ and CN, wherein $R^8$ and $R^9$ are independently selected from H and $C_{1-4}$alkyl. In some embodiments, $R^1$ is $C(O)NR^8R^9$, wherein $R^8$ and $R^9$ are independently selected from H and $CH$. In some embodiments $R^1$ is $C(O)NH_2$.

In some embodiments, $R^2$ and $R^3$ are independently selected from H, $C_{1-6}$alkyl and $C_{1-4}$alkylene-O—$C_{1-4}$alkyl. In some embodiments, $R^2$ and $R^3$ are independently selected from $C_{1-6}$alkyl and $C_{1-4}$alkylene-O—$C_{1-4}$alkyl. In some embodiments, $R^2$ and $R^3$ are independently selected from $C_{1-6}$alkyl.

In some embodiments, $R^2$ and $R^3$ are linked to form, together with the nitrogen atom to which they are attached, a 4-10-membered heterocycloalkyl ring, which optionally contains one to two additional heteroatoms selected from O, S, S(O), $SO_2$, NH and $NR^{10}$, and which is unsubstituted or substituted with one to four substituents selected from $R^{11}$. In some embodiments, $R^2$ and $R^3$ are linked to form, together with the nitrogen atom to which they are attached, a 5-10-membered heterocycloalkyl ring, which optionally contains one additional heteroatom selected from O, NH and $NR^{10}$, which is unsubstituted or substituted with one to four substituents selected from $R^{11}$. In some embodiments, $R^2$ and $R^3$ are linked to form, together with the nitrogen atom to which they are attached a heterocycloalkyl ring selected from:

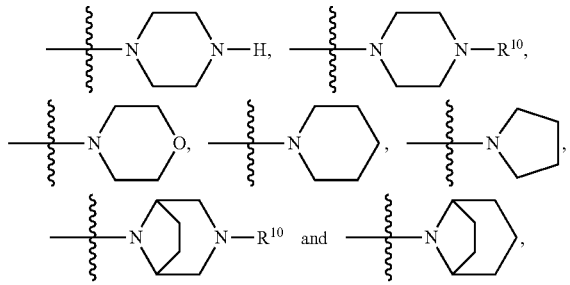

each of which is unsubstituted or substituted with one or two substituents selected from $R^{11}$.

In some embodiments, $R^{10}$ is selected from $C_{1-6}$alkyl, $ZC_{3-6}$cycloalkyl, $ZC_{3-6}$heterocycloalkyl, Zphenyl and $ZC_{5-6}$heteroaryl, each of which is unsubstituted or substituted with one to three substituents selected from $C_{1-4}$alkyl, $OC_{1-4}$alkyl, OH, Cl and F. In some embodiments, $R^{10}$ is selected from $CH_3$, $CH_2CH_3$, $C_{1-4}$alkyleneO$C_{1-4}$alkyl, $C_{1-4}$alkyleneCF$_3$, $C_{1-4}$alkyleneCF$_2$H, $CH_2CH(OCH_3)CH_3$, $CH_2CH(CH_2OH)_2$,

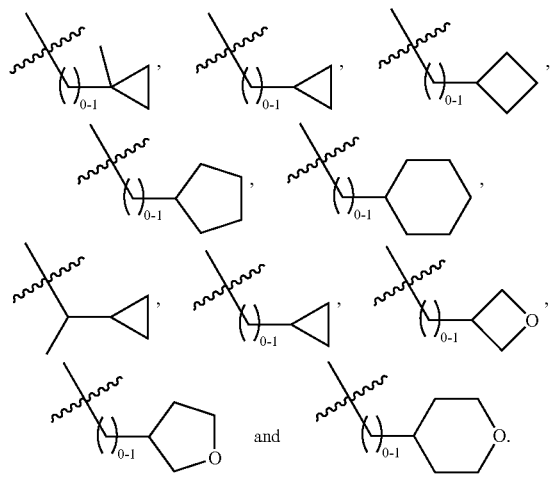

In some embodiments, $R^{11}$ is selected from $C_{1-6}$alkyl, $OC_{1-6}$alkyl, OH, $C_{1-6}$alkylene-O—$C_{1-6}$alkyl, $C_{1-6}$alkylene-OH $C_{1-6}$alkylene(OH)$_2$, Cl and F. In some embodiments, $R^{11}$ is selected from $C_{1-4}$alkyl, $OC_{4-6}$alkyl, OH, $C_{1-4}$alkylene-O—$C_{1-4}$alkyl, $C_{1-4}$alkylene-OH and $C_{1-4}$alkylene(OH)$_2$. In some embodiments, $R^{11}$ is selected from $C_{1-4}$alkyl. In some embodiments, $R^{11}$ is $CH_3$.

In some embodiments, Z is selected from a direct bond and $C_{1-4}$alkylene.

In some embodiments, n and m are independently selected from 0, 1 and 2. In some embodiments both n and m are 1. In some embodiments n is 0 and m is 1. In some embodiments, m is 0 and n is 1. In some embodiments, n is 2 and m is 1.

In some embodiments, all the fluoro-substituted alkyl groups are selected from $CF_3$, $CF_2H$ and $CFH_2$.

In some embodiments, the compound of Formula I is selected from compound number I-1 to I-98 in Table 1, or a pharmaceutically acceptable salt, solvent and/or prodrug thereof.

In some embodiments, the compound of Formula I is selected from the compound number I-1, I-2, I-5, I-6, I-7, I-8, I-20, I-22, I-23, I-24, I-25, I-33, I-34, I-35, I-37, I-38, I-39, I-40, I-41, I-43, I-44, I-47, I-48, I-55, I-57, I-58, I-59, I-60, I-61, I-62, I-63, I-65, I-66, I-74, I-75, I-76, I-77, I-78, I-79, I-80, I-81, I-82, I-84, I-85, I-86, I-87, I-88, I-89, I-90, I-92, I-93, I-94, I-96, I-97, and I-98 in Table 1, or a pharmaceutically acceptable salt, solvent and/or prodrug thereof.

In some embodiments, the compound of Formula I is selected from the compound number I-1, I-20, I-25, I-48, I-55, I-57, I-58, I-59, I-60, I-61, I-62, I-65, I-66, I-75, I-76, I-77, I-78, I-79, I-80, I-81, I-82, I-84, I-85, I-86, I-87, I-88, I-89, I-90, I-92, I-93, I-94, I-96, I-97, and I-98 in Table 1, or a pharmaceutically acceptable salt, solvent and/or prodrug thereof.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

The compounds of the application may be administered to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly. Administration can be by means of a pump for periodic or continuous delivery.

Parenteral administration includes intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

A compound of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines. For oral administration in a capsule form, useful carriers or diluents include lactose and dried corn starch.

Liquid preparations for oral administration may take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents may be added. Such liquid preparations for oral administration may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

A compound of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

The compounds of the application may be formulated for parenteral administration by injection, including using conventional catheterization techniques or infusion. Formulations for injection may be presented in unit dosage form, e.g., in ampoules or in multi-dose containers, with an added preservative. The compositions may take such forms as sterile suspensions, solutions or emulsions in oily or aqueous vehicles, and may contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

Compositions for nasal administration may conveniently be formulated as aerosols, drops, gels and powders.

For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

Compounds of the application may also be coupled with soluble polymers as targetable drug carriers. Such polymers can include polyvinylpyrrolidone, pyran copolymer, polyhydroxypropylmethacrylamide-phenol, polyhydroxy-ethyl-aspartamide-phenol, orpolyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of the application including pharmaceutically acceptable salts, solvates and prodrugs thereof are suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient (one or more compounds of the application), and from about 1 wt % to about 99.95 wt % or about 30 wt % to about 99.90 wt % of a pharmaceutically acceptable carrier, all percentages by weight being based on the total composition.

Compounds of the application may be used alone or in combination with other known agents useful for treating diseases, disorders or conditions treatable by inhibiting interactions with BCL6 BTB. When used in combination with other agents useful in treating diseases, disorders or conditions that are treatable by inhibiting interactions with BCL6 BTB, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application (e.g. a compound of Formula I), an additional therapeutic agent, and a pharmaceutically acceptable carrier.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. Dosages will generally be selected to maintain a serum level of compounds of the application from about 0.01 μg/cc to about 1000 μg/cc, or about 0.1 μg/cc to about 100 μg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. Compounds of the application may be administered in a single daily, weekly or monthly dose or the total daily dose may be divided into two, three or four daily doses.

To be clear, in the above, the term "a compound" also includes embodiments wherein one or more compounds are referenced.

III. Methods and Uses

The compounds of the application have been shown to be capable of inhibiting or blocking the interaction of BCL6 BTB binding domain with its corepressor binding partner SMRT/NCOR. The compounds have also been shown to inhibit tumor cell growth, specifically the Karpas-422 cell line.

Accordingly, the present application includes a method for inhibiting interactions with BCL6 BTB in a cell, either in a biological sample or in a patient, comprising administering an effective amount of one or more compounds of the application to the cell. The application also includes a use of one or more compounds of the application for inhibiting interactions with BCL6 BTB in a cell as well as a use of one or more compounds of the application for the preparation of a medicament for inhibiting interactions with BCL6 BTB interaction in a cell. The application further includes one or more compounds of the application for use in inhibiting interactions with BCL6 BTB protein.

As the compounds of the application have been shown to be capable of inhibiting interactions with BCL6 BTB, the compounds of the application are useful for treating diseases, disorders or conditions by inhibiting interactions with BCL6 BTB. Therefore the compounds of the present application are useful as medicaments. Accordingly, the present application includes a compound of the application for use as a medicament.

The present application also includes a method of treating a disease, disorder or condition that is treatable by inhibiting interactions with BCL6 BTB comprising administering a therapeutically effective amount of one or more compounds of the application to a subject in need thereof.

The present application also includes a use of one or more compounds of the application for treatment of a disease, disorder or condition that is treatable by inhibiting interactions with BCL6 BTB as well as a use of one or more compounds of the application for the preparation of a medicament for treatment of a disease, disorder or condition that is treatable by inhibiting interactions with BCL6 BTB. The application further includes one or more compounds of the application for use in treating a disease, disorder or condition that is treatable by inhibiting interactions with BCL6 BTB.

In an embodiment, the disease, disorder or condition is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Compounds of the application have been demonstrated to inhibit the growth of Karpas422 cells. Therefore in another embodiment of the present application, the disease, disorder or condition that is treatable by inhibiting interactions with BCL6 BTB is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from hematologic cancers, breast cancers, ovarian cancers and glioblastomas. In some embodiments, the cancer is a B-cell lymphoma. In some embodiments, the cancer is a non-Hodgkins lymphoma or a follicular lymphoma. In some embodiments, the cancer is diffuse large B cell lymphoma (DLBCL). In some embodiments, the cancer is a leukemia. In some embodiments, the cancer is BCR-ABL1-positive leukemia. In some embodiments, the cancer is chronic myeloid leukemia (CML) or acute lymphoblastic leukemia (ALL).

In an embodiment, the disease, disorder or condition that is treatable by inhibiting interactions with BCL6 BTB is a disease, disorder or condition associated with an uncontrolled and/or abnormal cellular activity affected directly or indirectly by inhibiting interactions with BCL6 BTB. In another embodiment, the uncontrolled and/or abnormal cellular activity that is affected directly or indirectly by inhibiting interactions with BCL6 BTB is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities affected directly or indirectly by inhibiting interactions with BCL6 BTB in a cell, either in a biological sample or in a subject, comprising administering an effective amount of one or more compounds of the application to the cell. The application also includes a use of one or more compounds of the application for inhibition of uncontrolled and/or abnormal cellular activities affected directly or indirectly by inhibiting interactions with BCL6 BTB in a cell as well as a use of one or more compounds of the application for the preparation of a medicament for inhibition of uncontrolled and/or abnormal cellular activities affected directly or indirectly by inhibiting interactions with BCL6 BTB in a cell. The application further includes one or more compounds of the application for use in inhibiting uncontrolled and/or abnormal cellular activities affected directly or indirectly by inhibiting interactions with BCL6 BTB in a cell.

Accordingly, the present application also includes a method of treating a disease, disorder or condition that is treatable by inhibiting interactions with BCL6 BTB comprising administering a therapeutically effective amount of one or more compounds of the application in combination with another known agent useful for treatment of a disease, disorder or condition that is treatable by inhibiting interactions with BCL6 BTB to a subject in need thereof. The present application also includes a use of one or more compounds of the application in combination with another known agent useful for treatment of a disease, disorder or condition that is treatable by inhibiting interactions with BCL6 BTB for treatment of a disease, disorder or condition that is treatable by inhibiting interactions with BCL6 BTB, as well as a use of one or more compounds of the application in combination with another known agent useful for treatment of a disease, disorder or condition that is treatable by inhibiting interactions with BCL6 BTB for the preparation of a medicament for treatment of a disease, disorder or condition that is treatable by inhibiting interactions with BCL6 BTB. The application further includes one or more compounds of the application in combination with another known agent useful for treatment of a disease, disorder or condition that is treatable by inhibiting interactions with BCL6 BTB for use in treating a disease, disorder or condition that is treatable by inhibiting interactions with BCL6 BTB. In an embodiment, the disease, disorder or condition treatable by inhibiting interactions with BCL6 BTB is cancer.

In a further embodiment, the disease, disorder or condition that is treatable by inhibiting interactions with BCL6 BTB is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors therapies, immunotherapy, hormonal therapy and anti-angiogenic therapies.

In some embodiments, the interactions that are being inhibited are protein-protein interactions between BCL6 BTB and another protein. In some embodiments, the other protein is a corepressor BCL6 BTB binding protein. In some embodiments the protein is selected from SMRT, NCOR and BCOR.

In some embodiments, the subject is a mammal. In some embodiments, the subject is human.

It will be appreciated by a person skilled in the art that the therapeutic methods and uses of the application would typically comprise administering or use an effective amount of the one or more compounds of the application in a pharmaceutical composition of the application.

IV. Methods of Preparation of Compounds of the Application

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art.

The compounds of Formula I generally can be prepared according to the processes illustrated in the Schemes below. In the structural formulae shown below the variables are as defined in Formula I unless otherwise stated. A person skilled in the art would appreciate that many of the reactions depicted in the Schemes below would be sensitive to oxygen and water and would know to perform the reaction under an anhydrous, inert atmosphere if needed. Reaction temperatures and times are presented for illustrative purposes only and may be varied to optimize yield as would be understood by a person skilled in the art.

Accordingly in some embodiments, the compounds of Formula I are prepared as shown in Scheme 1.

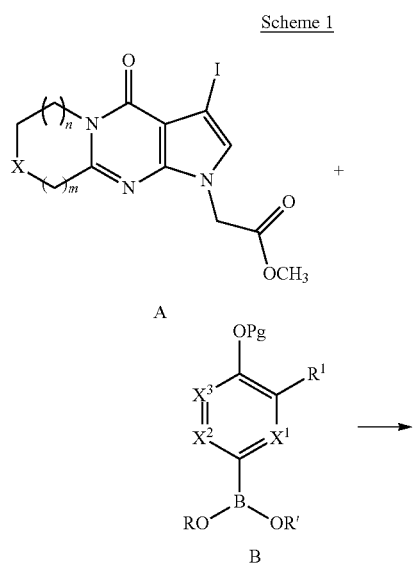

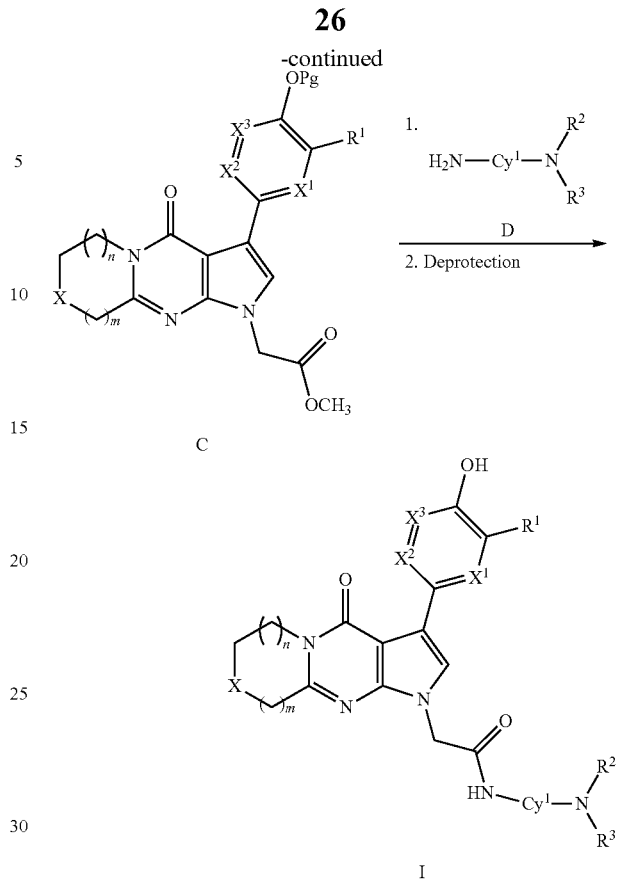

Therefore in some embodiments, compounds of Formula A are reacted under Suzuki coupling conditions with compounds of Formula B, wherein R and R' are, for example linked together to form a 4,4,5,5-tetramethylborolan-2-yl group, and Pg is a suitable protecting group, for example 2-trimethylsilylethyl, to provide compounds of Formula C. In some embodiments, the Suzuki coupling conditions comprise performing the reaction in the presence of a palladium catalyst, in an inert organic solvent and in a microwave at a temperature of about 40° C. to about 120° C., for about 1 minute to about 12 hours, or about 1 minute to about 1 hour. In some embodiments, the $R^1$ group in the compounds of Formula B also comprises a protecting group. Compounds of Formula C are then reacted with compounds of Formula D, for example in the presence of methyl magnesium chloride or equivalent, followed by removal of any protecting groups to provide compounds of Formula I. In some embodiments, the compounds of Formula D are first combined with the methyl magnesium chloride (or equivalent) in an inert organic solvent at for example room temperature, for about 1 minute to about 10 minutes, before the compounds of Formula C are added and the mixture allowed to react at a temperature of about 20° C. to about 80° C. until the reaction is complete. In some embodiments, additional methyl magnesium chloride (or equivalent) is added to the reaction mixture. In some embodiments, deprotection of the compounds of Formula D is carried out in the presence of an acid, such as trifluoroacetic acid, in an inert organic solvent at, for example, a slightly elevated temperature (such as about 30° C. to about 60° C.).

In an alternate embodiment, the compounds of Formula C are prepared by first synthesizing the corresponding boronic acid ester of the compounds of Formula A, i.e. compounds of Formula E, which are then reacted, via the corresponding boronic acid of Formula F, with compounds of Formula G, wherein Q is for example halo, such as Br, under Suzuki coupling conditions as shown in Scheme 2.

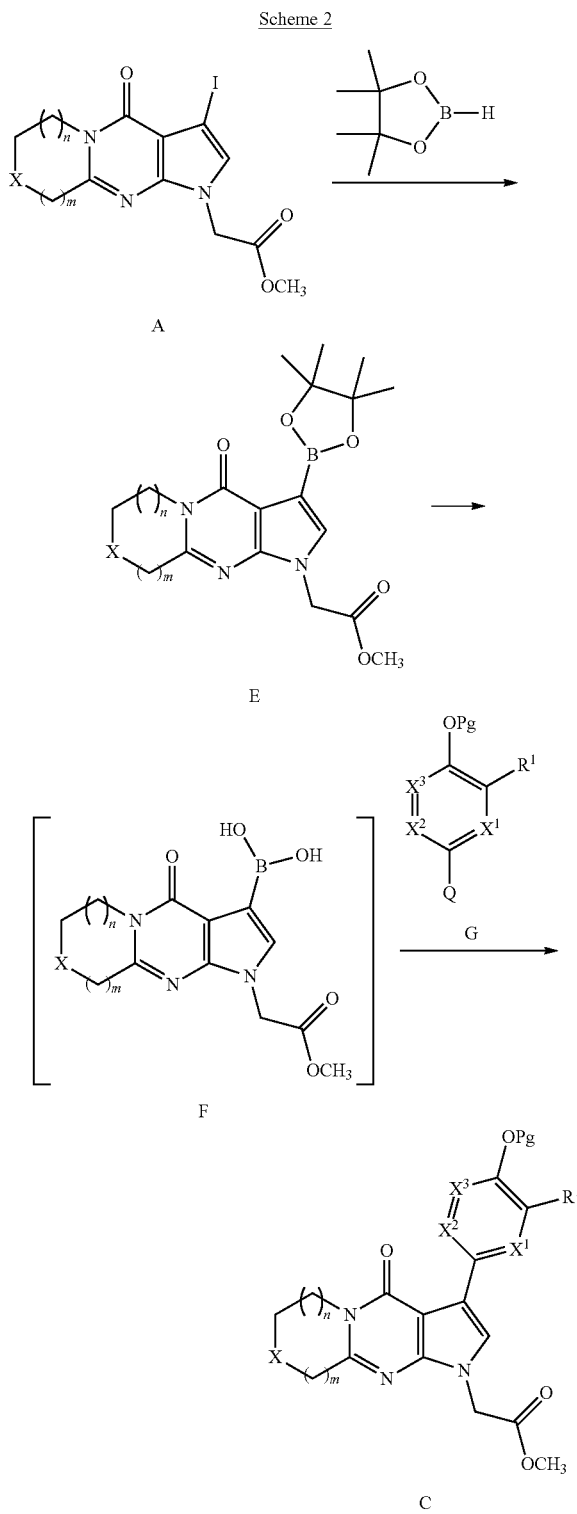

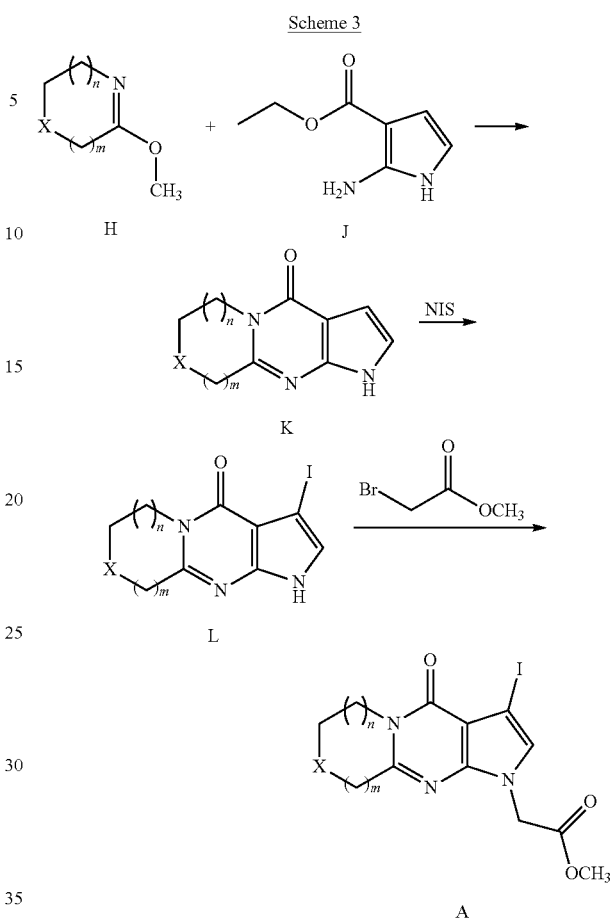

Therefore in some embodiments compounds of Formula H are reacted with compounds of Formula J, for example under neat conditions at a temperature of about 20° C. to about 120° C., to provide compounds of Formula K. Compounds of Formula K are iodinated, for example by reaction with N-iodosuccinimide in an inert organic solvent, at a temperature of for example 0° C. to about 30° C. to provide compounds of Formula L. Compounds of Formula L may then be reacted with methyl bromoacetate in the presence of a base in an inert organic solvent at a temperature of, for example, 20° C. to about 50° C., to provide compounds of Formula A.

Compounds of Formulae G and D are either commercially available or can be prepared from commercially available starting materials using methods known in the art, such as aromatic, nucleophilic and/or electrophic substitution reactions.

Examples of suitable inert organic solvents include, but are not limited to, dimethylformamide (DMF), dioxane, methylene chloride, chloroform, tetrahydrofuran (THF), toluene, and the like.

Salts of the compounds of the application are generally formed by dissolving the neutral compound in an inert organic solvent and adding either the desired acid or base and isolating the resulting salt by either filtration or other known means.

The formation of solvates of the compounds of the application will vary depending on the compound and the solvate. In general, solvates are formed by dissolving the compound in the appropriate solvent and isolating the sol- In some embodiments, compounds of Formula A are prepared as shown in Scheme 3.

vate by cooling or using an antisolvent. The solvate is typically dried or azeotroped under ambient conditions. The selection of suitable conditions to form a particular solvate can be made by a person skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine).

The following non-limiting examples are illustrative of the present application:

EXAMPLES

Example 1: Synthesis and Characterization of Compounds

Typical Synthesis of the Iodo Tricyclic Ester Illustrated with the Synthesis of methyl 2-(3-iodo-4-oxo-4,6,7,8-tetrahydro-1H-dipyrrolo[1,2-a:2',3'-d]pyrimidin-1-yl)acetate

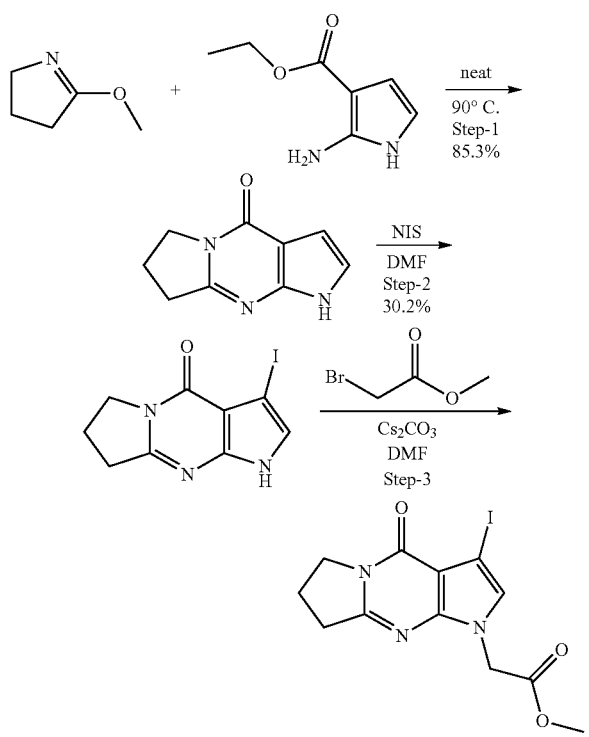

Step 1: A 2 L 3-necked flask equipped with a mechanical stirrer was charged with ethyl 2-amino-1H-pyrrole-3-carboxylate (100 g, 0.648 mol) and 5-methoxy-3,4-dihydro-2H-pyrrole (128.6 g, 1.5 mol) and the mixture was stirred at 90° C. After 8 h, 5-methoxy-3,4-dihydro-2H-pyrrole (45 g, 0.454 mol) was added then the mixture was kept at the same temperature overnight. It was purged with argon for 4 h then cooled to room temperature (rt). EtOAc (1 L) was added, the mixture was sonicated for 1 h and left to stand at rt overnight. The suspension was stirred for 4 h, then filtered. The solid was washed with EtOAc and dried to afford 1,6,7,8-tetrahydro-4H-dipyrrolo[1,2-a:2',3'-d]pyrimidin-4-one as a greenish solid (96.8 g, 85.3% yield); LCMS [M+H]⁺ 176.

In a similar manner the following compounds were synthesized:

| Structure | Name | Yield/LCMS |
|---|---|---|
| 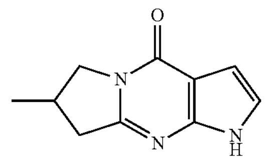 | 7-methyl-1,6,7,8-tetrahydro-4H-dipyrrolo[1,2-a:2',3'-d]pyrimidin-4-one | 46% yield LCMS [M + H]⁺ 190 |
| 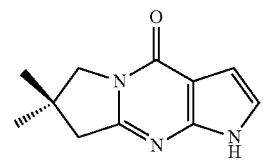 | 7,7-dimethyl-1,6,7,8-tetrahydro-4H-dipyrrolo[1,2-a:2',3'-d]pyrimidin-4-one | 46% yield LCMS [M + H]⁺ 204 |
| 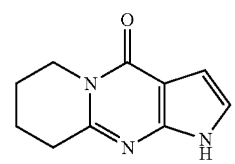 [SMILES: O=c1c2cc[nH]c2nc2n1CCCC2] | 6,7,8,9-tetrahydropyrido[1,2-a]pyrrolo[2,3-d]pyrimidin-4(1H)-one | 46% yield LCMS [M + H]⁺ 190 |
| 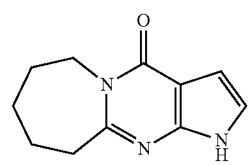 [SMILES: O=c1c2cc[nH]c2nc2n1CCCCC2] | 1,6,7,8,9,10-hexahydro-4H-pyrrolo[2',3':4,5]pyrimido[1,2-a]azepin-4-one | 91% yield LCMS [M + H]⁺ 204 |
| 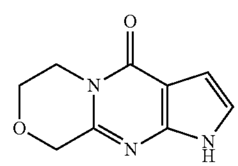 [SMILES: O=c1c2cc[nH]c2nc2n1CCOC2] | 1,6,7,9-tetrahydro-4H-pyrrolo[2',3':4,5]pyrimido[2,1-c][1,4]oxazin-4-one | 100% yield LCMS [M + H]⁺ 192 |

Step 2: 1,6,7,8-Tetrahydro-4H-dipyrrolo[1,2-a:2',3'-d]pyrimidin-4-one (100 g, 0.57 mmol) was dissolved in in anhydrous DMF (2.75 L) and stirred at rt for 10 min. The mixture was then filtered by gravity through a filter paper. An N-iodosuccinimide solution (128.42 g, 0.57 mmol) in anhydrous DMF (690 mL) was added in one portion. The mixture was vigorously stirred at 10° C. for 10 min. The solvent was removed via rotary evaporation at 60° C. The flask was then left in the water bath to cool slowly to rt and left at room temperature overnight upon which a precipitate formed. EtOAc (200 mL) was added then the mixture was shaken. The solid was filtered off and washed with EtOAc then dried under high vacuum to afford 3-iodo-1,6,7,8-tetrahydro-4H-dipyrrolo[1,2-a:2',3'-d]pyrimidin-4-one as a dark solid (54.8 g, 30.2% yield); LCMS [M+H]⁺ 302.

In a similar manner the following compounds were synthesized:

| Structure | Name | Yield/LCMS |
|---|---|---|
| 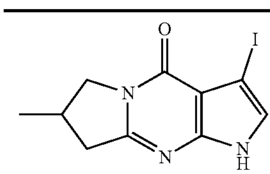 | 3-iodo-7-methyl-1,6,7,8-tetrahydro-4H-dipyrrolo[1,2-a:2',3'-d]pyrimidin-4-one | 97% yield LCMS [M + H]⁺ 316 |

| | | |
|---|---|---|
| 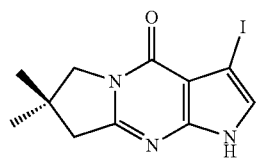 | 3-iodo-7,7-dimethyl-1,6,7,8-tetrahydro-4H-dipyrrolo[1,2-a:2',3'-d]pyrimidin-4-one | 100% yield LCMS [M + H]⁺ 330 |
| 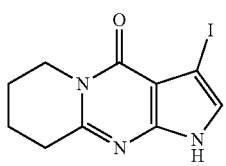 [SMILES: O=c1c2c(I)c[nH]c2nc2n1CCCC2] | 3-iodo-6,7,8,9-tetrahydropyrido[1,2-a]pyrrolo[2,3-d]pyrimidin-4(1H)-one | quantitative yield LCMS [M + H]⁺ 316 |
| 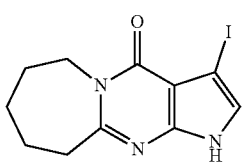 [SMILES: O=c1c2c(I)c[nH]c2nc2n1CCCCC2] | 3-iodo-1,6,7,8,9,10-hexahydro-4H-pyrrolo[2',3':4,5]pyrimido[1,2-a]azepin-4-one | quantitative yield LCMS [M + H]⁺ 330 |
| 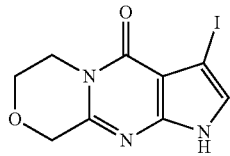 [SMILES: O=c1c2c(I)c[nH]c2nc2n1CCOC2] | 3-iodo-1,6,7,9-tetrahydro-4H-pyrrolo[2',3':4,5]pyrimido[2,1-c][1,4]oxazin-4-one | quantitative yield LCMS [M + H]⁺ 318 |

Step 3: A 1 L 3-necked flask was charged with 3-iodo-1,6,7,8-tetrahydro-4H-dipyrrolo[1,2-a:2',3'-d]pyrimidin-4-one (20 g, 66.43 mmol) and anhydrous DMF (300 mL). This suspension was stirred under argon then cesium carbonate (43.29 g, 132.85 mmol) was added. A solution of methyl bromoacetate (11.18 g, 73.07 mmol) in 20 mL of anhydrous DMF was added. The mixture was stirred for 30 min at rt upon which liquid chromatography-mass spectrometry (LCMS) showed complete conversion. The suspension was filtered to remove excess salts. The solid was washed with DMF. The combined organic layers were concentrated down to form a solid. 50 mL of (1:1) a solution of EtOAc:hexanes was added then the mixture was stirred. The mixture was filtered and the pad was washed with hexanes. The residue was dried with an air pump to afford methyl 2-(3-iodo-4-oxo-4,6,7,8-tetrahydro-1H-dipyrrolo[1,2-a:2',3'-d]pyrimidin-1-yl)acetate as an earth-colored solid (24.7 g, 99.7% yield); LCMS [M+H]⁺ 374.

In a similar manner the following compounds were synthesized:

| | | |
|---|---|---|
| 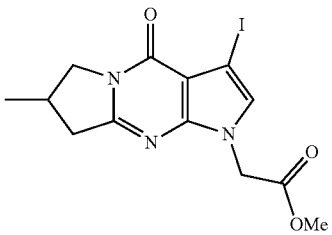 | methyl 2-(3-iodo-7-methyl-4-oxo-4,6,7,8-tetrahydro-1H-dipyrrolo[1,2-a:2',3'-d]pyrimidin-1-yl)acetate | 44% yield LCMS [M + H]⁺ 294 |
| 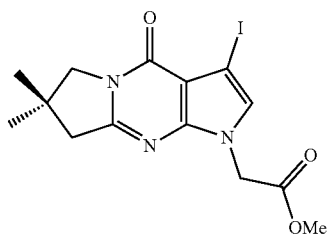 | methyl 2-(3-iodo-7,7-dimethyl-4-oxo-4,6,7,8-tetrahydro-1H-dipyrrolo[1,2-a:2',3'-d]pyrimidin-1-yl)acetate | 56% yield LCMS [M + H]⁺ 402 |
| 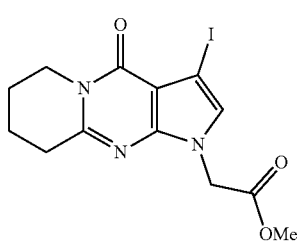 [SMILES: COC(=O)Cn1cc(I)c2c(=O)n3c(nc21)CCCC3] | methyl 2-(3-iodo-4-oxo-6,7,8,9-tetrahydropyrido[1,2-a]pyrrolo[2,3-d]pyrimidin-1(4H)-yl)acetate | 21% yield LCMS [M + H]⁺ 388 |

| | | |
|---|---|---|
| 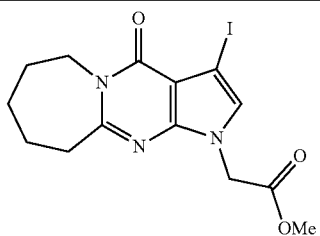 | methyl 2-(3-iodo-4-oxo-4,6,7,8,9,10-hexahydro-1H-pyrrolo[2',3':4,5]pyrimido[1,2-a]azepin-1-yl)acetate | 21% yield<br>LCMS [M + H]⁺ 402 |
| 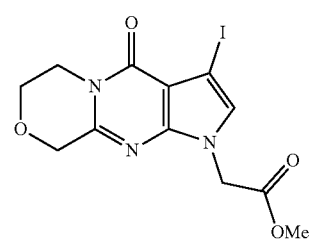 [SMILES: COC(=O)Cn1cc(I)c2c(=O)n3c(nc21)COCC3] | methyl 2-(3-iodo-4-oxo-4,6,7,9-tetrahydro-1H-pyrrolo[2',3':4,5]pyrimido[2,1-c][1,4]oxazin-1-yl)acetate | 25% yield<br>LCMS [M + H]⁺ 390 |

Synthesis of Compounds of Formula I

The general scheme for Suzuki-Coupling/Amidation/Deprotection Procedures (Method A) is as follows:

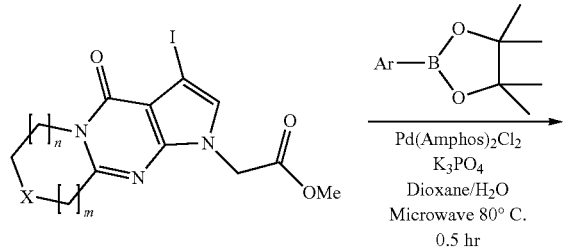
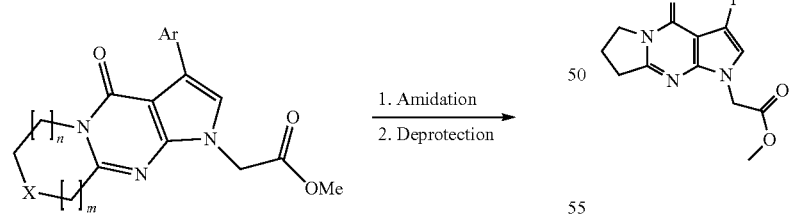
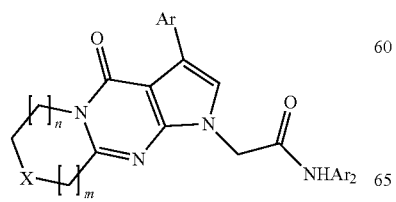

Synthesis of (S)-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide

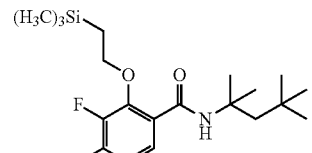
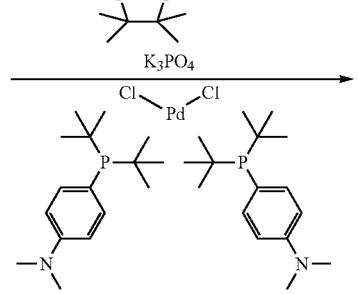

1,4-Dioxane/water, 90° C. Step-1 81%

-continued

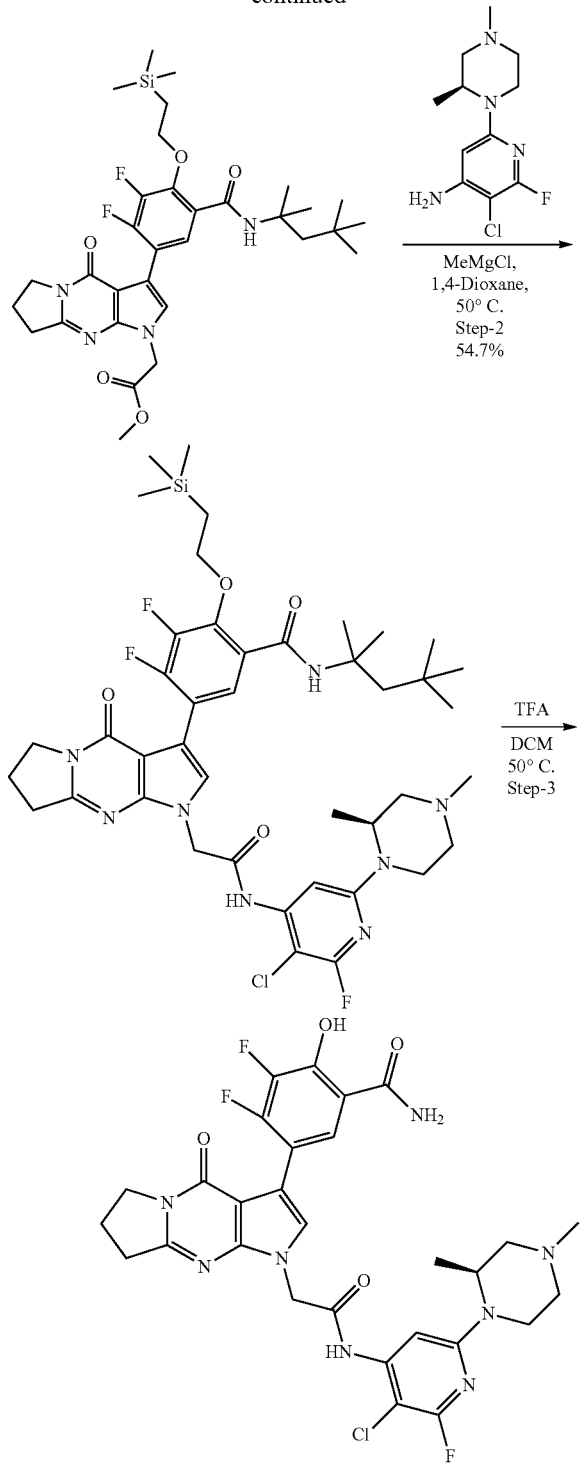

Step 1: A 20 mL microwave vial was charged with 3,4-difluoro-5-(4,4,5,5-tetramethyl-1,3,2-dioxaborolan-2-yl)-N-(2,4,4-trimethylpentan-2-yl)-2-(2-(trimethylsilyl) ethoxy)benzamide (960 mg, 1.876 mmol) and methyl 2-(3-iodo-4-oxo-4,6,7,8-tetrahydro-1H-dipyrrolo[1,2-a:2',3'-d] pyrimidin-1-yl)acetate (500 mg, 1.340 mmol) then 1,4-dioxane (12 mL) was added. The mixture was stirred at rt. Potassium phosphate tribasic (569 mg, 2.68 mmol) was dissolved in water (1.2 mL) and cooled. It was then added to the mixture. The vial was flushed with $N_2$. Bis(di-tert-butyl(4-dimethylaminophenyl)phosphine)dichloropalladium(II) (76 mg, 0.107 mmol) was added then the flask was purged with $N_2$ and sealed. The mixture was heated in a microwave at 90° C. for 30 min upon which LCMS showed completion. The mixture was neutralized with 1N citric acid (2.68 mL) then diluted with DCM then water was added. The aqueous layer was extracted several times with DCM. It was dried over $Na_2SO_4$ and concentrated to afford crude. The crude was purified by Isco chromatography (24 g silica column: eluent: 0%, 0-50%, then 50% EtOAc:hexanes). The desired product was collected as an off-white fluffy powder (683.4 mg, 81% yield); LCMS [M+H]$^+$ 631.

Step 2: In a vial with magnetic stir bar was placed (S)-3-chloro-6-(2,4-dimethylpiperazin-1-yl)-2-fluoropyridin-4-amine (51.7 mg, 0.2 mmol) and 1,4-dioxane (4 mL). The solution was stirred at rt and 3M methylmagnesium chloride (MeMgCl; 0.074 mL, 0.222 mmol) was added all at once. The resulting turbid solution was stirred at rt for 5 min. Methyl 2-(3-(2,3-difluoro-5-((2,4,4-trimethylpentan-2-yl) carbamoyl)-4-(2-(trimethylsilyl)ethoxy)phenyl)-4-oxo-4,6,7,8-tetrahydro-1H-dipyrrolo[1,2-a:2',3'-d]pyrimidin-1-yl) acetate (70 mg, 0.111 mmol) was then added as solid. The mixture was stirred at 50° C. After 5 min, 0.08 mL of MeMgCl was added. The mixture was stirred for another 5 min upon which LCMS showed there was still some starting material left. Accordingly, an additional 0.02 mL of MeMgCl was added then the reaction was stirred for 2 to 3 min then stopped. The suspension was cooled. It was quenched with a small amount of MeOH. It was loaded on Celite™ and dried down. It was purified by reverse phase Isco (13 g C18 column: eluent 10%, 10-100% then 100% AcCN: water). The desired product was collected as a grey glassy solid (52 mg, 54.7% yield); LCMS [M+H]$^+$ 857.

Step 3: (S)-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-N-(2,4,4-trimethylpentan-2-yl)-2-(2-(trimethylsilyl)ethoxy)benzamide (52 mg, 0.061 mmol) was dissolved in dichloromethane (2 mL) then trifluoroacetic acid (2 mL) was added. The mixture was heated to 50° C. After 1 h, LCMS showed completion. The solvents were evaporated off. The resulting residue was dissolved in acetonitrile, and water was added. It was lyophilized overnight to afford the product as a light purple fluffy powder (TFA salt, 51.8 mg, 93% yield). $^1$H NMR (500 MHz, DMSO-$d_6$) δ=13.57 (br s, 1H), 10.05 (s, 1H), 9.46 (br s, 1H), 8.32 (br s, 1H), 8.00 (br s, 1H), 7.86 (br d, J=6.7 Hz, 1H), 7.42-7.37 (m, 1H), 7.12 (s, 1H), 5.14 (s, 2H), 4.41 (br s, 1H), 3.97 (br d, J=13.6 Hz, 2H), 3.86 (br t, J=7.2 Hz, 3H), 3.30 (br d, J=12.2 Hz, 2H), 3.05-2.96 (m, 2H), 2.93 (brt, J=7.8 Hz, 2H), 2.86 (br s, 1H), 2.68 (s, 3H), 2.03 (quin, J=7.5 Hz, 2H), 1.03 (d, J=7.1 Hz, 3H); LCMS [M+H]$^+$ 645.

The general scheme for Borylation-Suzuki-Coupling/Amidation/Deprotection Procedures (Method B) is as follows:

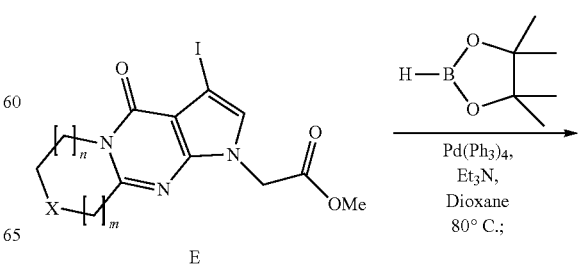

E

-continued
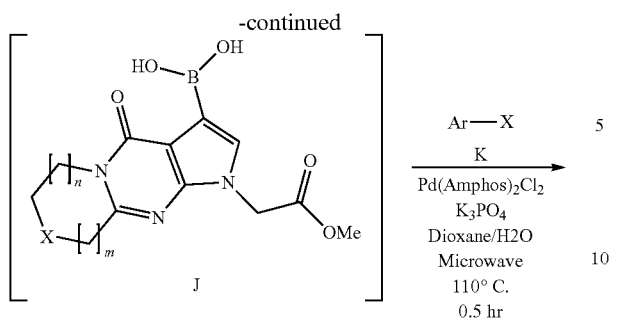
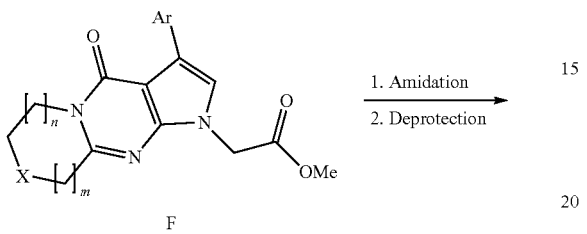
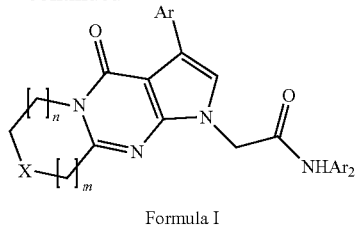
Synthesis of (S)-7-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-hydroxybenzo[d][1,3]dioxole-5-carboxamide
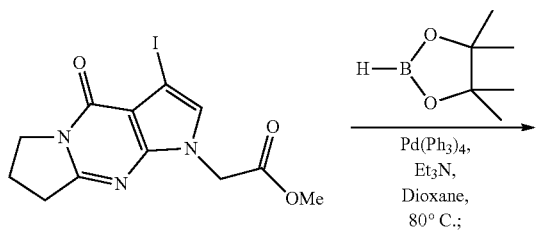
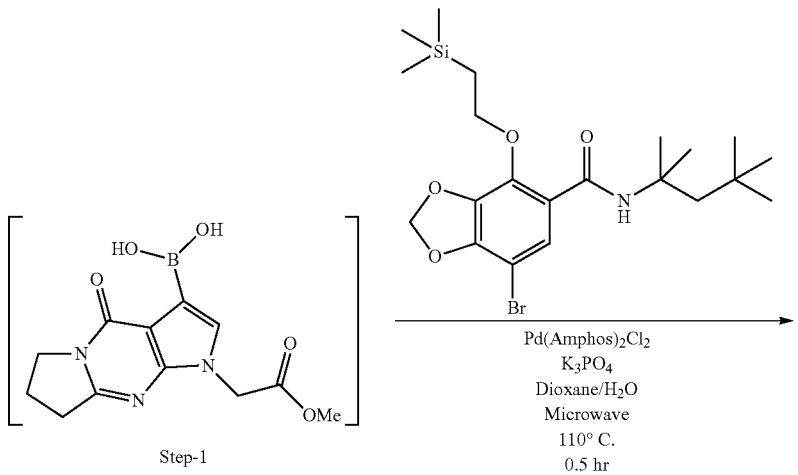

-continued

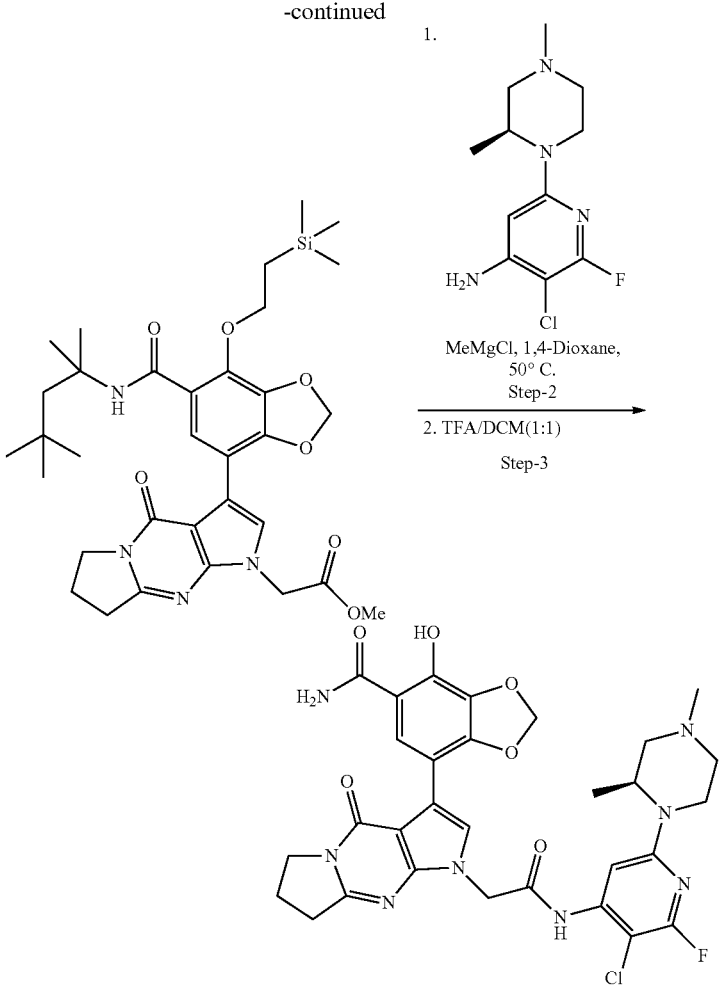

Step 1: A microwave vial equipped with a magnetic stir bar was charged with methyl 2-(3-iodo-4-oxo-4,6,7,8-tetrahydro-1H-dipyrrolo[1,2-a:2',3'-d]pyrimidin-1-yl)acetate (280 mg, 0.750 mmol) and tetrakis(triphenylphosphine)palladium(0) (0.052 g, 0.045 mmol). The flask was sealed with a septum and was evacuated and flushed with $N_2$ three times. Then 1,4-dioxane (10 mL), triethylamine (2.1 mL, 15.1 mmol) and 4,4,5,5-tetramethyl-1,3,2-dioxaborolane (0.241 mL, 1.66 mmol) were added to the flask, which was heated to 80° C. for 1 hour. LCMS analysis indicated complete formation of the boronic acid instead of the boronate ester. The crude reaction mixture was cooled to RT, and used directly in the next step without further purification (quantitative conversion). To a microwave vial charged with (1-(2-methoxy-2-oxoethyl)-4-oxo-4,6,7,8-tetrahydro-1H-dipyrrolo[1,2-a:2',3'-d]pyrimidin-3-yl)boronic acid (100 mg, 0.344 mmol), 7-bromo-N-(2,4,4-trimethylpentan-2-yl)-4-(2-(trimethylsilyl)ethoxy)benzo[d][1,3]dioxole-5-carboxamide (243 mg, 0.515 mmol), was added dioxane (10 mL). $K_3PO_4$ (146 mg, 0.687 mmol) dissolved in water (1 mL) and the reaction vial was flushed with nitrogen. Bis(di-tert-butyl (4-dimethylaminophenyl)phosphine)dichloropalladium(II) (0.0036 g, 0.052 mmol) was added, the vial was sealed, and the mixture heated in a microwave reactor to 110° C. for 30 minutes. The mixture was neutralized with citric acid (1N, 1 mL). The crude mixture was concentrated onto celite and purified using silica gel column chromatography (water: AcCN gradient 0-100%). The product was dried under vacuum to give methyl 2-(4-oxo-3-(6-((2,4,4-trimethylpentan-2-yl)carbamoyl)-7-(2-(trimethylsilyl)ethoxy)benzo[d][1,3]dioxol-4-yl)-4,6,7,8-tetrahydro-1H-dipyrrolo[1,2-a:2',3'-d]pyrimidin-1-yl)acetate as a light yellow solid (0.095 g, 43%). LCMS $[M+H]^+$ 639.

Step 2: To a solution of (S)-3-chloro-6-(2,4-dimethylpiperazin-1-yl)-2-fluoropyridin-4-amine (65.6 mg, 0.254 mmol) in 1,4-dioxane (8.0 mL) was added 3M methylmagnesium chloride (0.085 mL, 0.254 mmol) dropwise under nitrogen. The yellow suspension was allowed to stir at RT for 5 min. Methyl 2-(4-oxo-3-(6-((2,4,4-trimethylpentan-2-yl)carbamoyl)-7-(2-(trimethylsilyl)ethoxy)benzo[d][1,3]dioxol-4-yl)-4,6,7,8-tetrahydro-1H-dipyrrolo[1,2-a:2',3'-d]pyrimidin-1-yl)acetate (90 mg, 0.141 mmol) was slowly added and stirred at 40° C. for 10 min. Additional 3M methylmagnesium chloride (0.085 mL, 0.254 mmol) was added. The mixture was stirred at 40° C. for 1 hour. LCMS showed complete conversion. The reaction was quenched with methanol and concentrated onto celite. The crude mixture was purified on a Biotage™ (reverse phase silica gel) eluting with 0-100% ACN/$H_2O$. The desired fractions were collected, concentrated and dried under vacuum to afford (S)-7-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-N-(2,4,4-trimethylpentan-2-yl)-4-(2-(trimethylsilyl)ethoxy)benzo[d][1,3]dioxole-5-carboxamide as a yellow residue. LCMS $[M+H]^+$ 865.

Step 3: To a solution of (S)-7-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-N-(2,4,4-trimethylpentan-2-yl)-4-(2-(trimethylsilyl)ethoxy)benzo[d][1,3]dioxole-5-carboxamide in dichloromethane (DCM) (1.00 mL) was added trifluoroacetic acid (1.079 mL, 14.09 mmol). The mixture was stirred at 40° C. for 2 hours. LCMS showed complete conversion. The reaction was concentrated in vacuo to remove the volatiles, followed by trituration with diethyl ether. The filtered solid was dried under vacuum to afford (S)-7-(1-(2-((3-chloro-6-(2,4-dimethylpiperazin-1-yl)-2-fluoropyridin-4-yl)amino)-2-oxoethyl)-4-oxo-4,6,7,8-tetrahydro-1H dipyrrolo[1,2-a:2',3'-d]pyrimidin-3-yl)-N-(2,4,4-trimethylpentan-2-yl)-4-(2 (trimethylsilyl)ethoxy)benzo[d][1,3]dioxole-5-carboxamide as a beige solid. (TFA salt, 59 mg, 48% yield). $^1$H NMR (500 MHz, DMSO-$d_6$) δ=12.98 (br s, 1H), 10.17 (s, 1H), 9.51 (br d, J=1.2 Hz, 1H), 8.30 (s, 1H), 7.86 (br s, 2H), 7.55 (s, 1H), 7.36 (s, 1H), 6.11 (s, 2H), 5.27 (s, 2H), 4.56 (br s, 1H), 4.11 (br d, J=13.9 Hz, 1H), 4.04 (br t, J=7.2 Hz, 2H), 3.44 (br d, J=12.0 Hz, 2H), 3.14 (br d, J=12.5 Hz, 1H), 3.08 (br t, J=7.9 Hz, 2H), 3.00 (br d, J=10.5 Hz, 1H), 2.82 (br s, 3H), 2.18 (quin, J=7.5 Hz, 2H), 1.17 (d, J=7.0 Hz, 3H); [M+1]$^+$ 654.

Synthesis of (S)-5-(1-(2-((3-chloro-2-fluoro-6-(4-(3-hydroxy-2-(hydroxymethyl)propyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide

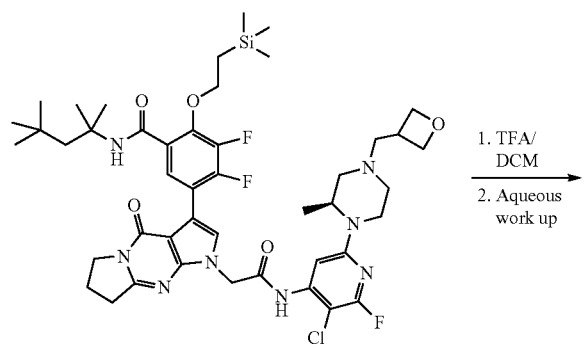

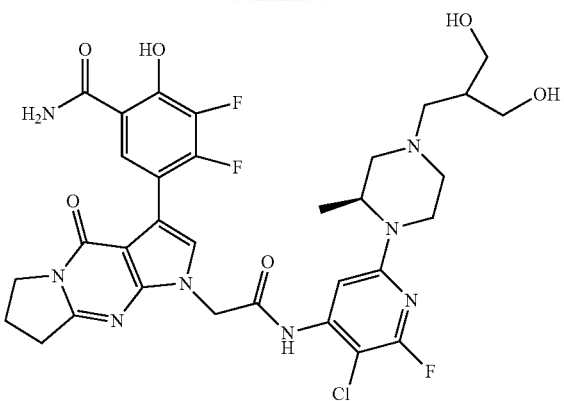

To a solution of (S)-5-(1-(2-((3-chloro-2-fluoro-6-(2-methyl-4-(oxetan-3-ylmethyl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-N-(2,4,4-trimethylpentan-2-yl)-2-(2-(trimethylsilyl)ethoxy)benzamide (38 mg, 0.042 mmol) in dichloromethane (DCM) (1.00 mL) was added trifluoroacetic acid (0.910 mL, 11.89 mmol). The mixture was stirred at 40° C. for 1 hour. LCMS analysis showed only ring-opened product with and without the octyl protecting group observed. The reaction was heated overnight at 40° C. overnight then concentrated in vacuo and purified on a Biotage (reverse phase silica gel) eluting with 0-80% ACN/H$_2$O. The desired fractions were collected, concentrated in vacuo and dried under vacuum at RT to afford the diol (S)-5-(1-(2-((3-chloro-2-fluoro-6-(4-(3-hydroxy-2-(hydroxymethyl)propyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide, 2 trifluoroacetic acid, CF$_3$COOH [D] (0.014 mmol, 11.54% yield) as a beige solid.

Using the general approach described in Method A or B the following compounds of Formula I were synthesized:

| Structure | Yield | NMR & LCMS |
|---|---|---|
| 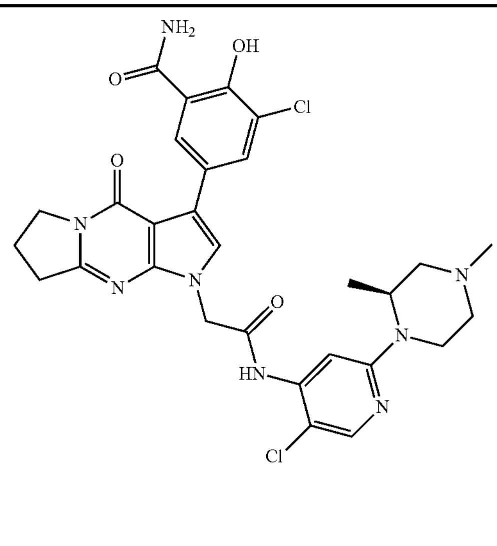 | 78% | $^1$H NMR (500 MHz, DMSO-$d_6$) δ = 13.66 (s, 1H), 9.86 (s, 1H), 9.51-9.20 (m, 1H), 8.47 (br s, 1H), 8.43 (d, J = 1.7 Hz, 1H), 8.07-7.97 (m, 2H), 7.47 (s, 1), 7.32 (s, 1H), 5.09 (s, 2H), 4.52-4.35 (m, 2H), 4.06-3.95 (m, 2H), 3.90 (br t, J = 7.2 Hz, 2H), 3.62-3.38 (m, 2H), 3.28 (br d, J = 12.1 Hz, 2H), 2.92 (br t, J = 7.8 Hz, 1H), 2.66 (br s, 3H), 2.09-1.95 (m, 2H), 0.98 (br d, J = 7.0 Hz, 3H); LCMS [M + H]$^+$ 625. |

| Structure | Yield | NMR & LCMS |
|---|---|---|
| 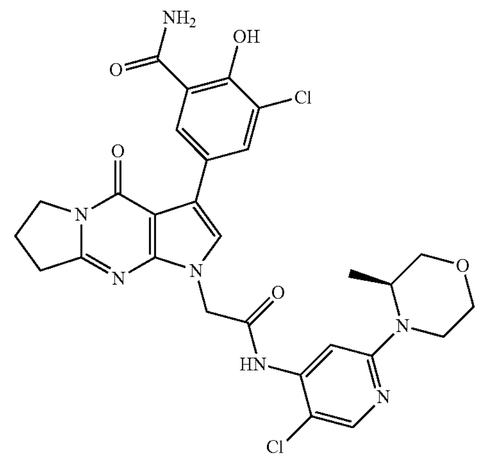 [SMILES: C[C@H]1COCCN1c1cc(NC(=O)Cn2cc(-c3cc(Cl)c(O)c(C(N)=O)c3)c3c(=O)n4c(nc32)CCC4)c(Cl)cn1] | 72% | $^1$H NMR (500 MHz, DMSO-$d_6$) δ = 13.67 (br s, 1H), 9.76 (s, 1H), 8.48 (br s, 1H), 8.43 (d, J = 2.0 Hz, 1H), 8.04-7.96 (m, 2H), 7.37 (s, 1H), 7.31 (s,1H), 5.07 (s, 2H), 4.01-3.93 (m, 2H), 3.89 (br t, J = 7.2 Hz, 1H), 3.72 (br dd, J = 3.2, 11.5 Hz, 1H), 3.50 (br d, J = 10.9 Hz, 2H), 3.40 (dd, J = 2.8, 11.3 Hz, 1H), 3.25 (br d, J = 3.1 Hz, 1H), 2.93 (t, J = 7.8 Hz, 1H), 2.89-2.76 (m, 1H), 2.08-1.96 (m, 2H), 0.90 (d, J = 6.6 Hz, 3H); LCMS [M + H]$^+$ 612. |
| 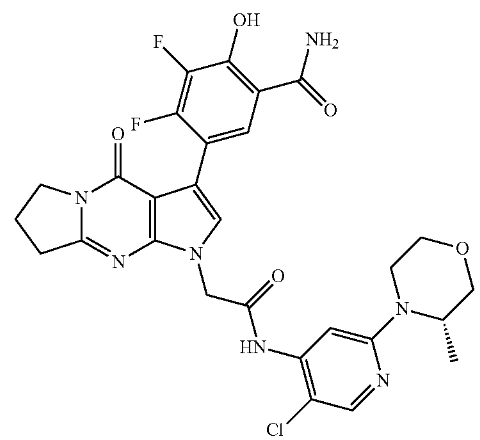 [SMILES: C[C@H]1COCCN1c1cc(NC(=O)Cn2cc(-c3cc(C(N)=O)c(O)c(F)c3F)c3c(=O)n4c(nc32)CCC4)c(Cl)cn1] | Quant. | $^1$H NMR (500 MHz, DMSO-$d_6$) δ = 13.73-13.39 (m, 1H), 9.75 (s, 1H), 8.38-8.31 (m, 1H), 8.01 (s, 1H), 8.00 (br s, 1H), 7.85 (br d, J = 6.7 Hz, 1H), 7.40 (s, 1H), 7.15-7.08 (m, 1H), 5.10 (s, 2H), 3.99 (br d, J = 4.5 Hz, 1H), 3.86 (br t, J = 7.2 Hz, 2H), 3.74 (br dd, J = 3.2, 11.4 Hz, 1H), 3.28 (dt, J = 2.9, 11.8 Hz, 2H), 2.94 (t, J = 7.9 Hz, 2H), 2.86 (dt, J = 3.9, 12.6 Hz, 1H), 2.03 (quin, J = 7.5 Hz, 2H), 0.92 (d, J = 6.7 Hz, 3H); LCMS [M + H]$^+$ 614. |
| 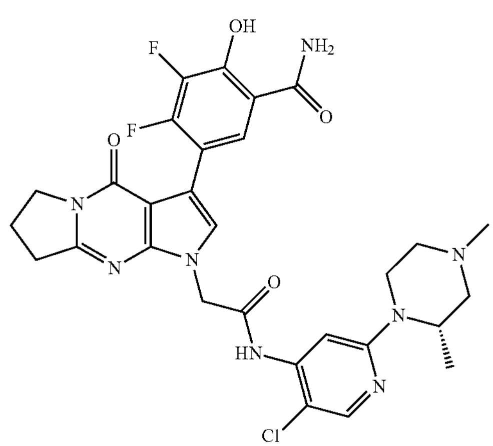 | 99% | $^1$H NMR (500 MHz, DMSO-$d_6$) δ = 13.56 (br s, 1H), 9.85 (s, 1H), 9.34 (br s, 1H), 8.32 (br s, 1H), 8.06 (s, 1H), 8.00 (br s, 1H), 7.85 (br d, J = 6.5 Hz, 1H), 7.51 (s, 1H), 7.14-7.07 (m, 1H), 5.11 (s, 2H), 4.53-4.36 (m, 1H), 4.03 (br d, J = 13.6 Hz, 1H), 3.86 (br t, J = 7.2 Hz, 2H), 3.30 (br d, J = 12.2 Hz, 2H), 3.02 (br s, 2H), 2.93 (br t, J = 7.9 Hz, 2H), 2.91-2.80 (m, 1H), 2.69 (br s, 3H), 2.03 (quin, J = 7.6 Hz, 2H), 1.01 (d, J = 7.0 Hz, 3H); LCMS [M + H]$^+$ 627. |

| Structure | Yield | NMR & LCMS |
|---|---|---|
| 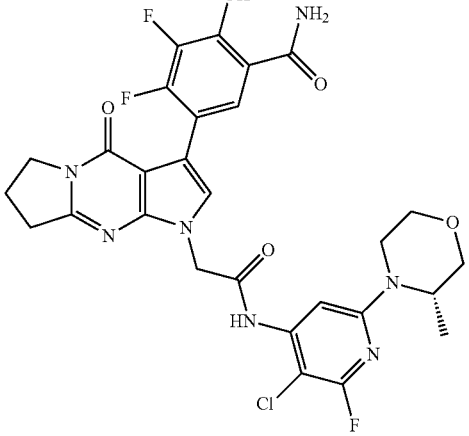 | Quant. | ¹H NMR (500 MHz, DMF) δ = 10.51 (s, 1H), 8.92 (br s, 1H), 8.57 (br s, 1H), 8.42 (br d, J = 6.6 Hz, 1H), 7.88 (s, 1H), 7.71-7.65 (m, 1H), 5.69 (s, 2H), 4.53-4.46 (m, 1H), 4.43 (t, J = 7.2 Hz, 2H), 4.31 (br dd, J = 3.4, 11.3 Hz, 1H), 4.10 (d, J = 11.4 Hz, 1H), 4.04 (br d, J = 11.6 Hz, 1H), 3.98 (br dd, J = 2.8, 11.4 Hz, 1H), 3.51 (t, J = 7.9 Hz, 2H), 3.47-3.42 (m, 1H), 2.60 (quin, J = 7.5 Hz, 2H), 1.52 (d, J = 6.7 Hz, 3H); LCMS [M + H]⁺ 632. |
| 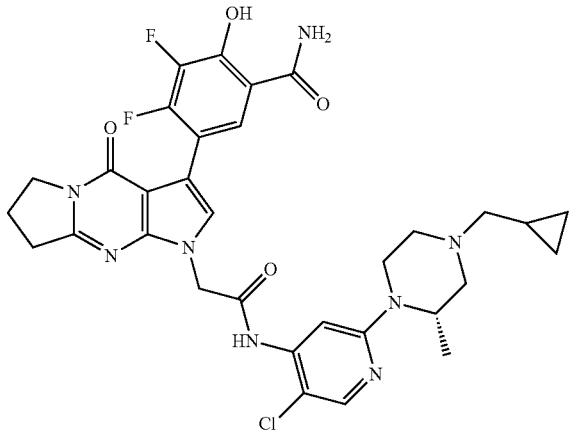 [SMILES: C[C@H]1CN(CC2CC2)CCN1c1cc(NC(=O)Cn2cc(-c3cc(C(N)=O)c(O)c(F)c3F)c3c(=O)n4c(nc32)CCC4)c(Cl)cn1] | 100% | ¹H NMR (500 MHz, DMSO-d₆) δ ppm 0.22 (br d, J = 3.55 Hz, 2 H) 0.51 (br d, J = 7.83 Hz, 2 H) 0.86-0.96 (m, 1 H) 1.05 (br d, J = 6.97 Hz, 3 H) 1.94-2.09 (m, 2 H) 2.79-2.89 (m, 2 H) 2.93 (br t, J = 7.83 Hz, 2 H) 2.98-3.07 (m, 3 H) 3.86 (br t, J = 7.09 Hz, 2 H) 4.05 (br d, J = 13.82 Hz, 1 H) 4.51 (br s, 1 H) 5.11 (s, 2 H) 7.11-7.14 (m, 1 H) 7.51 (s, 1 H) 7.86 (br d, J = 6.85 Hz, 1 H) 8.00 (br s, 1 H) 8.07 (s, 1 H) 8.32 (br s, 1 H) 9.22 (br d, J = 0.98 Hz, 1 H) 9.85 (s, 1 H) 13.43-13.63 (m, 1 H); LCMS [M + H]⁺ 667. |
| 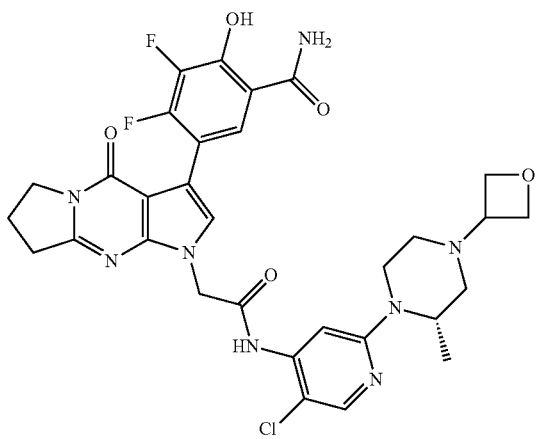 | 97% | ¹H NMR (500 MHz, DMSO-d₆) δ ppm 1.06 (br d, J = 6.72 Hz, 3 H) 2.03 (quin, J = 7.55 Hz, 2 H) 2.93 (br t, J = 7.83 Hz, 3 H) 2.96-3.01 (m, 1 H) 3.86 (br t, J = 7.15 Hz, 2 H) 4.02 (br d, J = 10.64 Hz, 1 H) 4.44 (br s, 1 H) 4.53-4.56 (m, 1 H) 4.58 (br d, J = 6.11 Hz, 2 H) 4.59-4.65 (m, 1 H) 5.11 (s, 2H) 7.11-7.14 (m, 1 H) 7.48 (s, 1 H) 7.86 (br d, J = 6.72 Hz, 1 H) 8.00 (br s, 1 H) 8.06 (s, 1 H) 8.32 (br s, 1 H) 9.83 (s, 1 H) 13.56 (br d, J = 1.10 Hz, 1H); LCMS [M + H]⁺ 669. |

-continued

| Structure | Yield | NMR & LCMS |
|---|---|---|
| 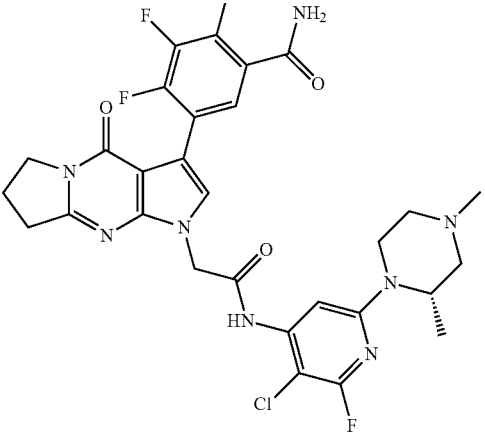 | 93% | $^1$H NMR (500 MHz, DMSO-$d_6$) δ = 13.57 (br s, 1H), 10.05 (s, 1H), 9.46 (br s, 1H), 8.32 (br s, 1H), 8.00 (br s, 1H), 7.86 (br d, J = 6.7 Hz, 1H), 7.42-7.37 (m, 1H), 7.12 (s, 1H), 5.14 (s, 2H), 4.41 (br s, 1H), 3.97 (br d, J = 13.6 Hz, 2H), 3.86 (br t, J = 7.2 Hz, 3H), 3.30 (br d, J = 12.2 Hz, 2H), 3.05-2.96 (m, 2H), 2.93 (br t, J = 7.8 Hz, 2H), 2.86 (br s, 1H), 2.68 (s, 3H), 2.03 (quin, J = 7.5 Hz, 2H), 1.03 (d, J = 7.1 Hz, 3H); LCMS [M + H]$^+$ 645. |
| 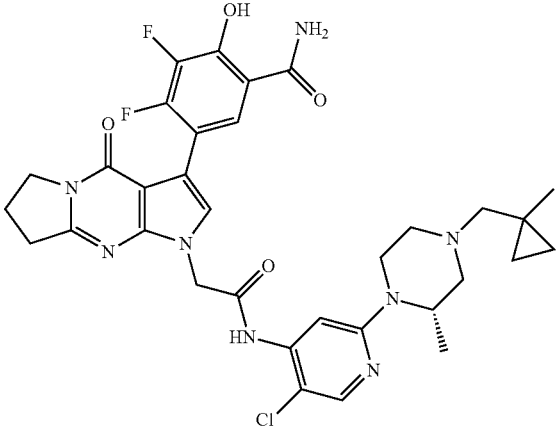 [SMILES: C[C@H]1CN(CC2(C)CC2)CCN1c1cc(NC(=O)Cn2cc(-c3cc(C(N)=O)c(O)c(F)c3F)c3c(=O)n4c(nc32)CCC4)c(Cl)cn1] | 98% | $^1$H NMR (500 MHz, DMSO-$d_6$) δ = 13.56 (br s, 1H), 9.85 (s, 1H), 8.99 (br s, 1H), 8.32 (br s, 1H), 8.07 (s, 1H), 8.00 (br s, 1H), 7.86 (br d, J = 6.6 Hz, 1H), 7.51 (s, 1H), 7.14-7.08 (m, 1H), 5.11 (s, 2H), 4.54 (br s, 1H), 4.01 (br d, J = 14.1 Hz, 3H), 3.87 (br t, J = 7.1 Hz, 2H), 3.41 (br d, J = 12.3 Hz, 1H), 3.33 (br d, J = 11.9 Hz, 1H), 3.18 (br d, J = 12.2 Hz, 1H), 3.12-2.99 (m, 2H), 2.93 (br t, J = 7.8 Hz, 2H), 2.90-2.80 (m, 1H), 2.68 (br dd, J = 6.8, 12.6 Hz, 1H), 2.03 (quin, J = 7.5 Hz, 2H), 1.08 (d, J = 7.0 Hz, 3H), 0.99 (s, 3H), 0.52-0.45 (m, 1H), 0.37 (br t, J = 5.5 Hz, 2H), 0.33-0.27 (m, 1H); LCMS [M + H]$^+$ 681. |
| 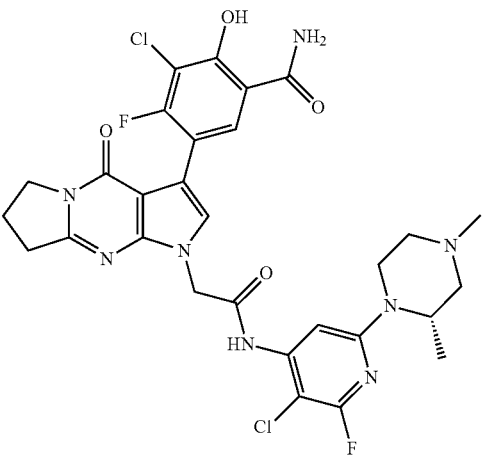 [SMILES: C[C@H]1CN(C)CCN1c1cc(NC(=O)Cn2cc(-c3cc(C(N)=O)c(O)c(Cl)c3F)c3c(=O)n4c(nc32)CCC4)c(Cl)c(F)n1] | 89% | $^1$H NMR (500 MHz, DMSO-$d_6$) δ = 10.13 (s, 1H), 9.52 (br s, 1H), 8.49 (br s, 1H), 8.14 (br s, 1H), 8.09 (d, J = 7.9 Hz, 1H), 7.49 (s, 1H), 7.22-7.15 (m, 1H), 5.21 (s, 2H), 4.49 (br s, 1H), 4.04 (br d, J = 13.9 Hz, 1H), 3.94 (br t, J = 7.2 Hz, 2H), 3.13-3.04 (m, 2H), 3.01 (br t, J = 7.9 Hz, 2H), 2.97-2.86 (m, 1H), 2.76 (s, 3H), 2.11 (quin, J = 7.5 Hz, 2H), 1.11 (d, J = 7.1 Hz, 3H); LCMS [M + H]$^+$ 661. |

| Structure | Yield | NMR & LCMS |
|---|---|---|
| 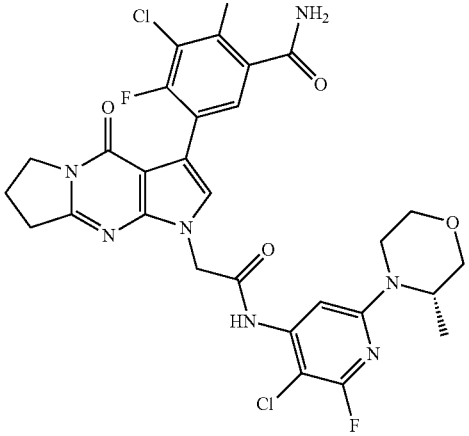 | 95% | ¹H NMR (500 MHz, DMSO-d$_6$) δ = 10.02 (s, 1H), 8.50 (br s, 1H), 8.13 (br s, 1H), 8.08 (d, J = 8.1 Hz, 1H), 7.38 (s, 1H), 7.21-7.16 (m, 1H), 5.20 (s, 2H), 4.00 (br d, J = 4.9 Hz, 1H), 3.93 (br t, J = 7.2 Hz, 2H), 3.81 (br dd, J = 3.3, 11.4 Hz, 1H), 3.55 (br d, J = 13.2 Hz, 2H), 3.48 (br dd, J = 2.7, 11.5 Hz, 1H), 3.34 (dt, J = 2.9, 11.8 Hz, 1H), 3.01 (br t, J = 7.9 Hz, 2H), 2.99-2.92 (m, 1H), 2.10 (quin, J = 7.5 Hz, 2H), 1.03 (d, J = 6.7 Hz, 3H); LCMS [M + H]⁺ 648. |
| 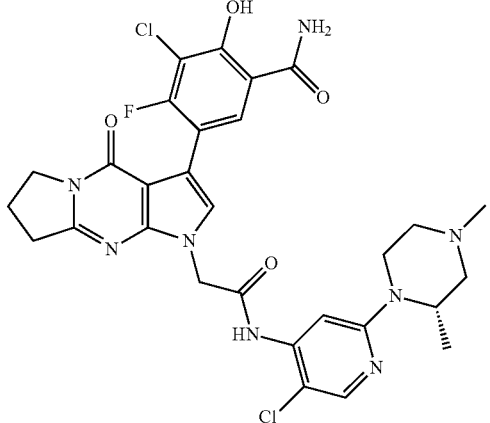 | 94% | ¹H NMR (500 MHz, DMSO-d$_6$) δ = 10.00 (s, 1H), 9.52 (br d, J = 1.6 Hz, 1H), 8.56 (br s, 1H), 8.25-8.19 (m, 2H), 8.17 (d, J = 7.9 Hz, 1H), 7.66 (s, 1H), 7.28-7.26 (m, 1H), 5.27 (s, 2H), 4.64 (br d, J = 5.5 Hz, 1H), 4.18 (br d, J = 13.9 Hz, 1H), 4.02 (br t, J = 7.2 Hz, 3H), 3.46 (br d, J = 12.2 Hz, 3H), 3.21-3.13 (m, 2H), 3.11 (br s, 1H), 3.09 (br t, J = 7.9 Hz, 2H), 3.05-2.93 (m, 1H), 2.84 (br s, 3H), 2.18 (quin, J = 7.5 Hz, 2H), 1.16 (d, J = 7.0 Hz, 3H); LCMS [M + H]⁺ 643. |
| 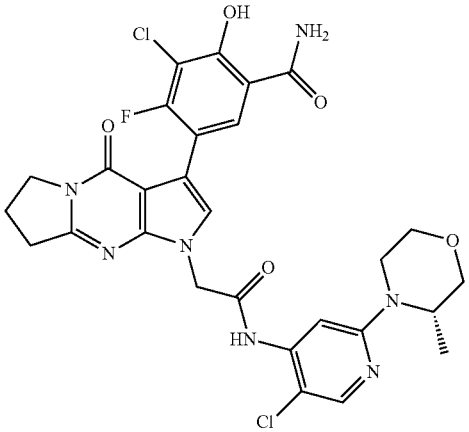 [SMILES: C[C@H]1COCCN1c1cc(NC(=O)Cn2cc(-c3cc(C(N)=O)c(O)c(Cl)c3F)c3c(=O)n4c(nc32)CCC4)c(Cl)cn1] | 94% | ¹H NMR (500 MHz, DMSO-d$_6$) δ = 9.91 (s, 1H), 8.58 (br s, 1H), 8.24-8.18 (m, 1H), 8.18-8.14 (m, 2H), 7.56 (s, 1H), 7.28-7.25 (m, 1H), 5.25 (s, 2H), 4.19-4.09 (m, 2H), 4.01 (br t, J = 7.2 Hz, 3H), 3.70-3.64 (m, 3H), 3.58 (br dd, J = 2.7, 11.4 Hz, 1H), 3.43 (dt, J = 2.9, 11.8 Hz, 1H), 3.09 (t, J = 7.8 Hz, 2H), 3.02 (dt, J = 3.8, 12.6 Hz, 1H), 2.18 (quin, J = 7.5 Hz, 2H), 1.08 (d, J = 6.6 Hz, 3H); LCMS [M + H]⁺ 630. |

| Structure | Yield | NMR & LCMS |
|---|---|---|
| 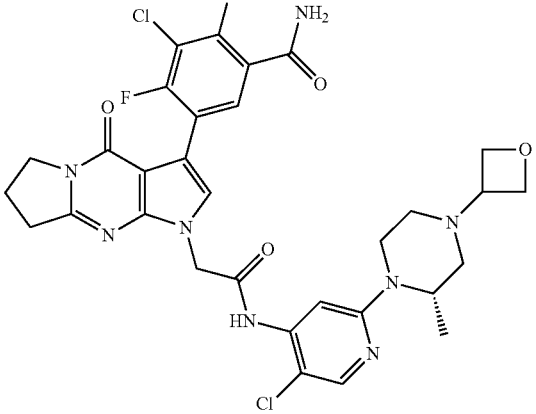 | Quant. | $^1$H NMR (500 MHz, DMSO-$d_6$) δ = 9.99 (s, 1H), 8.56 (br s, 1H), 8.21 (s, 2H), 8.17 (d, J = 8.1 Hz, 1H), 7.64 (s, 1H), 7.30-7.24 (m, 1H), 5.26 (s, 2H), 4.81-4.68 (m, 4H), 4.60 (br s, 1H), 4.37-4.26 (m, 1H), 4.19 (br d, J = 13.6 Hz, 1H), 4.01 (br t, J = 7.2 Hz, 2H), 3.41 (br d, J = 1.5 Hz, 2H), 3.28 (br d, J = 9.0 Hz, 1H), 3.13 (br s, 1H), 3.09 (br t, J = 7.9 Hz, 2H), 3.01-2.87 (m, 1H), 2.84-2.70 (m, 1H), 2.18 (quin, J = 7.5 Hz, 2H), 1.21 (br d, J = 6.7 Hz, 3H); LCMS [M + H]$^+$ 685. |
| 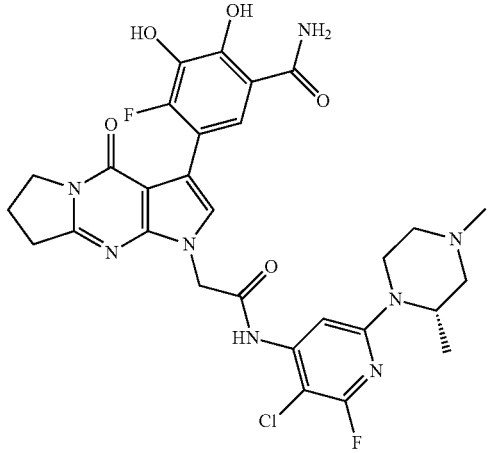 | 93% | $^1$H NMR (500 MHz, DMSO-$d_6$) δ = 13.48 (br s, 1H), 10.11 (s, 1H), 9.52 (br s, 1H), 7.92 (br s, 1H), 7.83 (d, J = 7.8 Hz, 1H), 7.50 (s, 1H), 7.16-7.12 (m, 1H), 5.20 (s, 2H), 4.49 (br s, 2H), 4.05 (br d, J = 13.6 Hz, 2H), 3.94 (br t, J = 7.2 Hz, 3H), 3.77 (s, 3H), 3.38 (br d, J = 12.2 Hz, 3H), 3.13-3.04 (m, 2H), 3.01 (br t, J = 7.8 Hz, 2H), 2.94 (br d, J = 7.9 Hz, 1H), 2.76 (br s, 3H), 2.11 (quin, J = 7.5 Hz, 2H), 1.11 (d, J = 7.0 Hz, 3H); LCMS [M + H]$^+$ 657. |
| 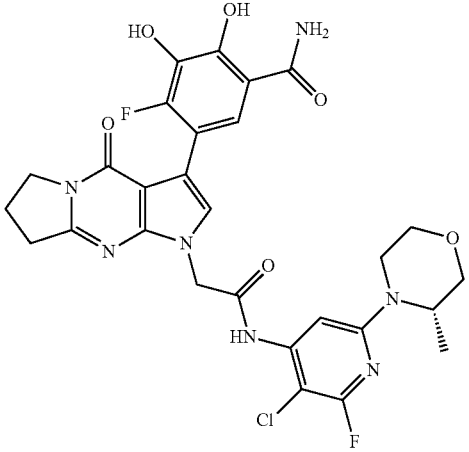 | Quant. | $^1$H NMR (500 MHz, DMSO-$d_6$) δ = 13.81-13.11 (m, 1H), 10.00 (s, 1H), 8.28 (br s, 1H), 7.91 (br s, 1H), 7.82 (d, J = 7.8 Hz, 1H), 7.38 (s, 1H), 7.14 (s, 1H), 5.18 (s, 2H), 4.00 (br d, J = 4.8 Hz, 1H), 3.93 (br t, J = 7.2 Hz, 2H), 3.81 (br dd, J = 3.3, 11.4 Hz, 1H), 3.77 (s, 3H), 3.60 (d, J = 11.5 Hz, 1H), 3.55 (br d, J = 11.9 Hz, 1H), 3.48 (dd, J = 2.6, 11.4 Hz, 1H), 3.34 (dt, J = 2.8, 11.8 Hz, 1H), 3.01 (br t, J = 7.8 Hz, 2H), 2.98-2.92 (m, 1H), 2.10 (quin, J = 7.5 Hz, 2H), 1.03 (d, J = 6.7 Hz, 3H); LCMS [M + H]$^+$ 644. |

| Structure | Yield | NMR & LCMS |
|---|---|---|
| | Quant. | $^1$H NMR (500 MHz, DMSO-$d_6$) δ = 13.73-13.20 (m, 1H), 9.91 (s, 1H), 9.51 (br s, 1H), 8.26 (br s, 1H), 8.14 (s, 1H), 7.92 (br s, 1H), 7.83 (d, J = 7.8 Hz, 1H), 7.59 (s, 1H), 7.15 (s, 1H), 5.18 (s, 2H), 4.57 (br d, J = 5.0 Hz, 1H), 4.11 (br d, J = 13.6 Hz, 1H), 3.93 (br t, J = 7.2 Hz, 2H), 3.77 (s, 3H), 3.38 (br d, J = 12.2 Hz, 2H), 3.14-3.06 (m, 1H), 3.01 (br t, J = 7.8 Hz, 2H), 2.98-2.89 (m, 1H), 2.77 (br s, 3H), 2.10 (quin, J = 7.5 Hz, 2H), 1.09 (d, J = 7.0 Hz, 3H); LCMS [M + H]$^+$ 639. |
| | Quant. | $^1$H NMR (500 MHz, DMSO-$d_6$) δ = 13.66-12.99 (m, 1H), 9.73 (s, 1H), 8.19 (br s, 1H), 8.00 (s, 1H), 7.82 (br s, 1H), 7.73 (d, J = 7.8 Hz, 1H), 7.40 (s, 1H), 7.07-6.99 (m, 1H), 5.07 (s, 2H), 4.02-3.93 (m, 1H), 3.84 (t, J = 7.2 Hz, 2H), 3.77-3.70 (m, 1H), 3.68 (s, 3H), 3.54-3.47 (m, 2H), 3.44-3.38 (m, 1H), 3.27 (dt, J = 2.9, 11.8 Hz, 1H), 2.92 (t, J = 7.8 Hz, 2H), 2.86 (dt, J = 3.8, 12.6 Hz, 1H), 2.06-1.95 (m, 2H), 0.91 (d, J = 6.6 Hz, 3H); LCMS [M + H]$^+$ 626. |
| | Quant. | $^1$H NMR (500 MHz, DMSO-$d_6$) δ = 13.69-13.26 (m, 1H), 9.91 (s, 1H), 8.26 (br s, 1H), 8.14 (s, 1H), 7.92 (br s, 1H), 7.83 (d, J = 7.8 Hz, 1H), 7.57 (s, 1H), 7.16-7.13 (m, 1H), 5.18 (s, 2H), 4.76-4.61 (m, 4H), 4.54 (br s, 1H), 4.26 (br s, 1H), 4.12 (br d, J = 12.0 Hz, 1H), 3.93 (br t, J = 7.2 Hz, 2H), 3.77 (s, 3H), 3.36 (br s, 1H), 3.24 (br d, J = 3.7 Hz, 1H), 3.12-3.05 (m, 1H), 3.01 (br t, J = 7.9 Hz, 2H), 2.92 (br s, 1H), 2.75 (br dd, J = 2.0, 3.9 Hz, 1H), 2.15-2.04 (m, 2H), 1.14 (br d, J = 6.7 Hz, 3H); LCMS [M + H]$^+$ 681. |

-continued

| Structure | Yield | NMR & LCMS |
|---|---|---|
| 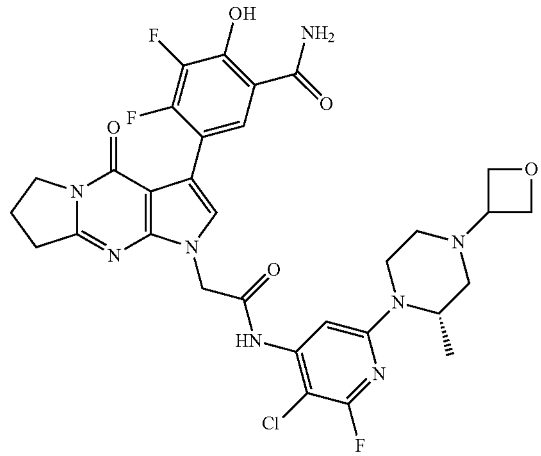 [SMILES: C[C@H]1CN(C2COC2)CCN1c1cc(NC(=O)Cn2cc(-c3cc(C(N)=O)c(O)c(F)c3F)c3c(=O)n4c(nc32)CCC4)c(Cl)c(F)n1] | 89% | ¹H NMR (500 MHz, DMSO-d₆) δ = 13.57 (br s, 1H), 10.01 (s, 1H), 8.33 (br s, 1H), 8.01 (br s, 1H), 7.89-7.83 (m, 1H), 7.37 (s, 1H), 7.12 (s, 1H), 5.13 (s, 2H), 4.55 (br s, 3H), 4.41-4.27 (m, 2H), 3.86 (br t, J = 7.2 Hz, 2H), 3.03-2.97 (m, 1H), 2.93 (br t, J = 7.8 Hz, 2H), 2.03 (quin, J = 7.5 Hz, 2H), 1.07 (br d, J = 6.6 Hz, 3H); LCMS [M + H]⁺ 687. |
| 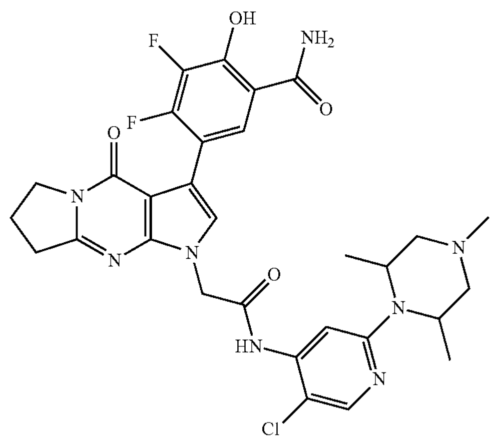 [SMILES: CC1CN(C)CC(C)N1c1cc(NC(=O)Cn2cc(-c3cc(C(N)=O)c(O)c(F)c3F)c3c(=O)n4c(nc32)CCC4)c(Cl)cn1] | 29% | ¹H NMR (500 MHz, DMSO-d₆) δ = 13.71 (br s, 1H), 9.96 (s, 1H), 9.72-9.56 (m, 1H), 8.47 (br s, 1H), 8.22 (s, 1H), 8.15 (br s, 1H), 8.00 (br d, J = 7.2 Hz, 1H), 7.60 (s, 1H), 7.27 (s, 1H), 5.26 (s, 2H), 4.60 (br s, 2H), 4.00 (br t, J = 6.9 Hz, 2H), 3.49-3.47 (m, 1H), 3.17 (br s, 2H), 3.08 (br t, J = 7.7 Hz, 2H), 2.90 (br s, 3H), 2.20-2.14 (m, 2H), 1.24 (br d, J = 6.8 Hz, 6H); [M + H]⁺ 641. |
| 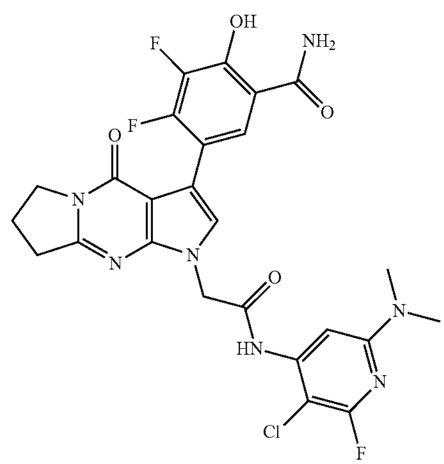 [SMILES: CN(C)c1cc(NC(=O)Cn2cc(-c3cc(C(N)=O)c(O)c(F)c3F)c3c(=O)n4c(nc32)CCC4)c(Cl)c(F)n1] | 53% | ¹H NMR (500 MHz, DMSO-d₆) δ = 13.74 (br s, 1H), 9.99 (s, 1H), 8.49 (br s, 1H), 8.14 (br s, 1H), 7.99 (br d, J = 7.1 Hz, 1H), 7.31 (s, 1H), 7.27 (s, 1H), 5.26 (s, 2H), 4.00 (br t, J = 7.2 Hz, 2H), 3.08 (br t, J = 7.8 Hz, 2H), 2.95 (s, 6H), 2.17 (quin, J = 7.5 Hz, 2H); LCMS [M + H]⁺ 577. |

-continued

| Structure | Yield | NMR & LCMS |
|---|---|---|
| 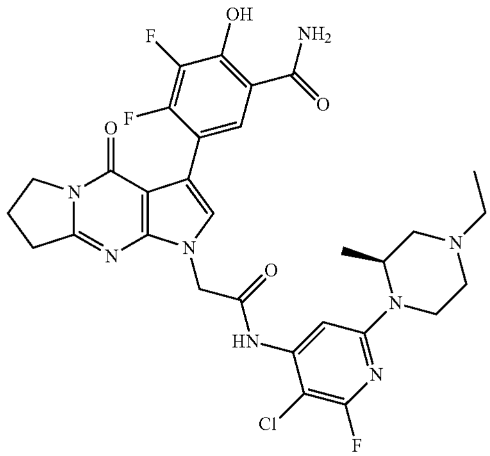 [SMILES: CCN1CCN(c2cc(NC(=O)Cn3cc(-c4cc(C(N)=O)c(O)c(F)c4F)c4c(=O)n5c(nc43)CCC5)c(Cl)c(F)n2)[C@@H](C)C1] | 47% | $^1$H NMR (500 MHz, DMSO-$d_6$) δ = 13.71 (br s, 1H), 10.19 (s, 1H), 9.20 (br s, 1H), 8.52-8.40 (m, 1H), 8.21-8.10 (m, 1H), 8.00 (br d, J = 6.7 Hz, 1H), 7.56 (s, 1H), 7.27 (s, 1H), 5.28 (s, 2H), 4.56 (br s, 1H), 4.12 (br d, J = 13.7 Hz, 1H), 4.01 (br t, J = 7.2 Hz, 2H), 3.20-3.11 (m, 4H), 3.08 (br t, J = 7.9 Hz, 2H), 3.02-2.92 (m, 1H), 2.18 (quin, J = 7.5 Hz, 2H), 1.23 (br t, J = 7.3 Hz, 3H), 1.20 (d, J = 7.1 Hz, 3H); LCMS [M + H]$^+$ 660. |
| 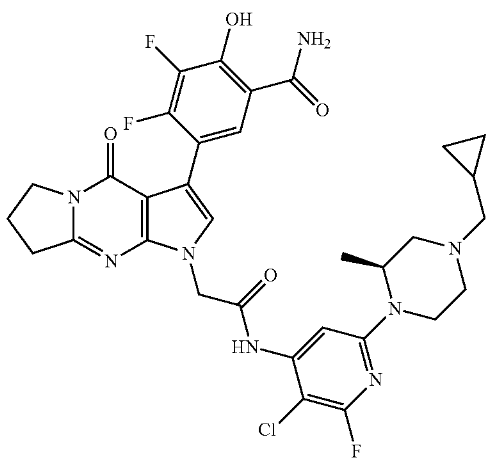 [SMILES: C[C@H]1CN(CC2CC2)CCN1c1cc(NC(=O)Cn2cc(-c3cc(C(N)=O)c(O)c(F)c3F)c3c(=O)n4c(nc32)CCC4)c(Cl)c(F)n1] | 41% | $^1$H NMR (500 MHz, DMSO-$d_6$) δ = 13.71 (br s, 1H), 10.19 (s, 1H), 9.37 (br s, 1H), 8.46 (br s, 1H), 8.15 (br s, 1H), 8.00 (br d, J = 6.7 Hz, 1H), 7.56 (s, 1H), 7.31-7.24 (m, 1H), 5.28 (s, 2H), 4.58 (br s, 1H), 4.14 (br d, J = 13.3 Hz, 1H), 4.01 (br t, J = 7.2 Hz, 2H), 3.23-3.13 (m, 3H), 3.08 (br t, J = 7.9 Hz, 2H), 3.04-2.93 (m, 2H), 2.18 (quin, J = 7.5 Hz, 2H), 1.22 (d, J = 7.1 Hz, 3H), 1.07-1.02 (m, 1H), 0.65 (br d, J = 7.9 Hz, 2H), 0.36 (br d, J = 3.8 Hz, 2H); LCMS [M + H]$^+$ 686. |
| 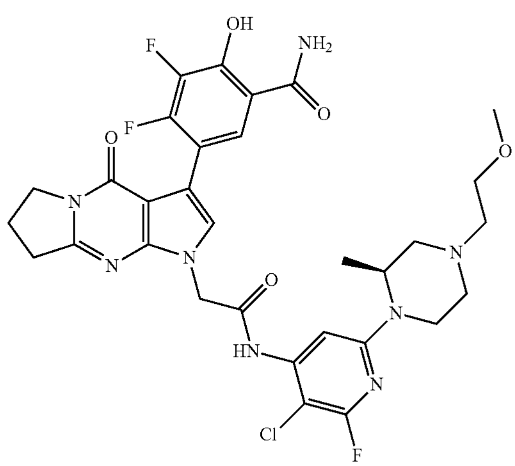 [SMILES: COCCN1CCN(c2cc(NC(=O)Cn3cc(-c4cc(C(N)=O)c(O)c(F)c4F)c4c(=O)n5c(nc43)CCC5)c(Cl)c(F)n2)[C@@H](C)C1] | 51% | $^1$H NMR (500 MHz, DMSO-$d_6$) δ = 13.71 (br s, 1H), 10.18 (br s, 1H), 9.57-9.36 (m, 1H), 8.55-8.40 (m, 1H), 8.21-8.09 (m, 1H), 8.00 (br d, J = 7.1 Hz, 1H), 7.54 (s, 1H), 7.27 (s, 1H), 5.28 (s, 2H), 4.56 (br d, J = 1.6 Hz, 1H), 4.14-4.05 (m, 1H), 4.01 (br t, J = 7.1 Hz, 2H), 3.73-3.62 (m, 2H), 3.30 (s, 3H), 3.20 (br s, 1H), 3.08 (br t, J = 7.8 Hz, 2H), 2.18 (quin, J = 7.5 Hz, 2H), 1.20 (br d, J = 6.7 Hz, 3H); [M + H]$^+$ 690. |

| Structure | Yield | NMR & LCMS |
|---|---|---|
| 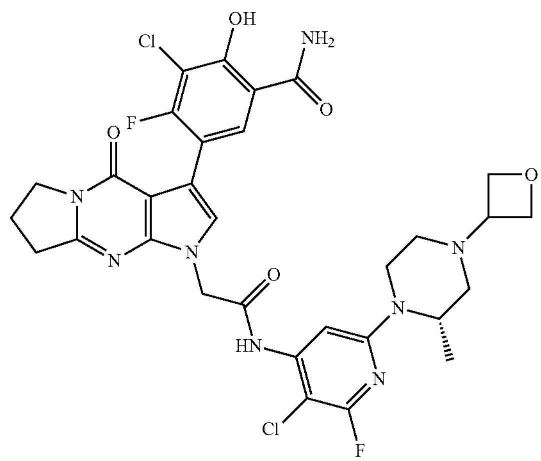 [SMILES: C[C@H]1CN(C2COC2)CCN1c1cc(NC(=O)Cn2cc(-c3cc(C(N)=O)c(O)c(Cl)c3F)c3c(=O)n4c(nc32)CCC4)c(Cl)c(F)n1] | 91% | ¹H NMR (500 MHz, DMSO-d$_6$) δ = 10.08 (br s, 1H), 8.55-8.43 (m, 1H), 8.14 (br s, 1H), 8.09 (d, J = 8.1 Hz, 1H), 7.45 (s, 1H), 7.21-7.17 (m, 1H), 5.20 (s, 2H), 4.61 (br s, 4H), 3.94 (br t, J = 7.1 Hz, 2H), 3.01 (br t, J = 7.9 Hz, 2H), 2.11 (quin, J = 7.5 Hz, 2H), 1.14 (br d, J = 6.0 Hz, 3H); [M + H]⁺ 703. |
| 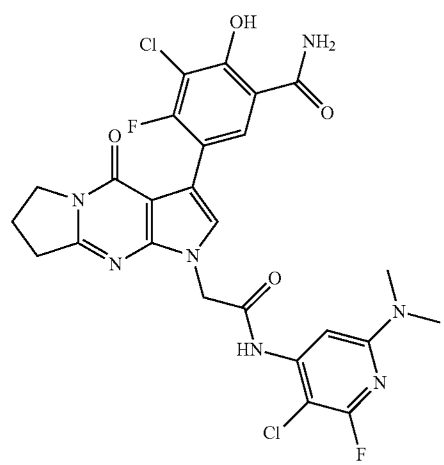 [SMILES: CN(C)c1cc(NC(=O)Cn2cc(-c3cc(C(N)=O)c(O)c(Cl)c3F)c3c(=O)n4c(nc32)CCC4)c(Cl)c(F)n1] | 89% | ¹H NMR (500 MHz, DMSO-d$_6$) δ = 9.92 (s, 1H), 8.51 (br s, 1H), 8.13 (br s, 1H), 8.08 (d, J = 8.1 Hz, 1H), 7.25 (s, 1H), 7.20 (s, 1H), 5.19 (s, 2H), 3.93 (t, J = 7.2 Hz, 2H), 3.02 (t, J = 7.9 Hz, 2H), 2.88 (s, 6H), 2.10 (quin, J = 7.5 Hz, 2H); [M + H]⁺ 592. |
| 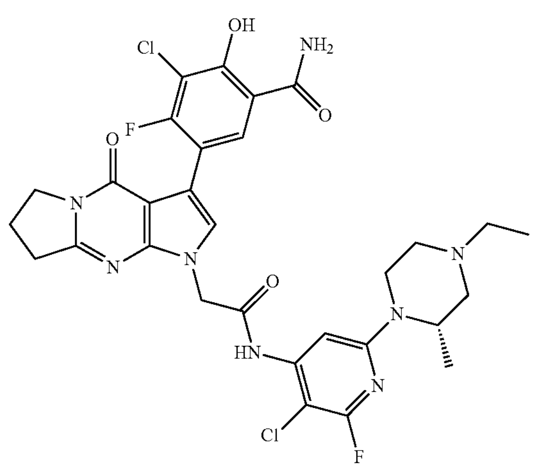 [SMILES: CCN1CCN(c2cc(NC(=O)Cn3cc(-c4cc(C(N)=O)c(O)c(Cl)c4F)c4c(=O)n5c(nc43)CCC5)c(Cl)c(F)n2)[C@@H](C)C1] | Quant. | ¹H NMR (500 MHz, DMSO-d$_6$) δ = 10.12 (s, 1H), 9.15 (br s, 1H), 8.49 (br s, 1H), 8.15 (br s, 1H), 8.09 (d, J = 8.1 Hz, 1H), 7.49 (s, 1H), 7.21-7.18 (m, 1H), 5.21 (s, 2H), 4.49 (br s, 1H), 4.05 (br d, J = 14.4 Hz, 1H), 3.94 (br t, J = 7.2 Hz, 3H), 3.09 (br t, J = 12.0 Hz, 4H), 3.01 (br t, J = 7.9 Hz, 2H), 2.94-2.83 (m, 1H), 2.11 (quin, J = 7.5 Hz, 2H), 1.16 (br t, J = 7.3 Hz, 3H), 1.13 (d, J = 7.1 Hz, 3H); [M + H]⁺ 675. |

| Structure | Yield | NMR & LCMS |
|---|---|---|
| 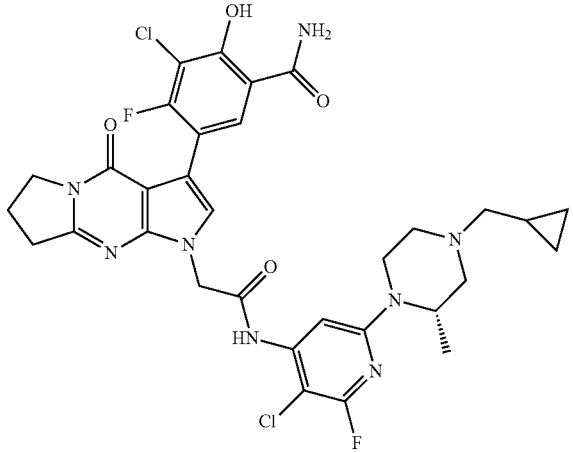 [SMILES: C[C@H]1CN(CC2CC2)CCN1c1cc(NC(=O)Cn2cc(-c3cc(C(N)=O)c(O)c(Cl)c3F)c3c(=O)n4c(nc32)CCC4)c(Cl)c(F)n1] | Quant. | $^{1}$H NMR (500 MHz, DMSO-d$_{6}$) δ = 10.13 (s, 1H), 9.40 (br s, 1H), 8.49 (br s, 1H), 8.14 (br s, 1H), 8.09 (d, J = 8.1 Hz, 1H), 7.49 (s, 1H), 7.21-7.16 (m, 1H), 5.21 (s, 2H), 4.51 (br s, 1H), 4.07 (br d, J = 14.1 Hz, 1H), 3.94 (br t, J = 7.2 Hz, 2H), 3.12 (br d, J = 12.5 Hz, 3H), 3.01 (br t, J = 7.9 Hz, 2H), 2.97-2.87 (m, 2H), 2.11 (quin, J = 7.5 Hz, 2H), 1.16 (d, J = 7.0 Hz, 3H), 1.04-0.94 (m, 1H), 0.58 (br d, J = 8.1 Hz, 2H), 0.29 (br d, J = 3.9 Hz, 2H); [M + H]$^{+}$ 701. |
| 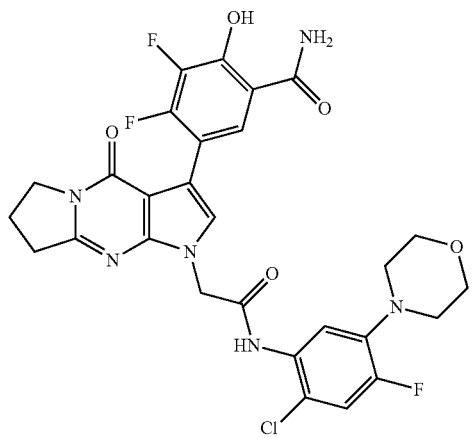 [SMILES: NC(=O)c1cc(-c2cn(CC(=O)Nc3cc(N4CCOCC4)c(F)cc3Cl)c3nc4n(c(=O)c23)CCC4)c(F)c(F)c1O] | 63% | $^{1}$H NMR (500 MHz, DMSO-d$_{6}$) δ = 13.88-13.48 (m, 1H), 9.90 (s, 1H), 8.62-8.34 (m, 1H), 8.26-8.04 (m, 1H), 8.04-7.84 (m, 1H), 7.58-7.38 (m, 2H), 7.26 (br s, 1H), 5.14 (s, 2H), 4.05-3.93 (m, 2H), 3.76-3.68 (m, 4H), 3.10 (s, 2H), 3.00-2.91 (m, 4H), 2.24-2.12 (m, 2H); [M + H]$^{+}$ 617. |
| 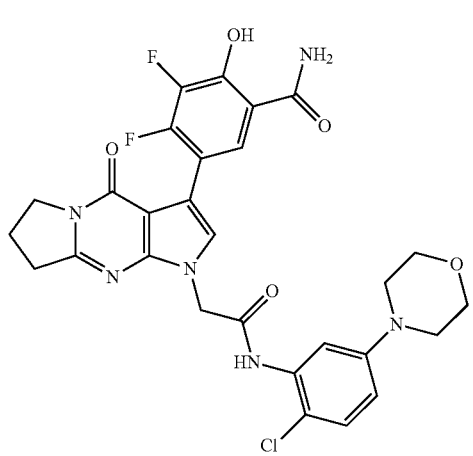 [SMILES: NC(=O)c1cc(-c2cn(CC(=O)Nc3cc(N4CCOCC4)ccc3Cl)c3nc4n(c(=O)c23)CCC4)c(F)c(F)c1O] | 63% | $^{1}$H NMR (500 MHz, DMSO-d$_{6}$) δ = 13.59 (s, 1H), 9.78-9.48 (m, 1H), 8.49-8.25 (m, 1H), 8.10-7.92 (m, 1H), 7.91-7.79 (m, 1H), 7.34-7.28 (m, 1H), 7.20-7.17 (m, 1H), 7.17-7.15 (m, 1H), 7.12 (s, 1H), 6.75-6.55 (m, 1H), 5.12-4.86 (m, 2H), 4.00-3.91 (m, 1H), 3.86 (br t, J = 7.2 Hz, 2H), 3.58-3.49 (m, 4H), 2.93-2.87 (m, 4H), 2.09-1.98 (m, 2H); [M + H]$^{+}$ 599. |

-continued

| Structure | Yield | NMR & LCMS |
|---|---|---|
| 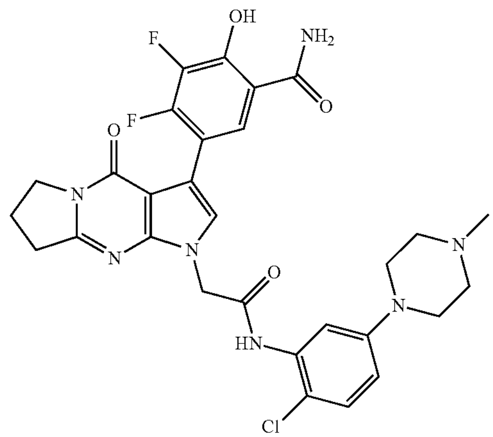 [SMILES: CN1CCN(c2ccc(Cl)c(NC(=O)Cn3cc(-c4cc(C(N)=O)c(O)c(F)c4F)c4c(=O)n5c(nc43)CCC5)c2)CC1] | 68% | ¹H NMR (500 MHz, DMSO-d₆) δ = 13.77-13.36 (m, 1H), 9.79-9.63 (m, 1H), 9.61-9.41 (m, 1H), 8.41-8.23 (m, 1H), 8.10-7.92 (m, 1H), 7.92-7.72 (m, 1H), 7.48-7.32 (m, 1H), 7.31-7.18 (m, 1H), 7.16-7.06 (m, 1H), 6.75-6.64 (m, 1H), 5.01 (s, 2H), 3.86 (m, 3H), 3.70-3.45 (m, 2H), 2.94-2.88 (m, 6H), 2.67 (br s, 4H), 2.03 (s, 2H); [M + H]⁺ 612. |
| 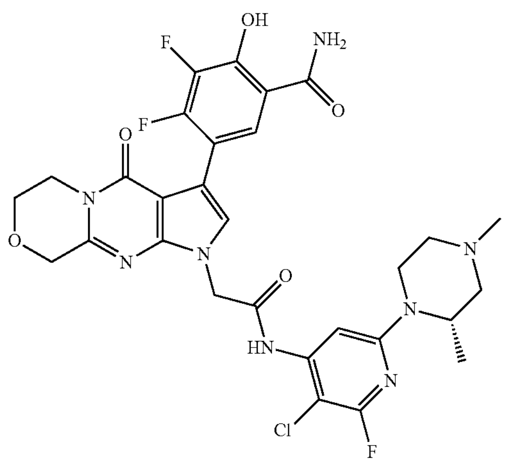 [SMILES: C[C@H]1CN(C)CCN1c1cc(NC(=O)Cn2cc(-c3cc(C(N)=O)c(O)c(F)c3F)c3c(=O)n4c(nc32)COCC4)c(Cl)c(F)n1] | 99% | ¹H NMR (500 MHz, DMSO-d₆) δ = 13.59 (br s, 1H), 10.05 (s, 1H), 9.36 (br d, J = 1.8 Hz, 1H), 8.34 (br s, 1H), 8.01 (br s, 1H), 7.83 (br d, J = 7.0 Hz, 1H), 7.40 (s, 1H), 7.18-7.08 (m, 1H), 5.12 (s, 2H), 4.54 (br s, 2H), 4.41 (br s, 1H), 4.00-3.94 (m, 1H), 3.92 (t, J = 5.3 Hz, 2H), 3.73 (br t, J = 5.2 Hz, 2H), 3.04-2.93 (m, 2H), 2.91-2.78 (m, 1H), 2.68 (br s, 3H), 1.03 (d, J = 7.0 Hz, 3H); [M + H]⁺ 661. |
| 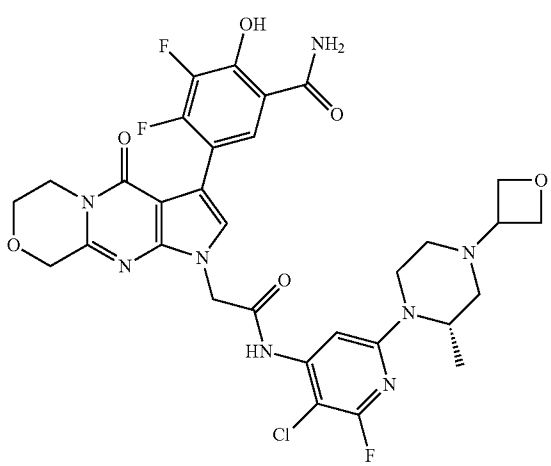 [SMILES: C[C@H]1CN(C2COC2)CCN1c1cc(NC(=O)Cn2cc(-c3cc(C(N)=O)c(O)c(F)c3F)c3c(=O)n4c(nc32)COCC4)c(Cl)c(F)n1] | 94% | ¹H NMR (500 MHz, DMSO-d₆) δ = 13.69 (br s, 1H), 10.07 (br s, 1H), 8.43 (br s, 1H), 8.09 (br s, 1H), 7.91 (br d, J = 6.4 Hz, 1H), 7.42 (br s, 1H), 7.25-7.22 (m, 1H), 5.20 (s, 2H), 4.63 (s, 2H), 4.60-4.52 (m, 2H), 4.00 (t, J = 5.3 Hz, 2H), 3.82-3.78 (m, 2H), 1.13 (br d, J = 5.5 Hz, 3H); [M + H]⁺ 703. |

| Structure | Yield | NMR & LCMS |
|---|---|---|
| 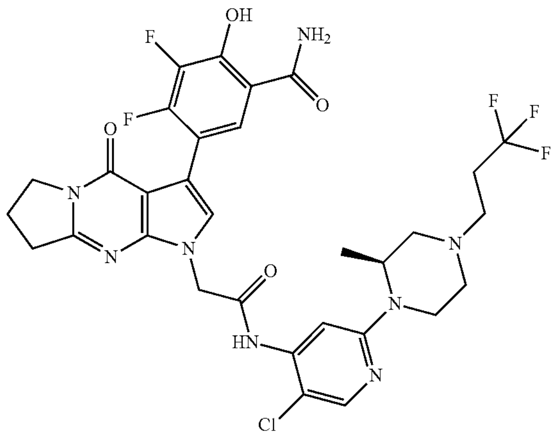 [SMILES: C[C@H]1CN(CCC(F)(F)F)CCN1c1cc(NC(=O)Cn2cc(-c3cc(C(N)=O)c(O)c(F)c3F)c3c(=O)n4c(nc32)CCC4)c(Cl)cn1] | 53% | $^1$H NMR (500 MHz, DMSO-$d_6$) δ = 13.71 (br s, 1H), 9.96 (br s, 1H), 8.47 (br s, 1H), 8.20 (s, 1H), 8.15 (br s, 1H), 8.00 (br d, J = 6.5 Hz, 1H), 7.62 (br s, 1H), 7.27 (s, 1H), 5.26 (s, 2H), 4.69-4.46 (m, 1H), 4.22-4.05 (m, 1H), 4.01 (br t, J = 7.2 Hz, 2H), 3.08 (br t, J = 7.8 Hz, 2H), 2.87-2.71 (m, 2H), 2.18 (quin, J = 7.5 Hz, 2H), 1.14 (br d, J = 6.6 Hz, 3H); [M + H]$^+$ 710. |
| 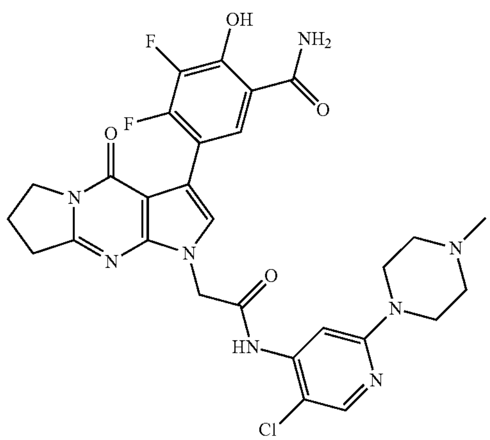 [SMILES: CN1CCN(c2cc(NC(=O)Cn3cc(-c4cc(C(N)=O)c(O)c(F)c4F)c4c(=O)n5c(nc43)CCC5)c(Cl)cn2)CC1] | 75% | $^1$H NMR (500 MHz, methanol-$d_4$) δ = 7.95-7.93 (m, 1H), 7.93-7.89 (m, 1H), 7.59 (s, 1H), 7.08 (s, 1H), 5.06-5.01 (m, 2H), 4.49-4.25 (m, 3H), 3.99-3.91 (m, 2H), 3.72-3.40 (m, 4H), 3.01-2.93 (m, 3H), 2.66 (s, 3H), 2.16-2.03 (m, 2H); [M + H]$^+$ 613. |
| 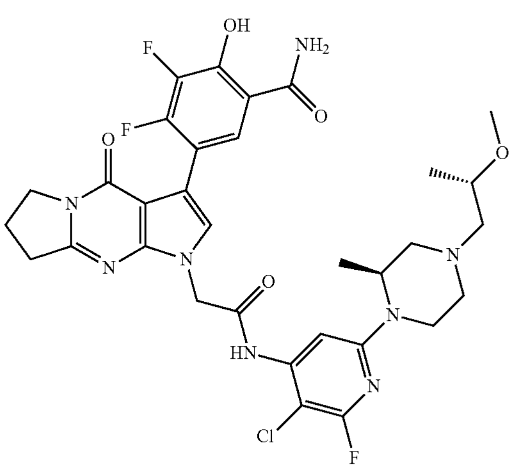 [SMILES: CO[C@@H](C)CN1CCN(c2cc(NC(=O)Cn3cc(-c4cc(C(N)=O)c(O)c(F)c4F)c4c(=O)n5c(nc43)CCC5)c(Cl)c(F)n2)[C@@H](C)C1] | 47% | $^1$H NMR (500 MHz, DMSO-$d_6$) δ = 13.72 (br s, 1H), 10.18 (br s, 1H), 9.23-9.04 (m, 1H), 8.47 (br s, 1H), 8.26-8.10 (m, 1H), 8.00 (br d, J = 6.7 Hz, 1H), 7.53 (br s, 1H), 7.27 (s, 1H), 5.28 (s, 2H), 4.57 (br s, 1H), 4.18-4.05 (m, 1H), 4.01 (br t, J = 7.1 Hz, 2H), 3.69 (br d, J = 2.6 Hz, 1H), 3.53 (br d, J = 8.8 Hz, 2H), 3.31 (br s, 3H), 3.08 (br t, J = 7.8 Hz, 2H), 2.18 (quin, J = 7.5 Hz, 2H), 1.37-1.28 (m, 2H), 1.21 (br s, 3H); [M + H]$^+$ 703. |

| Structure | Yield | NMR & LCMS |
|---|---|---|
| 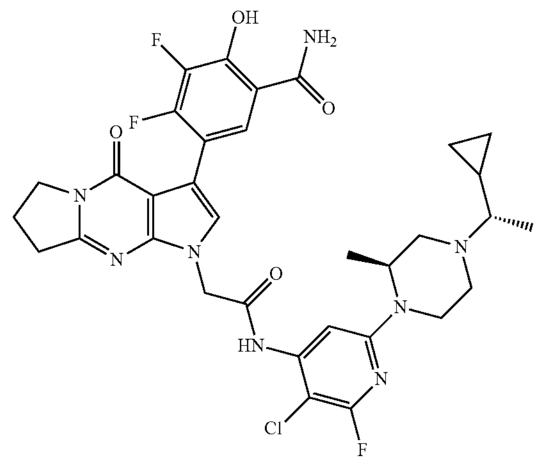 [SMILES: C[C@@H](C1CC1)N1CCN(c2cc(NC(=O)Cn3cc(-c4cc(C(N)=O)c(O)c(F)c4F)c4c(=O)n5c(nc43)CCC5)c(Cl)c(F)n2)[C@@H](C)C1] | 45% | ¹H NMR (500 MHz, DMSO-d₆) δ = 13.71 (br s, 1H), 10.19 (br s, 1H), 9.06 (br s, 1H), 8.47 (br s, 1H), 8.23-8.10 (m, 1H), 8.00 (br d, J = 6.6 Hz, 1H), 7.56 (s, 1H), 7.27 (s, 1H), 5.28 (s, 2H), 4.59 (br s, 1H), 4.16 (br d, J = 10.4 Hz, 1H), 4.01 (br t, J = 7.2 Hz, 2H), 3.65 (br d, J = 9.8 Hz, 1H), 3.50 (br d, J = 11.7 Hz, 1H), 3.24-3.18 (m, 1H), 3.08 (br t, J = 7.8 Hz, 2H), 2.77 (br s, 1H), 2.18 (quin, J = 7.5 Hz, 2H), 1.35 (br d, J = 5.5 Hz, 3H), 1.23 (br d, J = 6.7 Hz, 3H), 1.06-0.96 (m, 1H), 0.73-0.56 (m, 3H), 0.26 (br s, 1H); [M + H]⁺ 700. |
| 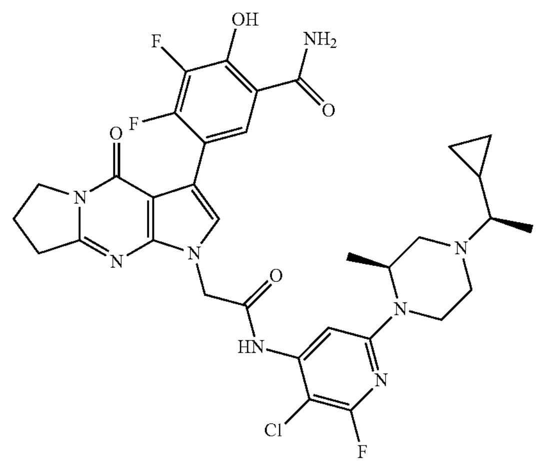 [SMILES: C[C@H](C1CC1)N1CCN(c2cc(NC(=O)Cn3cc(-c4cc(C(N)=O)c(O)c(F)c4F)c4c(=O)n5c(nc43)CCC5)c(Cl)c(F)n2)[C@@H](C)C1] | 49% | ¹H NMR (500 MHz, DMSO-d₆) δ = 13.71 (br s, 1H), 10.19 (s, 1H), 9.25-9.12 (m, 1H), 8.54-8.37 (m, 1H), 8.15 (br s, 1H), 8.01 (br d, J = 6.6 Hz, 1H), 7.56 (s, 1H), 7.27 (s, 1H), 5.28 (s, 2H), 4.61 (br s, 1H), 4.14 (br d, J = 12.0 Hz, 1H), 4.01 (br t, J = 7.2 Hz, 2H), 3.61-3.51 (m, 2H), 3.25-3.14 (m, 2H), 3.08 (br t, J = 7.8 Hz, 2H), 2.83 (br d, J = 4.0 Hz, 1H), 2.18 (quin, J = 7.5 Hz, 2H), 1.35 (br d, J = 6.1 Hz, 3H), 1.23 (br d, J = 6.7 Hz, 3H), 0.97 (br s, 1H), 0.71 (br d, J = 3.8 Hz, 1H), 0.59 (br d, J = 6.7 Hz, 2H), 0.25 (br d, J = 3.4 Hz, 1H); [M + H]⁺ 700. |
| 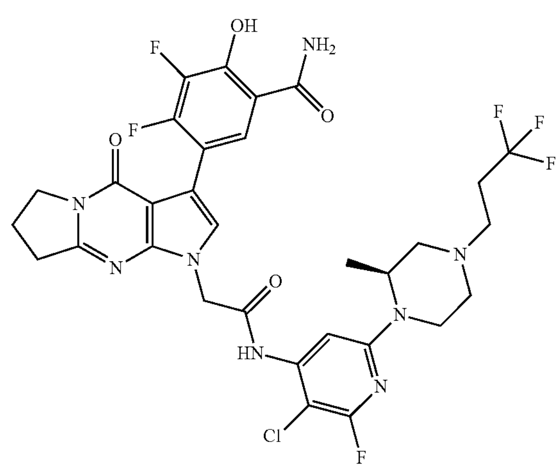 [SMILES: C[C@H]1CN(CCC(F)(F)F)CCN1c1cc(NC(=O)Cn2cc(-c3cc(C(N)=O)c(O)c(F)c3F)c3c(=O)n4c(nc32)CCC4)c(Cl)c(F)n1] | 48% | ¹H NMR (500 MHz, DMSO-d₆) δ = 13.72 (br s, 1H), 10.15 (br s, 1H), 8.54-8.38 (m, 1H), 8.15 (br s, 1H), 8.00 (br d, J = 6.5 Hz, 1H), 7.55-7.48 (m, 1H), 7.27 (s, 1H), 5.28 (s, 2H), 4.01 (br t, J = 7.2 Hz, 2H), 3.08 (br t, J = 7.8 Hz, 2H), 2.17 (quin, J = 7.5 Hz, 2H), 1.16 (br d, J = 5.4 Hz, 3H); [M + H]⁺ 728. |

| Structure | Yield | NMR & LCMS |
|---|---|---|
| 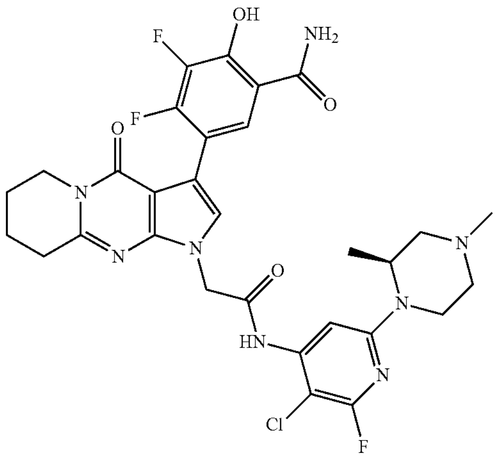 | 53% | $^1$H NMR (500 MHz, DMSO-d$_6$) δ = 13.73 (br s, 1H), 10.18 (s, 1H), 9.49 (br d, J = 3.2 Hz, 1H), 8.48 (br s, 1H), 8.15 (br s, 1H), 7.97 (br d, J = 6.5 Hz, 1H), 7.55 (s, 1H), 7.25 (s, 1H), 5.27 (s, 2H), 4.56 (br s, 1H), 4.19-4.05 (m, 1H), 3.92 (t, J = 6.1 Hz, 2H), 3.44 (br d, J = 9.4 Hz, 2H), 3.20-3.09 (m, 2H), 3.07-2.95 (m, 1H), 2.88 (t, J = 6.7 Hz, 2H), 2.83 (br s, 2H), 1.88 (quin, J = 6.5 Hz, 2H), 1.85-1.77 (m, 2H), 1.17 (d, J = 7.0 Hz, 3H); [M + H]$^+$ 728. |
| 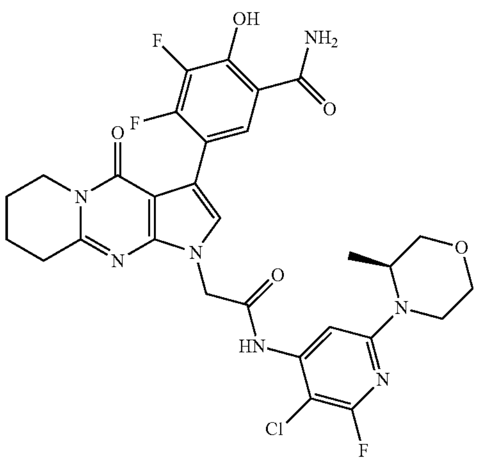 [SMILES: C[C@H]1COCCN1c1cc(NC(=O)Cn2cc(-c3cc(C(N)=O)c(O)c(F)c3F)c3c(=O)n4c(nc32)CCCC4)c(Cl)c(F)n1] | 34% | $^1$H NMR (500 MHz, DMSO-d$_6$) δ = 13.76 (s, 1H), 10.08 (s, 1H), 8.59-8.44 (m, 1H), 8.14 (br s, 1H), 7.96 (br d, J = 6.4 Hz, 1H), 7.45 (s, 1H), 7.25 (s, 1H), 5.25 (s, 2H), 4.07 (br d, J = 4.4 Hz, 1H), 3.91 (t, J = 6.1 Hz, 2H), 3.89-3.84 (m, 1H), 3.67 (d, J = 11.4 Hz, 1H), 3.65-3.59 (m, 1H), 3.55 (dd, J = 2.8, 11.4 Hz, 1H), 3.40 (dt, J = 3.0, 11.8 Hz, 1H), 3.03 (dt, J = 3.7, 12.6 Hz, 1H), 2.92-2.84 (m, 2H), 1.93-1.85 (m, 2H), 1.84-1.76 (m, 2H), 1.10 (d, J = 6.7 Hz, 3H); [M + H]$^+$ 647. |
| 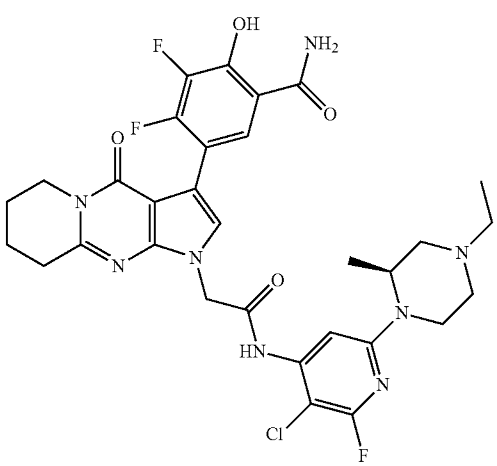 [SMILES: CCN1CCN(c2cc(NC(=O)Cn3cc(-c4cc(C(N)=O)c(O)c(F)c4F)c4c(=O)n5c(nc43)CCCC5)c(Cl)c(F)n2)[C@@H](C)C1] | 43% | $^1$H NMR (500 MHz, DMSO-d$_6$) δ = 13.85-13.59 (m, 1H), 10.19 (s, 1H), 9.32-9.11 (m, 1H), 8.59-8.38 (m, 1H), 8.25-8.06 (m, 1H), 7.97 (br d, J = 6.6 Hz, 1H), 7.61-7.50 (m, 1H), 7.25 (s, 1H), 5.27 (s, 2H), 4.56 (br s, 1H), 4.12 (br d, J = 13.0 Hz, 1H), 3.92 (br t, J = 6.1 Hz, 2H), 3.45 (br s, 2H), 3.21-3.10 (m, 4H), 3.01-2.92 (m, 1H), 2.88 (br t, J = 6.6 Hz, 2H), 1.92-1.85 (m, 2H), 1.85-1.78 (m, 2H), 1.25-1.22 (m, 2H), 1.20 (br d, J = 7.0 Hz, 3H); [M + H]$^+$ 674. |

-continued

| Structure | Yield | NMR & LCMS |
|---|---|---|
| 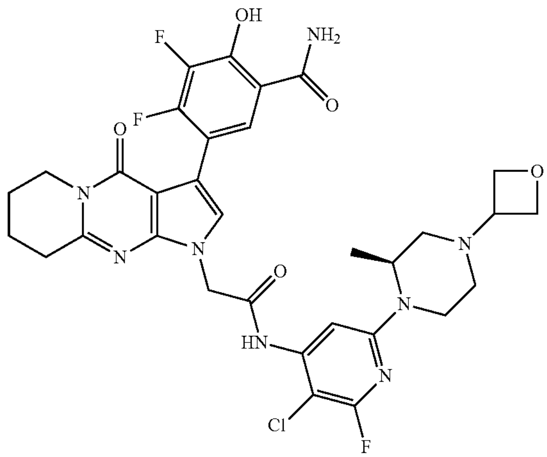 [SMILES: C[C@H]1CN(C2COC2)CCN1c1cc(NC(=O)Cn2cc(-c3cc(C(N)=O)c(O)c(F)c3F)c3c(=O)n4c(nc32)CCCC4)c(Cl)c(F)n1] | 38% | $^1$H NMR (500 MHz, DMSO-d$_6$) δ = 13.74 (br s, 1H), 10.11 (br s, 1H), 8.56-8.43 (m, 1H), 8.22-8.09 (m, 1H), 7.97 (br d, J = 6.5 Hz, 1H), 7.49 (br s, 1H), 7.25 (s, 1H), 5.31-5.19 (m, 2H), 4.80-4.45 (m, 4H), 4.45-4.28 (m, 1H), 3.91 (br t, J = 6.1 Hz, 2H), 3.12-3.01 (m, 1H), 2.88 (br t, J = 6.7 Hz, 2H), 1.91-1.84 (m, 2H), 1.84-1.77 (m, 2H), 1.18 (br d, J = 3.9 Hz, 3H); [M + H]$^+$ 702. |
| 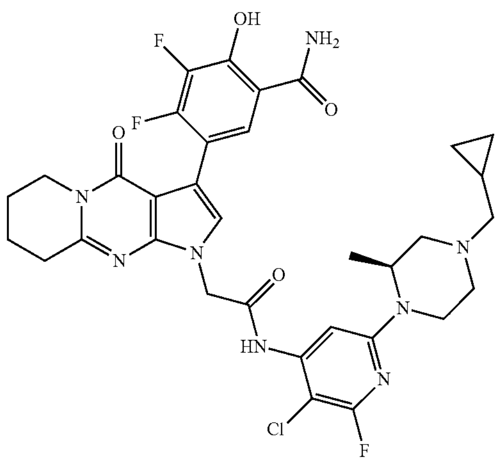 [SMILES: C[C@H]1CN(CC2CC2)CCN1c1cc(NC(=O)Cn2cc(-c3cc(C(N)=O)c(O)c(F)c3F)c3c(=O)n4c(nc32)CCCC4)c(Cl)c(F)n1] | 51% | $^1$H NMR (500 MHz, DMSO-d$_6$) δ = 13.73 (br s, 1H), 10.18 (s, 1H), 9.44-9.25 (m, 1H), 8.55-8.41 (m, 1H), 8.24-8.09 (m, 1H), 7.97 (br d, J = 6.6 Hz, 1H), 7.56 (s, 1H), 7.25 (s, 1H), 5.27 (s, 2H), 4.59 (br s, 1H), 4.20-4.10 (m, 1H), 3.92 (t, J = 6.1 Hz, 2H), 3.62-3.48 (m, 2H), 3.22-3.14 (m, 2H), 3.00 (br s, 2H), 2.88 (t, J = 6.7 Hz, 2H), 1.88 (td, J = 6.6, 12.7 Hz, 2H), 1.84-1.78 (m, 2H), 1.22 (br d, J = 6.8 Hz, 3H), 1.09-1.01 (m, 1H), 0.66 (br s, 2H), 0.36 (br s, 2H); [M + H]$^+$ 700. |
| 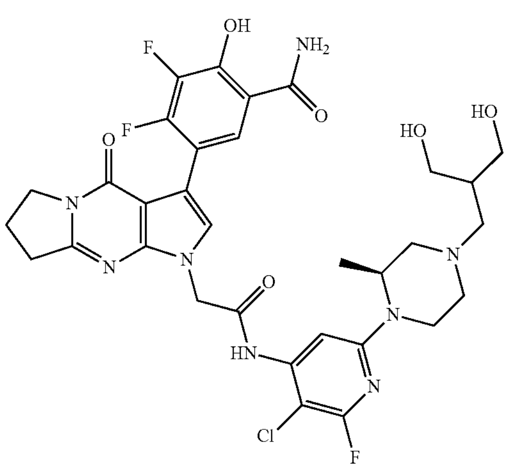 [SMILES: C[C@H]1CN(CC(CO)CO)CCN1c1cc(NC(=O)Cn2cc(-c3cc(C(N)=O)c(O)c(F)c3F)c3c(=O)n4c(nc32)CCC4)c(Cl)c(F)n1] | 12% | $^1$H NMR (500 MHz, DMSO-d$_6$) δ = 13.94-13.53 (m, 1H), 10.06 (br s, 1H), 8.58-8.40 (m, 1H), 8.14 (br s, 1H), 7.99 (br d, J = 6.7 Hz, 1H), 7.45 (br s, 1H), 7.26 (s, 1H), 5.26 (br s, 2H), 4.29-4.17 (m, 1H), 4.23 (br s, 1H), 4.00 (br t, J = 6.6 Hz, 2H), 3.79 (br d, J = 10.0 Hz, 1H), 3.42 (br d, J = 6.0 Hz, 4H), 3.08 (br t, J = 7.4 Hz, 2H), 3.03-2.87 (m, 2H), 2.87-2.73 (m, 1H), 2.38-2.27 (m, 1H), 2.20-2.13 (m, 2H), 2.06-1.89 (m, 1H), 1.88-1.72 (m, 1H), 1.11 (br d, J = 6.1 Hz, 3H); [M + H]$^+$ 720. |

-continued

| Structure | Yield | NMR & LCMS |
|---|---|---|
| 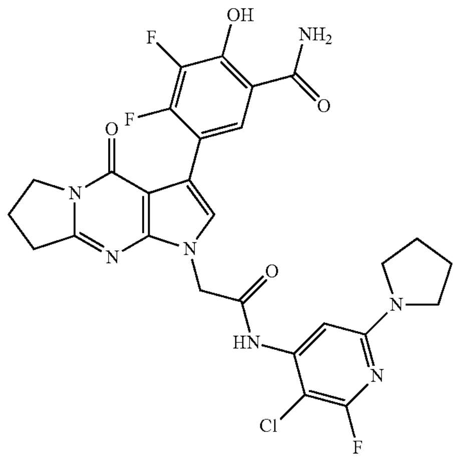 [SMILES: NC(=O)c1cc(-c2cn(CC(=O)Nc3cc(N4CCCC4)nc(F)c3Cl)c3nc4n(c(=O)c23)CCC4)c(F)c(F)c1O] | 35% | ¹H NMR (500 MHz, DMSO-d₆) δ = 13.75 (br s, 1H), 9.97 (s, 1H), 8.50 (br s, 1H), 8.14 (br s, 1H), 8.00 (br d, J = 6.6 Hz, 1H), 7.27 (s, 1H), 7.16 (s, 1H), 5.26 (s, 2H), 4.00 (br t, J = 7.2 Hz, 2H), 3.28 (br s, 4H), 3.08 (br t, J = 7.8 Hz, 2H), 2.17 (quin, J = 7.5 Hz, 2H), 1.90 (br s, 4H); [M + H]⁺ 603. |
| 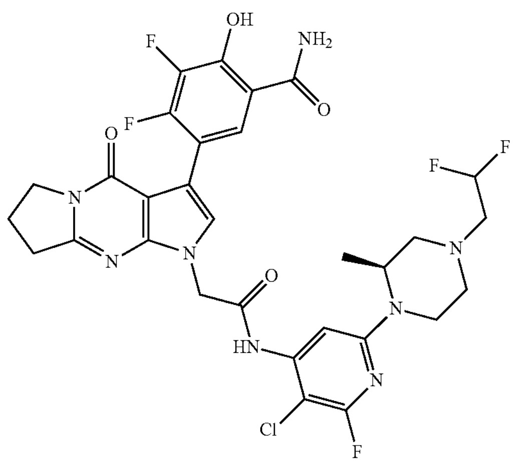 [SMILES: C[C@H]1CN(CC(F)F)CCN1c1cc(NC(=O)Cn2cc(-c3cc(C(N)=O)c(O)c(F)c3F)c3c(=O)n4c(nc32)CCC4)c(Cl)c(F)n1] | 27% | ¹H NMR (500 MHz, DMSO-d₆) δ = 13.74 (s, 1H), 10.06 (s, 1H), 8.60-8.40 (m, 1H), 8.22-8.07 (m, 1H), 7.99 (br d, J = 6.6 Hz, 1H), 7.44 (s, 1H), 7.26 (s, 1H), 6.29-5.99 (m, 1H), 5.26 (s, 2H), 4.21 (br s, 1H), 4.00 (t, J = 7.2 Hz, 2H), 3.76 (br d, J = 12.3 Hz, 1H), 3.08 (t, J = 7.8 Hz, 2H), 3.03-2.90 (m, 2H), 2.80 (br d, J = 11.1 Hz, 1H), 2.78-2.68 (m, 2H), 2.36 (br dd, J = 3.4, 11.2 Hz, 1H), 2.23-2.13 (m, 3H), 1.11 (d, J = 6.6 Hz, 3H); [M + H]⁺ 696. |
| 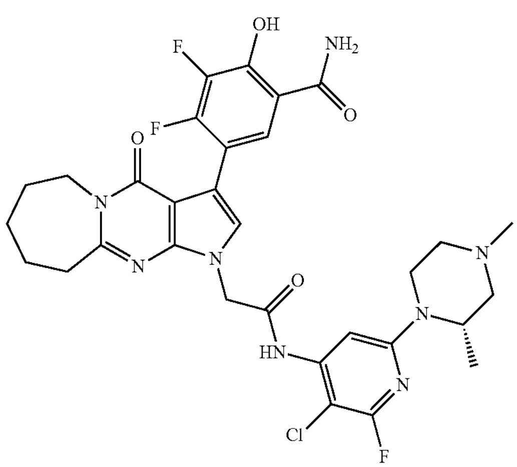 [SMILES: C[C@H]1CN(C)CCN1c1cc(NC(=O)Cn2cc(-c3cc(C(N)=O)c(O)c(F)c3F)c3c(=O)n4c(nc32)CCCCC4)c(Cl)c(F)n1] | 91% | ¹H NMR (500 MHz, DMSO-d₆) δ = 13.59 (br s, 1H), 10.05 (s, 1H), 9.37 (br s, 1H), 8.34 (br s, 1H), 8.00 (br s, 1H), 7.80 (br d, J = 7.0 Hz, 1H), 7.41 (s, 1H), 7.13-7.08 (m, 1H), 5.12 (s, 2H), 4.42 (br s, 1H), 4.16 (br d, J = 3.3 Hz, 2H), 3.97 (br d, J = 13.8 Hz, 1H), 3.30 (br d, J = 12.1 Hz, 2H), 3.05-2.96 (m, 2H), 2.88 (br d, J = 8.4 Hz, 3H), 2.68 (br s, 3H), 1.66-1.52 (m, 5H), 1.47 (br d, J = 13.2 Hz, 2H), 1.03 (d, J = 7.1 Hz, 3H); [M + H]⁺ 673. |

-continued

| Structure | Yield | NMR & LCMS |
|---|---|---|
| 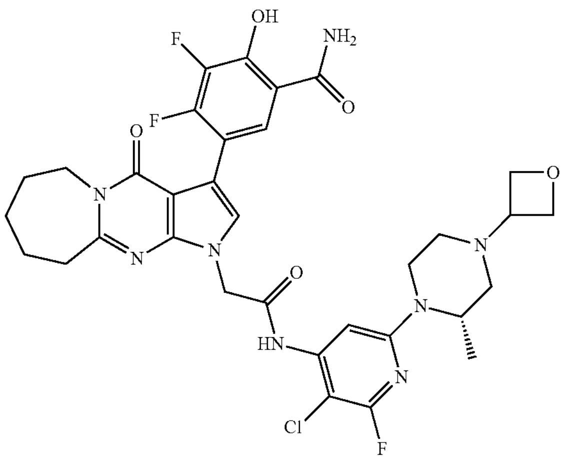 [SMILES: C[C@H]1CN(C2COC2)CCN1c1cc(NC(=O)Cn2cc(-c3cc(C(N)=O)c(O)c(F)c3F)c3c(=O)n4c(nc32)CCCCC4)c(Cl)c(F)n1] | 95% | ¹H NMR (500 MHz, DMSO-d₆) δ = 13.83-13.33 (m, 1H), 10.02 (s, 1H), 8.35 (br s, 1H), 8.00 (br s, 1H), 7.80 (br d, J = 6.5 Hz, 1H), 7.37 (s, 1H), 7.13-7.08 (m, 1H), 5.11 (s, 2H), 4.56 (br d, J = 4.4 Hz, 5H), 4.35 (br s, 2H), 4.16 (br d, J = 3.2 Hz, 3H), 3.17 (br s, 1H), 3.03-2.95 (m, 1H), 2.88 (br d, J = 8.9 Hz, 2H), 1.64-1.53 (m, 5H), 1.48 (br s, 2H), 1.08 (br d, J = 6.8 Hz, 3H); [M + H]⁺ 715. |
| 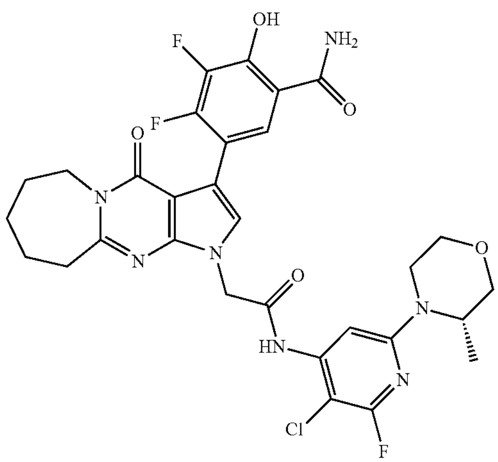 [SMILES: C[C@H]1COCCN1c1cc(NC(=O)Cn2cc(-c3cc(C(N)=O)c(O)c(F)c3F)c3c(=O)n4c(nc32)CCCCC4)c(Cl)c(F)n1] | 80% | ¹H NMR (500 MHz, DMSO-d₆) δ = 13.61 (br s, 1H), 9.94 (s, 1H), 8.36 (br s, 1H), 7.99 (br s, 1H), 7.79 (br d, J = 6.5 Hz, 1H), 7.29 (s, 1H), 7.13-7.06 (m, 1H), 5.10 (s, 2H), 4.21-4.11 (m, 2H), 3.92 (br dd, J = 1.9, 6.4 Hz, 1H), 3.74 (br dd, J = 3.5, 11.4 Hz, 1H), 3.52 (br d, J = 11.4 Hz, 1H), 3.47 (br d, J = 13.2 Hz, 2H), 2.90-2.82 (m, 3H), 1.64-1.53 (m, 5H), 1.48 (br s, 2H), 0.95 (d, J = 6.7 Hz, 3H); [M + H]⁺ 660. |
| 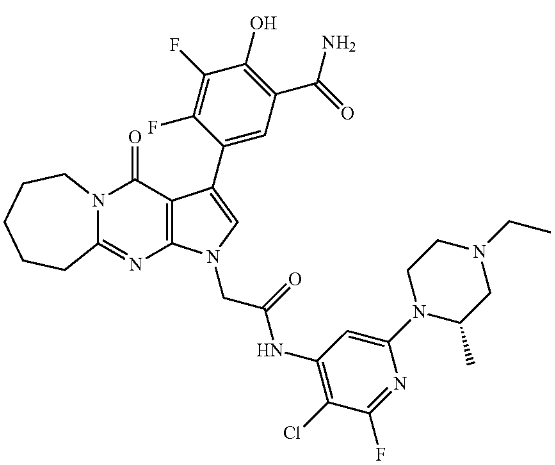 [SMILES: CCN1CCN(c2cc(NC(=O)Cn3cc(-c4cc(C(N)=O)c(O)c(F)c4F)c4c(=O)n5c(nc43)CCCCC5)c(Cl)c(F)n2)[C@@H](C)C1] | 84% | ¹H NMR (500 MHz, DMSO-d₆) δ = 13.58 (br s, 1H), 10.04 (s, 1H), 9.14 (br s, 1H), 8.34 (br s, 1H), 8.00 (br s, 1H), 7.80 (br d, J = 6.7 Hz, 1H), 7.40 (s, 1H), 7.14-7.06 (m, 1H), 5.12 (s, 2H), 4.42 (br s, 1H), 4.16 (br s, 2H), 3.98 (br d, J = 13.1 Hz, 1H), 3.01 (br d, J = 11.7 Hz, 6H), 2.88 (br d, J = 6.5 Hz, 2H), 2.81 (br d, J = 7.2 Hz, 1H), 1.67-1.52 (m, 5H), 1.48 (br s, 3H), 1.12-1.03 (m, 7H); [M + H]⁺ 687. |

| Structure | Yield | NMR & LCMS |
|---|---|---|
| 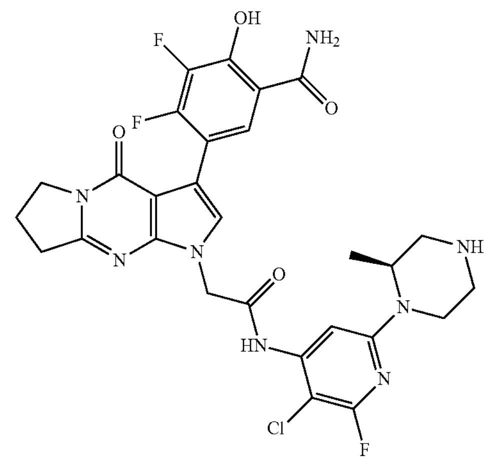 [SMILES: C[C@H]1CNCCN1c1cc(NC(=O)Cn2cc(-c3cc(C(N)=O)c(O)c(F)c3F)c3c(=O)n4c(nc32)CCC4)c(Cl)c(F)n1] | 17% | ¹H NMR (500 MHz, DMSO-d$_6$) δ = 10.01 (br s, 1H), 9.62-9.30 (m, 1H), 7.82 (br d, J = 5.3 Hz, 1H), 7.50 (br s, 1H), 7.44 (s, 1H), 7.15 (s, 1H), 5.23 (s, 2H), 4.15 (br s, 1H), 3.99 (br t, J = 7.2 Hz, 2H), 3.71 (br d, J = 11.9 Hz, 1H), 3.07 (br t, J = 7.8 Hz, 2H), 2.97 (br d, J = 12.1 Hz, 1H), 2.93-2.85 (m, 1H), 2.80 (br s, 2H), 2.62-2.54 (m, 1H), 2.17 (quin, J = 7.5 Hz, 2H), 1.10 (d, J = 6.7 Hz, 3H); [M + H]⁺ 631. |
| 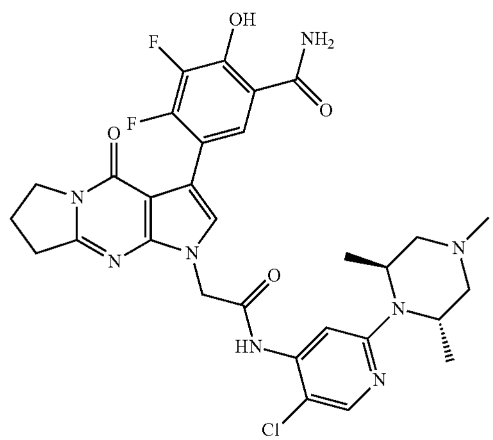 [SMILES: C[C@H]1CN(C)C[C@H](C)N1c1cc(NC(=O)Cn2cc(-c3cc(C(N)=O)c(O)c(F)c3F)c3c(=O)n4c(nc32)CCC4)c(Cl)cn1] | 18% | ¹H NMR (500 MHz, DMSO-d$_6$) δ = 13.78-13.64 (m, 1H), 10.10 (s, 1H), 9.49 (br d, J = 5.6 Hz, 1H), 8.46 (br d, J = 1.3 Hz, 1H), 8.34 (s, 1H), 8.15 (br s, 1H), 8.00 (br d, J = 7.2 Hz, 1H), 7.71 (s, 1H), 7.27 (s, 1H), 5.26 (s, 2H), 4.25-4.13 (m, 1H), 4.01 (br t, J = 7.2 Hz, 2H), 3.83-3.71 (m, 1H), 3.47 (br s, 2H), 3.08 (br t, J = 7.8 Hz, 2H), 2.85 (br s, 4H), 2.18 (quin, J = 7.5 Hz, 2H), 1.14 (br s, 3H), 0.98 (br d, J = 4.0 Hz, 3H); [M + H]⁺ 642. |
| 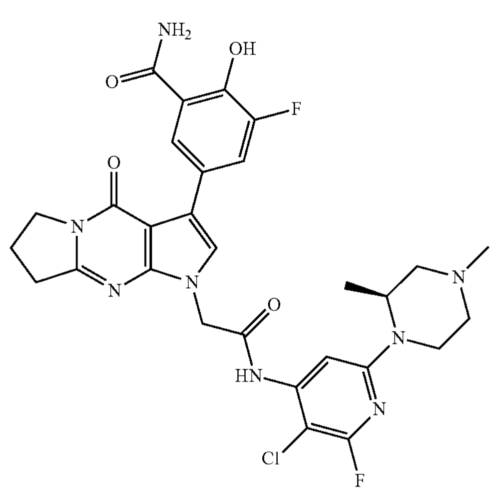 [SMILES: C[C@H]1CN(C)CCN1c1cc(NC(=O)Cn2cc(-c3cc(F)c(O)c(C(N)=O)c3)c3c(=O)n4c(nc32)CCC4)c(Cl)c(F)n1] | 47% | ¹H NMR (500 MHz, DMSO-d$_6$) δ = 13.14 (s, 1H), 10.26-10.17 (m, 1H), 9.53-9.37 (m, 1H), 8.53 (br s, 1H), 8.40 (dd, J = 1.7, 13.2 Hz, 1H), 8.11 (br s, 1H), 8.05 (s, 1H), 7.55 (s, 1H), 7.47 (s, 1H), 5.27 (s, 2H), 4.55 (br d, J = 1.7 Hz, 1H), 4.15-4.08 (m, 1H), 4.06 (br t, J = 7.2 Hz, 2H), 3.44 (br d, J = 12.0 Hz, 2H), 3.13 (br d, J = 14.3 Hz, 1H), 3.08 (br t, J = 7.8 Hz, 2H), 3.05-2.95 (m, 1H), 2.82 (br s, 3H), 2.19 (quin, J = 7.5 Hz, 2H), 1.17 (br d, J = 7.0 Hz, 3H); [M + H]⁺ 628. |

-continued

| Structure | Yield | NMR & LCMS |
|---|---|---|
| 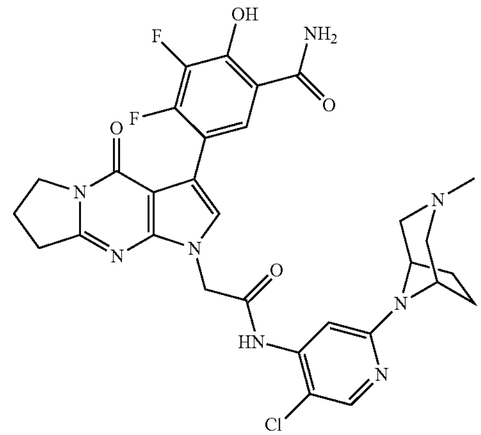 [SMILES: CN1CC2CCC(C1)N2c1cc(NC(=O)Cn2cc(-c3cc(C(N)=O)c(O)c(F)c3F)c3c(=O)n4c(nc32)CCC4)c(Cl)cn1] | 62% | $^1$H NMR (500 MHz, DMSO-$d_6$) δ 13.57 (br. s., 1H), 9.79 (s, 1H), 8.51 (br. s., 1H), 7.98-8.09 (m, 2H), 7.91 (d, J = 7.0 Hz, 1H), 7.39 (s, 1H), 7.19 (s, 1H), 5.16 (s, 2H), 4.27 (br. s., 2H), 3.93 (t, J = 7.2 Hz, 2H), 3.01 (t, J = 7.8 Hz, 2H), 2.47 (d, J = 11.6 Hz, 2H), 2.06-2.16 (m, 4H), 2.00 (s, 3H), 1.77-1.82 (m, 2H), 1.72 (d, J = 4.9 Hz, 2H); 19F NMR (471 MHz, DMSO-d6) δ −131.0 (br. s., 1F), −162.6 (d, J = 20.8 Hz, 1F); LCMS [M + 1]$^+$ 639.0 |
| 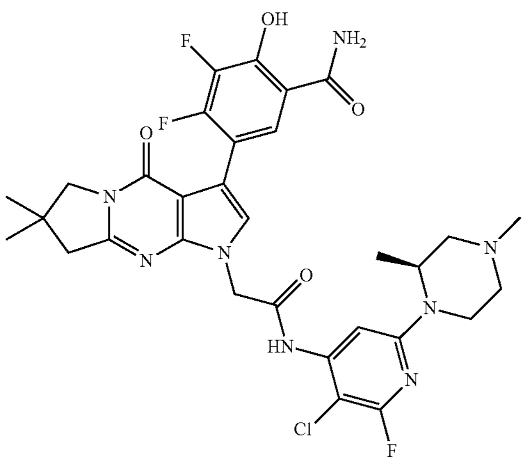 | 56% | $^1$H NMR (500 MHz, DMSO-$d_6$) δ = 13.71 (br s, 1H), 10.19 (s, 1H), 9.57-9.39 (m, 1H), 8.52-8.40 (m, 1H), 8.23-8.09 (m, 1H), 8.01 (br d, J = 6.7 Hz, 1H), 7.60-7.54 (m, 1H), 7.28 (s, 1H), 5.29 (s, 2H), 4.62-4.51 (m, 1H), 4.12 (br d, J = 12.6 Hz, 1H), 3.77 (s, 2H), 3.21-3.10 (m, 2H), 3.07-2.97 (m, 1H), 2.92 (s, 2H), 2.83 (br s, 3H), 1.18 (s, 9H); [M + H]$^+$ 674. |
| 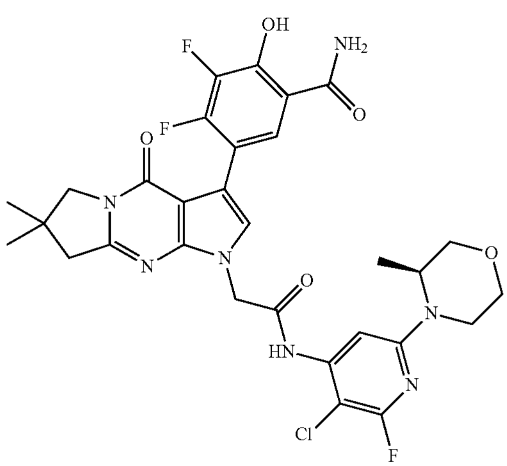 [SMILES: C[C@H]1COCCN1c1cc(NC(=O)Cn2cc(-c3cc(C(N)=O)c(O)c(F)c3F)c3c(=O)n4c(nc32)CC(C)(C)C4)c(Cl)c(F)n1] | 47% | $^1$H NMR (500 MHz, DMSO-$d_6$) δ = 13.74 (s, 1H), 10.08 (s, 1H), 8.56-8.40 (m, 1H), 8.14 (br s, 1H), 8.00 (br d, J = 6.6 Hz, 1H), 7.45 (s, 1H), 7.27 (s, 1H), 5.26 (s, 2H), 4.07 (br d, J = 4.8 Hz, 1H), 3.88 (br dd, J = 3.2, 11.4 Hz, 1H), 3.76 (s, 2H), 3.67 (br d, J = 11.4 Hz, 1H), 3.62 (br d, J = 11.9 Hz, 1H), 3.55 (dd, J = 2.6, 11.5 Hz, 1H), 3.44-3.38 (m, 1H), 3.04 (dt, J = 3.8, 12.6 Hz, 1H), 2.92 (s, 2H), 1.17 (s, 6H), 1.10 (d, J = 6.6 Hz, 3H); [M + H]$^+$ 661. |

| Structure | Yield | NMR & LCMS |
|---|---|---|
| 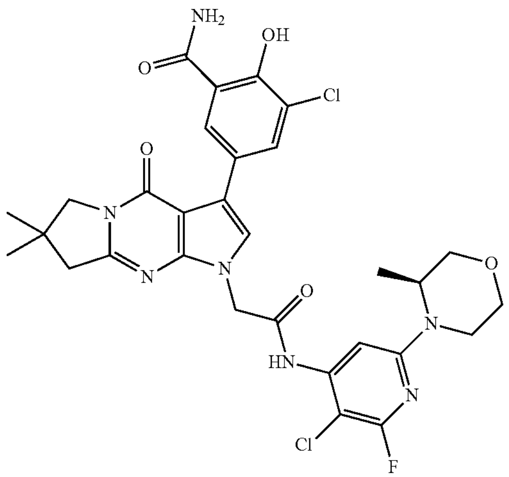 [SMILES: C[C@H]1COCCN1c1cc(NC(=O)Cn2cc(-c3cc(Cl)c(O)c(C(N)=O)c3)c3c(=O)n4c(nc32)CC(C)(C)C4)c(Cl)c(F)n1] | 55% | $^1$H NMR (500 MHz, DMSO-d$_6$) δ = 13.83 (s, 1H), 10.09 (s, 1H), 8.64 (br s, 1H), 8.56 (d, J = 1.5 Hz, 1H), 8.19 (d, J = 1.7 Hz, 1H), 8.16 (br s, 1H), 7.47 (s, 1H), 7.44 (s, 1H), 5.25 (s, 2H), 4.06 (br d, J = 4.6 Hz, 1H), 3.88 (br dd, J = 3.1, 11.3 Hz, 1H), 3.82 (s, 2H), 3.66 (d, J = 11.5 Hz, 1H), 3.61 (br d, J = 12.3 Hz, 1H), 3.55 (dd, J = 2.5, 11.4 Hz, 1H), 3.40 (dt, J = 2.8, 11.8 Hz, 1H), 3.03 (dt, J = 3.7, 12.6 Hz, 1H), 2.92 (s, 2H), 1.19 (s, 6H), 1.09 (d, J = 6.7 Hz, 3H); [M + H]$^+$ 659. |
| 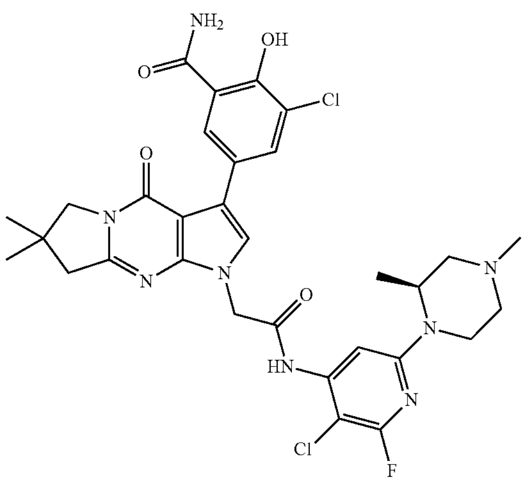 | 46% | $^1$H NMR (500 MHz, DMSO-d$_6$) δ = 13.82 (s, 1H), 10.21 (s, 1H), 9.56-9.41 (m, 1H), 8.62 (br s, 1H), 8.56 (d, J = 1.8 Hz, 1H), 8.20 (d, J = 1.8 Hz, 1H), 8.17 (br s, 1H), 7.55 (s, 1H), 7.48 (s, 1H), 5.27 (s, 2H), 4.55 (br s, 1H), 4.11 (br d, J = 14.5 Hz, 1H), 3.82 (s, 2H), 3.44 (br d, J = 12.1 Hz, 2H), 3.20-3.09 (m, 2H), 2.92 (s, 2H), 2.82 (br s, 3H), 1.19 (s, 6H), 1.17 (d, J = 7.1 Hz, 3H); [M + H]$^+$ 672. |
| 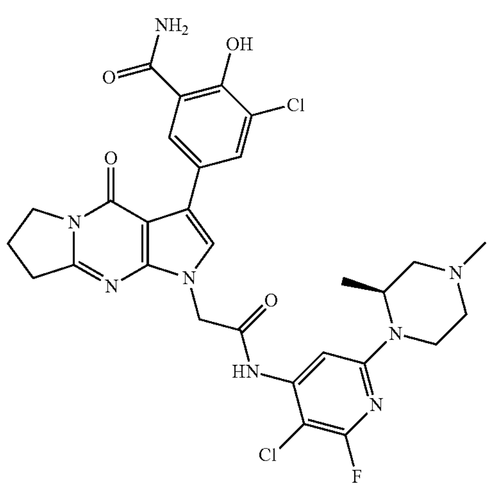 | 63% | $^1$H NMR (500 MHz, DMSO-d$_6$) δ = 13.82 (s, 1H), 10.22 (s, 1H), 9.56 (br s, 1H), 8.63 (br s, 1H), 8.59 (d, J = 1.8 Hz, 1H), 8.19 (d, J = 2.0 Hz, 1H), 8.18 (br s, 1H), 7.55 (s, 1H), 7.48 (s, 1H), 5.30-5.25 (m, 2H), 4.55 (br s, 1H), 4.11 (br d, J = 13.9 Hz, 1H), 4.06 (br t, J = 7.2 Hz, 2H), 3.14 (br d, J = 12.5 Hz, 2H), 3.09 (br t, J = 7.8 Hz, 2H), 3.00 (br d, J = 9.8 Hz, 1H), 2.82 (br s, 3H), 2.19 (quin, J = 7.5 Hz, 2H), 1.17 (d, J = 7.0 Hz, 3H); [M + H]$^+$ 644. |

| Structure | Yield | NMR & LCMS |
|---|---|---|
| 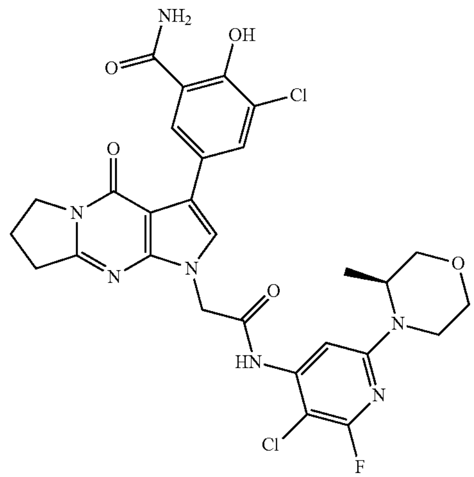 [SMILES: C[C@H]1COCCN1c1cc(NC(=O)Cn2cc(-c3cc(Cl)c(O)c(C(N)=O)c3)c3c(=O)n4c(nc32)CCC4)c(Cl)c(F)n1] | 27% | ¹H NMR (500 MHz, DMSO-$d_6$) δ = 13.83 (s, 1H), 10.11 (s, 1H), 8.64 (br s, 1H), 8.59 (d, J = 2.0 Hz, 1H), 8.19 (d, J = 2.0 Hz, 1H), 8.17 (br s, 1H), 7.47 (s, 1H), 7.44 (s, 1H), 5.26 (s, 2H), 4.06 (br t, J = 7.2 Hz, 3H), 3.88 (br dd, J = 3.3, 11.4 Hz, 1H), 3.66 (br d, J = 11.5 Hz, 1H), 3.61 (br d, J = 11.6 Hz, 1H), 3.54 (br dd, J = 2.8, 11.5 Hz, 1H), 3.44-3.36 (m, 1H), 3.09 (t, J = 7.9 Hz, 2H), 3.03 (dt, J = 3.9, 12.7 Hz, 1H), 2.19 (quin, J = 7.5 Hz, 2H), 1.09 (d, J = 6.6 Hz, 3H); [M + H]⁺ 631. |
| 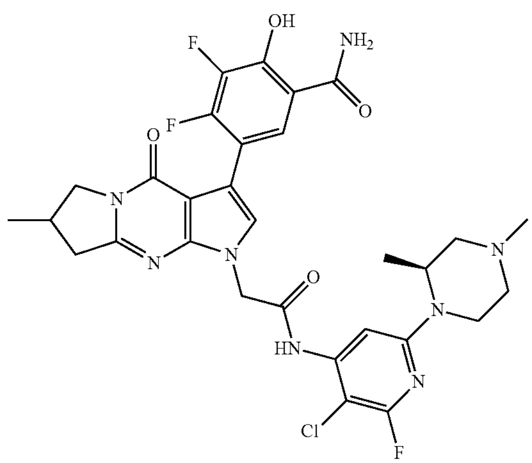 | 53% | ¹H NMR (500 MHz, DMSO-$d_6$) δ = 13.72 (br s, 1H), 10.26-10.16 (m, 1H), 9.63-9.44 (m, 1H), 8.47 (br s, 1H), 8.24-8.09 (m, 1H), 8.00 (br d, J = 6.5 Hz, 1H), 7.56 (s, 1H), 7.27 (s, 1H), 5.28 (s, 2H), 4.56 (br s, 1H), 4.21-4.14 (m, 1H), 4.11 (br d, J = 13.8 Hz, 1H), 3.24-3.18 (m, 1H), 3.17-3.10 (m, 2H), 3.05-2.95 (m, 1H), 2.83 (br s, 3H), 2.79-2.72 (m, 1H), 2.65 (qd, J = 7.1, 14.1 Hz, 1H), 1.18 (d, J = 7.0 Hz, 3H), 1.14 (d, J = 6.7 Hz, 3H); [M + H]⁺ 660 |
| 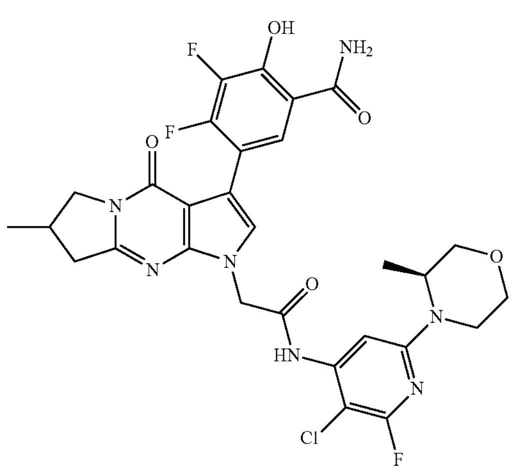 [SMILES: CC1Cc2nc3c(c(-c4cc(C(N)=O)c(O)c(F)c4F)cn3CC(=O)Nc3cc(N4CCOC[C@@H]4C)nc(F)c3Cl)c(=O)n2C1] | 40% | ¹H NMR (500 MHz, DMSO-$d_6$) δ = 13.74 (s, 1H), 10.08 (s, 1H), 8.49 (br s, 1H), 8.15 (br s, 1H), 7.99 (br d, J = 6.5 Hz, 1H), 7.45 (s, 1H), 7.26 (s, 1H), 5.26 (s, 2H), 4.16 (dd, J = 7.6, 11.6 Hz, 1H), 4.07 (br d, J = 4.5 Hz, 1H), 3.88 (br dd, J = 3.1, 11.3 Hz, 1H), 3.67 (br d, J = 11.4 Hz, 1H), 3.61 (br d, J = 13.0 Hz, 1H), 3.58-3.52 (m, 2H), 3.45-3.41 (m, 1H), 3.20 (dd, J = 7.9, 16.8 Hz, 1H), 3.03 (dt, J = 3.7, 12.6 Hz, 1H), 2.75 (dd, J = 7.3, 16.8 Hz, 1H), 2.65 (qd, J = 7.1, 14.2 Hz, 1H), 1.13 (d, J = 6.7 Hz, 3H), 1.10 (d, J = 6.5 Hz, 3H); [M + H]⁺ 646. |

| Structure | Yield | NMR & LCMS |
|---|---|---|
| (structure) | 55% | ¹H NMR (500 MHz, DMSO-d$_6$) δ = 13.83 (s, 1H), 10.21 (s, 1H), 9.53 (br d, J = 1.6 Hz, 1H), 8.63 (br s, 1H), 8.58 (d, J = 1.8 Hz, 1H), 8.19 (d, J = 1.8 Hz, 1H), 8.18 (br s, 1H), 7.55 (s, 1H), 7.47 (s, 1H), 5.27 (s, 2H), 4.55 (br s, 1H), 4.22 (dd, J = 7.5, 11.6 Hz, 1H), 4.17-4.05 (m, 1H), 3.62 (br dd, J = 6.5, 11.6 Hz, 1H), 3.24-3.18 (m, 1H), 3.17-3.09 (m, 2H), 3.01 (br s, 1H), 2.82 (br s, 3H), 2.79-2.73 (m, 1H), 2.66 (td, J = 6.8, 14.1 Hz, 1H), 1.16 (dd, J = 7.0, 9.2 Hz, 6H); [M + H]⁺ 659. |
| (structure) | 48% | ¹H NMR (500 MHz, DMSO-d$_6$) δ = 13.83 (s, 1H), 10.10 (s, 1H), 8.64 (br s, 1H), 8.57 (d, J = 1.8 Hz, 1H), 8.19 (d, J = 2.0 Hz, 1H), 8.16 (br s, 1H), 7.45 (d, J = 14.8 Hz, 2H), 5.26 (s, 2H), 4.22 (dd, J = 7.6, 11.6 Hz, 1H), 4.06 (br d, J = 4.5 Hz, 1H), 3.88 (br dd, J = 3.1, 11.2 Hz, 1H), 3.66 (br d, J = 11.5 Hz, 1H), 3.64-3.58 (m, 2H), 3.54 (br dd, J = 2.5, 11.4 Hz, 1H), 3.21 (br dd, J = 7.9, 16.7 Hz, 1H), 3.03 (dt, J = 3.7, 12.7 Hz, 1H), 2.76 (dd, J = 7.3, 16.7 Hz, 1H), 2.67 (qd, J = 7.1, 14.2 Hz, 1H), 1.15 (d, J = 6.7 Hz, 3H), 1.11-1.07 (m, 4H); [M + H]⁺ 644. |
| (structure) | 37% | ¹H NMR (500 MHz, DMSO-d$_6$) δ = 10.07-9.94 (m, 1H), 8.63 (s, 1H), 7.51 (s, 2H), 7.45-7.35 (m, 1H), 6.46 (s, 1H), 6.15 (s, 2H), 5.21 (s, 2H), 4.00 (br t, J = 7.2 Hz, 2H), 3.03 (br t, J = 7.2 Hz, 3H), 3.02 (br t, J = 7.9 Hz, 3H), 2.12 (td, J = 7.7, 14.9 Hz, 4H), 1.17 (br s, 1H), 1.06 (br d, J = 5.9 Hz, 3H); [M + H]⁺ 635. |

-continued

| Structure | Yield | NMR & LCMS |
|---|---|---|
| 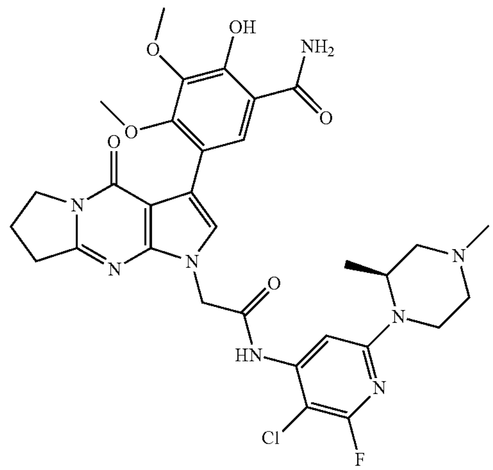 [SMILES: COc1c(-c2cn(CC(=O)Nc3cc(N4CCN(C)C[C@@H]4C)nc(F)c3Cl)c3nc4n(c(=O)c23)CCC4)cc(C(N)=O)c(O)c1OC] | 93% | $^1$H NMR (500 MHz, DMSO-d$_6$) δ = 13.50-13.16 (m, 1H), 10.15 (br s, 1H), 9.66-9.34 (m, 1H), 8.30-8.03 (m, 1H), 7.89-7.57 (m, 3H), 7.14 (br s, 1H), 5.25 (br s, 3H), 4.72-4.47 (m, 2H), 4.12 (br d, J = 12.2 Hz, 2H), 4.00 (br d, J = 6.4 Hz, 2H), 3.22-3.12 (m, 3H), 3.08 (br d, J = 6.8 Hz, 3H), 3.02-2.96 (m, 1H), 2.84 (br s, 2H), 2.18 (br d, J = 6.6 Hz, 3H), 1.19 (br s, 3H) [M + H]$^+$ 669. |
| 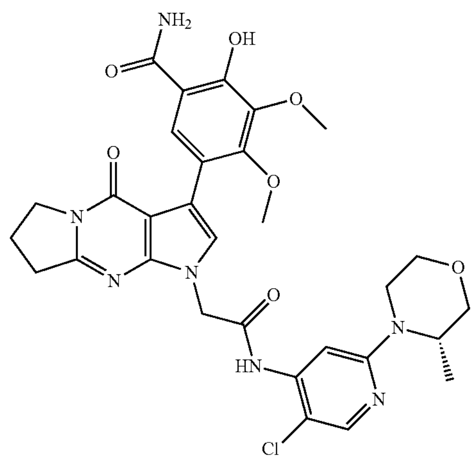 [SMILES: COc1c(-c2cn(CC(=O)Nc3cc(N4CCOC[C@@H]4C)ncc3Cl)c3nc4n(c(=O)c23)CCC4)cc(C(N)=O)c(O)c1OC] | 92% | $^1$H NMR (500 MHz, DMSO-d$_6$) δ = 13.80-12.44 (m, 1H), 9.85 (s, 1H), 8.21-8.17 (m, 1H), 8.17 (s, 1H), 7.82 (br s, 1H), 7.77 (s, 1H), 7.58-7.51 (m, 1H), 7.14 (s, 1H), 5.22 (s, 2H), 4.15 (br d, J = 4.9 Hz, 1H), 3.99 (br t, J = 7.1 Hz, 2H), 3.92-3.87 (m, 1H), 3.81 (s, 3H), 3.76 (s, 3H), 3.71-3.64 (m, 2H), 3.58 (br dd, J = 2.5, 11.2 Hz, 1H), 3.43 (dt, J = 2.8, 11.7 Hz, 1H), 3.08 (br t, J = 7.8 Hz, 2H), 3.02 (dt, J = 3.8, 12.6 Hz, 1H), 2.17 (quin, J = 7.4 Hz, 2H), 1.08 (br d, J = 6.6 Hz, 3H); [M + H]$^+$ 638. |
| 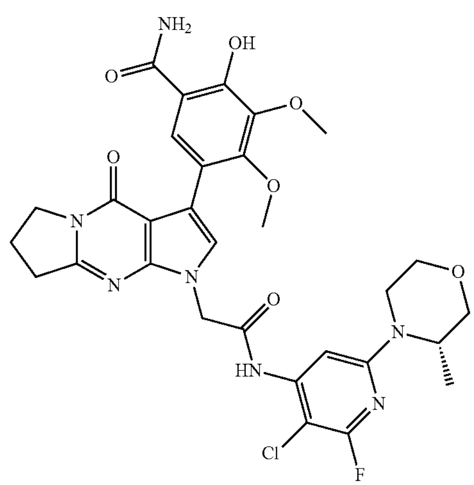 [SMILES: COc1c(-c2cn(CC(=O)Nc3cc(N4CCOC[C@@H]4C)nc(F)c3Cl)c3nc4n(c(=O)c23)CCC4)cc(C(N)=O)c(O)c1OC] | 79% | $^1$H NMR (500 MHz, DMSO-d$_6$) δ = 13.64-13.01 (m, 1H), 10.04 (s, 1H), 8.17 (br s, 1H), 7.82 (br s, 1H), 7.77 (s, 1H), 7.45 (s, 1H), 7.16-7.10 (m, 1H), 5.24 (s, 2H), 4.10-4.05 (m, 1H), 3.99 (br t, J = 7.0 Hz, 3H), 3.89 (br d, J = 10.1 Hz, 3H), 3.80 (s, 3H), 3.76 (s, 3H), 3.68 (br d, J = 11.5 Hz, 2H), 3.65-3.54 (m, 4H), 3.42 (br t, J = 11.2 Hz, 1H), 3.11-3.06 (m, 2H), 3.06-2.98 (m, 1H), 2.17 (quin, J = 7.3 Hz, 2H), 1.10 (br d, J = 6.6 Hz, 3H); [M + H]$^+$ 656. |

| Structure | Yield | NMR & LCMS |
|---|---|---|
| | 92% | ¹H NMR (500 MHz, DMSO-d₆) δ = 13.48-13.08 (m, 1H), 10.15 (s, 1H), 9.42 (br s, 1H), 8.15 (br s, 1H), 7.83 (br s, 1H), 7.78 (s, 1H), 7.55 (s, 1H), 7.17-7.12 (m, 1H), 5.26 (s, 2H), 4.58 (br s, 1H), 4.10 (br d, J = 13.4 Hz, 1H), 4.00 (br t, J = 7.0 Hz, 2H), 3.81 (s, 3H), 3.76 (s, 3H), 3.75-3.68 (m, 2H), 3.55-3.45 (m, 5H), 3.42-3.30 (m, 2H), 3.22 (br t, J = 12.2 Hz, 2H), 3.08 (br t, J = 7.7 Hz, 2H), 2.17 (quin, J = 7.3 Hz, 2H), 1.21 (br d, J = 6.8 Hz, 3H), 1.15 (br t, J = 6.9 Hz, 3H); [M + H]⁺ 727. |
| | 92% | ¹H NMR (500 MHz, DMSO-d₆) δ = 13.52-13.08 (m, 1H), 10.27-10.00 (m, 1H), 8.16 (br s, 1H), 7.83 (br s, 1H), 7.78 (s, 1H), 7.52 (br s, 1H), 7.16-7.12 (m, 1H), 5.25 (s, 2H), 4.69 (br s, 4H), 4.00 (br t, J = 6.9 Hz, 2H), 3.81 (s, 3H), 3.76 (s, 3H), 3.12 (br s, 1H), 3.08 (br t, J = 7.8 Hz, 2H), 2.17 (quin, J = 7.4 Hz, 2H), 1.22 (br d, J = 5.7 Hz, 3H); [M + H]⁺ 711. |
| 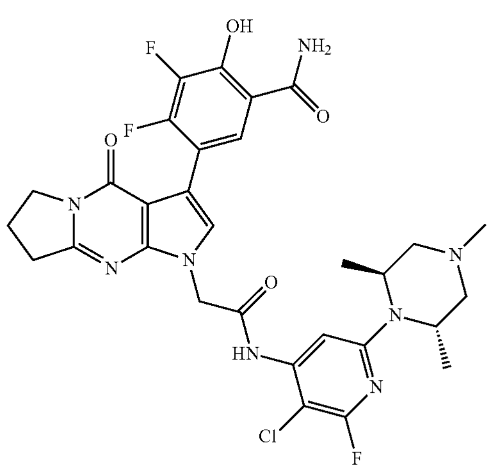 [SMILES: C[C@H]1CN(C)C[C@H](C)N1c1cc(NC(=O)Cn2cc(-c3cc(C(N)=O)c(O)c(F)c3F)c3c(=O)n4c(nc32)CCC4)c(Cl)c(F)n1] | 40% | ¹H NMR (500 MHz, DMSO-d₆) δ = 13.56 (br s, 1H), 10.16-10.09 (m, 1H), 9.46 (br s, 1H), 8.39-8.24 (m, 1H), 8.01 (br s, 1H), 7.86 (br d, J = 7.2 Hz, 1H), 7.43 (s, 1H), 7.16-7.07 (m, 1H), 5.14 (s, 2H), 4.12 (br s, 1H), 3.86 (br t, J = 6.9 Hz, 2H), 3.65 (br d, J = 1.3 Hz, 1H), 3.23 (br d, J = 8.4 Hz, 1H), 2.93 (br t, J = 7.6 Hz, 2H), 2.87-2.78 (m, 1H), 2.72 (br s, 3H), 2.03 (quin, J = 7.2 Hz, 2H), 1.08 (br d, J = 5.4 Hz, 3H), 0.92 (br d, J = 6.4 Hz, 3H); [M + H]⁺ 660. |

| Structure | Yield | NMR & LCMS |
|---|---|---|
| 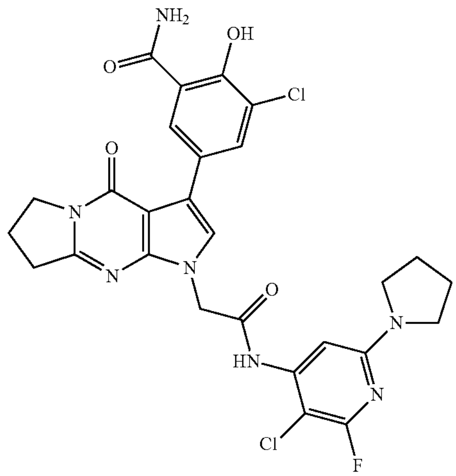 | 48% | ¹H NMR (500 MHz, DMSO-d₆) δ = 13.83 (br s, 1H), 9.99 (s, 1H), 8.64 (br s, 1H), 8.59 (s, 1H), 8.19 (s, 1H), 8.16 (br s, 1H), 7.47 (s, 1H), 7.15 (s, 1H), 5.25 (s, 2H), 4.06 (br t, J = 7.0 Hz, 2H), 3.27 (br s, 4H), 3.09 (br t, J = 7.7 Hz, 2H), 2.19 (quin, J = 7.2 Hz, 2H), 1.90 (br s, 4H); [M + H]⁺ 600. |
| 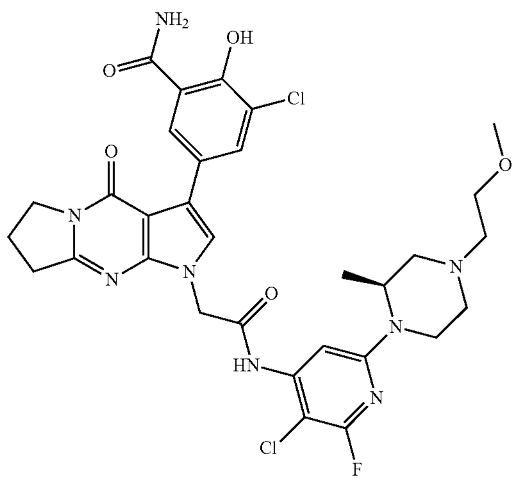 [SMILES: COCCN1CCN(c2cc(NC(=O)Cn3cc(-c4cc(Cl)c(O)c(C(N)=O)c4)c4c(=O)n5c(nc43)CCC5)c(Cl)c(F)n2)[C@@H](C)C1] | 50% | ¹H NMR (500 MHz, DMSO-d₆) δ = 13.82 (s, 1H), 10.21 (s, 1H), 9.59-9.36 (m, 1H), 8.63 (br s, 1H), 8.59 (s, 1H), 8.20 (s, 1H), 8.17 (br s, 1H), 7.53 (s, 1H), 7.48 (s, 1H), 5.27 (s, 2H), 4.55 (br s, 1H), 4.06 (br t, J = 6.9 Hz, 2H), 3.75-3.61 (m, 4H), 3.53-3.43 (m, 2H), 3.41-3.35 (m, 1H), 3.30 (s, 3H), 3.20 (br t, J = 12.5 Hz, 2H), 3.09 (br t, J = 7.7 Hz, 2H), 2.19 (quin, J = 7.4 Hz, 2H), 1.20 (br d, J = 6.7 Hz, 3H); [M + H]⁺ 688. |
| 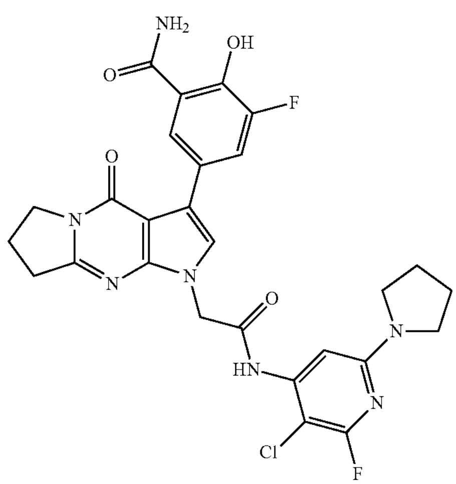 [SMILES: NC(=O)c1cc(-c2cn(CC(=O)Nc3cc(N4CCCC4)nc(F)c3Cl)c3nc4n(c(=O)c23)CCC4)cc(F)c1O] | 41% | ¹H NMR (500 MHz, DMSO-d₆) δ = 13.18 (br s, 1H), 9.98 (s, 1H), 8.55 (br s, 1H), 8.41 (br d, J = 13.1 Hz, 1H), 8.10 (br s, 1H), 8.05 (s, 1H), 7.47 (s, 1H), 7.15 (s, 1H), 5.25 (s, 2H), 4.05 (br t, J = 7.0 Hz, 2H), 3.27 (br s, 4H), 3.09 (br t, J = 7.7 Hz, 2H), 2.19 (quin, J = 7.3 Hz, 2H), 1.90 (br s, 4H); [M + H]⁺ 585. |

| Structure | Yield | NMR & LCMS |
|---|---|---|
| 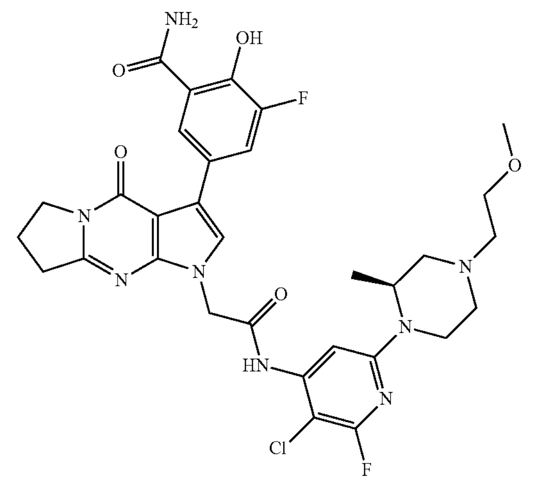 [SMILES: COCCN1CCN(c2cc(NC(=O)Cn3cc(-c4cc(F)c(O)c(C(N)=O)c4)c4c(=O)n5c(nc43)CCC5)c(Cl)c(F)n2)[C@@H](C)C1] | 53% | ¹H NMR (500 MHz, DMSO-d$_6$) δ = 13.14 (br s, 1H), 10.20 (br s, 1H), 9.48-9.30 (m, 1H), 8.52 (br s, 1H), 8.40 (br d, J = 13.1 Hz, 1H), 8.14-8.09 (m, 1H), 8.05 (br s, 1H), 7.53 (br s, 1H), 7.47 (s, 1H), 5.27 (br s, 2H), 4.60-4.48 (m, 1H), 4.12-3.98 (m, 4H), 3.75-3.63 (m, 4H), 3.30 (br s, 3H), 3.22-3.16 (m, 2H), 3.08 (br t, J = 7.6 Hz, 2H), 2.24-2.16 (m, 2H), 1.20 (br d, J = 6.2 Hz, 3H); [M + H]⁺ 672. |
| 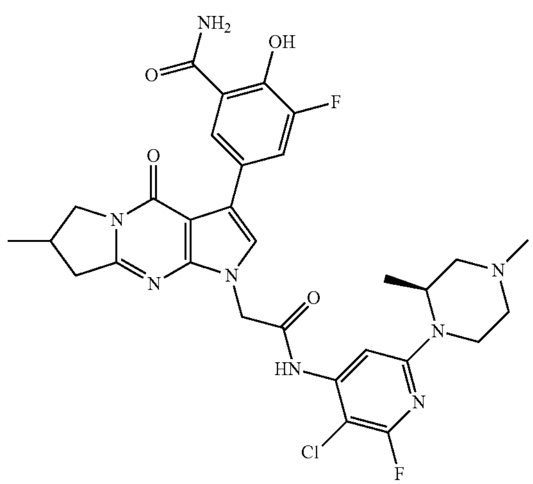 | 35% | ¹H NMR (500 MHz, DMSO-d$_6$) δ = 13.15 (s, 1H), 10.21 (s, 1H), 9.55-9.41 (m, 1H), 8.53 (br s, 1H), 8.39 (dd, J = 1.6, 13.1 Hz, 1H), 8.10 (br s, 1H), 8.05 (s, 1H), 7.55 (s, 1H), 7.47 (s, 1H), 5.27 (s, 2H), 4.61-4.48 (m, 1H), 4.22 (dd, J = 7.5, 11.6 Hz, 1H), 4.11 (br d, J = 13.0 Hz, 1H), 3.61 (br dd, J = 6.5, 11.6 Hz, 1H), 3.25-3.09 (m, 4H), 3.00 (br d, J = 9.0 Hz, 1H), 2.82 (br s, 3H), 2.75 (br dd, J = 7.0, 16.9 Hz, 1H), 2.67 (dt, J = 6.8, 14.0 Hz, 1H), 1.16 (dd, J = 7.1, 9.0 Hz, 6H); [M + H]⁺ 642. |
| 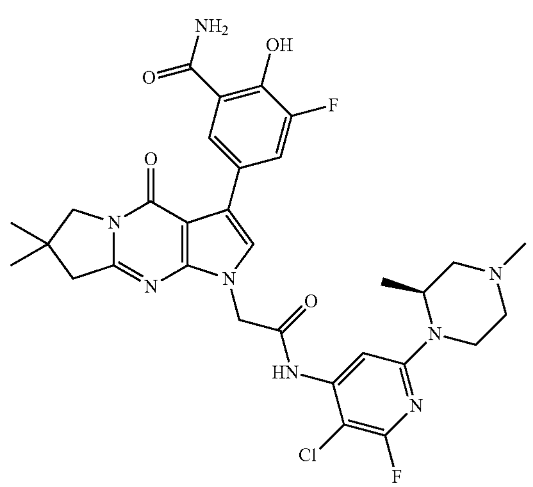 | 54% | ¹H NMR (500 MHz, DMSO-d$_6$) δ = 13.15 (s, 1H), 10.21 (s, 1H), 9.44 (br s, 1H), 8.52 (br s, 1H), 8.38 (dd, J = 1.5, 13.1 Hz, 1H), 8.11 (br s, 1H), 8.05 (s, 1H), 7.55 (s, 1H), 7.47 (s, 1H), 5.27 (s, 2H), 4.55 (br s, 1H), 4.11 (br d, J = 14.3 Hz, 1H), 3.82 (s, 2H), 3.18-3.09 (m, 2H), 3.05-2.96 (m, 1H), 2.92 (s, 2H), 2.82 (br s, 3H), 1.19 (s, 6H), 1.17 (br d, J = 7.1 Hz, 3H); [M + 1]⁺ 656. |

-continued

| Structure | Yield | NMR & LCMS |
|---|---|---|
| 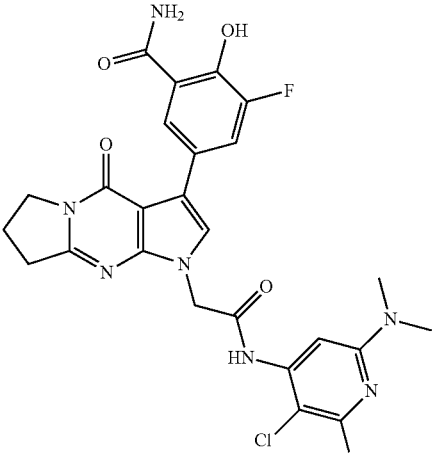 | 56% | ¹H NMR (500 MHz, DMSO-$d_6$) δ = 13.18 (s, 1H), 10.01 (s, 1H), 8.55 (br s, 1H), 8.41 (dd, J = 1.7, 13.1 Hz, 1H), 8.10 (br s, 1H), 8.05 (s, 1H), 7.47 (s, 1H), 7.30 (s, 1H), 5.25 (s, 2H), 4.05 (br t, J = 7.2 Hz, 2H), 3.09 (br t, J = 7.8 Hz, 2H), 2.94 (s, 6H), 2.19 (quin, J = 7.5 Hz, 2H); [M + 1]⁺ 559. |
| 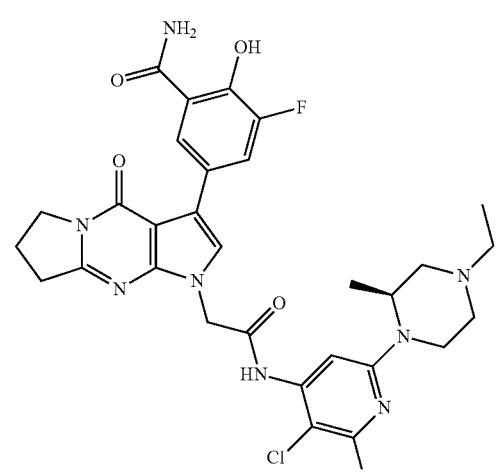 | 56% | ¹H NMR (500 MHz, DMSO-$d_6$) δ = 13.14 (s, 1H), 10.21 (s, 1H), 9.28-9.12 (m, 1H), 8.53 (br s, 1H), 8.41 (dd, J = 1.8, 13.1 Hz, 1H), 8.11 (br s, 1H), 8.05 (s, 1H), 7.54 (s, 1H), 7.48 (s, 1H), 5.27 (s, 2H), 4.55 (br s, 1H), 4.12 (br d, J = 14.3 Hz, 1H), 4.06 (br t, J = 7.2 Hz, 2H), 3.50 (br s, 1H), 3.22-3.11 (m, 4H), 3.08 (br t, J = 7.9 Hz, 2H), 3.00-2.89 (m, 1H), 2.19 (quin, J = 7.6 Hz, 2H), 1.22 (br t, J = 7.2 Hz, 3H), 1.19 (br d, J = 7.0 Hz, 3H); [M + 1]⁺ 642. |
| 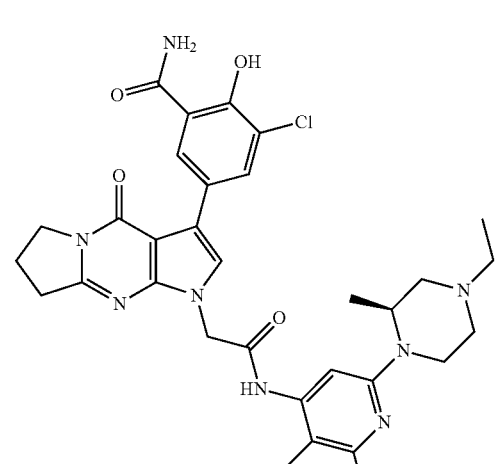 | 48% | ¹H NMR (500 MHz, DMSO-$d_6$) δ = 13.82 (s, 1H), 10.21 (s, 1H), 9.20 (br s, 1H), 8.63 (br s, 1H), 8.59 (d, J = 1.8 Hz, 1H), 8.20 (d, J = 1.8 Hz, 1H), 8.18 (br s, 1H), 7.54 (s, 1H), 7.48 (s, 1H), 5.27 (s, 2H), 4.55 (br s, 1H), 4.12 (br d, J = 14.2 Hz, 1H), 4.06 (br t, J = 7.2 Hz, 2H), 3.45 (br d, J = 12.7 Hz, 2H), 3.19-3.12 (m, 3H), 3.09 (br t, J = 7.9 Hz, 2H), 3.01-2.90 (m, 1H), 2.19 (quin, J = 7.5 Hz, 2H), 1.23 (br t, J = 7.2 Hz, 3H), 1.19 (br d, J = 7.0 Hz, 3H); [M + 1]⁺ 659. |

-continued

| Structure | Yield | NMR & LCMS |
|---|---|---|
| | 48% | $^1$H NMR (500 MHz, DMSO-d$_6$) δ = 13.14 (s, 1H), 10.31 (s, 1H), 9.63 (br s, 1H), 8.52 (br s, 1H), 8.41 (dd, J = 1.8, 13.1 Hz, 1H), 8.11 (br s, 1H), 8.05 (s, 1H), 7.57 (s, 1H), 7.47 (s, 1H), 5.27 (s, 2H), 4.30-4.22 (m, 1H), 4.06 (br t, J = 7.2 Hz, 2H), 3.79 (br s, 1H), 3.39-3.33 (m, 2H), 3.09 (br t, J = 7.8 Hz, 2H), 3.01-2.93 (m, 1H), 2.86 (br s, 3H), 2.19 (quin, J = 7.5 Hz, 2H), 1.22 (br d, J = 5.7 Hz, 3H), 1.06 (br d, J = 6.8 Hz, 3H); [M + 1]$^+$ 641. |
| | 48% | $^1$H NMR (500 MHz, DMSO-d$_6$) δ = 12.98 (br s, 1H), 10.17 (s, 1H), 9.51 (br d, J = 1.2 Hz, 1H), 8.30 (s, 1H), 7.86 (br s, 2H), 7.55 (s, 1H), 7.36 (s, 1H), 6.11 (s, 2H), 5.27 (s, 2H), 4.56 (br s, 1H), 4.11 (br d, J = 13.9 Hz, 1H), 4.04 (br t, J = 7.2 Hz, 2H), 3.44 (br d, J = 12.0 Hz, 2H), 3.14 (br d, J = 12.5 Hz, 1H), 3.08 (br t, J = 7.9 Hz, 2H), 3.00 (br d, J = 10.5 Hz, 1H), 2.82 (br s, 3H), 2.18 (quin, J = 7.5 Hz, 2H), 1.17 (d, J = 7.0 Hz, 3H); [M + 1]$^+$ 654. |
| 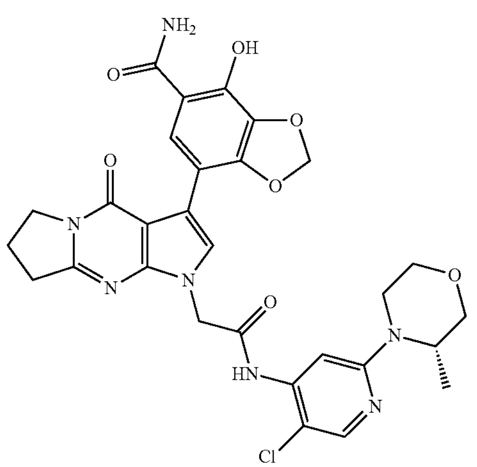 [SMILES: C[C@H]1COCCN1c1cc(NC(=O)Cn2cc(-c3cc(C(N)=O)c(O)c4c3OCO4)c3c(=O)n4c(nc32)CCC4)c(Cl)cn1] | Quant. | $^1$H NMR (500 MHz, DMSO-d$_6$) δ = 9.80 (s, 1H), 8.21 (s, 1H), 8.10-8.04 (m, 1H), 7.79 (s, 2H), 7.47 (s, 1H), 7.28 (s, 1H), 6.03 (s, 2H), 5.16 (s, 2H), 4.07 (br d, J = 4.5 Hz, 1H), 3.97 (br t, J = 7.2 Hz, 2H), 3.81 (br dd, J = 3.2, 11.2 Hz, 1H), 3.60 (br d, J = 10.9 Hz, 2H), 3.50 (dd, J = 2.6, 11.3 Hz, 1H), 3.35 (dt, J = 3.0, 11.8 Hz, 1H), 3.02 (t, J = 7.8 Hz, 2H), 2.94 (dt, J = 3.8, 12.6 Hz, 1H), 2.11 (quin, J = 7.5 Hz, 2H), 1.00 (d, J = 6.6 Hz, 3H); [M + H]$^+$ 622. |

-continued

| Structure | Yield | NMR & LCMS |
|---|---|---|
| 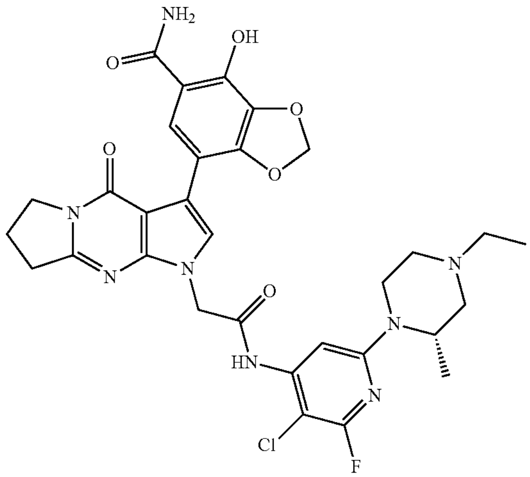 [SMILES: CCN1CCN(c2cc(NC(=O)Cn3cc(-c4cc(C(N)=O)c(O)c5c4OCO5)c4c(=O)n5c(nc43)CCC5)c(Cl)c(F)n2)[C@@H](C)C1] | 93% | $^1$H NMR (500 MHz, DMSO-d$_6$) δ = 13.09-12.64 (m, 1H), 10.10 (s, 1H), 9.24 (br s, 1H), 8.23 (s, 1H), 7.79 (br s, 2H), 7.48 (s, 1H), 7.31-7.26 (m, 1H), 6.04 (s, 2H), 5.21 (s, 2H), 4.49 (br s, 1H), 4.05 (br d, J = 14.2 Hz, 1H), 3.97 (br t, J = 7.2 Hz, 2H), 3.44 (br d, J = 11.7 Hz, 1H), 3.39 (br d, J = 12.3 Hz, 1H), 3.14-3.05 (m, 4H), 3.02 (br t, J = 7.8 Hz, 2H), 2.94-2.84 (m, 1H), 2.11 (quin, J = 7.5 Hz, 2H), 1.16 (br t, J = 7.3 Hz, 3H), 1.13 (d, J = 7.1 Hz, 3H); [M + H]$^+$ 667. |
| 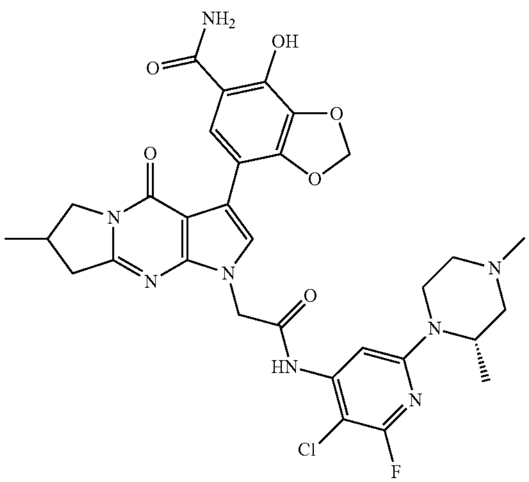 | 91% | $^1$H NMR (500 MHz, DMSO-d$_6$) δ = 13.07-12.80 (m, 1H), 10.10 (s, 1H), 9.55-9.30 (m, 1H), 8.21 (s, 1H), 7.80 (br s, 2H), 7.48 (s, 1H), 7.30-7.26 (m, 1H), 6.04 (s, 2H), 5.20 (s, 2H), 4.60-4.41 (m, 1H), 4.13 (dd, J = 7.5, 11.7 Hz, 1H), 4.04 (br d, J = 13.3 Hz, 1H), 3.18-3.03 (m, 4H), 2.93 (br d, J = 9.8 Hz, 1H), 2.68 (br dd, J = 6.9, 16.4 Hz, 1H), 2.59 (qd, J = 7.2, 14.0 Hz, 1H), 1.10 (d, J = 7.0 Hz, 3H), 1.07 (d, J = 6.7 Hz, 3H); [M + H]$^+$ 667. |
| 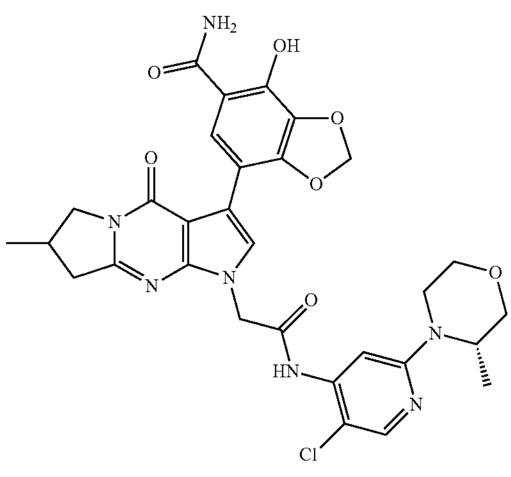 [SMILES: CC1Cc2nc3c(c(-c4cc(C(N)=O)c(O)c5c4OCO5)cn3CC(=O)Nc3cc(N4CCOC[C@@H]4C)ncc3Cl)c(=O)n2C1] | Quant. | $^1$H NMR (500 MHz, DMSO-d$_6$) δ = 13.35-12.49 (m, 1H), 9.80 (s, 1H), 8.19 (s, 1H), 8.08 (s, 1H), 7.80 (br s, 2H), 7.49-7.42 (m, 1H), 7.28 (s, 1H), 6.03 (s, 2H), 5.16 (s, 2H), 4.12 (dd, J = 7.6, 11.6 Hz, 1H), 4.07 (br d J = 4.8 Hz, 1H), 3.81 (br dd, J = 3.0, 10.9 Hz, 1H), 3.35 (dt, J = 2.9, 11.7 Hz, 1H), 3.14 (br dd, J = 7.8, 16.8 Hz, 1H), 2.93 (dt, J = 3.7, 12.7 Hz, 1H), 2.72-2.65 (m, 1H), 2.63-2.54 (m, 1H), 1.07 (d, J = 6.7 Hz, 3H), 1.00 (d, J = 6.7 Hz, 3H); [M + H]$^+$ 636. |

| Structure | Yield | NMR & LCMS |
|---|---|---|
| 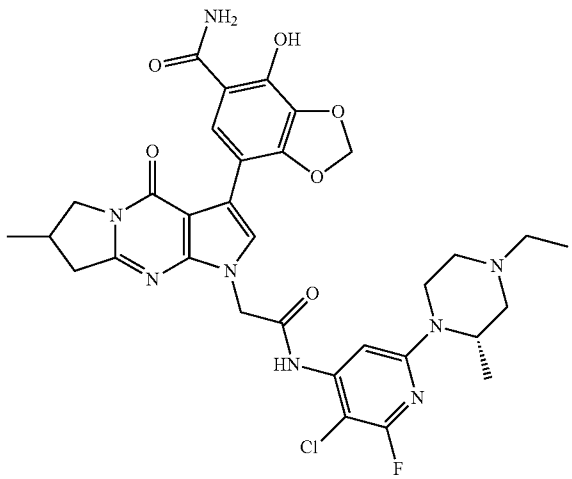 [SMILES: CCN1CCN(c2cc(NC(=O)Cn3cc(-c4cc(C(N)=O)c(O)c5c4OCO5)c4c(=O)n5c(nc43)CC(C)C5)c(Cl)c(F)n2)[C@@H](C)C1] | 93% | $^1$H NMR (500 MHz, DMSO-d$_6$) δ = 12.93 (br s, 1H), 10.10 (s, 1H), 9.14 (br d, J = 1.6 Hz, 1H), 8.21 (s, 1H), 7.80 (br s, 2H), 7.48 (s, 1H), 7.31-7.25 (m, 1H), 6.04 (s, 2H), 5.20 (s, 2H), 4.49 (br s, 1H), 4.13 (dd, J = 7.6, 11.6 Hz, 1H), 4.06 (br d, J = 13.7 Hz, 1H), 3.54 (br dd, J = 6.4, 11.6 Hz, 1H), 3.18-3.04 (m, 6H), 2.94-2.84 (m, 1H), 2.72-2.66 (m, 1H), 2.59 (qd, J = 7.0, 14.0 Hz, 1H), 1.16 (br t, J = 6.9 Hz, 4H), 1.13 (br d, J = 7.0 Hz, 3H), 1.07 (d, J = 6.7 Hz, 3H); [M + H]$^+$ 681 |
| 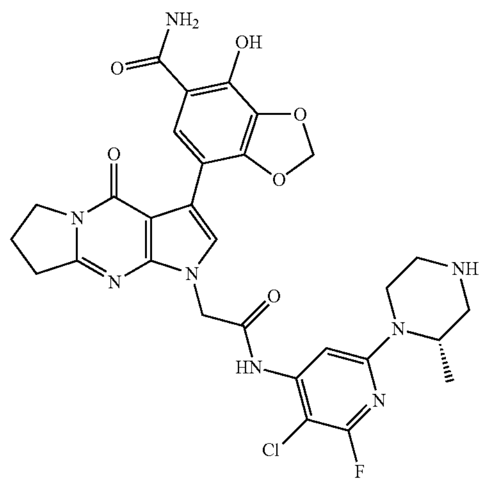 [SMILES: C[C@H]1CNCCN1c1cc(NC(=O)Cn2cc(-c3cc(C(N)=O)c(O)c4c3OCO4)c3c(=O)n4c(nc32)CCC4)c(Cl)c(F)n1] | 71% | $^1$H NMR (500 MHz, DMSO-d$_6$) δ = 12.91 (br s, 1H), 10.08 (s, 1H), 8.97-8.83 (m, 1H), 8.50-8.35 (m, 1H), 8.22 (s, 1H), 7.79 (br s, 2H), 7.47 (s, 1H), 7.30-7.27 (m, 1H), 6.04 (s, 2H), 5.20 (s, 2H), 4.41 (br s, 1H), 3.97 (br t, J = 7.0 Hz, 2H), 3.95-3.90 (m, 1H), 3.11-3.04 (m, 2H), 3.01 (br t, J = 7.9 Hz, 2H), 2.96-2.87 (m, 1H), 2.76 (br s, 1H), 2.14-2.09 (m, 2H), 1.09 (br d, J = 7.0 Hz, 3H); [M + H]$^+$ 639. |
| 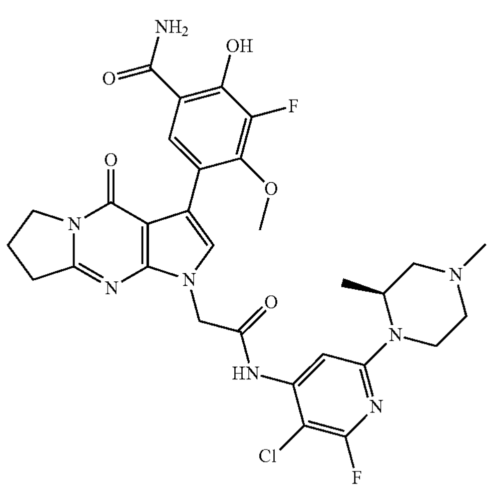 [SMILES: COc1c(-c2cn(CC(=O)Nc3cc(N4CCN(C)C[C@@H]4C)nc(F)c3Cl)c3nc4n(c(=O)c23)CCC4)cc(C(N)=O)c(O)c1F] | 41% | $^1$H NMR (500 MHz, DMSO-d$_6$) δ ppm 1.18 (d, J = 6.97 Hz, 3 H), 2.17 (quin, J = 7.52 Hz, 2 H), 2.83 (br s, 3 H), 3.07 (br t, J = 7.83 Hz, 2 H), 3.11-3.19 (m, 2 H), 3.45 (br d, J = 12.23 Hz, 2 H), 3.82 (d, J = 1.96 Hz, 3 H), 3.99 (br t, J = 7.15 Hz, 2 H), 4.11 (br d, J = 13.69 Hz, 1 H), 4.56 (br s, 1 H), 5.26 (s, 2 H), 7.17 (s, 1 H), 7.55 (s, 1 H), 7.83 (s, 1 H), 7.98 (br s, 1 H), 8.29 (br s, 1 H), 9.56-9.70 (m, 1 H), 10.16 (s, 1 H), 13.48 (br s, 1 H); [M + 1]$^+$ 657. |

| Structure | Yield | NMR & LCMS |
|---|---|---|
| 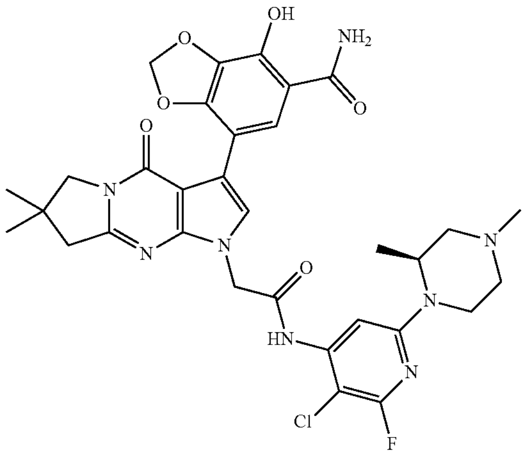 | 52% | $^1$H NMR (500 MHz, DMSO-d$_6$) δ ppm 1.16 (br s, 3 H), 1.18 (s, 6 H), 2.83 (br s, 3 H), 2.92 (s, 2 H), 3.09-3.19 (m, 2 H), 3.44 (br d, J = 11.62 Hz, 2 H), 3.80 (s, 2 H), 4.11 (br d, J = 12.96 Hz, 1 H), 4.56 (br s, 1 H), 5.27 (s, 2 H), 6.11 (s, 2 H), 7.36 (s, 1 H), 7.55 (s, 1 H), 7.87 (br s, 2 H), 8.27 (s, 1 H), 9.46 (br s, 1 H), 10.16 (s, 1 H), 13.00 (s, 1 H); [M + 1]$^+$ 681. |
| 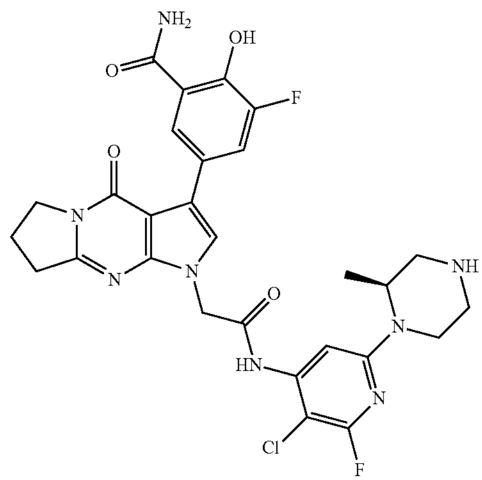 [SMILES: C[C@H]1CNCCN1c1cc(NC(=O)Cn2cc(-c3cc(F)c(O)c(C(N)=O)c3)c3c(=O)n4c(nc32)CCC4)c(Cl)c(F)n1] | 32% | $^1$H NMR (500 MHz, DMSO-d$_6$) δ = 13.15 (s, 1H), 10.19 (s, 1H), 9.03 (br s, 1H), 8.53 (br s, 2H), 8.40 (dd, J = 1.7, 13.1 Hz, 1H), 8.10 (br s, 1H), 8.05 (s, 1H), 7.53 (s, 1H), 7.47 (s, 1H), 5.31-5.23 (m, 2H), 4.51-4.43 (m, 1H), 4.08-3.99 (m, 3H), 3.30-3.23 (m, 2H), 3.14 (br s, 2H), 3.08 (br t, J = 7.9 Hz, 2H), 2.19 (quin, J = 7.5 Hz, 2H), 1.16 (d, J = 7.0 Hz, 3H); [M + 1]$^+$ 613. |
| 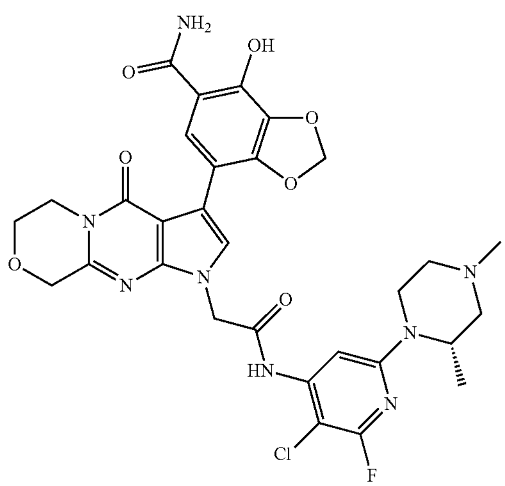 [SMILES: C[C@H]1CN(C)CCN1c1cc(NC(=O)Cn2cc(-c3cc(C(N)=O)c(O)c4c3OCO4)c3c(=O)n4c(nc32)COCC4)c(Cl)c(F)n1] | 97% | $^1$H NMR (500 MHz, DMSO-d$_6$) δ = 12.97 (br s, 1H), 10.11 (s, 1H), 9.46 (br s, 1H), 8.12 (s, 1H), 7.84 (br dd, J = 1.9, 4.5 Hz, 2H), 7.47 (s, 1H), 7.34-7.27 (m, 1H), 6.04 (s, 2H), 5.19 (s, 2H), 4.63 (s, 2H), 4.49 (br s, 1H), 4.10-4.03 (m, 1H), 4.01 (br t, J = 5.3 Hz, 2H), 3.84 (br t, J = 5.1 Hz, 2H), 3.12-3.02 (m, 2H), 2.93 (br d, J = 8.2 Hz, 1H), 2.76 (br s, 3H), 1.10 (d, J = 7.0 Hz, 3H); [M + H]$^+$ 669. |

-continued

| Structure | Yield | NMR & LCMS |
|---|---|---|
| 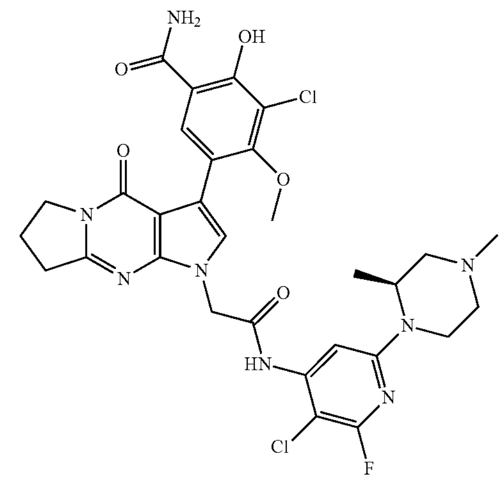 | 70% | ¹H NMR (500 MHz, DMSO-d₆) δ = 14.15-14.11 (m, 1H), 10.17 (s, 1H), 9.66-9.48 (m, 1H), 8.38 (br s, 1H), 8.07 (br s, 1H), 8.05 (s, 1H), 7.53 (s, 1H), 7.24 (s, 1H), 5.27 (s, 2H), 4.56 (br s, 1H), 4.10 (br d, J = 13.4 Hz, 1H), 4.00 (br t, J = 7.1 Hz, 2H), 3.60 (s, 3H), 3.14 (br t, J = 12.7 Hz, 2H), 3.08 (br t, J = 7.8 Hz, 2H), 3.01 (br d, J = 7.9 Hz, 1H), 2.83 (br s, 3H), 2.17 (quin, J = 7.5 Hz, 2H), 1.18 (d, J = 7.0 Hz, 3H); [M + 1]⁺ 674. |
| 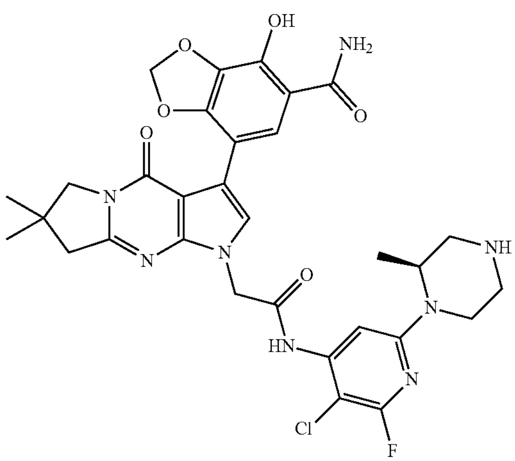 [SMILES: C[C@H]1CNCCN1c1cc(NC(=O)Cn2cc(-c3cc(C(N)=O)c(O)c4c3OCO4)c3c(=O)n4c(nc32)CC(C)(C)C4)c(Cl)c(F)n1] | 52% | ¹H NMR (500 MHz, DMSO-d₆) δ ppm 1.16 (d, J = 6.97 Hz, 3 H) 1.18 (s, 6 H) 2.92 (s, 2 H) 2.94-3.03 (m, 1 H) 3.07-3.18 (m, 2 H) 3.25 (br d, J = 13.82 Hz, 1 H) 3.80 (s, 2 H) 4.03 (br d, J = 13.57 Hz, 1 H) 4.44-4.52 (m, 1 H) 5.27 (s, 2 H) 6.11 (s, 2 H) 7.35 (s, 1 H) 7.49-7.54 (m, 1 H) 7.87 (s, 2 H) 8.27 (s, 1 H) 8.53 (br s, 1 H) 8.99 (br d, J = 3.06 Hz, 1 H) 10.15 (s, 1 H) 13.01 (s, 1 H); [M + 1]⁺ 668. |
| 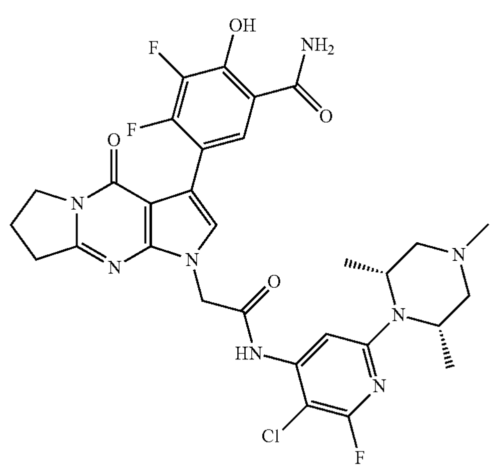 [SMILES: C[C@@H]1CN(C)C[C@H](C)N1c1cc(NC(=O)Cn2cc(-c3cc(C(N)=O)c(O)c(F)c3F)c3c(=O)n4c(nc32)CCC4)c(Cl)c(F)n1] | 49% | ¹H NMR (500 MHz, DMSO-d₆) δ ppm 1.25 (br d, J = 6.97 Hz, 6 H), 2.17 (quin, J = 7.55 Hz, 2 H), 2.89 (br s, 2 H), 3.08 (br t, J = 7.83 Hz, 2 H), 3.12-3.22 (m, 2 H), 3.43-3.54 (m, 2 H), 4.00 (br t, J = 7.21 Hz, 2 H), 4.52 (br d, J = 0.86 Hz, 2 H), 5.28 (s, 2 H), 7.25-7.30 (m, 1 H), 7.51 (br s, 1 H), 8.00 (br d, J = 6.36 Hz, 1 H), 8.08-8.23 (m, 1 H), 8.47 (br s, 1 H), 9.64-9.82 (m, 1 H), 10.16 (br s, 1 H), 13.71 (br s, 1 H); [M + 1]⁺ 659. |

| Structure | Yield | NMR & LCMS |
|---|---|---|
| 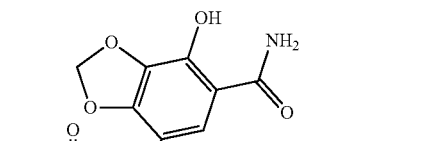 | 58% | $^1$H NMR (500 MHz, DMSO-$d_6$) δ ppm 1.25 (br d, J = 7.09 Hz, 6 H), 2.18 (quin, J = 7.55 Hz, 2 H), 2.89 (br s, 3 H), 3.08 (br t, J = 7.83 Hz, 2 H), 3.16 (br s, 2 H), 4.04 (br t, J = 7.21 Hz, 2 H), 4.52 (br s, 2 H), 5.27 (s, 2 H), 6.11 (s, 2 H), 7.36 (s, 1 H), 7.51 (s, 1 H), 7.86 (br s, 2 H), 8.30 (s, 1 H), 9.64-9.80 (m, 1 H), 10.14 (s, 1 H), 12.98 (br s, 1 H); [M + 1]$^+$ 668. |

Preparation of Trimethylsilylethyl (TMSE)-Protected Boronate Esters (a) Synthesis of 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide Method 1

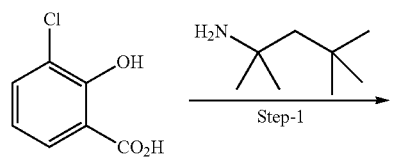

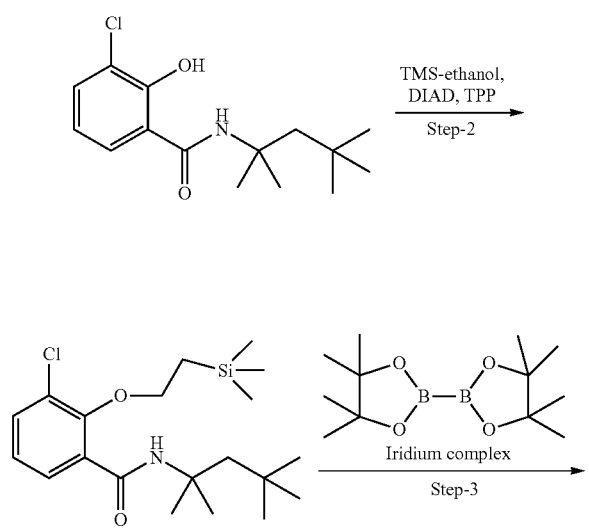

-continued

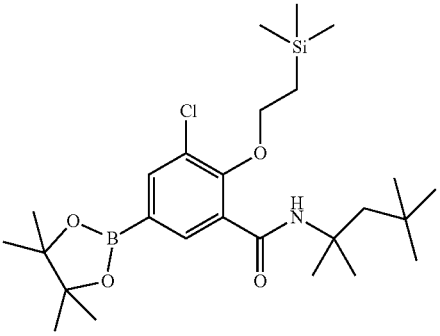

Step 1: To a stirred solution of 3-chloro-2-hydroxybenzoic acid (50 g, 290.6 mmol, 1 eq) in DMF (1000 mL) was added EDC.HCl (66.8 g, 348.7 mmol, 1.2 eq) and HOBt (47.11 g, 348.7 mmol, 1.2 eq) at 0° C. under an argon atmosphere followed by DiPEA (180.12 mL, 1017.1 mmol, 3.5 eq) and the mixture stirred for 15 min at the same temperature. Then, t-octylamine (58.8 mL, 248.7 mmol, 1.2 eq) was added dropwise at 0° C. and the mixture allowed to warm to RT and stirred 16 h. TLC analysis indicated formation of a less polar spot. The reaction mixture was diluted with water (5 L) and extracted with EtOAc (3×1 L). The organic layer was washed with water (2×1 L), dried over Na$_2$SO$_4$ and concentrated under reduced pressure to give crude product. The crude product was purified by column chromatography (silica gel, 100-200 mesh) using 5-10% EtOAc in petroleum ether as an eluent to provide 3-chloro-2-hydroxy-N-(2,4,4-trimethylpentan-2-yl)benzamide (30 g, 36.58%) as an off-white solid. LCMS [M+H]$^+$ 284.

Step 2: To a solution of triphenylphosphine (18.51 g, 70.47 mmol, 2 eq) in dry THF (350 mL), a solution of diisopropyl azodicarboxylate (14.24 g, 70.47 mmol, 2 eq) was added dropwise over 30 min at 0° C. and stirred at the same temperature for 30 minutes. Then, a solution of 2-(trimethylsilyl)ethanol (5.9 g, 70.47 mmol, 2 eq) was added followed by dropwise addition of 3-chloro-2-hydroxy-N-(2,4,4-trimethylpentan-2-yl)benzamide (10 g, 35.24 mmol, 1 eq) in dry THF (70 mL) over 20 min at 0° C. and allowed to stir at RT overnight under an argon atmosphere. TLC analysis indicated formation of a nonpolar spot.

The reaction mixture was diluted with EtOAc (1 L), washed with water (2×250 mL) and saturated brine (2×250 mL). The separated organic layer was dried over $Na_2SO_4$ and concentrated under reduced pressure to give crude product; which was purified by column chromatography (silica gel, 100-200 mesh) using 0-4% EtOAc in petroleum ether as an eluent to afford 3-chloro-N-(2,4,4-trimethylpentan-2-yl)-2-(2-(trimethylsilyl)ethoxy)benzamide (8 g, 59.25%) as a reddish oil. LCMS [M+H]$^+$ 384.

Step 3: A solution of bis(pinacolato)diboron (22.8 g, 90 mmol, 2.3 eq) and 4,4'-di-tert-butyl-2,2'-bipyridine (DTBPY; 620 mg, 2.34 mmol, 0.06 eq) in degassed dry n-hexane (450 mL) was degassed with argon for 30 min. After 10 min, di-mu-methoxobis(1,5-cyclooctadiene) diiridium (I) (770 mg, 1.17 mmol, 0.03 eq) was added and stirred for 5 min (a color change was observed from yellow to wine red). After 5 min, 3-chloro-N-(2,4,4-trimethylpentan-2-yl)-2-(2-(trimethylsilyl)ethoxy)benzamide (15 g, 33.6 mmol, 1 eq) was added to the wine red solution at RT under an argon atmosphere. Then, the round bottomed flask was immersed in a preheated oil bath at 65° C. and stirred for 1.5 h. TLC analysis indicated formation of a nonpolar spot. Then, the reaction mixture was cooled to RT, filtered through celite, and the celite bed was washed with n-hexane. The filtrate obtained was concentrated under reduced pressure to give crude residual oil, which was adsorbed on celite and purified by column chromatography (silica gel, 100-200 mesh) using 5-10% EtOAc in petroleum ether as an eluent to afford 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (12 g, 70.13%) as an off-white solid.

Method 2

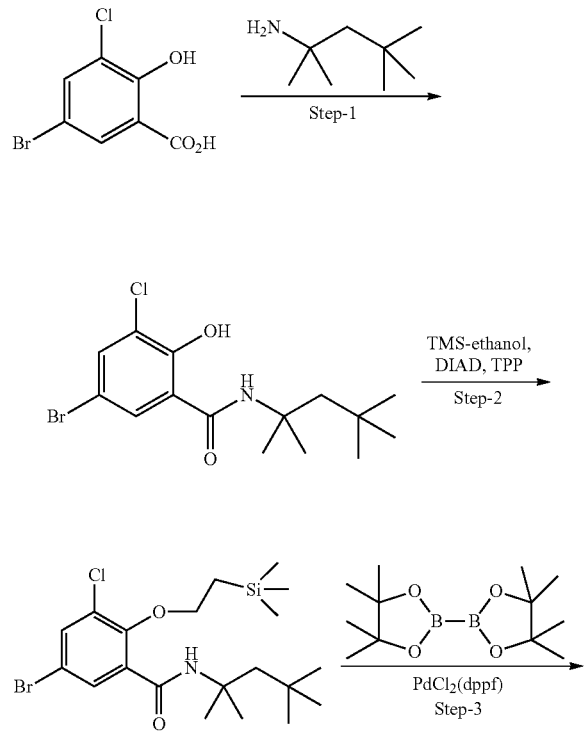

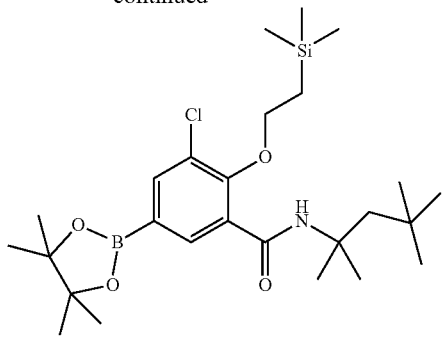

Step 1: To a solution of 5-bromo-3-chloro-2-hydroxybenzoic acid (25.91 g, 103 mmol) in N,N-dimethylformamide (DMF) (Volume: 250 mL) was added HBTU (42.93 g, 113 mmol) and N,N-diisopropylethylamine (53.8 mL, 309 mmol). The reaction mixture was stirred for 10 minutes before adding tert-octylamine (24.81 mL, 155 mmol). Then the reaction mixture was stirred at room temperature and followed via LCMS. After stirring overnight, the reaction was partitioned between water and EtOAc. The layers were separated and the aqueous layer was extracted with EtOAc. The combined organic layers were washed with water and brine and dried over magnesium sulfate. The crude material was loaded onto celite and purified by flash chromatography in 2 batches [5-50% EtOAc/hexanes] to give the desired 5-bromo-3-chloro-2-hydroxy-N-(2,4,4-trimethylpentan-2-yl)benzamide (35.1 g, 97 mmol, 94% yield) as a white solid.

Step 2: Di-tert-butyl azodicarboxylate 98% (1.071 g, 4.65 mmol) was added to a stirring solution of 5-bromo-3-chloro-2-hydroxy-N-(2,4,4-trimethylpentan-2-yl)benzamide (1.349 g, 3.72 mmol), 2-(trimethylsilyl)ethanol (0.666 mL, 4.65 mmol) and triphenylphosphine (1.219 g, 4.65 mmol) in dichloromethane (DCM) (volume: 35 mL) at room temperature. After stirring overnight, the mixture was concentrated, the residue was triturated with hexane and the filtrate was concentrated onto celite and flash chromatography was performed [0-15% EtOAc/hexanes] to afford 5-bromo-3-chloro-N-(2,4,4-trimethylpentan-2-yl)-2-(2-(trimethylsilyl)ethoxy)benzamide (1.616 g, 3.49 mmol, 94% yield) as a viscous yellow oil. $^1$H NMR (500 MHz, DMSO-$d_6$) δ=7.96 (s, 1H), 7.81 (d, J=2.4 Hz, 1H), 7.42 (d, J=2.4 Hz, 1H), 4.09-4.03 (m, 2H), 1.82 (s, 2H), 1.39 (s, 6H), 1.16-1.11 (m, 2H), 0.98 (s, 9H), 0.02 (s, 9H).

Step 3: A round bottomed flask was charged with 5-bromo-3-chloro-N-(2,4,4-trimethylpentan-2-yl)-2-(2-(trimethylsilyl)ethoxy)benzamide (7.09 g, 15.32 mmol), bis(pinacolato)diboron (7.94 g, 30.6 mmol), potassium acetate (6.07 g, 61.3 mmol) and 1,4-dioxane (volume: 120 mL). The reaction mixture was degassed using argon for 15 minutes and 1,12-bis(diphenylphosphino)ferrocene]dichloropalladium(II), DCM complex (1.251 g, 1.532 mmol) was added. The reaction mixture was heated to 110° C. and followed by LCMS. After 2 hours, the reaction mixture was concentrated onto celite and the crude compound was purified by flash chromatography [0-20% DCM/MeOH] to afford 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide (6.86 g, 13.45 mmol, 88% yield) as a slightly yellow oil that solidified on standing. $^1$H NMR (500 MHz, chloroform-d) δ=8.39 (d, J=1.5 Hz, 1H), 7.89 (d, J=1.5 Hz, 1H), 7.67 (s, 1H), 4.12-4.08 (m, 2H), 1.90 (s, 2H), 1.52 (s, 6H), 1.32 (s, 12H), 1.29-1.25 (m, 2H), 1.02 (s, 9H), 0.06 (s, 9H).

Method 3

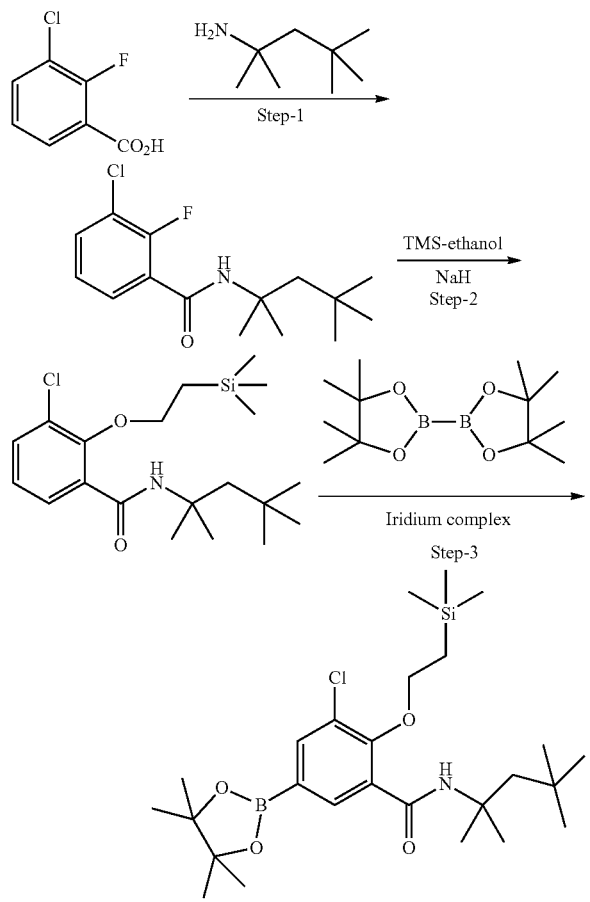

Step 1: To a flask charged with 3-chloro-2-fluorobenzoic acid (2 g, 8.66 mmol), was added thionyl chloride (10 mL) followed by triethylamine (0.5 mL) and the mixture was heated to 70° C. for 30 min. The thionyl chloride was removed in vacuo, the residue was dissolved in $CH_2Cl_2$ (10 mL), the amine was added, and the mixture was stirred at room temperature overnight. The mixture was then concentrated onto celite and purified by silica gel flash column chromatography (EtOAc:hexane 0-20% as eluent) to 3-chloro-2-fluoro-N-(2,4,4-trimethylpentan-2-yl)benzamide as a white solid (55%); LCMS $[M+H]^+$ 286.

Step 2: To a flask charged with 2-(trimethylsilyl)ethanol as solvent (50.2 mL, 350 mmol), was added NaH (3.35 g, 87 mmol) and the mixture was heated to 80° C. for 30 min. The 3-chloro-2-fluoro-N-(2,4,4-trimethylpentan-2-yl)benzamide (10 g, 35 mmol) was added as a solid portion-wise then the reaction mixture was stirred for 10 min after which LCMS analysis indicated that the reaction was complete. The mixture was cooled, diluted with ether (150 mL) and then washed with NaOH (1N, 75 mL) and brine. The organic layer was then dried over $Na_2SO_4$ (anhydrous), concentrated onto celite and purified by silica gel flash column chromatography (EtOAc:hexane 0-10% as eluent) to give 3-chloro-N-(2,4,4-trimethylpentan-2-yl)-2-(2-(trimethylsilyl)ethoxy) benzamide as a yellow oil (74% yield); $^1H$ NMR (500 MHz, chloroform-d) δ=7.89 (dd, J=1.8, 7.9 Hz, 1H), 7.77 (s, 1H), 7.41 (dd, J=1.7, 7.9 Hz, 1H), 7.08 (t, J=7.9 Hz, 1H), 4.20-3.75 (m, 3H), 1.83 (s, 2H), 1.46 (s, 6H), 1.26-1.18 (m, 2H), 0.95 (s, 9H); LCMS $[M+Na]^+$ 406.

Step 3: In a 250 mL round bottomed flask with magnetic stir bar was placed bis(pinacolato)diboron (2.91 g, 11.46 mmol), di-mu-methoxobis(1,5-cyclooctadiene)diiridium (I) (207 mg, 0.312 mmol) and 4,4'-di-tert-butyl-2,2'-dipyridyl (168 mg, 0.625 mmol). The flask was evacuated and filled with nitrogen and then dry hexane (volume: 50 mL) was added via syringe. This flask was stirred at rt for 5 min to activate the catalyst and dissolve the material. Then 3-chloro-N-(2,4,4-trimethylpentan-2-yl)-2-(2-(trimethylsilyl)ethoxy)benzamide (4 g, 10.42 mmol) was added and the reaction mixture was stirred for 2 h at 55° C. (LCMS indicated full conversion). The crude mixture was cooled to room temperature, concentrated onto celite and then purified by flash chromatography by ISCO chromatography ($SiO_2$, hexanes-EtOAc 0-20%) to yield 3-chloro-5-(4,4,5,5-tetramethyl-1,3,2-dioxaborolan-2-yl)-N-(2,4,4-trimethylpentan-2-yl)-2-(2-(trimethylsilyl)ethoxy)benzamide as a white solid (79% yield). $^1H$ NMR (500 MHz, chloroform-d) δ=8.34 (d, J=1.3 Hz, 1H), 7.83 (d, J=1.3 Hz, 1H), 7.61 (s, 1H), 4.11-3.94 (m, 3H), 1.84 (s, 2H), 1.47 (s, 6H), 1.26 (s, 12H), 1.24-1.19 (m, 3H), 0.96 (s, 9H), 0.00 (s, 9H); LCMS $[M+Na]^+$ 532.

(b) Synthesis of 3-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide

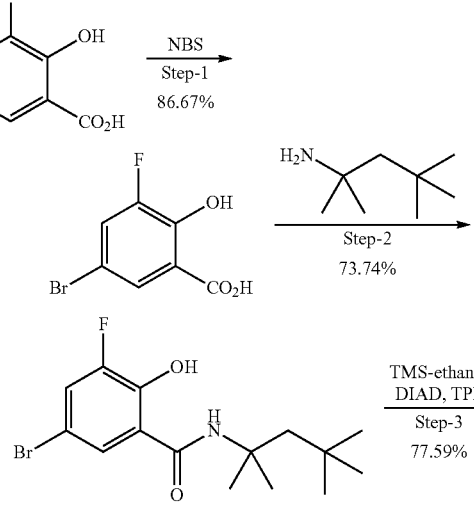

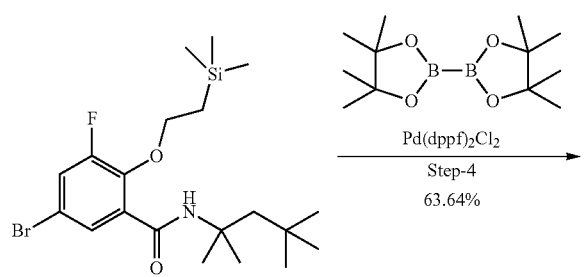

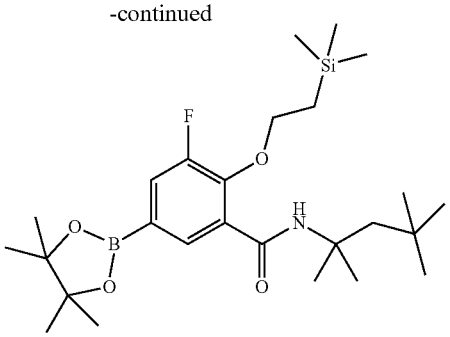

Step 1: To a stirred solution of 3-fluoro-2-hydroxybenzoic acid (10 g, 64.51 mmol, 1 eq) in ACN (200 mL) was added NBS (12.6 g, 70.96 mmol, 1.1 eq) at RT under an argon atmosphere and then stirring continued for 2 h. TLC analysis indicated formation of a polar spot. The reaction mixture was concentrated under reduced pressure to crude residue, which was diluted with water and filtered to obtain the solid compound, washed with petroleum ether (2×30 mL) then dried under vacuum to afford 5-bromo-3-fluoro-2-hydroxy-benzoic acid (13 g, 86.66%) as an off-white solid.

Step 2: To a stirred solution of 5-bromo-3-fluoro-2-hydroxybenzoic acid (13 g, 55.55 mmol, 1 eq) in DMF (150 mL) was added DIPEA (29.86 mL, 166.66 mmol, 3 eq) and HATU (25.33 g, 66.66 mmol, 1.2 eq) at RT under an argon atmosphere, and after 10 min, 2,4,4-trimethylpentan-2-amine (14.52 mL, 83.33 mmol, 1.5 eq) was added at RT and stirring continued for 16 h. TLC analysis indicated formation of a less polar spot. The reaction mixture was diluted with water and extracted with EtOAc (3×100 mL). The organic layer was washed with water (2×150 mL), dried over Na$_2$SO$_4$ and concentrated under reduced pressure to give crude product. The crude product was purified by column chromatography (silica gel, 100-200 mesh) using 0-5% EtOAc in petroleum ether as an eluent to give 5-bromo-3-fluoro-2-hydroxy-N-(2,4,4-trimethylpentan-2-yl)benzamide (11 g, 67.84% yield) as a white solid. LC-MS: 346.32 (M+H).

Step 3: To a stirred solution of tetrakistriphenylphosphine (11.39 g, 43.47 mmol, 1.5 eq) in THF (150 mL) was added DIAD (11.71 g, 57.97 mmol, 2 eq) at 0° C. under an argon atmosphere, and after 30 min, TMS-ethanol (8.55 mL, 57.97 mmol, 2 eq) was added followed by 5-bromo-3-fluoro-2-hydroxy-N-(2,4,4-trimethylpentan-2-yl)benzamide (10 g, 28.98 mmol, 1 eq) at the same temperature. The reaction mixture was allowed to react at RT for 16 h. TLC analysis indicated formation of a less polar spot. The reaction mixture was diluted with water and extracted with EtOAc (3×150 mL). The combined organic layer was washed with water, dried over Na$_2$SO$_4$ and concentrated under reduced pressure to give crude product. The crude compound was purified by column chromatography (silica gel, 100-200 mesh) using 0-3% EtOAc in petroleum ether as eluent to afford 5-bromo-3-fluoro-N-(2,4,4-trimethylpentan-2-yl)-2-(2-(trimethylsilyl)ethoxy)benzamide (9 g, 69.82%) as a pale yellow oil.

Step 4: A stirred solution of 5-bromo-3-fluoro-N-(2,4,4-trimethylpentan-2-yl)-2-(2-(trimethylsilyl)ethoxy)benzamide (9 g, 20.22 mmol, 1 eq) in dioxane (100 mL) was degassed with Ar for 20 min., then KOAc (5.94 g, 60.67 mmol, 3 eq), bis(pinacolato)diboron (5.65 g, 22.24 mmol, 1.1 eq) and PdCl$_2$(dppf) (1.65 g, 2.02 mmol, 0.1 eq) were added at RT and the mixture heated at 90° C. for 16 h. TLC analysis indicated formation of a polar spot. The reaction mixture was cooled to RT, filtered through a celite pad and the celite pad was washed with EtOAc (2×30 mL). The filtrate was concentrated to afford crude compound. The crude product was purified by column chromatography (silica gel, 100-200 mesh) using 0-4% EtOAc in petroleum ether as an eluent to afford 3-fluoro-5-(4,4,5,5-tetramethyl-1,3,2-dioxaborolan-2-yl)-N-(2,4,4-trimethylpentan-2-yl)-2-(2(trimethylsilyl)ethoxy)benzamide (7 g, 70.21%) as light yellow oil. $^1$H NMR (500 MHz, DMSO-d$_6$) δ=7.85 (s, 1H), 7.62 (s, 1H), 7.42 (br d, J=11.4 Hz, 1H), 4.21-4.14 (m, 2H), 1.81 (s, 2H), 1.37 (s, 6H), 1.26 (s, 12H), 1.12-1.07 (m, 2H), 0.95 (s, 9H), 0.00 (s, 9H).

(c) Synthesis of 3,4-difluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide

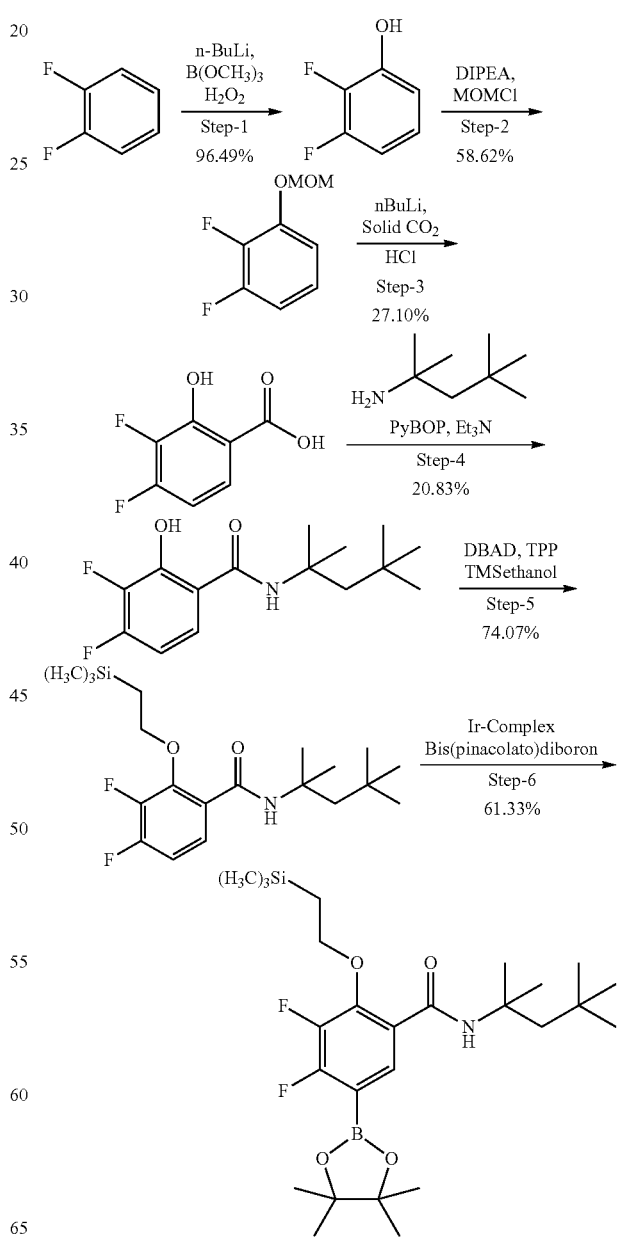

Step 1: To a suspension of 1,2-difluorobenzene (20.0 g, 175.4 mmol, 1.0 eq) in dry THF (250 mL), cooled to −78° C., n-BuLi (80 mL, 1.1 eq, 1.6 M) was added dropwise, then the reaction mass stirred at −78° C. for 1 h. After 1 h, the reaction was quenched with trimethylborate (30.0 mL, 263.157 mmol, 1.5 eq) then stirred for 16 h. TLC analysis indicated a polar spot. The reaction was then quenched with 30% hydrogen peroxide solution (80 mL) then stirred for 3 h. TLC analysis indicated a non-polar spot. The reaction mixture was extracted with diethyl ether (1 L) and washed with water (500 mL) The separated organic layer was dried over $Na_2SO_4$ and concentrated under reduced pressure to give the desired 2,3-difluorophenol (21.8 g, 93.96%) as a liquid.

Step 2: To a solution of 2,3-difluorophenol (18.0 g, 138.46 mmol, 1.0 eq) in DCM (250 mL), N,N-diisopropylamine (36.27 mL, 207.7 mmol, 1.5 eq) and MOM-Cl (15.7 mL, 207.691 mmol, 1.5 eq) were added at 0° C. and the reaction mixture was allowed to warm to RT and stirred for 16 h. TLC analysis indicated formation of a non-polar spot. The reaction mixture was concentrated under reduced pressure to give crude residue which was dissolved in diethyl ether (500 mL) and washed with brine (2×200 mL) & water (2×100 mL). The separated organic layer was dried over with $Na_2SO_4$ and concentrated under reduced pressure to afford crude product, which was purified by column chromatography (silica gel, 100-200 mesh) using 2% diethyl ether in petroleum ether as an eluent to afford 1,2-difluoro-3-(methoxymethoxy)benzene (17 g, 70.83%) as a liquid.

Step 3: To a suspension of 1,2-difluoro-3-(methoxymethoxy)benzene (15.0 g, 86.206 mmol, 1.0 eq) in dry THF (160 mL), cooled to −78° C., n-BuLi (55 mL, 1.6 eq, 2.5 M) was added dropwise, then the reaction mass stirred at −78° C. for 6 h. After 6 h, the reaction was quenched with dry ice, then the reaction mixture stirred at RT for 16 h. The reaction mixture was added to water (200 mL) and extracted with diethyl ether (500 mL), an aqueous layer was adjusted to pH 1 with concentrated HCl (50 mL) and extracted with diethyl ether (500 mL), the separated organic layer was dried over $Na_2SO_4$ and concentrated under reduced pressure to give crude compound; which was recrystallized from chloroform to give the desired compound 3,4-difluoro-2-hydroxybenzoic acid (8.3 g, 55.33%) as a solid.

Alternative Synthesis of
3,4-difluoro-2-hydroxybenzoic Acid from
2,3,4-trifluorobenzoic Acid

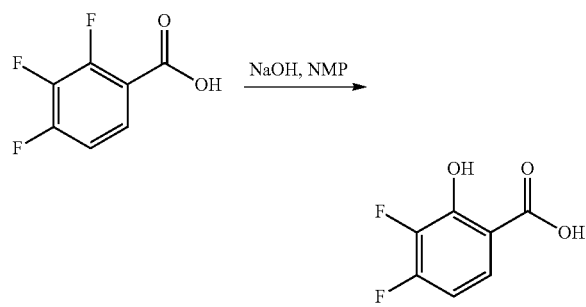

To a solution of 2,3,4-trifluorobenzoic acid (500 g, 2.84 mol) in NMP (3.5 L) under argon, was added sodium hydroxide (459 g, 11.47 mol) in portions. The reaction mixture was refluxed at 188° C. under argon for 3 hrs. The progress of the reaction was monitored by LCMS. The reaction was complete after 3 hrs. The reaction mixture was cooled to approximately 90-100° C. and NMP was removed by vacuum distillation at 112-115° C. using a rotary evaporator. The residue was diluted with water (16 L), cooled below 10° C. and acidified to pH 2 using pre-chilled 12N HCl. The precipitate was filtered, the solid was washed with cold water (1.5 L) and dried in a vacuum oven at 45° C. for at least 18 hrs to obtain the 3,4-difluoro-2-hydroxybenzoic acid as a 1:1 mixture with NMP. The actual weight of 3,4-difluoro-2-hydroxybenzoic acid was 393.6 g (80% yield).

Step 4: To a suspension of 3,4-difluoro-2-hydroxybenzoic acid (5.5 g, 31.609 mmol, 1.0 eq) in dry THF (60 mL), triethylamine (4.32 mL, 31.609 mmol, 1.0 eq), PyBOP (16.34 g, 31.609 mmol, 1.5 eq) and 2,4,4-trimethylpentan-2-amine (3.41 mL, 20.861 mmol, 0.66 eq) were added. The reaction mixture was refluxed for 16 h. TLC analysis indicated formation of a nonpolar spot. The reaction mixture was concentrated under reduced pressure and gave crude residue which was dissolved in diethyl ether (250 mL) and washed with brine (2×200 mL) and water (2×100 mL). The separated organic layer was dried over $Na_2SO_4$ and concentrated under reduced pressure to afford crude product; which was purified by column chromatography (silica gel, 100-200 mesh) using 2% EtOAc in petroleum ether as an eluent to afford 3,4-difluoro-2-hydroxy-N-(2,4,4-trimethylpentan-2-yl)benzamide (3.5 g, 38.88%) as a solid.

Step 5: To a solution of triphenylphosphine (8.65 g, 32.280 mmol, 2 eq) in dry toluene (80 mL), di-tert-butyl azodicarboxylate (13.0 g, 56.49 mmol, 3.5 eq) was added at room temperature over 30 min. Then, a solution of TMS ethanol (2.68 mL, 32.28 mmol, 2 eq) was added followed by addition of 3,4-difluoro-2-hydroxy-N-(2,4,4-trimethylpentan-2-yl)benzamide (4.6 g, 16.140 mmol, 1.0 eq) at room temperature. Then, the reaction mixture was stirred at RT overnight. TLC analysis indicated formation of a nonpolar spot. The reaction mixture was concentrated under reduced pressure and gave crude residue which was dissolved in EtOAc (300 mL) and washed with brine (2×100 mL) and water (2×100 mL). The separated organic layer was dried over $Na_2SO_4$ and concentrated under reduced pressure to afford crude product; which was purified by column chromatography (silica gel, 100-200 mesh) using 1-2% EtOAc in petroleum ether as an eluent to afford 3,4-difluoro-N-(2,4,4-trimethylpentan-2-yl)-2-(2-(trimethylsilyl)ethoxy)benzamide (5.8 g, 93.54%) as a solid compound.

Step 6: A solution of bis(pinacolato)diboron (9.25 g, 36.441 mmol, 2.3 eq), and DTBPY (254 mg, 0.950 mmol, 0.06 eq) in degassed dry n-hexane (80 mL) was degassed with argon for 20 min. After 20 min, iridium complex (315 mg, 0.475 mmol, 0.03 eq) was added and stirred for 5 min (a color change was observed from yellow to wine red). After 5 minutes, 3,4-difluoro-N-(2,4,4-trimethylpentan-2-yl)-2-(2-(trimethylsilyl)ethoxy)benzamide (6.1 g, 15.844 mmol, 1.0 eq) in n-hexane (20 mL) was added to the wine red solution at RT under an argon atmosphere. Then, the reaction mass was immersed in a preheated oil bath at 60° C. and stirred for 16 h. TLC analysis indicated formation of a polar spot. Then, the reaction mixture was cooled to RT, filtered through celite, and the celite bed was washed with n-hexane. The filtrate obtained was concentrated under reduced pressure and gave crude residual oil, which was adsorbed on celite and purified by column chromatography (silica gel, 100-200 mesh) with 0.5-2% EtOAc in petroleum ether as an eluent to afford 3,4-difluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (4.6 g, 61.33%) as an off-white solid.

(d) Synthesis of 3,4-dimethoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide

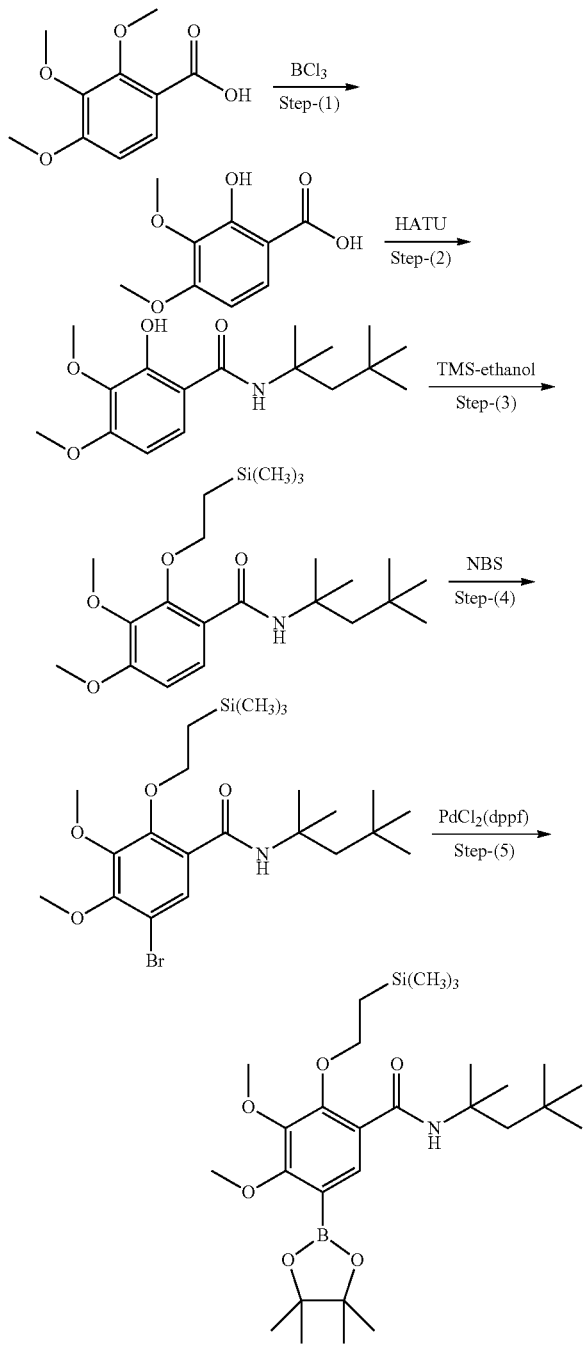

Step 1: To a stirred solution of 2,3,4-trimethoxybenzoic acid (1 g, 4.71 mmol, 1 eq) in DCM (20 mL) was added BCl$_3$ (4.7 mL, 4.71 mmol, 1 eq, 1 M in heptane) at −78° C. under an argon atmosphere, then the reaction mixture was allowed to stir at RT for 3 h. TLC analysis indicated formation of a polar spot. The reaction mixture was diluted with water and extracted with EtOAc (3×150 mL). The combined organic layer was washed with water (2×150 mL), dried over Na$_2$SO$_4$ and concentrated under reduced pressure to give 2-hydroxy-3,4-dimethoxybenzoic acid (900 mg, 96.4%) as an off-white solid. LCMS: m/z 199.33 (M+1).

Step 2: To a stirred solution of 2-hydroxy-3,4-dimethoxybenzoic acid (900 mg, 4.54 mmol, 1 eq) in DMF (10 mL) was added DIPEA (2.4 mL, 13.62 mmol, 3 eq) at RT under an argon atmosphere, then t-octylamine (0.96 mL, 5.45 mmol, 1.2 eq) was added at RT, and after 10 minutes, HATU (3.45 g, 9.08 mmol, 1.2 eq) was added. The reaction mixture was then heated to 80° C. for 16 h. TLC analysis indicated formation of a less polar spot. The reaction mixture was cooled to RT then diluted with water and extracted with EtOAc (3×150 mL). The combined organic layer was washed with water (2×150 mL), dried over Na$_2$SO$_4$ and concentrated under reduced pressure to give crude product. The crude product was purified by column chromatography (silica gel, 100-200 mesh) using 0-5% EtOAc in petroleum ether as an eluent to afford 2-hydroxy-3,4-dimethoxy-N-(2,4,4-trimethylpentan-2-yl)benzamide (1 g, 71.4%) as a brown oil. LCMS: m/z 310.57 (M+1).

Step 3: To a stirred solution of TPP (1.69 g, 6.47 mmol, 2 eq) in THF (40 mL) was added DIAD (1.43 g, 7.11 mmol, 2.2 eq) at 0° C. dropwise under an argon atmosphere, and after 30 min, TMS-ethanol (0.52 mL, 6.47 mmol, 2 eq) was added followed by a solution of 2-hydroxy-3,4-dimethoxy-N-(2,4,4-trimethylpentan-2-yl)benzamide (1 g, 3.23 mmol, 1 eq) in 10 mL of THF at the same temperature. Then, the reaction mixture was allowed to stir at RT for 16 h. TLC analysis indicated formation of a less polar spot. The reaction mixture was diluted with water and extracted with EtOAc (3×150 mL). The combined organic layer was washed with water, dried over Na$_2$SO$_4$ and concentrated under reduced pressure to give crude product. The crude compound was purified by column chromatography (silica gel, 100-200 mesh) using 0-10% EtOAc in petroleum ether as eluent to afford 3,4-dimethoxy-N-(2,4,4-trimethylpentan-2-yl)-2-(2-(trimethylsilyl)ethoxy)benzamide (1.1 g, 83.3%) as a light pink oil. LCMS: m/z 410.55 (M+1).

Step 4: To a stirred solution of 3,4-dimethoxy-N-(2,4,4-trimethylpentan-2-yl)-2-(2-(trimethylsilyl)ethoxy)benzamide (17 g, 41.56 mmol, 1 eq) in DMF (300 mL) was added NBS (7.39 g, 41.56 mmol, 1 eq) at RT under an argon atmosphere, then the reaction mixture was heated to 70° C. for 1 h. TLC analysis indicated formation of a less polar spot. The reaction mixture was diluted with water and extracted with EtOAc (3×300 mL). The organic layer was washed with water (2×250 mL), dried over Na$_2$SO$_4$ and concentrated under reduced pressure to give crude product. The crude compound was purified by column chromatography (silica gel, 100-200 mesh) using 0-3% EtOAc in petroleum ether as eluent to afford 5-bromo-3,4-dimethoxy-N-(2,4,4-trimethylpentan-2-yl)-2-(2-(trimethylsilyl)ethoxy)benzamide (8 g, 39.5%) as a light pink oil.

Step 5: To a stirred solution of 5-bromo-3,4-dimethoxy-N-(2,4,4-trimethylpentan-2-yl)-2-(2-(trimethylsilyl)ethoxy)benzamide (4.5 g, 9.23 mmol, 1 eq) in 1,2-dimethoxyethane (400 mL) was added KOAc (2.71 g, 27.7 mmol, 3 eq) at RT, and the mixture degassed with argon for 20 min. Subsequently, bis(pinacolato)diboron (2.81 g, 11.08 mmol, 1.2 eq) and PdCl$_2$(dppf).DCM (753 mg, 0.923 mmol, 0.1 eq) were added and the reaction mixture was heated to 90° C. for 16 h. TLC analysis indicated formation of a polar spot. The reaction mixture was cooled to RT and filtered through a celite pad, which was washed with EtOAc (3×50 mL). The filtrate was concentrated to afford crude compound. The crude compound was purified by column chromatography (silica gel, 100-200 mesh) using 0-2% EtOAc in petroleum ether as an eluent to afford 3,4-dimethoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (2.2 g, 44.5%) as a colourless oil. $^1$H NMR (500 MHz, DMSO-$d_6$) δ=7.91 (s, 1H), 7.72 (s, 1H), 4.20-4.15 (m, 2H), 3.79 (s, 3H), 3.78-3.76 (m, 3H), 1.85-1.82 (m, 2H), 1.41 (s, 6H), 1.29 (s, 12H), 0.97 (s, 9H), 0.04 (s, 9H).

(e) Synthesis of 4-fluoro-3-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide

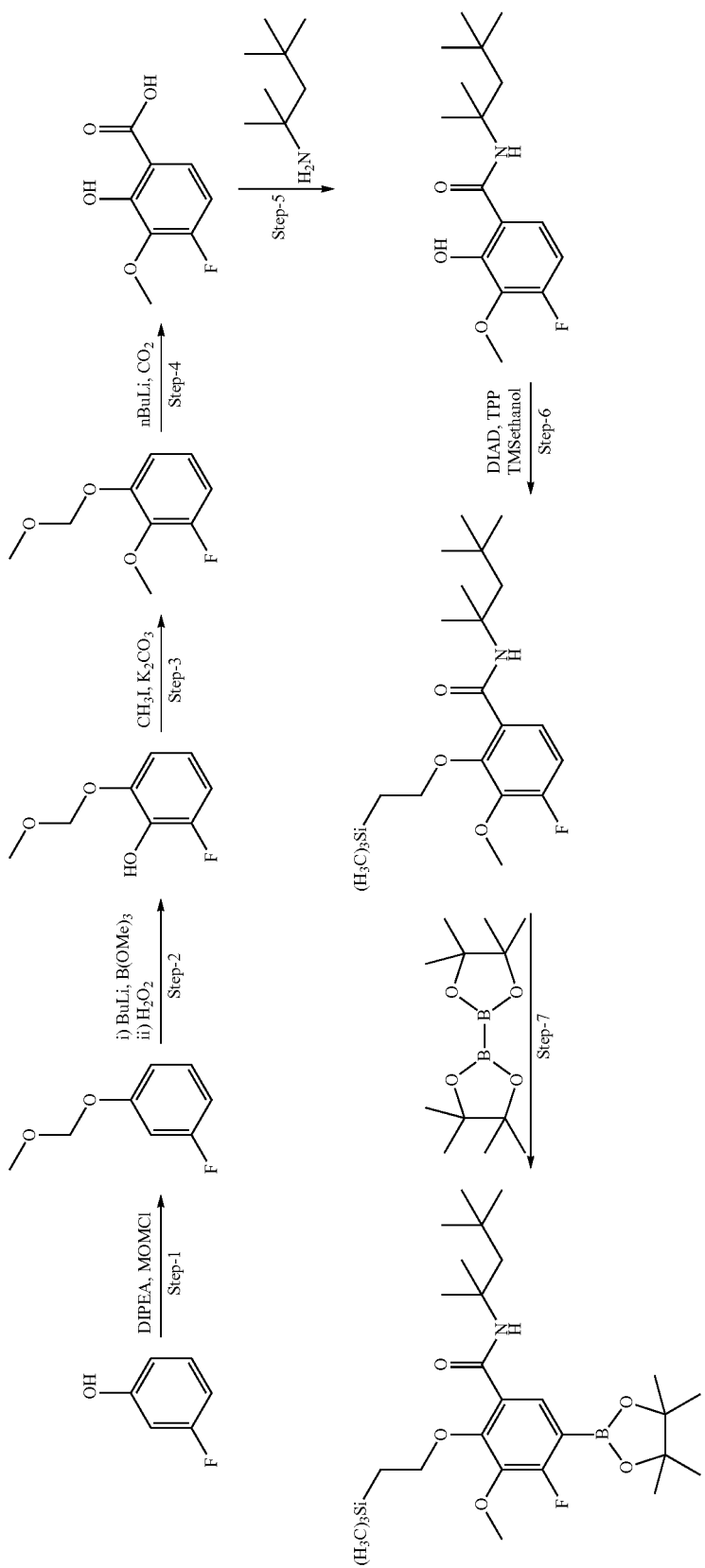

Step 1: To a stirred solution of 3-fluorophenol (50 g, 446.030 mmol, 1 eq) in DCM (500 mL) was added DIPEA (159.02 mL, 892.060 mmol, 2 eq) at 0° C. under an argon atmosphere and stirring continued for 30 min., after which MOM-Cl (40.65 mL, 535.236 mmol, 1.2 eq) was added at 0° C. The reaction was allowed to warm up to RT and stirred for 16 h. TLC analysis indicated formation of a nonpolar spot. The reaction mixture was quenched in ice water (500 mL) and extracted with EtOAc (3×300 mL). The organic layer was dried over $Na_2SO_4$ and concentrated under reduced pressure to give crude compound. The crude compound was purified by CombiFlash chromatography using 1% EtOAc in petroleum ether as an eluent to afford 1-fluoro-3-(methoxymethoxy)benzene (40 g, 57.47%) as a colorless liquid.

Step 2: To a solution of n-BuLi (76.85 mL, 192.122 mmol, 1 eq) in THF (300 mL) was added TMEDA (29.89 mL, 99.807 mmol, 1.04 eq) cooled to −78° C. and stirred for 1 h. 1-Fluoro-3-(methoxymethoxy)benzene (30 g, 192.122 mmol, 1 eq) in THF (75 mL) was added to the mixture dropwise under argon, then the reaction mass was stirred for 2 hr at −78° C., followed by addition of trimethylborate at the same temperature then slowly warmed to rt and stirred for 16 h. Then the reaction mass was cooled to 0° C., then 30% $H_2O_2$ (18 mL) solution was added slowly dropwise. The reaction mass was warmed to rt and stirred for 1 h. TLC analysis indicated formation of a polar spot. The reaction mixture was dissolved in EtOAc (300 mL) and washed with brine (2×50 mL) and water (2×50 mL). The separated organic layer was dried over $Na_2SO_4$ and concentrated under reduced pressure to afford crude product, which was purified by column chromatography (silica gel, 100-200 mesh) using 8% EtOAc in petroleum ether as an eluent to afford 2-fluoro-6-(methoxymethoxy)phenol (25 g, 75.55%) as a colorless oil.

Step 3: To a stirred solution of 2-fluoro-6-(methoxymethoxy)phenol (25 g, 145.222 mmol, 1 eq) in dry THF (250 mL) was added $K_2CO_3$ (30.11 g, 217.833 mmol, 1.5 eq) at 0° C. under an argon atmosphere and stirring continued for 30 min., after that methyl iodide (11.32 mL, 181.528 mmol, 1.25 eq) was added at 0° C. and the reaction was allowed to warm to RT and stirred for 16 h. TLC analysis indicated formation of a nonpolar spot. The reaction mixture was quenched in ice water (500 mL) and extracted with EtOAc (3×300 mL). The organic layer was dried over $Na_2SO_4$ and concentrated under reduced pressure to give crude compound. The crude compound was purified by CombiFlash chromatography using 2% EtOAc in petroleum ether as an eluent to afford 1-fluoro-2-methoxy-3-(methoxymethoxy)benzene (25 g, 92.42%) as a colorless liquid.

Step 4: To a solution of 1-fluoro-2-methoxy-3-(methoxymethoxy)benzene (25 g, 134.279 mmol, 1.0 eq) in dry THF (500 mL) was added n-BuLi (53.71 mL, 134.279 mmol, 1.0 eq, 2.5 M) dropwise at −78° C. under argon and stirred for 2 h at same temperature, then dry ice (saturated) was added to the reaction mixture portionwise at the same temperature then slowly warmed to rt and stirred overnight. TLC analysis indicated formation of a polar spot then the reaction mass was quenched with concentrated HCl (100 mL) solution down to pH of 2 and stirred for 1 h. The reaction mixture was then dissolved in EtOAc (2×500 mL) and washed with brine (2×200 mL) and water (2×200 mL). The separated organic layer was dried over $Na_2SO_4$ and concentrated under reduced pressure to give crude product; which was washed with pentane to afford 4-fluoro-2-hydroxy-3-methoxybenzoic acid (15 g, 60.06%) as an off-white solid.

Step 5: To a stirred solution of 4-fluoro-2-hydroxy-3-methoxybenzoic acid (14 g, 75.212 mmol, 1 eq) in THF (140 mL) was added triethylamine (31.49 mL, 225.636 mmol, 35 eq) and PYBOP (39.14 g, 75.212 mmol, 1 eq) at 0° C. under an argon atmosphere and the mixture stirred for 15 min at the same temperature. Then, 2,4,4-trimethylpentan-2-amine (15.14 mL, 90.255 mmol, 1.2 eq) was added dropwise at 0° C. and the mixture was allowed to warm to RT and stirred 16 h. TLC analysis indicated formation of a nonpolar spot. The reaction mixture was diluted with water (200 mL) and extracted with EtOAc (2×200 mL). The organic layer was washed with water (2×100 mL), dried over $Na_2SO_4$ and concentrated under reduced pressure to give crude product. The crude product was purified by column chromatography (silica gel, 100-200 mesh) using 4% EtOAc in petroleum ether as an eluent to afford 4-fluoro-2-hydroxy-3-methoxy-N-(2,4,4-trimethylpentan-2-yl)benzamide (10 g, 44.72%) as an off-white solid. LC-MS: 298.21 (M+H).

Step 6: To a solution of triphenylphosphine (17.67 g, 67.256 mmol, 2 eq) in dry toluene (150 mL) was added di-tert-butyl azodicarboxylate (23.23 g, 100.884 mmol, 3 eq) portionwise at RT and the mixture stirred at the same temperature over 30 min. Then, TMS ethanol (5.59 mL, 67.256 mmol, 2 eq) was added followed by addition of 4-fluoro-2-hydroxy-3-methoxy-N-(2,4,4-trimethylpentan-2-yl)benzamide (10 g, 33.628 mmol, 1 eq) in toluene (50 mL) at RT. Then, the reaction mixture was allowed to stir at RT overnight. TLC analysis indicated formation of a nonpolar spot. The reaction mixture was concentrated under reduced pressure to give crude residue which was dissolved in EtOAc (300 mL) and washed with brine (2×100 mL) and water (2×100 mL). The separated organic layer was dried over $Na_2SO_4$ and concentrated under reduced pressure to give crude product, which was purified by column chromatography (silica gel, 100-200 mesh) using 3% EtOAc in petroleum ether as an eluent to afford 4-fluoro-3-methoxy-N-(2,4,4-trimethylpentan-2-yl)-2-(2-(trimethylsilyl)ethoxy)benzamide (8 g, 59.83%) as a pale yellow colored liquid.

Step 7: A solution of bis(pinacolato)diboron (11.75 g, 46.278 mmol, 2.3 eq), DTBPY (324 mg, 1.208 mmol, 0.06 eq) in degassed dry n-hexane (100 mL) was degassed with argon for 10 min. After 10 min, Iridium complex (159 mg, 0.604 mmol, 0.03 eq) was added and stirred for 5 min (a color change was observed from yellow to wine red). After 5 min, 4-fluoro-3-methoxy-N-(2,4,4-trimethylpentan-2-yl)-2-(2-(trimethylsilyl)ethoxy)benzamide (8 g, 20.121 mmol, 1 eq) in n-hexane (20 mL) was added to the wine red solution at RT under an argon atmosphere. Then, the reaction mass was immersed in a preheated oil bath at 60° C. and stirred for 2 h. TLC analysis indicated formation of a polar spot. Then, the reaction mixture was cooled to RT, filtered through celite, and the celite bed was washed with n-hexane. The filtrate obtained was concentrated under reduced pressure to give crude residual oil, which was adsorbed on celite and purified by column chromatography (silica gel, 100-200 mesh) using 0-5% EtOAc in petroleum ether as an eluent to afford 4-fluoro-3-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (5 g, 47.46%) as a colorless liquid. $^1$H NMR (500 MHz, DMSO-$d_6$) δ=7.88 (s, 1H), 7.68 (br d, J=6.5 Hz, 1H), 4.25-4.18 (m, 2H), 3.85 (s, 3H), 1.83 (s, 2H), 1.40 (s, 6H), 1.29 (s, 12H), 1.16-1.14 (m, 2H), 0.97 (s, 9H), 0.04 (s, 9H).

(f) Synthesis of 4-(methoxymethoxy)-7-(4,4,5,5-tetramethyl-1,3,2-dioxaborolan-2-yl)benzo[d][1,3]dioxole-5-carbonitrile

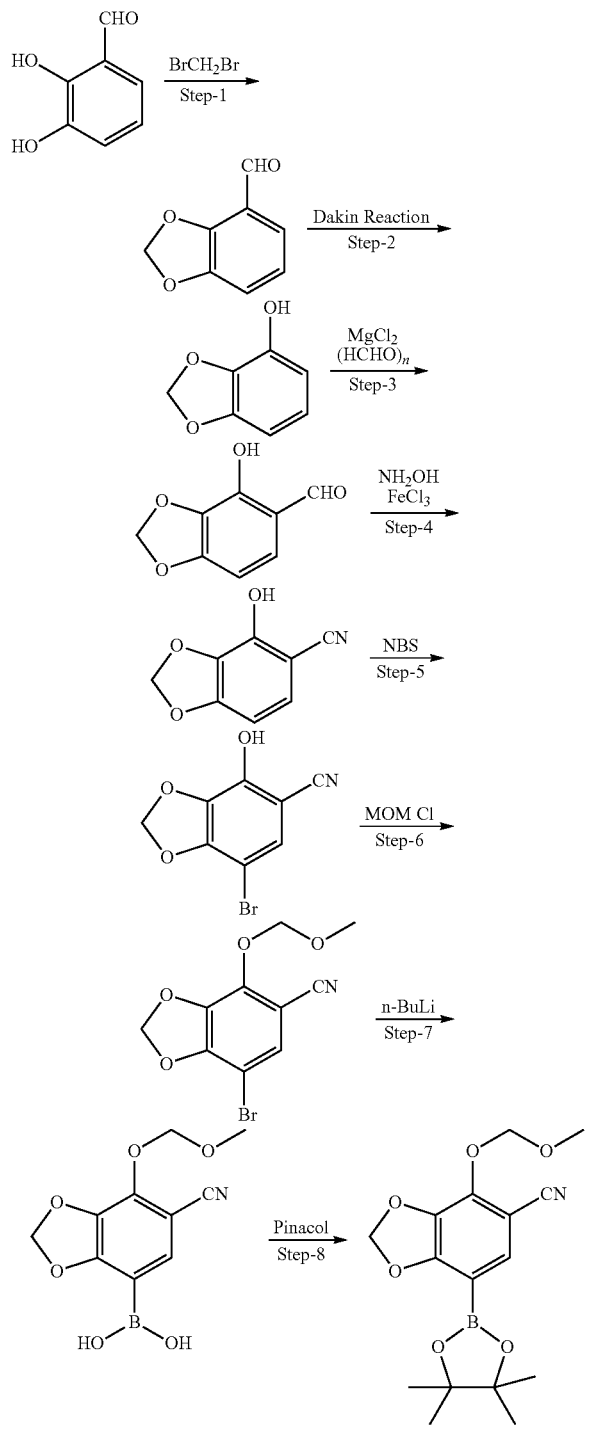

Step 1: To a solution of 2,3-dihydroxybenzaldehyde (25 g, 181.1 mmol, 1 eq) in DMF (250 mL) was added K$_2$CO$_3$ (27.5 g, 199.2 mmol, 1.22 eq) and CuO (1.57 g, 19.7 mmol, 0.11 eq) followed by dibromomethane (15.3 mL, 259.6 mmol, 1.22 eq) under an argon atmosphere and the reaction mixture heated to 120° C. for 8 h. Then, the reaction mixture was cooled to RT and poured on ice-water (600 mL). The reaction mixture was extracted with EtOAc (2×500 mL), and the combined organic layer was dried over Na$_2$SO$_4$ and concentrated under reduced pressure to give crude product. The crude product was purified by column chromatography using 5% EtOAc in petroleum ether as an eluent to afford benzo[d][1,3]dioxole-4-carbaldehyde (14 g, 74%) as a pale yellow liquid.

Step 2: To a solution of benzo[d][1,3]dioxole-4-carbaldehyde (20 g, 133.3 mmol, 1.2 eq) in DCM (400 mL) was added mCPBA (25.2 g, 146.6 mmol, 1.1 eq) at rt and heated to reflux for 24 h. TLC analysis indicated formation of a nonpolar spot. The reaction mass was then filtered through a celite bed washed with DCM (100 mL) and the filtrate evaporated under reduced pressure. Then, the crude reaction mass was dissolved in 10% ethanolic KOH (100 mL) solution, and stirred at rt for 2 h. TLC analysis indicated formation of a polar spot, the reaction mass was acidified with 2N HCL, extracted with DCM (2×500 mL), washed with water and brine, dried over Na$_2$SO$_4$ and concentrated under reduced pressure to give crude product. The crude product was purified by CombiFlash™ column chromatography using 1% EtOAc in petroleum ether as an eluent to afford benzo[d][1,3]dioxol-4-ol (11 g, 44%) as an off-white solid. LC-MS: m/z 139.07 (M+H).

Step 3: To a solution of benzo[d][1,3]dioxol-4-ol (10 g, 72.4 mmol, 1 eq), in ACN (200 mL) was added MgCl$_2$ (10.3 g, 108.6 mmol, 1.5 eq) and TEA (38.0 mL, 271.7 mmol, 3.75 eq). The resulting mixture was cooled to 0° C., paraformaldehyde (14.6 g, 489.1 mmol, 6.75 eq) was added portion-wise, the mixture was slowly warmed to rt then heated to 80° C. for 4 h. TLC analysis indicated formation of a nonpolar spot. Then, the reaction mass was quenched with 2N HCl, extracted with EtOAc (2×500 mL) and washed with saturated brine. The separated organic layer was dried over Na$_2$SO$_4$ and concentrated under reduced pressure to give crude product which was purified by CombiFlash column chromatography using 10% EtOAc in petroleum ether as an eluent to give 4-hydroxybenzo[d][1,3]dioxole-5-carbaldehyde (6 g, 36% yield) as a pale yellow solid.

Step 4: To a solution of 4-hydroxybenzo[d][1,3]dioxole-5-carbaldehyde (6 g, 36.1 mmol, 1 eq), in DMF (30 mL) was added hydroxylamine (3.01 g, 43.3 mmol, 1.2 eq) followed by FeCl$_3$ (2.92 g, 18.0 mmol, 0.5 eq) and the mixture was heated in a sealed tube at 150° C. for 3 h. After 3 h, TLC analysis indicated formation of a polar spot. Then, the reaction mass was poured into ice water, extracted with EtOAc (2×300 mL) and washed with saturated brine. The separated organic layer was dried over Na$_2$SO$_4$ and concentrated under reduced pressure to give crude product which was purified by CombiFlash column chromatography using 40% EtOAc in petroleum ether as an eluent to give 4-hydroxybenzo[d][1,3]dioxole-5-carbonitrile (4.5 g, 65.2%) as a pale yellow solid. LC-MS: m/z 164.06 (M+H).

Step 5: To a solution of 4-hydroxybenzo[d][1,3]dioxole-5-carbonitrile (7.5 g, 46.0 mmol, 1 eq) in ACN (150 mL) was added NBS (9.0 g, 50.6 mmol, 1.1 eq) in THF (50 mL) dropwise at 0° C. under argon. The mixture was then slowly warmed to rt and stirred for 2 h. TLC analysis indicated formation of a polar spot. Then, the reaction mixture was poured on ice water (200 mL). The reaction mixture was then extracted with EtOAc (2×200 mL), the combined organic layer was dried over Na$_2$SO$_4$ and concentrated under reduced pressure to give crude product that was purified by CombiFlash column chromatography using 60% EtOAc in petroleum ether as an eluent to give 7-bromo-4-hydroxybenzo[d][1,3]dioxole-5-carbonitrile (5 g, 68.4%) as a pale yellow solid. LC-MS: m/z 239.96 (M−H).

Step 6: To a solution of 7-bromo-4-hydroxybenzo[d][1,3]dioxole-5-carbonitrile (4.0 g, 16.5 mmol, 1 eq) in DMF (40 mL) was added $K_2CO_3$ (4.58 g, 33.1 mmol, 2.0 eq) at 0° C. under argon and the resulting mixture stirred for 30 mins. Then, MOM-Cl (1.87 mL, 24.7 mmol, 1.5 eq) was added to the mixture dropwise at the same temperature then the mixture was slowly warmed to rt and stirred for another 4 h at the same temperature. TLC analysis indicated formation of a nonpolar spot. Then, the reaction mixture was poured on ice water (200 mL). The reaction mixture was extracted with EtOAc (2×200 mL), the combined organic layer was dried over $Na_2SO_4$ and concentrated under reduced pressure to give crude product that was purified by CombiFlash column chromatography using 10% EtOAc in petroleum ether as an eluent to give 7-bromo-4-(methoxymethoxy) benzo[d][1,3]dioxole-5-carbonitrile (4 g, 88.8%) as an off-white solid.

Step 7: To a solution of 7-bromo-4-(methoxymethoxy)benzo[d][1,3]dioxole-5-carbonitrile (4.0 g, 14.0 mmol, 1 eq) in THF (80 mL) was added triisopropyl borate (3.95 mL, 21.05 mmol, 1.5 eq), the resulting mixture was cooled to −78° C., then n-BuLi (5.0 mL, 12.63 mmol, 0.9 eq) was added to the mixture dropwise under argon and the mixture stirred for 1 h at the same temperature. TLC analysis indicated formation of a polar spot. Then, the reaction mixture was quenched with ice water, washed with diethyl ether, then the aqueous layer was acidified with 2H HCl, extracted with EtOAc (2×100 mL). The combined organic layer was dried over $Na_2SO_4$ and concentrated under reduced pressure to give 6-cyano-7-(methoxymethoxy)benzo[d][1,3]dioxol-4-yl)boronic acid (2.7 g, 77.1%) as a pale yellow solid. LC-MS: m/z 252.1 (M+H).

Step 8: To a solution of 6-cyano-7-(methoxymethoxy)benzo[d][1,3]dioxol-4-yl)boronic acid (2.7 g, 10.7 mmol, 1 eq) in toluene (50 mL) was added pinacol (3.8 mL, 32.2 mmol, 3.0 eq) and the mixture heated to reflux using a Dean-Stark condenser for 4 h. TLC analysis indicated formation of a nonpolar spot. Then, the reaction mixture was concentrated under reduced pressure to give crude product. The crude compound was purified by CombiFlash column chromatography using 9% EtOAc in petroleum ether as an eluent to afford 4-(methoxymethoxy)-7-(4,4,5,5-tetramethyl-1,3,2-dioxaborolan-2-yl)benzo[d][1,3]dioxole-5-carbonitrile (2.2 g, 62.85%) as a colorless solid. $^1$H NMR (400 MHz, $CDCl_3$) δ=7.57 (s, 1H), 6.10 (s, 2H), 5.39 (s, 2H), 3.57 (s, 3H), 1.35 (s, 12H).

(g) Synthesis of 3-chloro-4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide

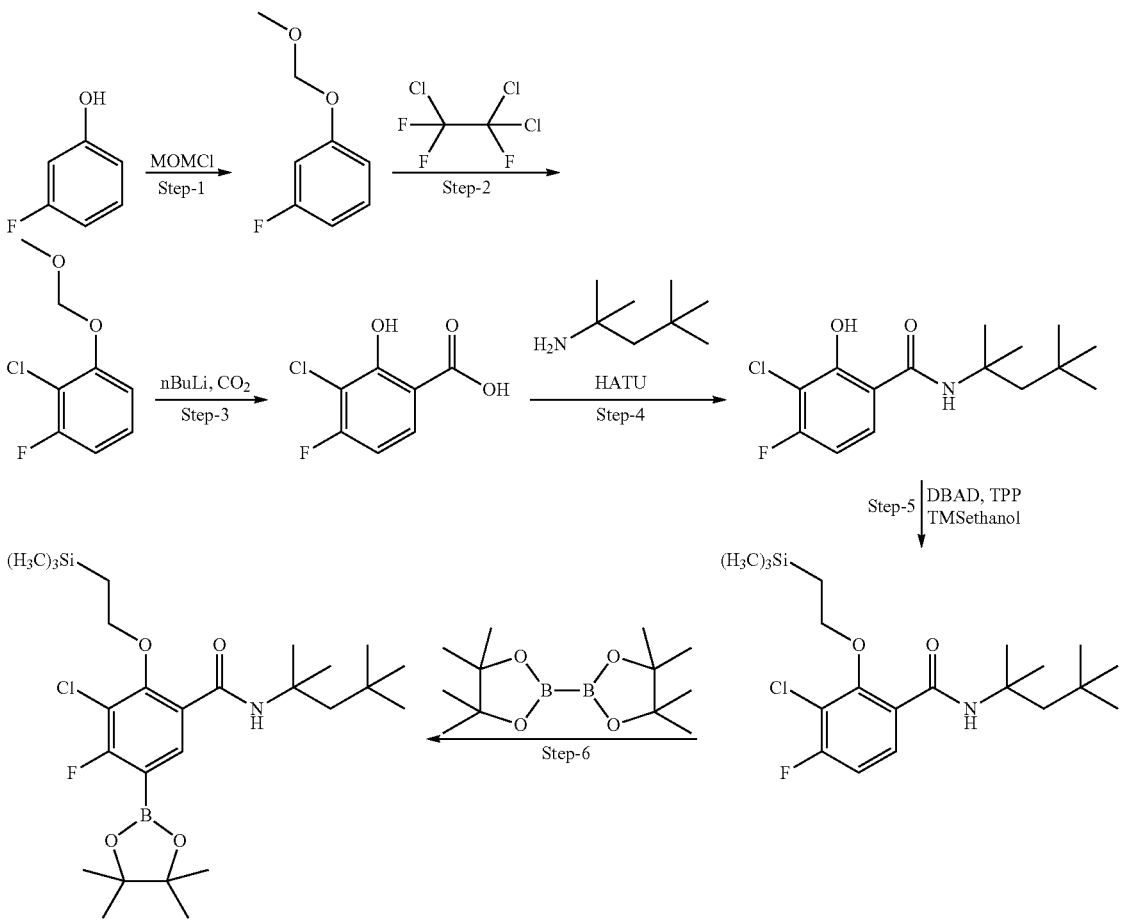

Step 1: To a solution of 3-fluorophenol (27.3 g, 223.21 mmol, 1 eq) in dry DCM (500 mL), was added diisopropyl ethylamine (79.86 mL, 446.42 mmol, 2.0 eq) followed by MOM chloride (20.18 mL, 267.85 mmol, 1.2 eq) dropwise at 0° C. then the mixture was allowed to warm up to rt and stirred overnight. TLC analysis indicated formation of a nonpolar spot. The reaction mixture was then dissolved in DCM (2×500 mL), and washed with brine (2×200 mL) and water (2×200 mL). The separated organic layer was dried over Na$_2$SO$_4$ and concentrated under reduced pressure to afford crude product which was purified by column chromatography (silica gel, 100-200 mesh) using 100% petroleum ether as an eluent to afford 1-fluoro-3-(methoxymethoxy)benzene (20 g, 57.97%) as a pale yellow colored liquid.

Step 2: To a solution of 1-fluoro-3-(methoxymethoxy) benzene (25 g, 130.2 mmol, 1.0 eq) in dry THF (250 mL) and dry cyclohexane (40 mL) was added sec-BuLi (121.82 mL, 195.3 mmol, 1.5 eq) dropwise at −78° C. under argon, the resulting mixture stirred for 2 h at the same temperature, then 1,1,2-trichloro-1,2,2-trifluoroethane (62 mL, 520.3 mmol, 4.0 eq) was added and the mixture stirred for 10 mins at the same temperature. TLC analysis indicated formation of a polar spot then the reaction mass was quenched with saturated NH$_4$Cl solution, and the reaction mixture was dissolved in ether (2×500 mL) and washed with brine (2×200 mL) and water (2×200 mL). The separated organic layer was dried over Na$_2$SO$_4$ and concentrated under reduced pressure to afford crude product which was purified by column chromatography (silica gel, 100-200 mesh) using 1% EtOAc in petroleum ether as an eluent to afford 2-chloro-1-fluoro-3-(methoxymethoxy)benzene (20 g, 45.1%) as a pale yellow colored liquid.

Step 3: To a solution of 2-chloro-1-fluoro-3-(methoxymethoxy)benzene (20 g, 104.7 mmol, 1.0 eq) in dry THF (400 mL) was added n-BuLi (41.8 mL, 104.7 mmol, 1.0 eq, 2.5 M) dropwise at −78° C. under argon and the resulting mixture was stirred for 4 h at same temperature. Then, dry ice (saturated) was added to the mixture portionwise at the same temperature then the mixture was slowly warmed to rt and stirred overnight. TLC analysis indicated formation of a polar spot then the reaction mass was quenched with concentrated HCl (50 mL) solution down to pH of 2 and stirred for 1 h. The reaction mixture was then dissolved in EtOAc (2×500 mL) and washed with brine (2×200 mL) and water (2×200 mL). The separated organic layer was dried over Na$_2$SO$_4$ and concentrated under reduced pressure to afford crude product which was washed with pentane to afford 3-chloro-4-fluoro-2-hydroxybenzoic acid (20 g, 60.2%) as an off-white solid.

Step 4: To a stirred solution of 3-chloro-4-fluoro-2-hydroxybenzoic acid (13 g, 68.4 mmol, 1 eq) in DMF (250 mL) was added HATU (31.2 g, 82.1 mmol, 1.2 eq) at 0° C. under an argon atmosphere followed by DiPEA (36.7 mL, 204.6 mmol, 3.0 eq) and the resulting mixture was stirred for 15 min at the same temperature. Then, 2,4,4-trimethylpentan-2-amine (17.1 mL, 102.3 mmol, 1.5 eq) was added dropwise at 0° C. and the mixture allowed to warm up to RT and stirred for 16 h. TLC analysis indicated formation of a less polar spot. The reaction mixture was diluted with water (1 L) and extracted with EtOAc (2×500 mL). The organic layer was washed with water (2×200 mL) and dried over Na$_2$SO$_4$ and concentrated under reduced pressure to give crude product. The crude product was purified by column chromatography (silica gel, 100-200 mesh) using 5-10% EtOAc in petroleum ether as an eluent to afford 3-chloro-4-fluoro-2-hydroxy-N-(2,4,4-trimethylpentan-2-yl)benzamide (10 g, 56.42%) as an off-white solid. LC-MS: m/z 302.01 (M+H).

Step 5: To a solution of triphenylphosphine (17.4 g, 66.59 mmol, 2 eq) in dry toluene (200 mL), di-tert-butyl azodiformate (DBAD; 22.92 g, 79.66 mmol, 3 eq) was added at RT and the mixture stirred for 30 min. Then, a solution of TMS ethanol (5.33 mL, 66.59 mmol, 2 eq) was added followed by addition of 3-chloro-4-fluoro-2-hydroxy-N-(2,4,4-trimethylpentan-2-yl)benzamide (10 g, 33.22 mmol, 1 eq) at rt and the mixture stirred overnight. TLC analysis indicated formation of a nonpolar spot. The reaction mixture was then dissolved in EtOAc (300 mL) and washed with brine (2×200 mL) and water (2×200 mL). The separated organic layer was dried over Na$_2$SO$_4$ and concentrated under reduced pressure to afford crude product which was purified by column chromatography (silica gel, 100-200 mesh) using 2% EtOAc in petroleum ether as an eluent to afford 3-chloro-4-fluoro-N-(2,4,4-trimethylpentan-2-yl)-2-(2-(trimethylsilyl)ethoxy)benzamide (10.5 g, 76.92%) as a pale yellow colored liquid.

Step 6: A solution of bis(pinacolato)diboron (15.29 g, 60.22 mmol, 2.3 eq) and DTBPY (420 mg, 0.06 eq) in degassed dry n-hexane (200 mL) was degassed with argon for 10 min. After 10 minutes, Iridium complex (520 mg, 0.78 mmol, 0.03 eq) was added and the mixture stirred for 5 min (a color change was observed from yellow to wine red). After 5 min, 3-chloro-4-fluoro-N-(2,4,4-trimethylpentan-2-yl)-2-(2-(trimethylsilyl)ethoxy)benzamide (10.5 g, 26.18 mmol, 1 eq) was added to the wine red solution at RT in a sealed tube under an argon atm. Then, the sealed tube was immersed in a preheated oil bath at 60° C. and stirred for 2 h. TLC analysis indicated formation of a polar spot. Then, the reaction mixture was cooled to RT, filtered through celite, and the celite bed was washed with n-hexane. The filtrate obtained was concentrated under reduced pressure to give crude residual oil, which was adsorbed on celite and purified by column chromatography (silica gel, 100-200 mesh) with 0-5% EtOAc in petroleum ether as an eluent to afford 3-chloro-4-fluoro-5-(4,4,5,5-tetramethyl-1,3,2-dioxaborolan-2-yl)-N-(2,4,4-trimethylpentan-2-yl)-2-(2-(trimethylsilyl)ethoxy)benzamide (11 g, 84.61%) as an off-white semi-solid. $^1$H NMR (500 MHz, DMSO-d$_6$) δ=7.89 (s, 1H), 7.66 (br d, J=6.5 Hz, 1H), 4.17-4.11 (m, 2H), 1.83 (s, 2H), 1.41 (s, 6H), 1.29 (s, 12H), 0.98 (s, 9H), 0.03 (s, 9H).

(i) Synthesis of 3-fluoro-4-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide

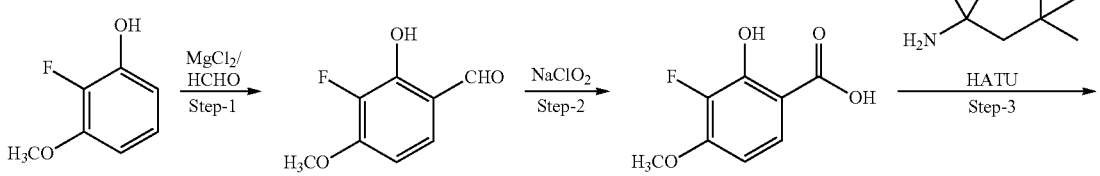

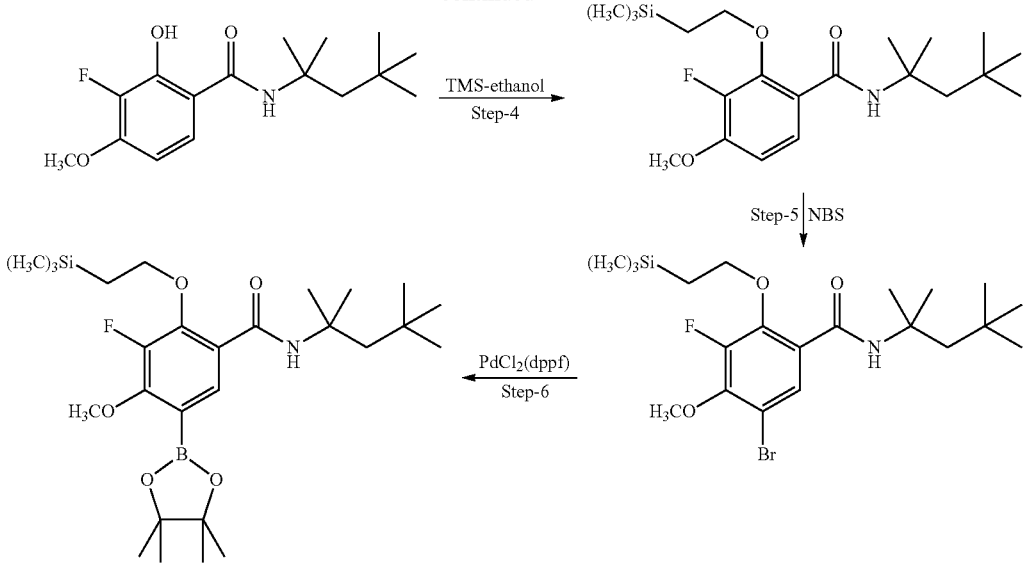

-continued

Step 1: To a stirred solution of MgCl₂ (20 g, 211.26 mmol, 3 eq) in ACN (100 mL) was added paraformaldehyde (11.5 g, 211.26 mmol, 3 eq) followed by TEA (50.5 mL, 352.11 mmol, 5 eq) at RT and the mixture stirred for 10 min. 2-Fluoro-3-methoxyphenol (10 g, 70.42 mmol, 1 eq) was then added and the resultant reaction mixture was heated at 80° C. for 5 h. The reaction was monitored with TLC, and TLC analysis indicated formation of a polar spot. The reaction mixture was poured into ice water (300 mL), acidified (pH: 1-2) with aqueous 6N HCl solution then extracted with EtOAc (2×200 mL). The combined organic layer was dried over Na₂SO₄ and concentrated under reduced pressure to afford 3-fluoro-2-hydroxy-4-methoxy-benzaldehyde (12.9 g, crude yield) as a yellow solid.

Step 2: A stirred solution of 3-fluoro-2-hydroxy-4-methoxybenzaldehyde (12 g, 70.58 mmol, 1 eq) in 1,4-dioxane:H₂O (150 mL:120 mL) was cooled to 0° C. and NH₃SO₃ (10.26 g, 105.81 mmol, 1.5 eq), and NaH₂PO₄.H₂O (38.88 g, 282.32 mmol, 4 eq) were added followed by NaClO₂ (8.71 g, 91.76 mmol, 1.3 eq) and the resultant reaction mixture was stirred for 2 h at 0° C. Na₂SO₃ (10.68 g, 84.69 mmol, 1.2 eq) was added at 0° C. and the mixture stirred for another 1 h at RT. The reaction was monitored by TLC, and TLC analysis indicated formation of a polar spot. The reaction mixture was concentrated under reduced pressure to afford crude product. The crude was acidified (pH 2) with aqueous 6N HCl solution, and the solid precipitated was filtered and dried under vacuum. The crude was triturated with ACN (2×4 mL), filtered and dried to afford 3-fluoro-2-hydroxy-4-methoxybenzoic acid (9.1 g, 69.35% yield) as a yellow solid. LCMS: m/z 186.96 (M+H).

Step 3: A stirred solution of 3-fluoro-2-hydroxy-4-methoxybenzoic acid (9 g, 48.38 mmol, 1 eq) in DMF (100 mL) was cooled to 0° C. and HATU (28.9 g, 72.58 mmol, 1.5 eq) was added, followed by DIPEA (27 mL, 145.14 mmol, 3 eq) and the resulting reaction mixture was stirred for 10 min at 0° C. 2,4,4-trimethylpentan-2-amine (12 mL, 72.58 mmol, 1.5 eq) was added and the mixture stirred overnight at RT. The reaction was monitored by TLC, and TLC analysis indicated formation of a non-polar spot. The reaction mixture was diluted with ice water and extracted with ethyl acetate (2×200 mL). The combined organic layer was dried over Na₂SO₄ and concentrated under reduced pressure. The crude product was purified by column chromatography (silica gel, 100-200 mesh) using 6-8% ethyl acetate in petroleum ether as an eluent to afford 3-fluoro-2-hydroxy-4-methoxy-N-(2,4,4-trimethylpentan-2-yl)benzamide (4.51 g, 31.5% yield) as an off-white solid.

Step 4: A stirred solution of TPP (7.94 g, 30.3 mmol, 2 eq) in THF (100 mL) was cooled to 0° C., DIAD (6.12 g, 30.3 mmol, 2 eq) was added and the resulting reaction mixture was stirred for 20 min at 0° C. TMS ethanol (3.58 g, 30.3 mmol, 2 eq) followed by 3-fluoro-2-hydroxy-4-methoxy-N-(2,4,4-trimethylpentan-2-yl)benzamide (4.5 g, 15.15 mmol, 1 eq) were added and the mixture stirred overnight at RT. The reaction was monitored by TLC, and TLC analysis indicated formation of a non-polar spot. The reaction mixture was concentrated under reduced pressure to give crude product. Petroleum ether was added to the crude mixture, which was then stirred for 30 min then filtered through celite. The filtrate was concentrated under reduced pressure to give crude product. The crude product was purified by column chromatography (silica gel, 230-400 mesh) using 10% ethyl acetate in petroleum ether as an eluent to afford 3-fluoro-4-methoxy-N-(2,4,4-trimethylpentan-2-yl)-2-(2-(trimethylsilyl)ethoxy)benzamide (5.41 g, 90% yield) as an off-white solid.

Step 5: To a stirred solution of 3-fluoro-4-methoxy-N-(2,4,4-trimethylpentan-2-yl)-2-(2-(trimethylsilyl)ethoxy)benzamide (4.9 g, 12.79 mmol, 1 eq) in DMF (50 mL), was added NBS (2.73 g, 15.35 mmol, 1.2 eq) at RT and the resultant reaction mixture was heated at 70° C. for 4 h in a preheated oil bath. The reaction was monitored by TLC, and TLC analysis indicated formation of a non-polar spot. The reaction mixture was diluted with ice water and extracted with ethyl acetate (2×150 mL). The combined organic layer was dried over Na₂SO₄ and concentrated under reduced pressure. The crude product was purified by column chromatography (silica gel, 100-200 mesh) using 5-7% ethyl acetate in petroleum ether as an eluent to afford 5-bromo-3-fluoro-4-methoxy-N-(2,4,4-trimethylpentan-2-yl)-2-(2-(trimethylsilyl)ethoxy)benzamide (4.45 g, 76% yield) as a colourless liquid.

Step 6: To a stirred solution of 5-bromo-3-fluoro-4-methoxy-N-(2,4,4-trimethylpentan-2-yl)-2-(2-(trimethylsilyl)ethoxy)benzamide (3 g, 6.31 mmol, 1 eq) in 1,2-dioxane (300 mL), was added bis(pinacolato)diboron (1.92 g, 7.57 mmol, 1.2 eq) followed by potassium acetate (1.85 g, 18.93 mmol, 3 eq) at RT. The resultant reaction mixture was degassed for 15 min under a nitrogen atmosphere, then PdCl$_2$(dppf)DCM (515 mg, 0.63 mmol, 0.1 eq) was added and the mixture was heated at 80° C. for 16 h. The reaction was monitored by TLC, and TLC analysis indicated formation of a polar spot. The reaction mixture was filtered through celite, and washed with ethyl acetate (200 mL). The filtrate was concentrated under reduced pressure to give crude product. The crude product was purified by column chromatography (silica gel, 100-200 mesh) using 2-5% ethyl acetate in petroleum ether as an eluent to afford 3-fluoro-4-methoxy-5-(4,4,5,5-tetramethyl-1,3,2-dioxaborolan-2-yl)-N-(2,4,4-trimethylpentan-2-yl)-2-(2-(trimethylsilyl)ethoxy)benzamide (1.2 g, 36.36% yield) as a brown solid. $^1$H NMR (500 MHz, DMSO-d$_6$) δ=7.93 (s, 1H), 7.70 (s, 1H), 4.26-4.21 (m, 2H), 3.84 (br s, 3H), 1.83 (s, 2H), 1.40 (br s, 6H), 1.29 (s, 12H), 0.97 (s, 9H), 0.04 (s, 9H).

Synthesis of 7-bromo-N-(2,4,4-trimethylpentan-2-yl)-4-(2-(trimethylsilyl)ethoxy)benzo[d][1,3]dioxole-5-carboxamide Step 2: A stirred solution of 4-methoxybenzo[d][1,3]dioxole (25 g, 164.4 mmol, 1 eq) in ACN (500 mL) was cooled to 0° C. and NaI (98.5 g, 657.8 mmol, 4 eq) was added, followed by TMS-Cl (71.4 g, 657.8 mmol, 4 eq) and the resultant reaction mixture was heated at 75° C. for 8 h. The reaction was monitored by TLC, and TLC analysis indicated formation of a polar spot. The reaction mixture was poured into ice water and extracted with ethyl acetate. The combined organic layer was dried over Na$_2$SO$_4$ and concentrated under reduced pressure. The crude product was purified by column chromatography (silica gel, 230-400 mesh) using 20-30% ethyl acetate in petroleum ether as an eluent to afford benzo[d][1,3]dioxol-4-ol (16 g, 70.5% yield) as a pale yellow solid. LCMS: m/z 139.31 (M+H).

Step 3: To a stirred solution of benzo[d][1,3]dioxol-4-ol (25 g, 183.8 mmol, 1 eq), in ACN (250 mL), was added TEA (89.2 mL, 680.1 mmol, 3.7 eq) followed by MgCl$_2$ (26.22 g, 275.7 mmol, 1.5 eq) at RT. The reaction mixture was cooled to 0° C., paraformaldehyde (37.22 g, 1240.8 mmol, 6.75 eq) was added and the resultant reaction mixture was refluxed for 4 h. The reaction was monitored by TLC, and TLC analysis indicated formation of a non-polar spot. The reaction mixture was cooled to 0° C., acidified with aqueous 2N HCl solution and extracted with ethyl acetate. The combined organic layer was dried over Na$_2$SO$_4$ and concentrated under reduced pressure to afford 4-hydroxybenzo[d][1,3]dioxole-5-carbaldehyde (21 g, 70% yield) as a pale yellow solid. LCMS: m/z 167.29 (M+H).

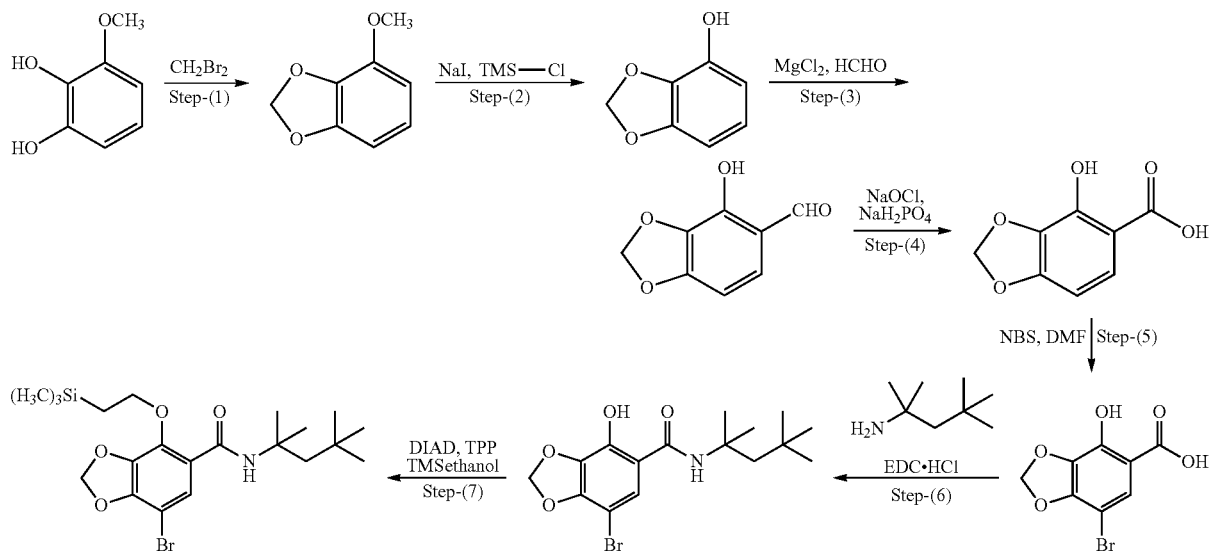

Step 1: To a stirred solution of 3-methoxybenzene-1,2-diol (50 g, 357.1 mmol, 1 eq) in DMF (500 mL), was added CuO (3.12 g, 39.2 mmol, 0.11 eq) followed by K$_2$CO$_3$ (60.1 g, 435.7 mmol, 1.22 eq) and dibromomethane (75.7 g, 435.7 mmol, 1.22 eq). The resultant reaction mixture was heated at 120° C. for 8 h. The reaction was monitored with TLC, and TLC analysis indicated formation of a non-polar spot. The reaction mixture was then poured into ice water and extracted with ethyl acetate. The combined organic layer was dried over Na$_2$SO$_4$ and concentrated under reduced pressure. The crude product was purified by column chromatography (silica gel, 100-200 mesh) using 0-10% ethyl acetate in petroleum ether as an eluent to afford 4-methoxybenzo[d][1,3]dioxole (40 g, 73.69% yield) as a white solid. LCMS: m/z 153.32 (M+H).

Step 4: To a stirred solution of 4-hydroxybenzo[d][1,3]dioxole-5-carbaldehyde (30 g, 179.6 mol, 1 eq) in 1,4-dioxane:H$_2$O (3:1, 800 mL), was added sulfamic acid (26.1 g, 269.2 mol, 1.5 eq) followed by Na$_2$H$_2$PO$_4$.H$_2$O (99.16 g, 718.5 mol, 4 eq). The reaction mixture was cooled to 0° C. and a solution of sodium chlorite (21.1 g, 233.5 mmol, 1.3 eq) in water (100 mL) was added dropwise and the resultant reaction mixture was stirred at RT for 1 h. The reaction was monitored by TLC, and TLC analysis indicated formation of a polar spot. The reaction mixture was cooled to 0° C., quenched with sodium sulphite (27.16 g, 215.5 mmol, 1.2 eq) and stirred for 30 min at RT. Then, the solvent was evaporated under reduced pressure, the crude was cooled to 0° C. and acidified with aqueous 2N HCl. The solid precipitated was filtered and dried under vacuum to afford 4-hydroxybenzo[d][1,3]dioxole-5-carboxylic acid (23 g, 69.9% yield) as a pale yellow solid. LCMS: m/z 183.34 (M+H).

Step 5: To a stirred solution of 4-hydroxybenzo[d][1,3]dioxole-5-carboxylic acid (20 g, 109.8 mmol, 1 eq) in ACN (200 mL), was added NBS (21.3 g, 120.8 mmol, 1.1 eq) and the resultant reaction mixture was stirred at RT for 3 h. The reaction was monitored by TLC, and TLC analysis indicated formation of a non-polar spot. The solid precipitated was filtered and dried under vacuum. The crude was triturated with n-pentane to afford 7-bromo-4-hydroxybenzo[d][1,3]dioxole-5-carboxylic acid (12 g, 42.1% yield) as a pale yellow solid. LCMS: m/z 259.17 (M−H).

Step 6: To a stirred solution of 7-bromo-4-hydroxybenzo[d][1,3]dioxole-5-carboxylic acid (20 g, 76.9 mmol, 1 eq) in DMF (200 mL), was added HATU (58.46 g, 253.8 mmol, 2 eq), and DIPEA (42.5 mL, 230.6 mmol, 3 eq) followed by 2,4,4-trimethylpentan-2-amine (14.88 g, 115.3 mmol, 1.5 eq) and the resultant reaction mixture was stirred at RT for 48 h. The reaction was monitored by TLC, and TLC analysis indicated formation of a non-polar spot. The reaction mixture was poured into ice water and extracted with ethyl acetate. The combined organic layer was dried over Na₂SO₄ and concentrated under reduced pressure. The crude product was purified by column chromatography (silica gel, 100-200 mesh) using 10-20% ethyl acetate in petroleum ether as an eluent to afford 7-bromo-4-hydroxy-N-(2,4,4-trimethylpentan-2-yl)benzo[d][1,3]dioxole-5-carboxamide (20 g, 70.1% yield) as a pale yellow solid. LCMS: m/z 372.28 (M+H).

Step 7: A stirred solution of TPP (28.2 g, 107.7 mmol, 2 eq) in THF (300 mL), was cooled to 0° C., DIAD (21.2 mL, 107.7 mmol, 2 eq) was added and the resultant reaction mixture was stirred at the same temperature for 20 min. TMS-ethanol (15.5 mL, 107.7 mmol, 2 eq) followed by a solution of 7-bromo-4-hydroxy-N-(2,4,4-trimethylpentan-2-yl)benzo[d][1,3]dioxole-5-carboxamide (20 g, 53.9 mmol, 1 eq) in THF (100 mL) was added and the resultant reaction mixture was stirred at RT for 16 h. The reaction was monitored by TLC, and TLC analysis indicated formation of a non-polar spot. The reaction mixture was quenched with ice water and extracted with ethyl acetate. The combined organic layer was dried over Na₂SO₄ and concentrated under reduced pressure. The crude product was purified by column chromatography (silica gel, 100-200 mesh) using 0-5% ethyl acetate in petroleum ether as an eluent to afford 7-bromo-N-(2,4,4-trimethylpentan-2-yl)-4-(2-(trimethylsilyl)ethoxy)benzo[d][1,3]dioxole-5-carboxamide (17 g, 67% yield) as an off-white solid. LCMS: m/z 471.98 (M+H).

Synthesis of 5-Bromo-3-chloro-2-hydroxy-4-methoxy-N-(2,4,4-trimethylpentan-2-yl)benzamide

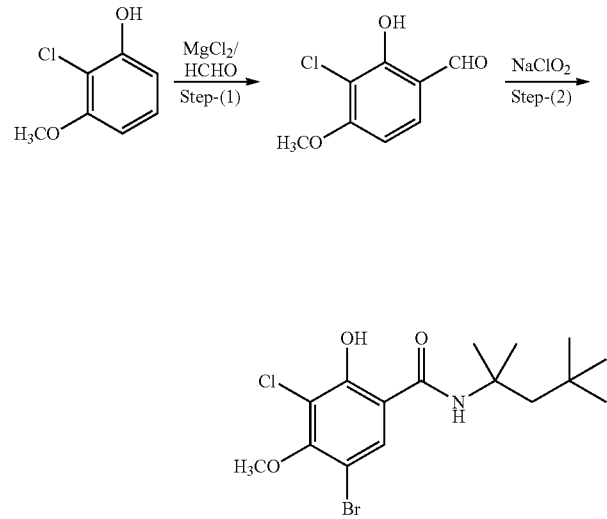
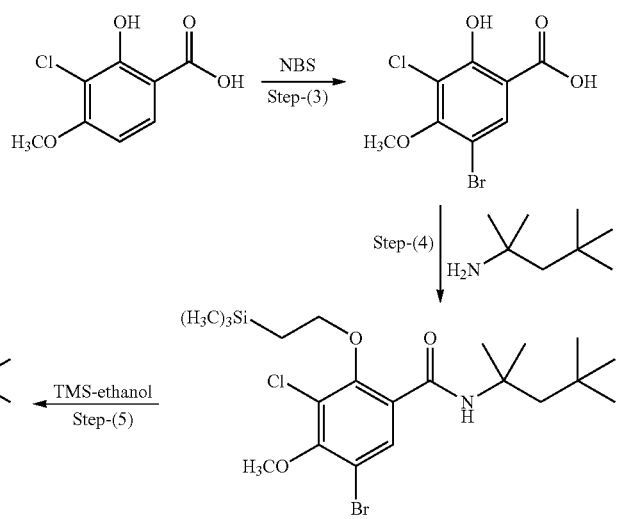

Step 1: A stirred solution of 2-chloro-3-methoxyphenol (10 g, 63.29 mmol, 1 eq) in ACN (200 mL) was cooled to 0° C. and MgCl₂ (9 g, 94.8 mmol, 1.5 eq) was added followed by TEA (32.7 mL, 233.8 mmol, 3.7 eq) and the resulting reaction mixture was stirred for 10 min. Paraformaldehyde (12.8 g, 426.6 mmol, 6.75 eq) was then added portionwise at 0° C. and the mixture heated at 75° C. for 4 h. TLC analysis indicated formation of a polar spot. The reaction mixture was concentrated under reduced pressure, acidified with aqueous 2N HCl solution and extracted with ethyl acetate (2×500 mL). The combined organic layer was dried over Na₂SO₄ and concentrated under reduced pressure. The crude product was triturated with diethyl ether to afford 3-chloro-2-hydroxy-4-methoxybenzaldehyde (9.2 g, 78.6% yield) as a pale yellow solid. LCMS: m/z 187.34 (M+H).

Step 2: A stirred solution of 3-chloro-2-hydroxy-4-methoxybenzaldehyde (9.2 g, 49.46 mmol, 1 eq) in 1,4-dioxane:H₂O (2:1, 600 mL) was cooled to 0° C. and NaH₂PO₄.H₂O (27.3 g, 197.8 mmol, 4 eq), and NaClO₂ (6.1 g, 64.3 mmol, 1.3 eq) were added followed by NH₃SO₃H (7.19 g, 74.19 mmol, 1.5 eq) and the resulting reaction mixture was stirred at the same temperature for 2 h. Na₂SO₃ (7.47 g, 60.3 mmol, 1.2 eq) was added and the resulting reaction mixture was stirred for 30 min. The reaction was monitored by TLC, and TLC analysis indicated formation of a polar spot. The reaction mixture was acidified with aqueous 2N HCl solution and extracted with ethyl acetate (2×500 mL). The combined organic layer was dried over Na₂SO₄ and concentrated under reduced pressure. The crude product was triturated with diethyl ether to afford 3-chloro-2-hydroxy-4-methoxybenzoic acid (8.2 g, 82.8% yield) as a pale yellow solid. LCMS: m/z 203.36 (M+H).

Step 3: To a stirred solution of 3-chloro-2-hydroxy-4-methoxybenzoic acid (8.1 g, 40.09 mmol, 1 eq) in ACN (180 mL), was added NBS (7.85 g, 41.1 mmol, 1.1 eq) and the resulting reaction mixture was stirred at RT for 6 h. The reaction was monitored by TLC, and TLC analysis indicated formation of a non-polar spot. The reaction mixture was diluted with cold water, filtered and washed with n-pentane to afford 5-bromo-3-chloro-2-hydroxy-4-methoxybenzoic acid (6.2 g, 55.3% yield) as an off-white solid.

Step 4: To a stirred solution of 5-bromo-3-chloro-2-hydroxy-4-methoxybenzoic acid (6.2 g, 22.14 mmol, 1.0 eq) in DMF (120 mL) was added DIPEA (11.5 mL, 66.42 mmol, 3 eq), and HATU (16.8 g, 44.28 mmol, 2 eq) followed by 2,4,4-trimethylpentan-2-amine (6.9 mL, 44.28 mmol, 2 eq). The resulting reaction mixture was stirred at RT for 24 h. The reaction was monitored by TLC, and TLC analysis indicated formation of a non-polar spot. The reaction mixture was diluted with water and extracted with EtOAc (3×200 mL). The combined organic layer was dried over $Na_2SO_4$ and concentrated under reduced pressure. The crude product was purified by column chromatography (silica gel, 100-200 mesh) using 0-10% ethyl acetate in petroleum ether as an eluent to afford 5-bromo-3-chloro-4-methoxy-N-(2,4,4-trimethylpentan-2-yl)-2-(2-(trimethylsilyl)ethoxy)benzamide (3 g, 34.8% yield) as an off-white-semi solid. LCMS: m/z 394.46 (M+2H).

Step 5: To a stirred solution of TPP (4.01 g, 15.3 mmol, 2 eq) in toluene (60 mL) was added DBAD (6.13 g, 26.5 mmol, 3.5 eq), and the resulting reaction mixture was stirred for 30 min. TMS-ethanol (2.17 mL, 15.24 mmol, 2 eq) followed by a solution of 5-bromo-3-chloro-4-methoxy-N-(2,4,4-trimethylpentan-2-yl)-2-(2-(trimethylsilyl)ethoxy)benzamide (3 g, 7.67 mmol, 1 eq) in toluene (60 mL) were added and the resulting reaction mixture was heated at 55° C. for 16 h. The reaction was monitored by TLC, and TLC analysis indicated formation of a non-polar spot. The reaction mixture was concentrated under reduced pressure to afford crude product. The crude product was purified by column chromatography (silica gel, 100-200 mesh) using 0-5% diethyl ether in petroleum ether as an eluent to afford 5-bromo-3-chloro-2-hydroxy-4-methoxy-N-(2,4,4-trimethylpentan-2-yl)benzamide (2.4 g, 64.8% yield) as an off-white semi solid. $^1$H NMR (500 MHz, DMSO-$d_6$) δ=7.91 (s, 1H), 7.56 (s, 1H), 4.12-4.04 (m, 2H), 3.82 (s, 3H), 1.82 (s, 2H), 1.39 (s, 6H), 1.20-1.13 (m, 2H), 0.98 (s, 9H), 0.03 (s, 9H).

Representative Synthetic Procedures for Aniline and Aminopyridine Intermediates

Synthesis of 5-chloro-2-(4-methylpiperazin-1-yl)pyridin-4-amine

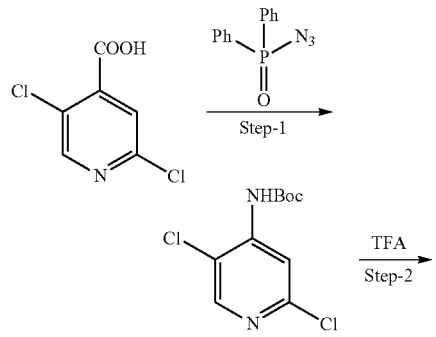

Step 1: To a solution of 2,5-dichloroisonicotinic acid (10 g, 52.35 mmol, 1 eq), and TEA (22 mL, 160.8 mmol, 3 eq) in t-BuOH:toluene (120 mL:120 mL) at 5-10° C., DPPA (17 mL, 78.53 mmol, 1.5 eq) was added in a dropwise manner at the same temperature. Then, the reaction mixture was heated to 85° C. for 6 h. TLC analysis indicated formation of a nonpolar spot. The reaction mixture was cooled to RT and concentrated under reduced pressure to give a residue, which was re-dissolved in EtOAc (150 mL) and washed with saturated brine. The separated organic layer was dried over $Na_2SO_4$ and concentrated under reduced pressure to give crude product which was purified by column chromatography (silica gel, 100-200 mesh) using 1-5% EtOAc in petroleum ether as an eluent to give tert-butyl (2,5-dichloropyridin-4-yl)carbamate (9.5 g, 97% yield) as a white solid. LC-MS: m/z 263.30 (M+H).

Step 2: To a solution of tert-butyl (2,5-dichloropyridin-4-yl)carbamate (10 g, 38.17 mmol, 1 eq) in DCM (100 mL) was added trifluoroacetic acid (34 mL, 12 eq) in a dropwise manner at 0° C. and the mixture allowed to warm to RT and stir for 16 h. TLC analysis indicated formation of a polar spot. Then, the reaction mixture was concentrated under reduced pressure to give the TFA salt of the desired product, which was dissolved in water (50 mL), basified with saturated $NaHCO_3$ and extracted in EtOAc (3×50 mL). The combined organic layer was dried over $Na_2SO_4$ and concentrated under reduced pressure to give crude product. The crude compound was purified by washing with n-pentane to give analytically pure 2,5-dichloropyridin-4-amine (6 g, 97%) as an off-white solid. LC-MS m/z 163.14 (M+H).

Step 3: A solution of 2,5-dichloropyridin-4-amine (3 g, 24.69 mmol, 1 eq) in 1-methyl piperazine (12 mL) was irradiated under microwave at 180° C. for 90 min in a 30 mL vial. TLC analysis indicated formation of a polar spot. Then, the reaction mixture was cooled to RT and poured on ice water to give an off-white precipitate, which was filtered and washed with ether followed by n-pentane to afford 5-chloro-2-(4-methylpiperazin-1-yl)pyridin-4-amine (3 g, 71.77% yield) as an off-white solid. LC-MS: m/z 227.0 (M+H);

General Scheme for the Synthesis of 2-Substituted amino-pyridine Derivatives from Commercially Available 2,5-dichloropyridin-4-amine

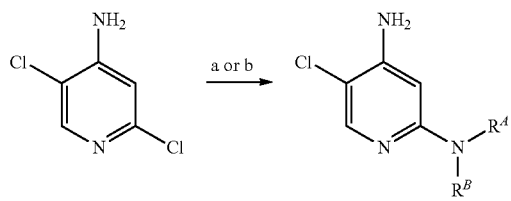

a) HNR$^A$R$^B$ neat, 210° C., mW; b) HNR$^A$R$^B$, EtNiPr$_2$, n-Butanol, 200° C., mW.

Synthesis of 5-chloro-2-(cis)-3,5-dimethylpiperazin-1-yl)pyridin-4-amine

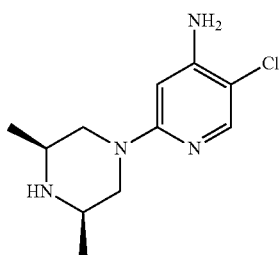 [SMILES: C[C@@H]1CN(c2cc(N)c(Cl)cn2)C[C@H](C)N1]

A solution of (2S,6R)-2,6-dimethylpiperazine (2 g, 12.36 mmol, 1.0 eq), and 2,5-dichloropyridin-4-amine (2.0 g, 17.52 mmol, 1.42 eq) in NMP (8 mL) was irradiated under microwave at 200° C. for 4 h. TLC analysis indicated formation of a polar spot. Then, the reaction mixture was cooled to RT and quenched with ice cold water (100 mL) followed by extraction with EtOAc (2×50 mL). The combined organic layer was dried over Na$_2$SO$_4$ and concentrated under reduced pressure to give crude product, which was triturated with n-pentane to afford 5-chloro-2-(cis)-3,5-dimethylpiperazin-1-yl)pyridin-4-amine (1.5 g, 50.67%) as an off-white solid. LC-MS: m/z 241.2 (M+H).

Synthesis of (S)-5-chloro-2-(3-methylmorpholino)pyridin-4-amine

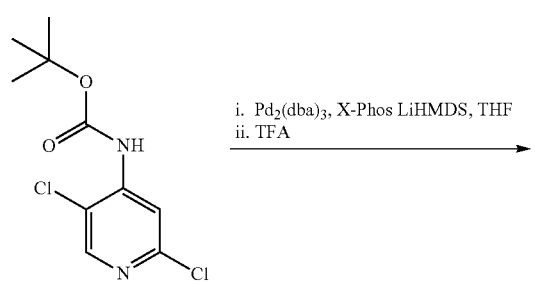

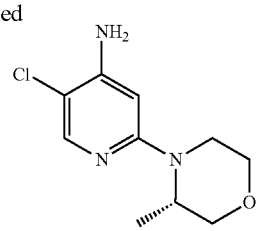

Step 1 (Coupling); A solution of tert-butyl (2,5-dichloro-pyridin-4-yl)carbamate (30 g, 114.4 mmol, 1.0 eq) in THF (300 mL) was degassed for 15 mins then (S)-3-methylmorpholine (17.37 mL, 71.73 mmol, 1.5 eq), and 2-dicyclohexylphospino-2,4,6-triisopropyl biphenyl (Xphos; 4.47 g, 9.3 mmol, 0.082 eq) were added at RT under an argon atmosphere, the solution was degassed for 5 min., then Pd$_2$(dba)$_3$ (2.62 g, 2.8 mmol, 0.025 eq) and LiHMDS (297 mL, 297.6 mmol, 2.6 eq) were added at RT and the total reaction mass was refluxed in a pre-heated oil bath for 1 h. TLC analysis indicated the formation of a polar spot. The reaction mixture was quenched with saturated NH$_4$Cl solution (150 mL) and extracted with EtOAc (2×500 mL). The combined organic layer was dried over Na$_2$SO$_4$ and concentrated under reduced pressure to give crude product which was purified by column chromatography (silica gel, 100-200 mesh) using 0-15% EtOAc in petroleum ether as an eluent to give tert-butyl (S)-(5-chloro-2-(3-methylmorpholino)pyridin-4-yl)carbamate (52 g, 72% yield) as a pale yellow solid. LC-MS: m/z 328.13 (M+H).

Step 2 (Deprotection): To a solution of tert-butyl (S)-(5-chloro-2-(3-methylmorpholino)pyridin-4-yl)carbamate (24 g, 73.3 mmol, 1.0 eq) in DCM (307 mL) was added TFA (307 mL, 12.8 vol) at 0° C. and the mixture allowed to stir at RT for 16 h. TLC analysis indicated the formation of a polar spot. The reaction mixture was concentrated under reduced pressure to give crude product. The crude was neutralized with saturated NaHCO$_3$ solution and extracted with EtOAc (2×500 mL). The combined organic layer was dried over Na$_2$SO$_4$ and concentrated under reduced pressure to give crude product which was purified by column chromatography (silica gel, 100-200 mesh) using 0-30% EtOAc in petroleum ether as an eluent to afford (S)-5-chloro-2-(3-methylmorpholino)pyridin-4-amine (15.5 g, 93% yield) as a pale yellow solid. LC-MS m/z 228.0 (M+H).

Below is a representative procedure for aniline and aminopyridine formation via a Buchwald coupling reaction:

Synthesis of (S)-5-chloro-2-(4-(cyclopropylmethyl)-2-methylpiperazin-1-yl) pyridin-4-amine

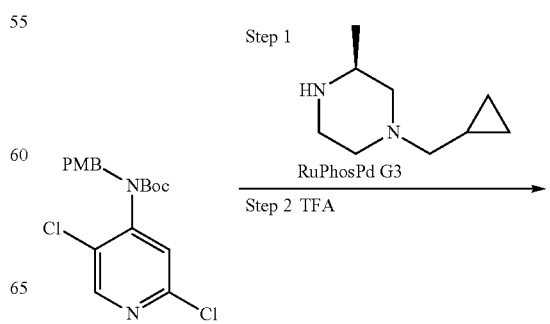

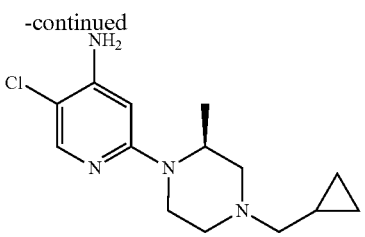

Step 1: A round bottomed flask was charged with tert-butyl (2,5-dichloropyridin-4-yl)(4-methoxybenzyl)carbamate (1700 mg, 4.44 mmol), (S)-1-(cyclopropylmethyl)-3-methylpiperazine dihydrochloride (1209 mg, 5.32 mmol), cesium carbonate (6503 mg, 19.96 mmol) and t-BuOH (12 mL). The system was flushed with nitrogen then 2-dicyclohexylphosphino-2',6'-di-i-propoxy-1,1'-biphenyl (83 mg, 0.177 mmol) and RuPhos Pd G3 (67.4 mg, 0.089 mmol) were added. The system was flushed with nitrogen and heated at 100° C. over a weekend. LCMS showed complete conversion. The reaction was loaded onto celite, and purified on a Biotage (silica gel) eluting with 0-10% MeOH/DCM. The desired fractions were collected and dried under vacuum to afford tert-butyl (S)-(5-chloro-2-(4-(cyclopropylmethyl)-2-methylpiperazin-1-yl)pyridin-4-yl)(4-methoxybenzyl)carbamate (2.2 g, 4.39 mmol, 99% yield) as an orange foam solid. The product was carried onto the next step.

Alternatively, if the amine is neutralized in the previous deprotection step to generate the free base, then 2.5 equivalents of cesium carbonate can be used for the Buchwald reaction. Additionally, either SPhos (CAS No. 657408-07-6) or RuPhos (CAS No. 787618-22-8) can be used as a ligand for this reaction. LCMS RT=1.52 min, [M]$^+$=501.5, Purity (UV 254)=90%.

Step 2: To a solution of tert-butyl tert-butyl (S)-(5-chloro-2-(4-(cyclopropylmethyl)-2-methylpiperazin-1-yl) pyridin-4-yl)(4 methoxybenzyl)carbamate (2.2 g, 4.39 mmol) in dichloromethane (DCM) (1.0 mL) was added trifluoroacetic acid (3.36 mL, 43.9 mmol). The mixture was heated at 40° C. overnight. LCMS showed complete deprotection of Boc and PMB groups. The reaction was concentrated to dryness and partitioned between DCM and saturated NaHCO$_3$ (aq). The aqueous layer was extracted with DCM and the combined organic layers were washed with water and brine. The organic layers were dried over magnesium sulfate, filtered and then concentrated to dryness to afford (S)-5-chloro-2-(4-(cyclopropylmethyl)-2-methylpiperazin-1-yl)pyridin-4-amine (4.20 mmol, 96% yield) as a sticky yellow foam solid. The product was used in the next step without further purification. LCMS: RT=0.17 min, [M+1]$^+$=281.4, Purity (UV 254)=about 90%.

In some cases, the product was purified by one of two methods described below:

Method A: Upon completion of the reaction as judged by LCMS, the reaction was concentrated to dryness and purified on the Biotage (reverse phase silica gel) eluting with 0%-20% ACN/H$_2$O. The desired fractions were collected, and dried under vacuum to afford the desired compound.

Method B: Upon completion of the reaction as judged by LCMS, the reaction was diluted with DCM and partitioned between DCM and water. The aqueous layer was neutralized with the addition of NaHCO$_3$ [both saturated solution and extra solid]. The layers were separated and the aqueous layer was extracted with DCM. The combined organic layers were dried over Na$_2$SO$_4$, filtered and concentrated in vacuo. The product was then used in the next step without further purification.

| Method | Aniline | Name | Yield & Mass |
|---|---|---|---|
| B | ![aniline structure] | 5-chloro-2-(2,4,6-trimethylpiperazin-1-yl)pyridin-4-amine | 41% yield over 2 steps LCMS [M]$^+$ 255.6 |

Synthesis of (S)-3-chloro-2-fluoro-6-(2-methylpiperazin-1-yl)pyridin-4-amine

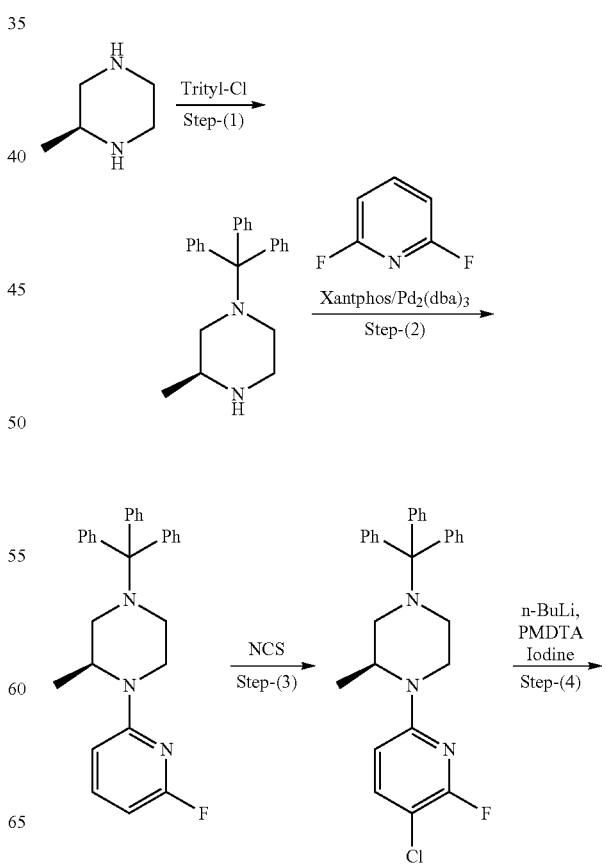

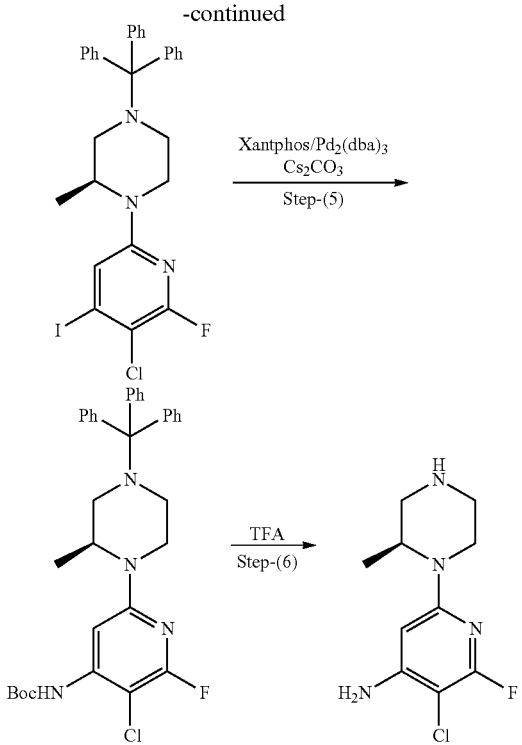

Step 1: To a solution of (S)-2-methylpiperazine (1 g, 10 mmol, 1 eq) in DCM (30 mL) was added Trityl-Cl (2.78 g, 10 mmol, 1 eq) portionwise at RT, then the reaction mixture was continued for 2 h. TLC analysis indicated formation of a less polar spot. The reaction mixture was quenched with water and extracted with EtOAc (3×50 mL). The combined organic layer was dried over $Na_2SO_4$ then concentrated to give (S)-3-methyl-1-tritylpiperazine (3.3 g, 96%) as a colorless oil.

Step 2: To a stirred solution of (S)-3-methyl-1-tritylpiperazine (3 g, 8.77 mmol, 1 eq) was added 2,6-difluoropyridine (1.51 g, 13.15 mmol, 1.5 eq), xantphos (152 mg, 0.026 mmol, 0.03 eq), $Pd_2(dba)_3$ (241 mg, 0.026 mmol, 0.03 eq) and Li-HMDS (43.8 mL, 43.85 mmol, 5 eq) at RT under an argon atmosphere, then the reaction mixture was heated to 90° C. for 16 h. TLC analysis indicated formation of a less polar spot. The reaction mixture was cooled to RT then filtered through a celite pad, which was washed with EtOAc (3×20 mL). The filtrate was diluted with water and extracted with EtOAc (3×100 mL). The combined organic layer was dried over $Na_2SO_4$ then concentrated to afford crude compound. The crude compound was purified by column chromatography (silica gel, 100-200 mesh) using 0-2% EtOAc in petroleum ether as eluent to afford (S)-1-(6-fluoropyridin-2-yl)-2-methyl-4-tritylpiperazine (3 g, 78%) as a colorless oil.

Step 3: To a stirred solution of (S)-1-(6-fluoropyridin-2-yl)-2-methyl-4-tritylpiperazine (3 g, 6.86 mmol, 1 eq) in DMF (40 mL) was added NCS (913 mg, 6.86 mmol, 1 eq) at RT then the mixture heated to 60° C. for 16 h. TLC analysis indicated formation of a less polar spot, which was very close to starting material. The reaction mixture was diluted with water then extracted with EtOAc (3×50 mL). The combined organic layer was dried over $Na_2SO_4$ then concentrated to afford crude compound. The crude compound was purified by column chromatography (silica gel, 100-200 mesh) using 0-2% EtOAc in petroleum ether as eluent to afford (S)-1-(5-chloro-6-fluoropyridin-2-yl)-2-methyl-4-tritylpiperazine (3 g, semi-pure) as a colorless oil.

Step 4: To a stirred solution of (S)-1-(5-chloro-6-fluoropyridin-2-yl)-2-methyl-4-tritylpiperazine (3 g, 6.36 mmol, 1 eq) in THF (50 mL) was added PMDTA (2.65 mL, 12.73 mmol, 2 eq) and n-BuLi (5.0 mL, 12.73 mmol, 2 eq) at −78° C. then the reaction mixture was continued for 2 h. A solution of 12 (3.23 g, 12.73 mmol, 2 eq, in THF) was added at −78° C., the mixture was slowly allowed to warm to RT then stirred for 16 h. TLC analysis indicated formation of a less polar spot. The reaction mixture was quenched in an aqueous solution of sodium thiosulphate then extracted with EtOAc (2×50 mL). The combined organic layer was dried over $Na_2SO_4$ then concentrated under reduced pressure to give crude (S)-1-(5-chloro-6-fluoro-4-iodopyridin-2-yl)-2-methyl-4-tritylpiperazine (4.5 g, crude) as a brown oil.

Step 5: To a stirred solution of (S)-1-(5-chloro-6-fluoro-4-iodopyridin-2-yl)-2-methyl-4-tritylpiperazine (4.5 g, 7.53 mmol, 1 eq) in toluene (80 mL) was added $Cs_2CO_3$ (4.89 g, 15.07 mmol, 2 eq) and $NH_2Boc$ (1.04 g, 9.04 mmol, 1.2 eq) at RT then the reaction mixture was de-gassed with argon for 5 min., then xantphos (130 mg, 0.22 mmol, 0.03 eq) and $Pd_2(dba)_3$ (207 mg, 0.22 mmol, 0.03 eq) were added at RT, and after that, the reaction mixture was heated to 90° C. for 16 h. TLC analysis indicated formation of a polar spot. The reaction mixture was filtered through a celite pad then the filtrate was concentrated to crude compound. The crude compound was purified by column chromatography (silica gel, 100-200 mesh) using 0-3% EtOAc in petroleum ether as eluent to afford (S)-tert-butyl (3-chloro-2-fluoro-6-(2-methyl-4-tritylpiperazin-1-yl)pyridin-4-yl)carbamate (800 mg, 19% after three steps) as a pale yellow gummy liquid.

Step 6: To stirred (S)-tert-butyl (3-chloro-2-fluoro-6-(2-methyl-4-tritylpiperazin-1-yl)pyridin-4-yl)carbamate (800 mg, 1.36 mmol, 1 eq) was added TFA (5 mL) at RT and stirring continued for 16 h. TLC analysis indicated formation of a polar spot. The reaction mixture was concentrated to crude, which was basified by aqueous $NaHCO_3$ solution then extracted with EtOAc (3×50 mL). The combined organic layer was dried over $Na_2SO_4$ then concentrated under reduced pressure to crude compound. The crude compound was purified by column chromatography (silica gel, 100-200 mesh) using 0-40% EtOAc in petroleum ether as eluent to afford (S)-3-chloro-2-fluoro-6-(2-methylpiperazin-1-yl)pyridin-4-amine (120 mg 36%) as a pale yellow semi-solid. LC-MS: m/z 245.01 (M+H+).

Representative Procedure for Aminopyridine Formation Via Alkylation

To a vial containing (S)-3-chloro-2-fluoro-6-(2-methylpiperazin-1-yl)pyridin-4-amine (322 mg, 1.316 mmol) in acetonitrile (1.0 mL) was added potassium carbonate (200 mg, 1.448 mmol) followed by 2-bromoethyl methyl ether (201 mg, 1.448 mmol). The reaction was stirred at RT overnight. Additional equivalents of potassium carbonate and 2-bromoethyl methyl ether were added until the reaction was judged complete by LCMS. Methanol was added to the reaction then the mixture concentrated onto celite. The crude product was purified on a Biotage (reverse phase silica gel) eluting with 0-40% $ACN/H_2O$. The desired fractions were collected, concentrated and dried under vacuum to afford (S)-3-chloro-2-fluoro-6-(4-(2-methoxyethyl)-2-methylpiperazin-1-yl) pyridin-4-amine (0.796 mmol, 60.5% yield) as a yellow oil.

In a similar manner, the following compounds were prepared:

| Aniline | Name | Yield & Mass |
|---|---|---|
| [structure] | (S)-5-chloro-2-(4-(2-methoxyethyl)-2-methylpiperazin-1-yl)pyridin-4-amine | 61% yield<br>LCMS [M]+ 303.5 |
| [structure] | 3-chloro-2-fluoro-6-((S)-4-((S)-2-methoxypropyl)-2-methylpiperazin-1-yl)pyridin-4-amine | 38% yield<br>LCMS [M]+ 317.5 |
| [structure] | (S)-3-chloro-2-fluoro-6-(2-methyl-4-(oxetan-3-ylmethyl)piperazin-1-yl)pyridin-4-amine | 56% yield<br>LCMS [M]+ 315.6 |
| [structure] | (S)-3-chloro-6-(4-(2,2-difluoroethyl)-2-methyl-piperazin-1-yl)-2-fluoro-pyridin-4-amine | 42% yield<br>LCMS [M]+ 309.4 |

Representative Procedure for Aminopyridine Formation Via Reductive Amination

To a screw-cap vial was added 3,3,3-trifluoropropanal (0.076 mL, 0.882 mmol) and (S)-5-chloro-2-(2-methylpiperazin-1-yl)pyridin-4-amine (200 mg, 0.882 mmol) in 1,2-dichloroethane (DCE) (1.0 mL) followed by acetic acid (5.0 mL) and sodium triacetoxyborohydride (561 mg, 2.65 mmol). The reaction was stirred at RT for 2 hours.

Method A: Upon completion of the reaction as judged by LCMS, the reaction was concentrated to dryness and purified on a Biotage (reverse phase silica gel) eluting with 0%-50% ACN/H$_2$O. The desired fractions were collected, concentrated in vacuo and dried under vacuum to afford the desired product.

Method B: Upon completion of the reaction as judged by LCMS, the reaction was diluted with DCM and partitioned between DCM and water. The aqueous layer was neutralized with the addition of NaHCO$_3$ [both saturated solution and extra solid]. The layers were separated and the aqueous layer was extracted with DCM. The combined organic layers were dried over Na$_2$SO$_4$, filtered and concentrated in vacuo. The crude material was purified on a Biotage (reverse phase silica gel) eluting with 0-80% ACN/H$_2$O. The desired fractions were collected, concentrated and dried on the h/v at room temperature to afford the desired product.

In a similar manner, the following compounds were prepared:

| Method | Aniline | Name | Yield & Mass |
|---|---|---|---|
| A | [structure] | (S)-5-chloro-2-(2-methyl-4-(3,3,3-trifluoropropyl)piperazin-1-yl)pyridin-4-amine | 22% yield<br>LCMS [M]+ 323.5 |

| Method | Aniline | Name | Yield & Mass |
|---|---|---|---|
| B | | (S)-3-chloro-2-fluoro-6-(2-methyl-4-(3,3,3-trifluoropropyl)piperazin-1-yl)pyridin-4-amine | 22% yield LCMS [M]+ 341.5 |

Synthesis of tert-butyl (2,5-dichloropyridin-4-yl)(4-methoxybenzyl)carbamate

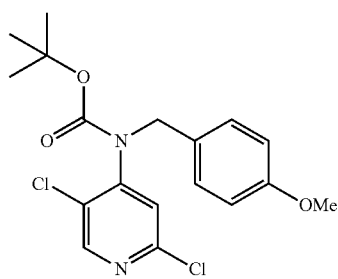 [SMILES: COc1ccc(CN(C(=O)OC(C)(C)C)c2cc(Cl)ncc2Cl)cc1]

Sodium hydride (60% in mineral oil, 0.340 g, 8.86 mmol) was added in portions to a stirring solution of tert-butyl (2,5-dichloropyridin-4-yl)carbamate (2.12 g, 8.06 mmol) in N,N-dimethylformamide (DMF) (Volume: 20 mL) at 0° C. After stirring for 30 minutes, 4-methoxybenzylchloride (1.197 mL, 8.86 mmol) was added dropwise and the reaction was warmed to room temperature. The mixture was then warmed to 50-55° C. for an hour. LCMS indicated near complete conversion. The reaction was concentrated directly onto celite and purified by flash chromatography [0-25% EtOAc/hexanes] to afford tert-butyl (2,5-dichloropyridin-4-yl)(4-methoxybenzyl)carbamate (3.17 g, 7.86 mmol, 98% yield) as a clear colourless oil. $^1$H NMR (500 MHz, DMSO-$d_6$) δ=8.50 (s, 1H), 7.64 (s, 1H), 7.14 (d, J=8.6 Hz, 2H), 6.84 (d, J=8.6 Hz, 2H), 4.77 (br. s., 2H), 3.71 (s, 3H), 1.38 (s, 9H); LCMS [M+H]+ 383.24.

Synthesis of tert-butyl (S)-4-(cyclopropylmethyl)-2-methylpiperazine-1-carboxylate

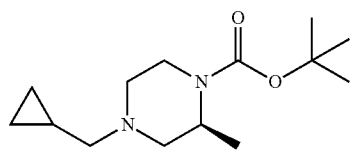 [SMILES: C[C@H]1CN(CC2CC2)CCN1C(=O)OC(C)(C)C]

To (S)-1-N-Boc-2-methyl piperazine (1.595 g, 7.96 mmol) in acetonitrile (20 mL) was added potassium carbonate (ACS) (1.321 g, 9.56 mmol) followed by (bromomethyl)cyclopropane (0.850 mL, 8.76 mmol). The mixture was heated at 80° C. over a weekend. The solvent was removed in vacuo, and the residue was taken up in water and extracted with DCM. The organic extract was dried over sodium sulfate, and the solvent removed in vacuo to afford tert-butyl (S)-4-(cyclopropylmethyl)-2-methylpiperazine-1-carboxylate (1.96 g, 7.69 mmol, 97% yield) as a colorless oil. $^1$H NMR (500 MHz, DMSO-$d_6$) δ=4.11-4.02 (m, 1H), 3.65 (d, J=13.1 Hz, 1H), 3.00-2.92 (m, 1H), 2.87 (d, J=11.2 Hz, 1H), 2.75 (d, J=11.2 Hz, 1H), 2.14 (d, J=6.2 Hz, 2H), 2.00 (dd, J=3.9, 11.2 Hz, 1H), 1.81 (dt, J=3.5, 11.7 Hz, 1H), 1.39 (s, 9H), 1.15 (d, J=6.7 Hz, 3H), 0.84-0.75 (m, 1H), 0.48-0.42 (m, 2H), 0.09-0.03 (m, 2H). Ref: WO 2001/085173 A1.

Synthesis of (S)-1-(cyclopropylmethyl)-3-methylpiperazine, 2 Hydrochloride (WO 2006/040192)

To a 0° C. solution of tert-butyl (S)-4-(cyclopropylmethyl)-2-methylpiperazine-1-carboxylate (1.957 g, 7.69 mmol) in dioxane (10 mL) was added hydrogen chloride solution (4.0 M in dioxane, 9.62 mL, 38.5 mmol) dropwise. The mixture was allowed to warm up to room temperature and stir at RT overnight. The white suspension was concentrated in vacuo, triturated from ether (ether was decanted as the HCl salt was very hydroscopic) and dried under high vacuum at RT to afford (S)-1-(cyclopropylmethyl)-3-methylpiperazine, 2HCl (1.57 g, 6.90 mmol, 90% yield) as a white solid.

General Scheme and Procedures for the Synthesis of 2-Substituted Amino-Pyridines Via a Buchwald Coupling Reaction i) HNR$^A$R$^B$ RuPhos Pd G$_3$, RuPhos, CsCO$_3$, n-Butanol, mW
ii) TFA, mW -continued

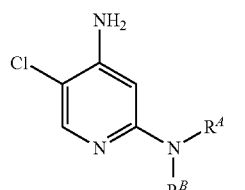

A microwave vial was charged with tert-butyl (2,5-dichloropyridin-4-yl)(4-methoxybenzyl)carbamate (780 mg, 2.035 mmol), 2,3-dimethylmorpholine hydrochloride (401 mg, 2.65 mmol), $Cs_2CO_3$ (2652 mg, 8.14 mmol), RuPhos Pd G3 (30.9 mg, 0.041 mmol) and 2-dicyclohexylphosphino-2',6'-di-i-propoxy-1,1'-biphenyl (38.0 mg, 0.081 mmol) (RuPhos). The system was flushed with nitrogen then t-BuOH (10 mL) was added. The system was flushed with nitrogen and heated at 100° C. to complete conversion as determined by LCMS. The reaction was concentrated onto celite, and purified by flash chromatography (silica gel) eluting with 0-10% MeOH/DCM+1% $NH_4OH$. The desired fractions were collected and dried on the h/v at RT to afford tert-butyl (5-chloro-2-(2,3-dimethylmorpholino)pyridin-4-yl)(4-methoxybenzyl)carbamate (598 mg, 1.294 mmol, 63.6% yield) as a yellow oil. To a stirring solution of the tert-butyl (5-chloro-2-(2,3-dimethylmorpholino)pyridin-4-yl)(4-methoxybenzyl)carbamate (598 mg, 1.294 mmol) in dichloromethane (1.0 mL) was added TFA (2.99 mL, 38.8 mmol) at room temperature.

Work up procedure A: Upon completion of the reaction as judged by LCMS, the reaction was concentrated to dryness and purified on a Biotage (reverse phase silica gel) eluting with 0%-20% $ACN/H_2O$. The desired fractions were collected, and dried under vacuum to afford 5-chloro-2-(2,3-dimethylmorpholino)pyridin-4-amine trifluoroacetate (321 mg, 0.902 mmol, 69.7% yield) as a yellow residue.

Work up procedure B: Upon completion of the reaction as judged by LCMS, the reaction was diluted with DCM and partitioned between DCM and water. The aqueous layer was neutralized with the addition of $NaHCO_3$ [both saturated solution and extra solid]. The layers were separated and the aqueous layer was extracted with DCM. The combined organics were dried over $Na_2SO_4$, filtered and concentrated in vacuo. The product was used in next step without further purification.

Synthesis of (S)-3-chloro-6-(2,4-dimethylpiperazin-1-yl)-2-fluoropyridin-4-amine

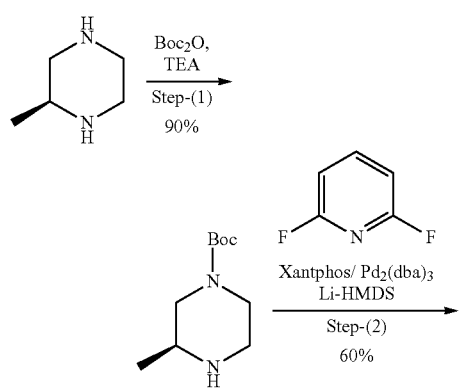

-continued

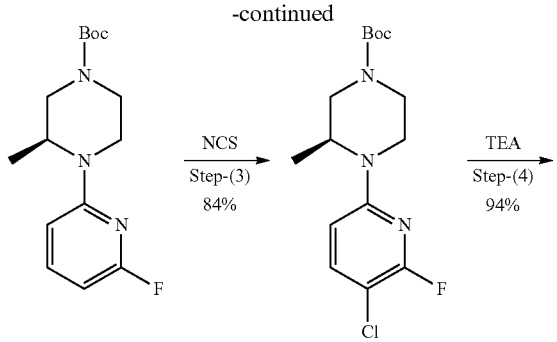

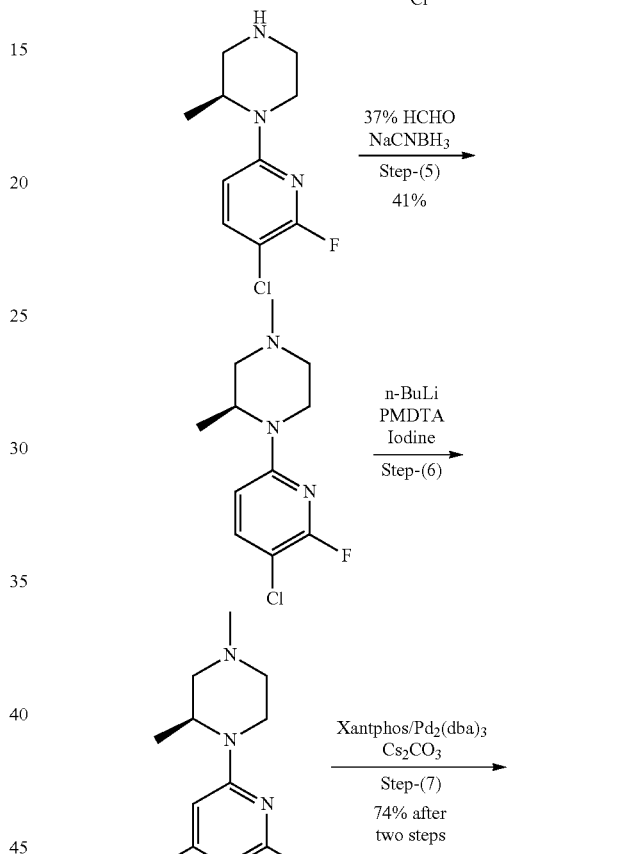

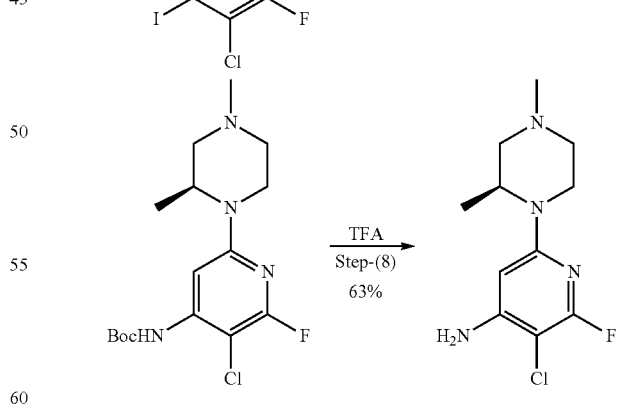

Step 1: To a solution of (S)-2-methylpiperazine (10 g, 100 mmol, eq) in EtOH (200 mL) was added DIPEA (43.58 mL, 250 mmol, 2.5 eq) and $Boc_2O$ (21.8 mL, 100 mmol, 1 eq) at RT, then the reaction mixture was continued for 16 h. TLC analysis indicated formation of a less polar spot. The reaction mixture was concentrated to crude compound, which was diluted with water and extracted with EtOAc (3×100 mL). The combined organic layer was dried over $Na_2SO_4$ then concentrated to give (S)-tert-butyl 3-methylpiperazine-1-carboxylate (18 g, 90%) as a colorless oil.

Step 2: To a stirred solution of (S)-tert-butyl 3-methylpiperazine-1-carboxylate (18 g, 90 mmol, 1 eq) was added 2,6-difluoropyridine (20.7 g, 180 mmol, 2 eq), xantphos (1.56 g, 2.7 mmol, 0.03 eq), $Pd_2(dba)_3$ (2.47 g, 2.7 mmol, 0.03 eq) and Li-HMDS (450 mL, 450 mmol, 5 eq) at RT under an argon atmosphere, then the reaction mixture was heated to 90° C. for 16 h. TLC analysis indicated formation of a less polar spot. The reaction mixture was cooled to RT then filtered through a celite pad, which was washed with EtOAc (3 times). The filtrate was diluted with water and extracted with EtOAc (3×100 ml). The combined organic layer was dried over $Na_2SO_4$ then concentrated to crude compound. The crude compound was purified by column chromatography (silica gel, 100-200 mesh) using 0-1% MeOH in DCM as eluent to afford (S)-tert-butyl 4-(6-fluoropyridin-2-yl)-3-methylpiperazine-1-carboxylate (23 g, 86%) as a pale yellow oil. LC-MS: m/z 396.24 (M+H).

Step 3: To a stirred solution of (S)-tert-butyl 4-(6-fluoropyridin-2-yl)-3-methylpiperazine-1-carboxylate (22 g, 74.57 mmol, 1 eq) in DMF (250 mL) was added NCS (9.91 g, 74.57 mmol, 1 eq) at RT then the mixture heated to 60° C. for 2 h. TLC analysis indicated formation of a polar spot, which very close to starting material. The reaction mixture was diluted with water then extracted with EtOAc (3×100 mL). The combined organic layer was dried over $Na_2SO_4$ then concentrated to crude compound. The crude compound was purified by column chromatography (silica gel, 100-200 mesh) using 0-5% EtOAc in petroleum ether as eluent to afford (S)-tert-butyl 4-(5-chloro-6-fluoropyridin-2-yl)-3-methylpiperazine-1-carboxylate (14 g, 57%) as a pale yellow oil. LC-MS: m/z 329.98 (M+H).

Step 4: To a stirred solution of (S)-tert-butyl 4-(5-chloro-6-fluoropyridin-2-yl)-3-methylpiperazine-1-carboxylate (14 g, 42.55 mmol, 1 eq) in DCM (100 mL) was added TFA (32.34 mL, 425.53 mmol, 10 eq) at 0° C. then the mixture allowed to warm up to RT and stir for 16 h. TLC analysis indicated formation of a polar spot. The reaction mixture was concentrated to crude residue, which was basified with aqueous $NaHCO_3$ solution then extracted with EtOAc (3×100 mL). The combined organic layer was dried over $Na_2SO_4$ then concentrated to afford (S)-1-(5-chloro-6-fluoropyridin-2-yl)-2-methylpiperazine (9 g, 92%) as a brown oil. LC-MS: m/z 230.34 (M+H).

Step 5A: Reductive amination (Method A) To a stirred solution of (S)-3-chloro-2-fluoro-6-(2-methylpiperazin-1-yl)pyridin-4-amine (8 g, 34.93 mmol, 1 eq) in DCM (100 mL) was added 37% HCHO (4.25 mL, 52.40 mmol, 1.5 eq) and AcOH (30 mL) at RT then stirring continued for 2 h. $NaCNBH_3$ (3.3 g, 52.40 mmol, 1.5 eq) was then added at 0° C. then the mixture was allowed to warm up to RT and stir for 2 h. TLC analysis indicated formation of a less polar spot. The reaction mixture was basified with aqueous $NaHCO_3$ solution then extracted with EtOAc (3×90 mL). The combined organic layer was dried over $Na_2SO_4$ then concentrated to crude compound. The crude compound was purified by column chromatography (silica gel, 100-200 mesh) using 0-1% MeOH in DCM as eluent to afford (S)-1-(5-chloro-6-fluoropyridin-2-yl)-2,4-dimethylpiperazine (5.4 g, 63%) as a brown oil. LC-MS: 73.12% with m/z 244.38 (M+H).

Step 5B: General procedure for alkylation (Method B): To a vial containing (S)-3-chloro-2-fluoro-6-(2-methylpiperazin-1-yl)pyridin-4-amine (1 equivalent) in acetonitrile was added potassium carbonate (1.1 eq) followed by alkyl halide (1.1 eq). The reaction was stirred at RT overnight. Additional equivalents of potassium carbonate and alkyl halide were added until the reaction was judged complete by LCMS. Methanol was added to the reaction then concentrated onto celite. The crude product was purified on a Biotage (reverse phase silica gel) eluting with 0-40% $ACN/H_2O$. The desired fractions were collected, concentrated and dried under vacuum to afford the desired compound (S)-1-(5-chloro-6-fluoropyridin-2-yl)-2,4-dimethylpiperazine.

Step 6: To a stirred solution of (S)-1-(5-chloro-6-fluoropyridin-2-yl)-2,4-dimethylpiperazine (5.4 g, 22.22 mmol, 1 eq) in THF (80 mL) was added PMDTA (10.19 mL, 48.88 mmol, 2.2 eq) and n-BuLi (19.55 mL, 48.88 mmol, 2.2 eq) at −78° C. then the reaction was continued for 3 h. A solution of 12 (11.29 g, 44.44 mmol, 2 eq, in THF) was then added at −78° C., and after that the mixture was slowly allowed to warm up to RT and stir for 16 h. TLC analysis indicated formation of a less polar spot. The reaction mixture was quenched in an aqueous solution of sodium thiosulphate then extracted with EtOAc (2×100 mL). The combined organic layer was dried over $Na_2SO_4$ then concentrated under reduced pressure to give crude (S)-1-(5-chloro-6-fluoro-4-iodopyridin-2-yl)-2,4-dimethylpiperazine (8 g, crude) as a brown semi-solid. LC-MS: m/z 370.16 (M+H).

Step 7: To a stirred solution of (S)-1-(5-chloro-6-fluoro-4-iodopyridin-2-yl)-2,4-dimethylpiperazine (8 g, 21.68 mmol, 1 eq) in toluene (100 mL) was added $Cs_2CO_3$ (14.1 g, 43.36 mmol, 2 eq) and $NH_2Boc$ (3.01 g, 26.01 mmol, 1.2 eq) at RT then the reaction mixture was degassed with argon for 5 min., then xantphos (376 mg, 0.65 mmol, 0.03 eq) and $Pd_2(dba)_3$ (595 mg, 0.65 mmol, 0.03 eq) were added at RT. After that, the reaction mixture was heated to 90° C. for 16 h. TLC analysis indicated formation of a polar spot. The reaction mixture was filtered through a celite pad then the filtrate was concentrated to crude compound. The crude compound was purified by column chromatography (silica gel, 100-200 mesh) using 0-1% MeOH in DCM as eluent to afford (S)-tert-butyl (3-chloro-6-(2,4-dimethylpiperazin-1-yl)-2-fluoropyridin-4-yl)carbamate (5 g, 62% per two steps) as a pale yellow gum. LC-MS: m/z 359.59 (M+H).

Step 8: To a stirred solution of (S)-tert-butyl (3-chloro-6-(2,4-dimethylpiperazin-1-yl)-2-fluoropyridin-4-yl)carbamate (5.0 g, 13.96 mmol, 1 eq) in DCM (50 mL) was added TFA (10.61 mL, 139.66 mmol, 10 eq) at RT and stirring continued for 16 h. TLC analysis indicated formation of a polar spot. The reaction mixture was concentrated to crude, which was basified by aqueous $NaHCO_3$ solution then extracted with EtOAc (3×50 mL). The combined organic layer was dried over $Na_2SO_4$ then concentrated under reduced pressure to crude compound. The crude compound was purified by column chromatography (silica gel, 100-200 mesh) using 0-2% MeOH in DCM as eluent to afford (S)-3-chloro-6-(2,4-dimethylpiperazin-1-yl)-2-fluoropyridin-4-amine (2.6 g 72%) as a pale yellow gum. $^1$H NMR ($CDCl_3$, 400 MHz): δ 5.69 (s, 1H), 4.49 (brs, 2H), 4.30 (m, 1H), 3.76 (d, j=12.4 MHz, 1H), 3.10 (m, 1H), 2.85 (m, 1H), 2.68 (d, j=11.2 MHz, 1H), 2.27 (s, 3H), 2.20 (m, 1H), 2.02 (m, 1H), 1.21 (d, j=6.8 MHz, 3H). LC-MS: m/z 259.16 (M+H).

In a similar manner, the following compounds were prepared

| Method in Step 5 | Aniline | Name | Yield & Mass |
|---|---|---|---|
| B | | (S)-3-chloro-2-fluoro-6-(2-methyl-4-(oxetan-3-yl)piperazin-1-yl)pyridin-4-amine | 60% yield LCMS [M]$^+$ 301 |
| B | | (S)-5-chloro-2-(4-(2-ethoxyethyl)-2-methylpiperazin-1-yl)pyridin-4-amine Exact Mass: 298.16 | 61% yield LCMS [M]$^+$ 299 |
| A | | (S)-3-chloro-2-fluoro-6-(4-(2-methoxyethyl)-2-methylpiperazin-1-yl)pyridin-4-amine | 57% yield LCMS [M]$^+$ 303 |
| A | | 3-chloro-2-fluoro-6-((S)-4-((S)-2-methoxypropyl)-2-methylpiperazin-1-yl)pyridin-4-amine | 38% yield LCMS [M]$^+$ 317 |
| B | | 3-chloro-6-(4-(cyclopropylmethyl)piperazin-1-yl)-2-fluoropyridin-4-amine | 69% yield LCMS [M]$^+$ 285 |
| A | | (S)-3-chloro-6-(4-ethyl-2-methylpiperazin-1-yl)-2-fluoropyridin-4-amine | 56% yield LCMS [M]$^+$ 273 |

Synthesis of (S)-3-chloro-2-fluoro-6-(3-methylmorpholino)pyridin-4-amine

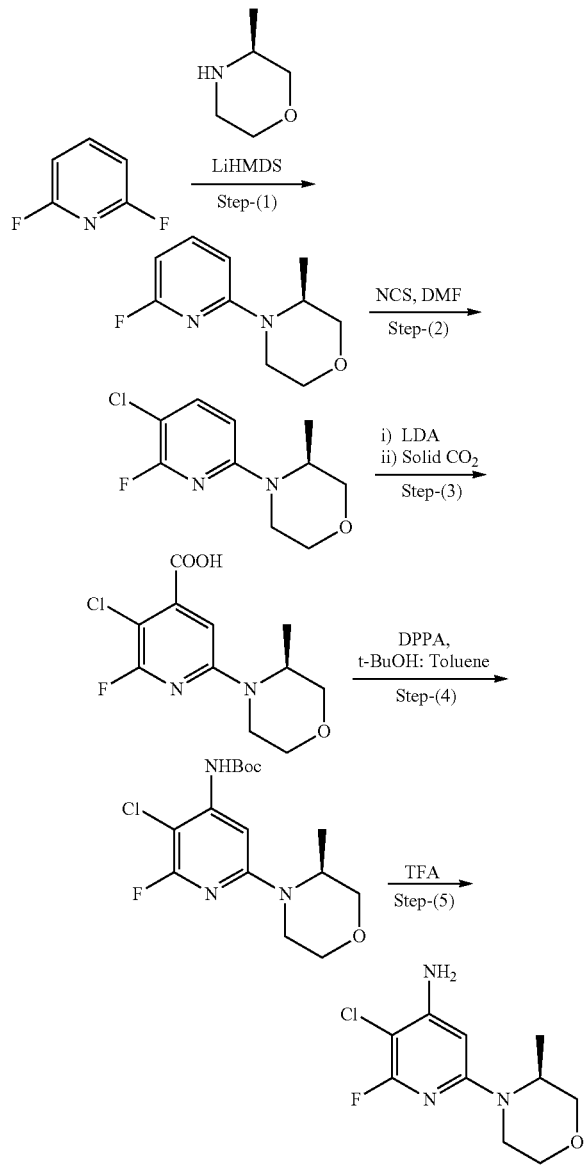

Step 1: To a solution of 2,6-difluoropyridine (25 g, 217.3 mmol, 1.0 eq) and (S)-3-methylmorpholine (26.3 g, 260 mmol, 1.2 eq), was added Xantphos (3.76 g, 6.52 mmol, 0.03 eq) then Pd$_2$(dba)$_3$ (5.97 g, 6.52 mmol, 0.03 eq) at RT under an argon atmosphere and the mixture degassed for 5 min. Then LiHMDS (250 mL, 1M soln in THF was added at RT and the total reaction mass was refluxed for 16 h. TLC analysis indicated the formation of a polar spot. The reaction mixture was quenched with saturated NH$_4$Cl solution (250 mL) and extracted with EtOAc (2×500 mL). The combined organic layer was dried over Na$_2$SO$_4$ and concentrated under reduced pressure to give crude product which was purified by column chromatography (silica gel, 100-200 mesh) using 0-10% EtOAc in petroleum ether as an eluent to give (S)-4-(6-fluoropyridin-2-yl)-3-methylmorpholine (27 g, 63.38% yield) as a pale yellow liquid. LC-MS: m/z 197.14 (M+H).

Step 2: To a solution of (S)-4-(6-fluoropyridin-2-yl)-3-methylmorpholine (27 g, 137.7 mmol, 1 eq) in DMF (550 mL) was added NCS (18.39 g, 137.7 mmol, 0.8 eq) at 0° C. to 50° C. for 2 h. TLC analysis indicated formation of a polar spot. Then, the reaction mixture was cooled to RT and poured on ice water (300 mL). The reaction mixture was extracted with EtOAc (2×200 mL), then the combined organic layer was dried over Na$_2$SO$_4$ and concentrated under reduced pressure to give crude product which was purified by CombiFlash column chromatography using 0-10% EtOAc in petroleum ether as an eluent to afford (S)-4-(5-chloro-6-fluoropyridin-2-yl)-3-methylmorpholine (13 g, 45%) as a pale yellow colored liquid. LC-MS: m/z 231.02 (M+H).

Step 3: To a mixture of DiPA (18.2 mL, 130.4 mmol, 2 eq) and LiCl (2.73 g, 65.2 mmol, 1.0 eq) in dry THF (150 mL) was added n-BuLi (1.6 M in n-hexane, 81.5 mL, 130.4 mmol, 2 eq) at −78° C. and the mixture allowed warm up to −30° C. over 30 min. Then freshly prepared LDA was added to a solution of (S)-4-(5-chloro-6-fluoropyridin-2-yl)-3-methylmorpholine (15 g, 65.2 mmol, 1 eq) in dry THF (350 mL) at −78° C. under an argon atmosphere and maintained for 4 h at the same temperature. Then, powdered dry ice was added slowly at the same temperature and the mixture allowed to warm up to RT and stirred for 16 h. TLC analysis indicated formation of a polar spot. Then, the reaction mixture was quenched with saturated NH$_4$Cl (150 mL) and washed with ether (2×150 mL). The aqueous layer was acidified with 1M HCl and extracted with EtOAc (4×200 mL). The combined organic layer was dried with Na$_2$SO$_4$ and concentrated under reduced pressure to give crude product which was washed with n-pentane and ether to afford (S)-3-chloro-2-fluoro-6-(3-methylmorpholino)isonicotinic acid (10 g, 76.9%) as a brown colored liquid. LC-MS: m/z 275.23 (M+H).

Step 4: To a solution of (S)-3-chloro-2-fluoro-6-(3-methylmorpholino)isonicotinic acid (25 g, 91.2 mmol, 1 eq), TEA (14 mL, 100.3 mmol, 1.1 eq) in tBuOH:toluene (250 mL:250 mL) at 5-10° C., DPPA (31.95 mL, 102.1 mmol, 1.12 eq) was added in a dropwise manner at the same temperature. Then, the reaction mixture was heated to 85° C. for 16 h. TLC analysis indicated formation of a nonpolar spot. The reaction mixture was cooled to RT and concentrated under reduced pressure to give residue which was re-dissolved in EtOAc (200 mL) and washed with saturated brine. The separated organic layer was dried over Na$_2$SO$_4$ and concentrated under reduced pressure to give crude product which was purified by CombiFlash column chromatography using 0-20% EtOAc in petroleum ether as an eluent to give (S)-tert-butyl (3-chloro-2-fluoro-6-(3-methylmorpholino)pyridin-4-yl)carbamate (21 g, 80% yield) as an off-white solid.

Step 5: To a solution of (S)-tert-butyl (3-chloro-2-fluoro-6-(3-methylmorpholino)pyridin-4-yl)carbamate (21 g, 60.8 mmol, 1 eq) in DCM (210 mL) was added trifluoroacetic acid (55.5 mL, 730.4 mmol, 12 eq) in a dropwise manner at 0° C. then the mixture was allowed to warm up to RT and stirred for 16 h. TLC analysis indicated formation of a polar spot. Then, the reaction mixture was concentrated under reduced pressure to give the TFA salt of the desired product which was dissolved in water (100 mL), basified with saturated NaHCO$_3$ and extracted in EtOAc (3×100 mL). The combined organic layer was dried over Na$_2$SO$_4$ and concentrated under reduced pressure to give crude product. The crude compound was purified by washing with n-pentane to give (S)-3-chloro-2-fluoro-6-(3-methylmorpholino)pyridin-4-amine (13.5 g, 93.1%) as an off-white solid. LC-MS: m/z 246.0 (M+H).

Synthesis of 3-chloro-6-((S)-4-((S)-1-cyclopropylethyl)-2-methylpiperazin-1-yl)-2-fluoropyridin-4-amine and 3-chloro-6-((S)-4-((R)-1-cyclopropylethyl)-2-methylpiperazin-1-yl)-2-fluoropyridin-4-amine

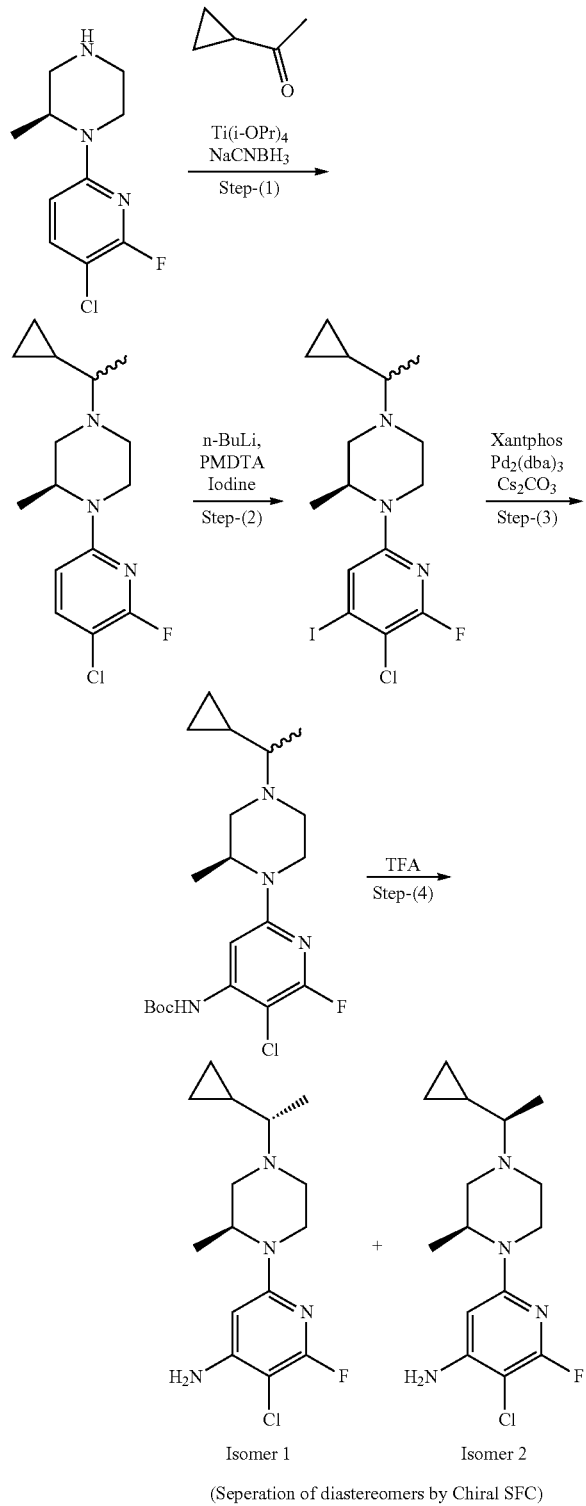

(Seperation of diastereomers by Chiral SFC)

Step 1: To a stirred solution of (S)-1-(5-chloro-6-fluoropyridin-2-yl)-2-methylpiperazine (5 g, 21.83 mmol, 1 eq) in MeOH (100 mL) was added cyclopropyl methyl ketone (2.75 g, 32.75 mmol, 1.5 eq), Ti(i-OPr)$_4$ (9.68 mL, 32.75 mmol, 1.5 eq) and Na(OAc)$_3$BH (9.25 g, 43.66 mmol, 2 eq) at RT under an argon atmosphere and stirring continued for 2 h, after which NaCNBH$_3$ (2.75 g, 43.66 mmol, 2 eq) was added at RT and stirring continued for 2 h. Additional cyclopropyl methyl ketone (2.75 g, 32.75 mmol, 1.5 eq) and NaCNBH$_3$ (2.75 g, 43.66 mmol, 2 eq) were added then stirring continued for 16 h. TLC analysis indicated formation of a less polar spot. The reaction mixture was diluted with water and filtered through a celite pad and the filtrate was extracted with EtOAc (3×100 mL). The combined organic layer was dried over Na$_2$SO$_4$ then concentrated to crude compound. The crude compound was purified by column chromatography (silica gel, 100-200 mesh) using 0-20% EtOAc in petroleum ether as eluent to afford (2S)-1-(5-chloro-6-fluoropyridin-2-yl)-4-(1-cyclopropylethyl)-2-methylpiperazine (2.5 g, 38.5%) as pale yellow oil. LCMS: m/z 298.08 (M+H).

Step 2: To a stirred solution of (2S)-1-(5-chloro-6-fluoropyridin-2-yl)-4-(1-cyclopropylethyl)-2-methylpiperazine (700 mg, 2.35 mmol, 1 eq) in THF (15 mL) was added PMDTA (0.98 mL, 4.71 mmol, 2 eq) and n-BuLi (1.88 mL, 4.71 mmol, 2 eq, 2.5 M in THF) at −78° C. under an argon atmosphere then the reaction mixture was continued for 2 h. A solution of 12 (1.19 g, 4.71 mmol, 2 eq, in THF) was then added at −78° C., and after that the mixture slowly allowed to warm to RT and stirred for 16 h. TLC analysis indicated formation of a less polar spot. The reaction mixture was quenched in an aqueous solution of sodium thiosulphate then extracted with EtOAc (3×50 mL). The combined organic layer was dried over Na$_2$SO$_4$ then concentrated under reduced pressure to give crude (2S)-1-(5-chloro-6-fluoro-4-iodopyridin-2-yl)-4-(1-cyclopropylethyl)-2-methylpiperazine (950 mg, crude) as a brown oil. LC-MS: m/z 423.94 (M+H).

Step 3: To a stirred solution of (2S)-1-(5-chloro-6-fluoro-4-iodopyridin-2-yl)-4-(1-cyclopropylethyl)-2-methylpiperazine (950 mg, 2.24 mmol, 1 eq) in toluene (15 mL) was added Cs$_2$CO$_3$ (1.45 g, 4.49 mmol, 2 eq) and NH$_2$Boc (312 mg, 2.69 mmol, 1.2 eq) at RT then the reaction mixture was degassed with argon for 20 min. Then xantphos (39 mg, 0.067 mmol, 0.03 eq) and Pd$_2$(dba)$_3$ (61.7 mg, 0.067 mmol, 0.03 eq) were added at RT, and after that the reaction mixture was heated to 90° C. for 16 h. TLC analysis indicated formation of a polar spot. The reaction mixture was filtered through a celite pad then the filtrate was concentrated to crude compound. The crude compound was purified by column chromatography (silica gel, 100-200 mesh) using 0-5% EtOAc in petroleum ether as eluent to afford tert-butyl (3-chloro-6-((2S)-4-(1-cyclopropylethyl)-2-methylpiperazin-1-yl)-2-fluoropyridin-4-yl)carbamate (600 mg, 61.7% per two steps) as a light yellow oil. LC-MS: m/z 413.10 (M+H).

Step 4: To a stirred solution of tert-butyl (3-chloro-6-((2S)-4-(1-cyclopropylethyl)-2-methylpiperazin-1-yl)-2-fluoropyridin-4-yl)carbamate (6 g, 14.56 mmol, 1 eq) in DCM (60 mL) was added TFA (11.16 mL, 145.63 mmol, 10 eq) at RT and stirring continued for 16 h. TLC analysis indicated formation of a polar spot. The reaction mixture was concentrated to crude, which was basified by aqueous NaHCO$_3$ solution then extracted with EtOAc (4×100 mL). The combined organic layer was dried over Na$_2$SO$_4$ then concentrated under reduced pressure to crude compound. The crude compound was purified by column chromatography (silica gel, 100-200 mesh) using 0-20% EtOAc in petroleum ether as eluent to afford a mixture of 3-chloro-6-((S)-4-((S)-1-cyclopropylethyl)-2-methylpiperazin-1-yl)-2-fluoropyridin-4-amine (Isomer 1) and 3-chloro-6-((S)-4-((R)-1-cyclopropylethyl)-2-methylpiperazin-1-yl)-2-fluoropyridin-4-amine (Isomer 2) (3.9 g, 85.9%) as an off-white semi-solid. This mixture of isomers was separated by chiral SFC and isolated to afford 1.4 g of Isomer 1 as an off-white solid [LC-MS: m/z 313.32 (M+H)]; and 1.8 g of Isomer 2 as a brown oil. LC-MS: m/z 313.32 (M+H).

Synthesis of 5-chloro-6-fluoro-N2,N2-dimethylpyridine-2,4-diamine

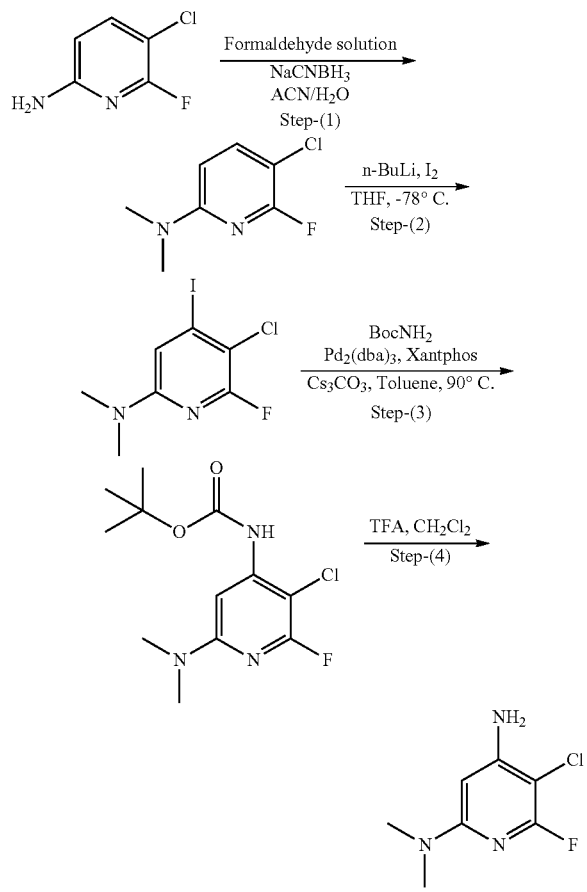

Step 1: To an ice-cold mixture of 5-chloro-6-fluoropyridin-2-ylamine (2.0 g, 13.65 mmol) in acetonitrile (60 mL) was added sequentially water (10 mL) followed by formaldehyde solution (37% wt in water, 20.32 mL, 273 mmol) and sodium cyanoborohydride (4.29 g, 68.2 mmol). The resulting reaction was stirred at 0° C. for 10 min followed by dropwise addition of acetic acid (5.0 mL). The reaction mixture was then allowed to stir at RT overnight. Additional formaldehyde solution (37% wt in water, 20.32 mL, 273 mmol), sodium cyanoborohydride (4.29 g, 68.2 mmol) and acetic acid (5.0 mL) were added. The reaction was allowed to stir overnight. The solvent was evaporated and the residue was treated with 1N NaOH$_{(aq)}$ solution and extracted three times with EtOAc. The combined organic layers were dried with Na$_2$SO$_4$, filtered and concentrated. The residue was purified on a Biotage eluting with 0-5% EtOAc/hexane to give 5-chloro-6-fluoro-N,N-dimethylpyridin-2-amine (5.74 mmol, 42.1% yield). $^1$H NMR (500 MHz, DMSO-d$_6$) δ=8.12 (dd, J=8.9, 9.7 Hz, 1H), 6.93 (d, J=8.8 Hz, 1H), 3.41 (s, 6H); LCMS (m/z): 175.3 [M+1]$^+$.

Step 2: To a −78° C. solution of 5-chloro-6-fluoro-N,N-dimethylpyridin-2-amine (1.00 g, 5.74 mmol) in anhydrous tetrahydrofuran (15 mL) was added 1,1,4,7,7-pentamethyldiethylenetriamine (2.64 mL, 12.63 mmol) and n-butyllithium solution (2.5 M in hexanes, 5.05 mL, 12.63 mmol). The reaction was stirred at −78° C. for 1.5 h and then a solution of iodine (resublimed) (2.92 g, 11.49 mmol) in tetrahydrofuran (3.0 mL) was added, followed by warming up to RT overnight. The reaction mixture was quenched with a saturated aqueous solution of sodium thiosulfate then extracted with EtOAc (2×). The combined organic layers were dried over Na$_2$SO$_4$ then concentrated and dried on the h/v overnight to give 5-chloro-6-fluoro-4-iodo-N,N-dimethylpyridin-2-amine (5.37 mmol, 93% yield) as a brown solid. The crude product was carried onto the next step without purification. LCMS (m/z): 301.2 [M+1]$^+$.

Step 3: To a stirred solution of 5-chloro-6-fluoro-4-iodo-N,N-dimethylpyridin-2-amine (1.376 g, 4.58 mmol) in toluene (20 mL) was added cesium carbonate (2.98 g, 9.16 mmol) and tert-butyl carbamate (0.644 g, 5.49 mmol). The system was flushed with nitrogen for 5 minutes, then Xantphos (0.159 g, 0.275 mmol) and tris(dibenzylideneacetone)dipalladium(0) (0.252 g, 0.275 mmol) were added. The system was flushed with nitrogen then heated at 90° C. for 16 h. The reaction mixture was concentrated onto celite and purified by column chromatography (silica gel) eluting with 0-5% MeOH/DCM. The desired fractions were collected, concentrated, and dried under vacuum to afford tert-butyl (3-chloro-6-(dimethylamino)-2-fluoropyridin-4-yl) carbamate (4.18 mmol, 91% yield). $^1$H NMR (500 MHz, DMSO-d$_6$) δ=8.69-8.66 (m, 1H), 7.02 (s, 1H), 2.97 (s, 6H), 1.48 (s, 9H); LCMS (m/z): 290.4 [M+1]$^+$.

Step 4: To a solution of tert-butyl (3-chloro-6-(dimethylamino)-2-fluoropyridin-4-yl)carbamate (1.211 g, 4.18 mmol) in dichloromethane (1 mL) was added trifluoroacetic acid (3.20 mL, 41.8 mmol) and the mixture stirred at room temperature for 1 h. Upon completion of the reaction as judged by LCMS, the reaction was concentrated to remove the volatiles. The reaction was diluted with EtOAc and partitioned between EtOAc and water. The aqueous layer was neutralized with the addition of NaHCO$_3$ [both saturated solution and extra solid]. The layers were separated and the aqueous layer was extracted with EtOAc. The combined organic layers were dried over Na$_2$SO$_4$, filtered and concentrated in vacuo. The crude compound was purified on a Biotage (reverse phase silica gel) eluting with 0-40% ACN/H$_2$O. The fractions were collected, concentrated, and dried under vacuum to afford 5-chloro-6-fluoro-N2,N2-dimethylpyridine-2,4-diamine (2.73 mmol, 65.2% yield) as a white solid.

Synthesis of 3-chloro-2-fluoro-6-(pyrrolidin-1-yl)pyridin-4-amine

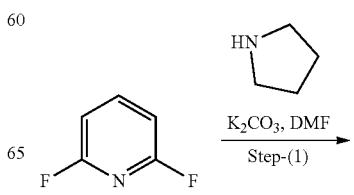

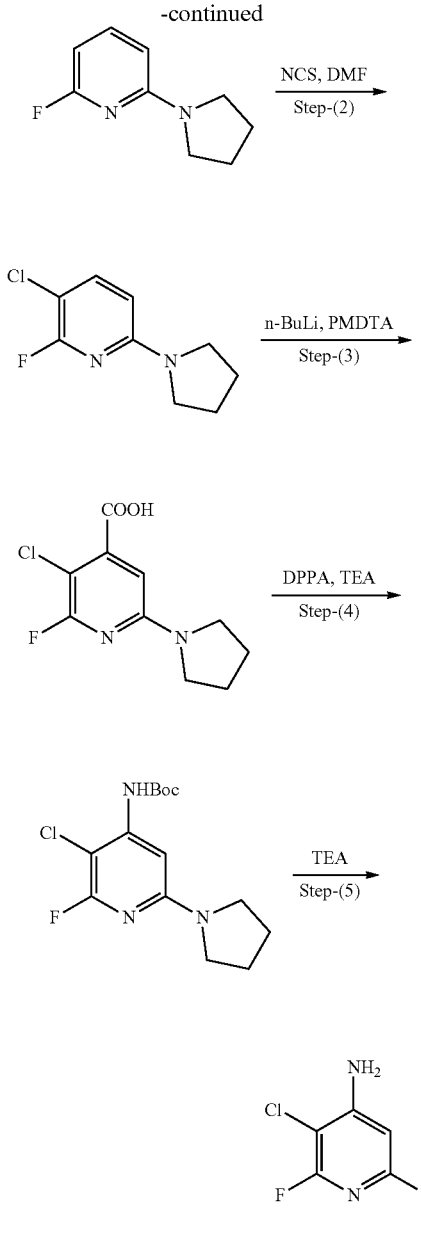

Step 1: To a stirred solution of 2,6-difluoropyridine (10 g, 86.9 mmol, 1 eq) in DMF (100 mL) was added K$_2$CO$_3$ (24 g, 173.9 mmol, 2 eq) followed by pyrrolidine (10.7 mL, 130.4 mmol, 1.5 eq) at RT and the resultant reaction mixture was heated at 90° C. for 16 h. The reaction was monitored by TLC, and TLC analysis indicated formation of a polar spot. The reaction mixture was quenched with ice water and extracted with ethyl acetate (2×200 mL). The combined organic layer was dried over Na$_2$SO$_4$ and concentrated under reduced pressure. The crude product was purified by column chromatography (silica gel, 100-200 mesh) using 0-4% ethyl acetate in petroleum ether as an eluent to afford 2-fluoro-6-(pyrrolidin-1-yl)pyridine (9 g, 62.5% yield) as a pale yellow liquid. LCMS: m/z 167.36 (M+H).

Step 2: To a stirred solution of 2-fluoro-6-(pyrrolidin-1-yl)pyridine (10 g, 60.24 mmol, 1 eq) in DMF (200 mL), was added NCS (8.8 g, 66.2 mmol, 1.1 eq) and the resultant reaction mixture was heated at 60° C. for 2 h. The reaction was monitored by TLC, and TLC analysis indicated formation of a non-polar spot. The reaction mixture was quenched with ice water and extracted with ethyl acetate (2×500 mL). The combined organic layer was dried over Na$_2$SO$_4$ and concentrated under reduced pressure. The crude product was purified by column chromatography (silica gel, 230-400 mesh) using 0-10% ethyl acetate in petroleum ether as an eluent to afford 3-chloro-2-fluoro-6-(pyrrolidin-1-yl)pyridine (8 g, 67.2% yield) as an off-white solid. LCMS: m/z 201.34 (M+H).

Step 3: A stirred solution of 3-chloro-2-fluoro-6-(pyrrolidin-1-yl)pyridine (8 g, 40.2 mmol, 1 eq) in dry THF (160 mL) was cooled to −78° C. and PMDTA (33.57 mL, 160.8 mmol, 4 eq) was added followed by dropwise addition of n-BuLi (2.5 M in hexane, 64.3 mL, 160.8 mmol, 4 eq) and the resultant reaction mixture was stirred at the same temperature for 3 h. The reaction mixture was quenched with crushed dry CO$_2$ and stirred at RT for 16 h. The reaction was monitored by TLC, and TLC analysis indicated formation of a polar spot. The reaction mixture was diluted with water and ethyl acetate, and the aqueous layer was acidified with 1N HCl and extracted with ethyl acetate. The combined organic layer was dried over Na$_2$SO$_4$ and concentrated under reduced pressure to afford 3-chloro-2-fluoro-6-(pyrrolidin-1-yl)isonicotinic acid (8 g, 81.6% yield) as a pale yellow solid. LCMS: m/z 245.34% (M+H).

Step 4: A stirred solution of 3-chloro-2-fluoro-6-(pyrrolidin-1-yl)isonicotinic acid (8 g, 32.7 mmol, 1 eq) in t-BuOH:toluene (1:1) (160 mL), was cooled to 0° C. and TEA (3.8 mL, 49.18 mmol, 1.5 eq) was added followed by DPPA (18.7 mL, 49.18 mmol, 1.5 eq) and the resultant reaction mixture was heated at 85° C. for 16 h. The reaction was monitored by TLC, and TLC analysis indicated formation of a non-polar spot. The solvent was concentrated under reduced pressure to yield crude product. The crude product was diluted with ethyl acetate (300 mL) and washed with saturated brine solution. The combined organic layer was dried over Na$_2$SO$_4$ and concentrated under reduced pressure. The crude product was purified by column chromatography (silica gel, 230-400 mesh) using 0-20% ethyl acetate in petroleum ether as an eluent to afford tert-butyl (3-chloro-2-fluoro-6-(pyrrolidin-1-yl)pyridin-4-yl)carbamate (5 g, 48.5% yield) as a pale yellow solid. LCMS: m/z 316.40 (M+H).

Step 5: To a stirred solution of tert-butyl (3-chloro-2-fluoro-6-(pyrrolidin-1-yl)pyridin-4-yl)carbamate (5 g, 15.87 mmol, 1 eq) in DCM (50 mL), was added TFA (12.9 mL, 158.7 mmol, 10 eq) dropwise and the resultant reaction mixture was stirred at RT for 16 h. The reaction was monitored by TLC, and TLC analysis indicated formation of a polar spot. The reaction mixture was concentrated under reduced pressure, basified with saturated aqueous NaHCO$_3$ solution and extracted with ethyl acetate (2×200 mL). The combined organic layer was dried over Na$_2$SO$_4$ and concentrated under reduced pressure. The crude was triturated with n-pentane to afford 3-chloro-2-fluoro-6-(pyrrolidin-1-yl)pyridin-4-amine (3 g, 88.2% yield) as a pale brown solid. LCMS: m/z 216.36 (M+H).

Synthesis of 3-chloro-2-fluoro-6-((2R,6S)-2,4,6-trimethylpiperazin-1-yl)pyridin-4-amine

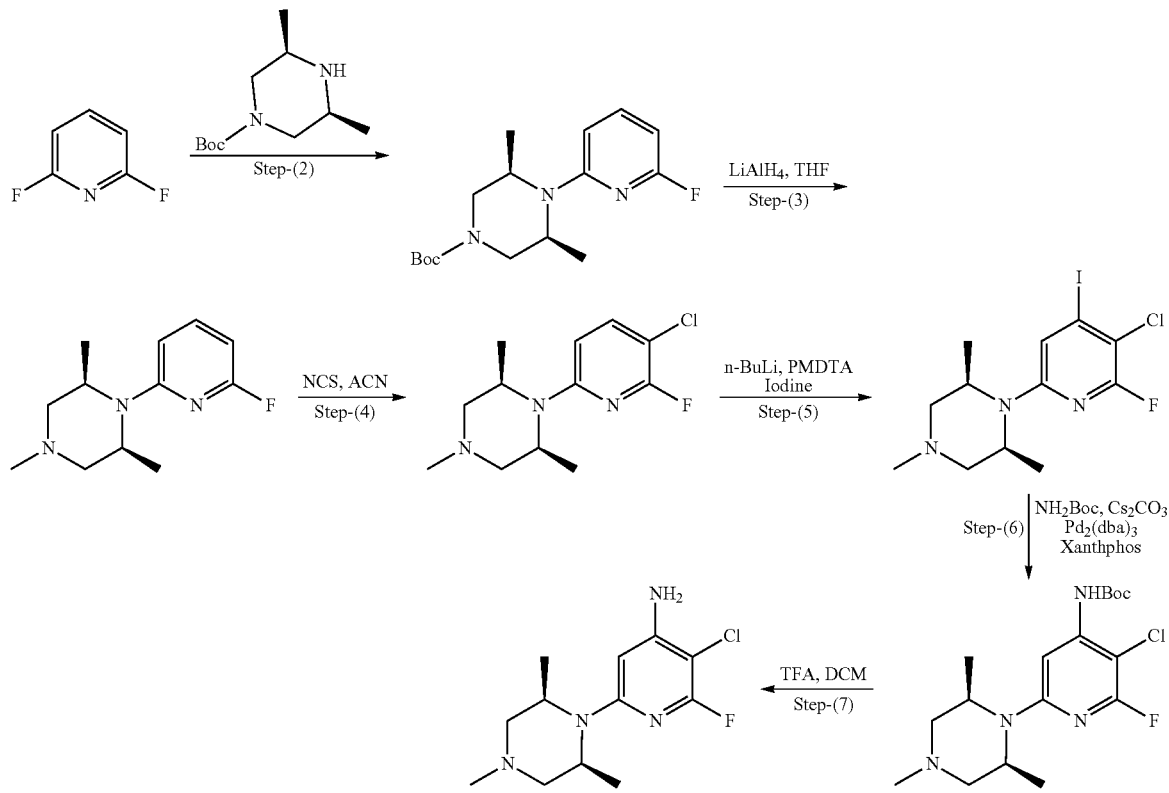

Step 1: A stirred solution of (2S,6R)-2,6-dimethylpiperazine (25 g, 219.1 mmol, 1 eq) in DCM (250 mL) was cooled to 0° C., (Boc)₂O (55.36 mL, 241.01 mmol, 1.1 eq) was added and the resultant reaction mixture was stirred overnight at room temperature. The reaction was monitored with TLC, and TLC indicated formation of a non-polar spot. The reaction mixture was diluted with water (100 mL) and extracted with EtOAc (3×300 mL). The combined organic layer was dried over Na₂SO₄, and concentrated under reduced pressure to give crude product. The crude product was purified by filtered column chromatography (silica gel, 230-400 mesh) using 0-5% methanol in DCM as an eluent to afford (3S,5R)-tert-butyl 3,5-dimethylpiperazine-1-carboxylate (37 g, 78.89% yield) as a pale brown semi-solid.

Step 2: A stirred solution of (3S,5R)-tert-butyl 3,5-dimethylpiperazine-1-carboxylate (20 g, 93.0 mmol, 1 eq) in LiHMDS (200 mL) was cooled to 0° C. and 2,6-difluoropyridine (26.8 mL, 280.3 mmol, 3 eq), and xanthophos (3.24 g, 5 mmol, 0.06 eq) were added followed by Pd₂(dba)₃ (2.5 g, 2.7 mmol, 0.03 eq). Then, the resultant reaction mixture was stirred overnight at 80° C. The reaction was monitored with TLC, and TLC indicated formation of a non-polar spot. The reaction mixture was quenched with ice water (100 mL), filtered through celite and washed with ethyl acetate. The layers were separated, and the aqueous layer extracted with ethyl acetate (2×150 mL) and washed with brine solution (1×100 mL). The combined organic layer was dried over Na₂SO₄, and concentrated under reduced pressure to give crude product. The crude product was purified by column chromatography (silica gel, 100-200 mesh) using 0-5% ethyl acetate in petroleum ether as an eluent to afford (3R,5S)-tert-butyl 4-(6-fluoropyridin-2-yl)-3,5-dimethylpiperazine-1-carboxylate (20 g, 37.73% yield) as a brown liquid. LCMS: m/z 310.54 (M+H).

Step 3: A stirred solution of (3R,5S)-tert-butyl 4-(6-fluoropyridin-2-yl)-3,5-dimethylpiperazine-1-carboxylate (10 g, 32.36 mmol, 1 eq) in THF (90 mL) was cooled to 0° C. and LAH (4.91 g, 129.4 mmol, 4 eq) added portionwise. Then, the reaction mass was stirred overnight at room temperature. The reaction was monitored by TLC, and TLC analysis indicated formation of a polar spot. The reaction mixture was quenched with H₂O (10 mL), and aqueous 2N NaOH solution (5 mL) and the resulting suspension was stirred for 15 min, filtered through celite and washed with ethyl acetate. The layers were separated, and the organic layer was dried over Na₂SO₄ and concentrated under reduced pressure to give crude product. The crude product was purified by column chromatography (silica gel, 100-200 mesh) using 15-20% ethyl acetate in petroleum ether as an eluent to afford (2R,6S)-1-(6-fluoropyridin-2-yl)-2,4,6-trimethylpiperazine (6.13 g, 85% yield) as a brown liquid. LCMS: m/z 224.46 (M+H).

Step 4: To a stirred solution of (2R,6S)-1-(6-fluoropyridin-2-yl)-2,4,6-trimethylpiperazine (5 g, 22.42 mmol, 1 eq) in ACN (100 mL) was added NCS (3.3 g, 24.66 mmol, 1.1 eq) and the resultant reaction mixture was heated at 75° C. for 3-4 h in a preheated oil bath. The reaction was monitored by TLC, and TLC analysis indicated formation of a non-polar spot. The solvent was concentrated under reduced pressure to give crude product. The crude product was purified by column chromatography (silica gel, 230-400 mesh) using 0-5% methanol in DCM as an eluent to afford (2R,6S)-1-(5-chloro-6-fluoropyridin-2-yl)-2,4,6-trimethylpiperazine (4 g, 71.42% yield) as a pale brown liquid. LCMS: m/z 258.44 (M+H).

Step 5: To a stirred solution of (2R,6S)-1-(5-chloro-6-fluoropyridin-2-yl)-2,4,6-trimethylpiperazine (10 g, 38.8 mmol, 1 eq) in dry THF (400 mL) was added PMDTA (30 mL, 155.2 mmol, 4 eq), then the mixture cooled to −78° C. and n-BuLi (2.5 M in hexane, 60 mL, 155.2 mmol, 4 eq) added dropwise. Then, the resultant reaction mixture was stirred for 2 h at the same temperature. To the reaction mixture was added a solution of iodine (19.7 g, 77.6 mmol, 2 eq) in dry THF (200 mL) at −78° C. and the mixture stirred for 10 min. The reaction was monitored by TLC, and TLC analysis indicated formation of a non-polar spot. The reaction was quenched with sodium thiosulphate (hypo solution; 100 mL), extracted with ethyl acetate (2×200 mL) and washed with brine solution (1×100 mL). The combined organic layer was dried over $Na_2SO_4$, and concentrated under reduced pressure to give crude product. The crude product was purified by column chromatography (silica gel, 100-200 mesh) using 10-20% ethyl acetate in petroleum ether as an eluent to afford (2R,6S)-1-(5-chloro-6-fluoro-4-iodopyridin-2-yl)-2,4,6-trimethylpiperazine (7.3 g, 48.99% yield) as a pale yellow liquid. LCMS: m/z 384.1 (M+H).

Step 6: To a stirred solution of (2R,6S)-1-(5-chloro-6-fluoro-4-iodopyridin-2-yl)-2,4,6-trimethylpiperazine (7.3 g, 19.06 mmol, 1 eq) in toluene (70 mL) was added $NH_2Boc$ (2.67 g, 22.3 mmol, 1.2 eq), and $Cs_2CO_3$ (12.38 g, 38.4 mmol, 2 eq) followed by xantphos (0.66 g, 1.1 mmol, 0.06 eq). Then, the resultant reaction mixture was degassed under a nitrogen atmosphere for 20 min, and $Pd_2(dba)_3$ (0.52 g, 0.52 mmol, 0.03 eq) was added. Then, the resultant reaction mixture was stirred overnight at 95° C. The reaction was monitored with TLC, and TLC indicated formation of a polar spot. The reaction mixture was filtered through celite and washed with ethyl acetate. The filtrate was dried over $Na_2SO_4$ and concentrated under reduced pressure to give crude product. The crude product was purified by column chromatography (silica gel, 100-200 mesh) using 0-1% methanol in DCM as an eluent to afford tert-butyl (3-chloro-2-fluoro-6-((2R,6S)-2,4,6-trimethylpiperazin-1-yl)pyridin-4-yl)carbamate (5 g, 70.52% yield) as a pale brown liquid. LCMS: m/z 373.54 (M+H).

Step 7: A stirred solution of tert-butyl (3-chloro-2-fluoro-6-((2R,6S)-2,4,6-trimethylpiperazin-1-yl)pyridin-4-yl)carbamate (5 g, 13.4 mmol, 1 eq) in DCM (100 mL) was cooled to 0° C. and TFA (15.6 mL, 134.0 mmol, 10 eq) added. Then, the resultant reaction mixture was stirred overnight at room temperature. The reaction was monitored by TLC, and TLC analysis indicated formation of a polar spot. The solvent was concentrated under reduced pressure and the crude was basified (pH 8) with aqueous $NaHCO_3$ solution and extracted with ethyl acetate (2×100 mL). The combined organic layer was dried over $Na_2SO_4$, and concentrated under reduced pressure to give crude product. The crude product was washed with pentane and diethyl ether, filtered and dried to afford 3-chloro-2-fluoro-6-((2R,6S)-2,4,6-trimethylpiperazin-1-yl)pyridin-4-amine (2.1 g, 57.53% yield) as a pale brown solid. LCMS: m/z 273.05 (M+H).

Synthesis of 3-chloro-2-fluoro-6-((2S,6S)-2,4,6-trimethylpiperazin-1-yl)pyridin-4-amine

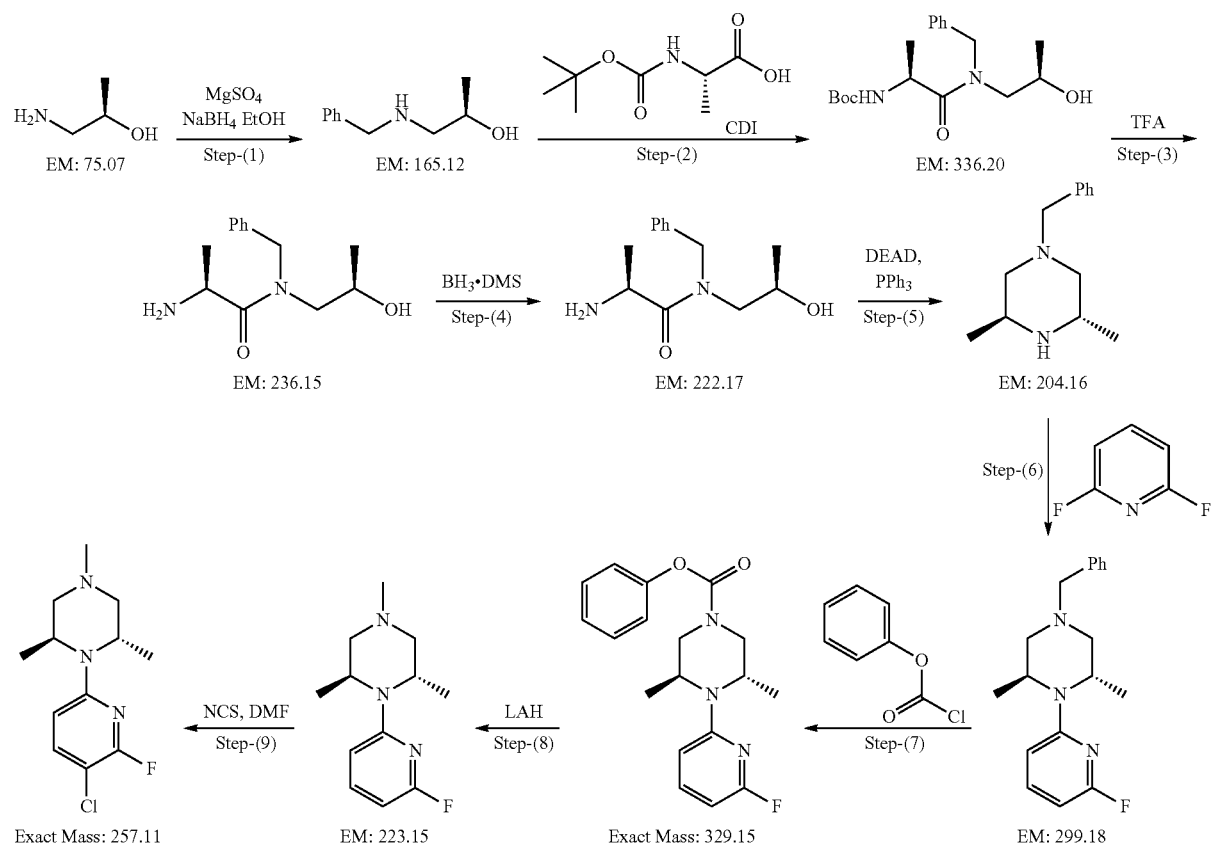

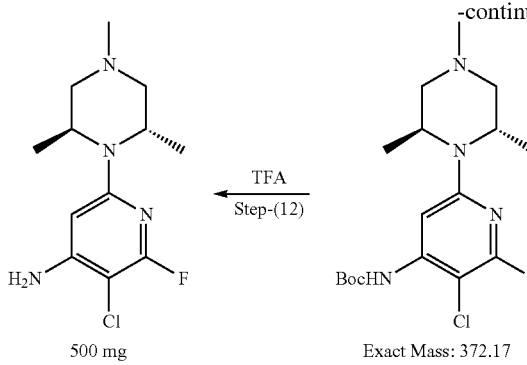 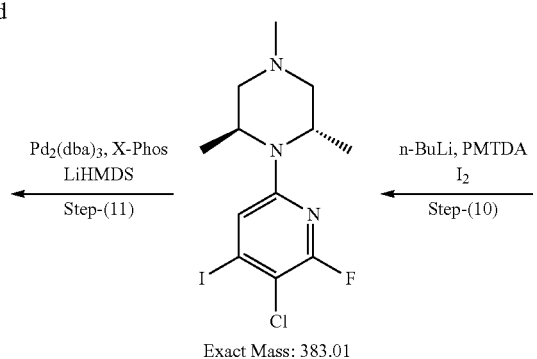

Step 1: A stirred solution of (R)-1-aminopropan-2-ol (50 g, 665 mmol, 1 eq) in THF (1680 mL), was cooled to 0° C. and MgSO₄ (41 g, 340 mmol, 0.5 eq) was added followed by benzaldehyde (81.5 mL, 798 mmol, 1.5 eq) dropwise and the resultant reaction mixture was stirred at RT for 4 h. The reaction mixture was filtered, and the filtrate was concentrated under reduced pressure. The crude was diluted with ethanol (1680 mL), cooled to 0° C. and NaBH₄ (8.4 g, 222 mmol, 0.325 eq) added and the resultant reaction mixture was stirred at RT for an additional 2 h before additional NaBH₄ (8.4 g, 222 mmol, 0.325 eq) was added at 0° C. The mixture was then slowly warmed to rt and stirred for 72 h. The reaction was monitored with TLC, and TLC analysis indicated formation of a non-polar spot. The solvent was evaporated under reduced pressure, then the crude was diluted with ethyl acetate and extracted with aqueous 2N HCl solution. The aqueous layer was basified with saturated NaHCO₃ solution and extracted with 5% methanol:DCM. The combined organic layer was dried over Na₂SO₄ and concentrated under reduced pressure to afford (R)-1-(benzylamino)propan-2-ol (91 g, 82.7% yield) as a brown semisolid.

Step 2: To a stirred solution of (S)-2-((tert-butoxycarbonyl)amino)propanoic acid (104.5 g, 551.5 mmol, 1 eq) in DCM (1820 mL) was added CDI (89.43 g, 551.5 mmol, 1 eq) and the resultant reaction mixture was stirred at RT for 1 h. (R)-1-(Benzylamino)propan-2-ol (91 g, 551.5 mmol, 1 eq) was added and the resultant reaction mixture was stirred at RT for 16 h. The reaction was monitored by TLC, and TLC analysis indicated formation of a polar spot. The reaction mixture was concentrated under reduced pressure and the crude was purified by column chromatography (silica gel, 100-200 mesh) using 20%-50% ethyl acetate in petroleum ether as an eluent to afford tert-butyl ((S)-1-(benzyl((R)-2-hydroxypropyl)amino)-1-oxopropan-2-yl)carbamate (98 g, 52.9% yield) as a pale brown liquid. LCMS m/z 337.32 (M+H).

Step 3: To a stirred solution of tert-butyl ((S)-1-(benzyl((R)-2-hydroxypropyl)amino)-1-oxopropan-2-yl)carbamate (98 g, 291 mmol, 1 eq) in DCM (980 mL), was added TFA (490 mL, 6403 mmol, 5 eq) dropwise and the resultant reaction mixture was stirred at RT for 30 min. The reaction was monitored by TLC, and TLC analysis indicated formation of a polar spot. The reaction mixture was concentrated under reduced pressure, basified with saturated aqueous NaHCO₃ solution and extracted with 5% methanol:DCM (2×500 mL). The combined organic layer was dried over Na₂SO₄ and concentrated under reduced pressure to afford (S)-2-amino-N-benzyl-N—((R)-2-hydroxypropyl)propanamide (67 g, 97.3% yield) as a pale brown liquid. LCMS: m/z 237.05 (M+H).

Step 4: A stirred solution of (S)-2-amino-N-benzyl-N—((R)-2-hydroxypropyl)propanamide (30 g, 127 mmol, 1 eq) in THF (570 mL), was cooled to 0° C. and Borane DMS (44.4 mL, 444 mmol, 3.5 eq) was added. The resultant reaction mixture was stirred at RT for 16 h. The reaction mixture was quenched with 20% aqueous HCl (100 mL) followed by a solution of KOH (200 g) in H₂O (400 mL) and the resultant reaction mixture was heated at 70° C. for 24 h. The reaction mixture was cooled to 0° C., methanol (100 mL) was added and the resultant reaction mixture was refluxed at 75° C. for 24 h. The reaction was monitored by TLC, and TLC analysis indicated formation of a non-polar spot. The solvent was concentrated under reduced pressure to yield crude product. The crude was diluted with water and extracted with DCM. The combined organic layer was dried over Na₂SO₄ and concentrated under reduced pressure. The crude product was purified by column chromatography (neutral alumina) using 5-10% methanol in DCM as an eluent to afford (R)-1-(((S)-2-aminopropyl)(benzyl)amino)propan-2-ol (16.5 g, 58.5% yield) as a pale brown liquid. LCMS: m/z 223.26 (M+H).

Step 5: A stirred solution of (R)-1-(((S)-2-aminopropyl)(benzyl)amino)propan-2-ol (14 g, 63 mmol, 1 eq) in THF (560 mL), was cooled to 0° C. and TPP (33 g, 126 mmol, 2 eq) was added, followed by DIAD (25 mL, 126 mmol, 2 eq) dropwise and the resultant reaction mixture was stirred at RT for 16 h. The reaction was monitored by TLC, and TLC analysis indicated formation of a non-polar spot. The solvent was concentrated under reduced pressure to yield crude product. The crude product was purified by column chromatography (silica gel, 230-400 mesh) using 5-8% methanol in DCM as an eluent to afford (3S,5S)-1-benzyl-3,5-dimethylpiperazine (4.7 g, 36.7% yield) as a pale yellow liquid. LCMS: 76.55% with m/z 205.24% (M+H).

Step 6: To (3S,5S)-1-benzyl-3,5-dimethylpiperazine (2 g, 9.7 mmol, 1 eq) in LiHMDS (20 mL), was added 2,6-difluoropyridine (2.66 mL, 29.3 mmol, 3 eq), and Pd(OAc)₂ (0.22 g, 0.97 mmol, 0.1 eq) followed by BINAP (0.65 g, 0.97 mmol, 0.1 eq) and the resultant reaction mixture was heated in a sealed tube at 85° C. for 16 h. The reaction was monitored by TLC, and TLC analysis indicated formation of a non-polar spot. The reaction mixture was quenched with ice cold water, filtered through celite and washed with ethyl acetate. The filtrate was dried over Na₂SO₄ and concentrated under reduced pressure to afford (2S,6S)-4-benzyl-1-(6-fluoropyridin-2-yl)-2,6-dimethylpiperazine (770 mg, 26.2% yield) as a pale yellow liquid. LCMS: m/z 300.34 (M+H).

Step 7: To a stirred solution of (2S,6S)-4-benzyl-1-(6-fluoropyridin-2-yl)-2,6-dimethylpiperazine (2.15 g, 7.1 mmol, 1 eq) in DCM (43 mL), was added phenyl chloroformate (2.7 mL, 21.5 mmol, 3 eq) followed by sodium bicarbonate (1.81 g, 21.5 mmol, 3 eq) and the resultant reaction mixture was stirred at RT for 16 h. The reaction was monitored by TLC, and TLC analysis indicated formation of a polar spot. The reaction mixture was diluted with water and extracted with DCM. The combined organic layer was dried over $Na_2SO_4$ and concentrated under reduced pressure. The crude product was purified by column chromatography (neutral alumina) using 4% ethyl acetate in petroleum ether as an eluent to afford (3S,5S)-phenyl 4-(6-fluoropyridin-2-yl)-3,5-dimethylpiperazine-1-carboxylate (1.71 g, 72.45% yield) as an off-white solid. LCMS: m/z 330.24 (M+H).

Step 8: A stirred solution of (3S,5S)-phenyl 4-(6-fluoropyridin-2-yl)-3,5-dimethylpiperazine-1-carboxylate (1.71 g, 5.1 mmol, 1 eq) in THF (35 mL) was cooled to 0° C. and LAH (0.39 g, 10.3 mmol, 2 eq) added portionwise. The resultant reaction mixture was stirred at RT for 16 h. The reaction was monitored by TLC, and TLC analysis indicated formation of a polar spot. The reaction mixture was quenched with saturated aqueous sodium sulphate and stirred for 30 min, then filtered through celite. The filtrate was dried over $Na_2SO_4$ and concentrated under reduced pressure to afford (2S,6S)-1-(6-fluoropyridin-2-yl)-2,4,6-trimethylpiperazine (1 g, 86.9% yield) as a pale yellow liquid. LCMS: m/z 224.27 (M+H).

Step 9: To a stirred solution of (2S,6S)-1-(6-fluoropyridin-2-yl)-2,4,6-trimethylpiperazine (1 g, 4.4 mmol, 1 eq) in DMF (10 mL), was added NCS (0.717 g, 5.3 mmol, 1.2 eq) and the resultant reaction mixture was heated at 50° C. for 1 h in a preheated oil bath. The reaction was monitored by TLC, and TLC analysis indicated formation of a non-polar spot. The reaction mixture was quenched with ice cold water and extracted with ethyl acetate. The combined organic layer was washed with brine solution, dried over $Na_2SO_4$ and concentrated under reduced pressure. The crude product was purified by column chromatography (neutral alumina) using 10-30% ethyl acetate in petroleum ether as an eluent to afford (2S,6S)-1-(5-chloro-6-fluoropyridin-2-yl)-2,4,6-trimethylpiperazine (0.8 g, 69.5% yield) as a pale yellow liquid. LCMS: m/z 257.98 (M+H).

Step 10: A stirred solution of (2S,6S)-1-(5-chloro-6-fluoropyridin-2-yl)-2,4,6-trimethylpiperazine (1 g, 3.88 mmol, 1 eq) in THF (60 mL), was cooled to −78° C. and PMDTA (2.68 g, 15.52 mmol, 4 eq) was added followed by n-BuLi (2.5 M in hexane, 6.2 mL, 15.52 mmol, 4 eq) dropwise and the resultant reaction mixture was stirred at the same temperature for 2 h. A solution of iodine (1.96 g, 7.76 mmol, 2 eq) in THF (30 mL) was then added at −78° C. and the resultant reaction mixture was stirred for 15 min. The reaction was monitored by TLC, and TLC analysis indicated formation of a non-polar spot. The reaction mixture was quenched with ice cold water and extracted with ethyl acetate. The combined organic layer was dried over $Na_2SO_4$ and concentrated under reduced pressure to afford (2S,6S)-1-(5-chloro-6-fluoro-4-iodopyridin-2-yl)-2,4,6-trimethylpiperazine (1.2 g, 80.59% yield) as a pale brown liquid. LCMS: m/z 383.94% (M+H).

Step 11: To a stirred solution of (2S,6S)-1-(5-chloro-6-fluoro-4-iodopyridin-2-yl)-2,4,6-trimethylpiperazine (1 g, 3.1 mmol, 1 eq) in toluene (48 mL), was added $Cs_2CO_3$ (1.69 g, 5.2 mmol, 2 eq), and Boc amine (440 mg, 3.7 mmol, 1.2 eq) followed by xanthophos (91 mg, 0.15 mmol, 0.06 eq) and the resultant reaction mixture was degassed for 15 min under a nitrogen atmosphere. $Pd_2(dba)_3$ (72 mg, 0.07 mmol, 0.03 eq) was then added and the resultant reaction mixture was stirred at 110° C. for 16 h. The reaction was monitored by TLC, and TLC analysis indicated formation of a non-polar spot. The reaction mixture was filtered through celite and washed with ethyl acetate. The combined organic layer was dried over $Na_2SO_4$ and concentrated under reduced pressure. The crude product was purified by column chromatography (silica gel, 230-400 mesh) using 1-10% methanol in DCM as an eluent to afford tert-butyl (3-chloro-2-fluoro-6-((2S,6S)-2,4,6-trimethylpiperazin-1-yl)pyridin-4-yl)carbamate (0.87 g, 90% yield) as a pale yellow liquid. LCMS: m/z 373.09 (M+H).

Step 12: To a stirred solution of tert-butyl (3-chloro-2-fluoro-6-((2S,6S)-2,4,6-trimethylpiperazin-1-yl)pyridin-4-yl)carbamate (0.5 g, 1.34 mmol, 1 eq) in DCM (10 mL), was added TFA (1.03 mL, 13.4 mmol, 10 eq) dropwise and the resultant reaction mixture was stirred at RT for 16 h. The reaction was monitored by TLC, and TLC analysis indicated formation of a polar spot. The reaction mixture was concentrated under reduced pressure, and the crude was diluted with water and washed with ethyl acetate. The aqueous layer was basified with aqueous saturated $NaHCO_3$ solution and extracted with ethyl acetate (2×50 mL). The combined organic layer was dried over $Na_2SO_4$ and concentrated under reduced pressure. The crude product was purified by column chromatography (neutral alumina) using 1-10% methanol in DCM as an eluent to afford 3-chloro-2-fluoro-6-((2S,6S)-2,4,6-trimethylpiperazin-1-yl)pyridin-4-amine (0.185 g, 50.6% yield) as pale yellow liquid. LCMS: m/z 273.42 (M+H).

In a similar manner, the following compound was prepared:

| Aniline | Name | Yield & Mass |
|---|---|---|
| ![structure] | 5-chloro-2-((2S,6S)-2,4,6-trimethyl-piperazin-1-yl)pyridin-4-amine | 51% yield LCMS [M]+ 273.6 |

Synthesis of (S)-5-chloro-2-(2,4-dimethylpiperazin-1-yl)pyridin-4-amine

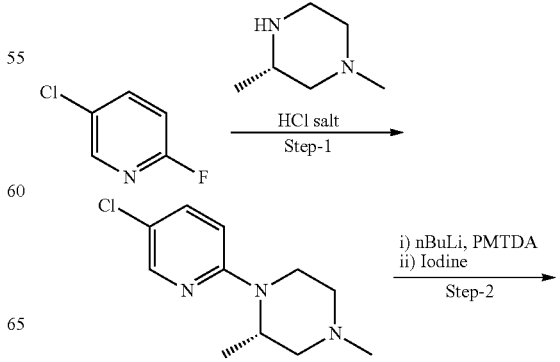

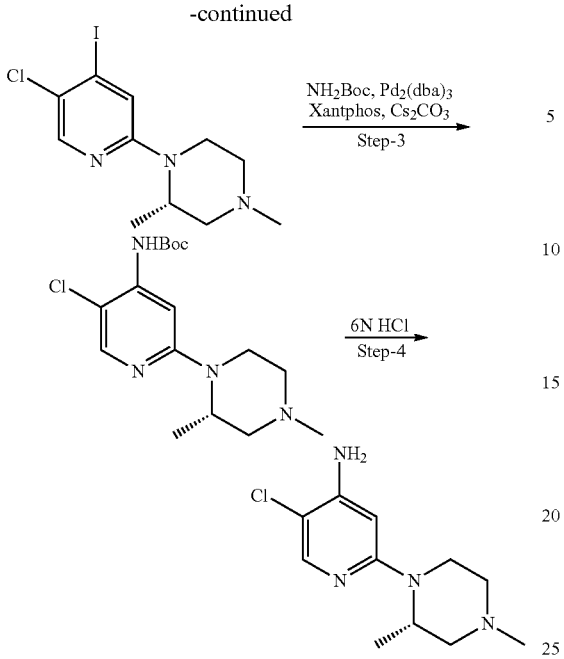

Step 1: To a stirred solution of the HCl salt of (S)-1,3-dimethylpiperazine (1 g, 5.43 mmol, 1 eq) in 1M Li-HMDS (54.3 mL, 54.34 mmol, 10 eq) was added 5-chloro-2-fluoropyridine (711 mg, 5.43 mmol, 1 eq), Xantphos (188 mg, 0.326 mmol, 0.06 eq) and $Pd_2(dba)_3$ (149 mg, 0.163 mmol, 0.03 eq) at RT and then the mixture heated to 70° C. for 6 h. The reaction mixture was quenched in ice water then extracted with EtOAc (3×50 mL). The combined organic layer was dried over $Na_2SO_4$ and concentrated under reduced pressure to give crude product. The crude product was purified by column chromatography (silica gel, 100-200 mesh) using 0-100% EtOAc in petroleum ether as an eluent to afford (S)-1-(5-chloropyridin-2-yl)-2,4-dimethylpiperazine (600 mg, 49.18%) as a brown oil. LC-MS: m/z 226.07 (M+H).

Step 2: To a stirred solution of (S)-1-(5-chloropyridin-2-yl)-2,4-dimethylpiperazine (1.2 g, 5.33 mmol, 1 eq) in THF (30 mL) was added PMDTA (1.66 mL, 7.99 mmol, 1.5 eq) and n-BuLi (2.13 mL, 7.99 mmol, 1.5 eq, 2.5 M in hexane) at −78° C. The mixture was then stirred for 1 h, quenched with $I_2$ (2.7 g, 10.66 mmol, 2 eq) at −78° C. and allowed to warm to RT and stir for 16 h. The reaction mixture was quenched in aqueous sodium thiosulphate and then extracted with EtOAc (3×70 mL). The combined organic layer was dried over $Na_2SO_4$ and concentrated under reduced pressure to give crude (S)-1-(5-chloro-4-iodopyridin-2-yl)-2,4-dimethylpiperazine (1.4 g, 74.86%) as a light brown oil. LC-MS: m/z 352.11 (M+H).

Step 3: To a stirred solution of (S)-1-(5-chloro-4-iodopyridin-2-yl)-2,4-dimethylpiperazine (1.8 g, 5.12 mmol, 1 eq) in toluene (30 mL) was added $NH_2Boc$ (714 mg, 6.15 mmol, 1.2 eq), $Cs_2CO_3$ (3.33 g, 10.25 mmol, 2 eq) and Xantphos (177 mg, 0.307 mmol, 0.06 eq) at RT then the mixture was degassed with argon for 10 min. After that, $Pd_2(dba)_3$ (141 mg, 0.153 mmol, 0.03 eq) was added at RT and then the mixture was heated to 100° C. for 16 h. The reaction mixture was filtered through a celite pad and the filtrate was concentrated to afford crude compound. The crude compound was purified by column chromatography (silica gel, 100-200 mesh) using 0-60% EtOAc in petroleum ether as an eluent to afford (S)-tert-butyl (5-chloro-2-(2,4-dimethylpiperazin-1-yl)pyridin-4-yl)carbamate (1 g, 57.47%) as a light brown oil. LC-MS: m/z 341.25 (M+H).

Step 4: To a stirred solution of (S)-tert-butyl (5-chloro-2-(2,4-dimethylpiperazin-1-yl)pyridin-4-yl)carbamate (1 g, 2.93 mmol, 1 eq) in THF (10 mL) was added 6N HCl (10 mL) at RT then the mixture stirred for 6 h. The reaction mixture was quenched in aqueous $NaHCO_3$ solution then extracted with EtOAc (3×50 mL). The combined organic layer was dried over $Na_2SO_4$ and concentrated under reduced pressure to give crude product. The crude product was purified by CombiFlash chromatography using 0-5% MeOH in DCM as eluent to afford (S)-5-chloro-2-(2,4-dimethylpiperazin-1-yl)pyridin-4-amine (650 mg, 92.19%) as a light brown oil. LC-MS: m/z 241.2 (M+H).

Synthesis of 5-chloro-2-((1R,5S)-3-methyl-3,8-diazabicyclo[3.2.1]octan-8-yl)pyridin-4-amine

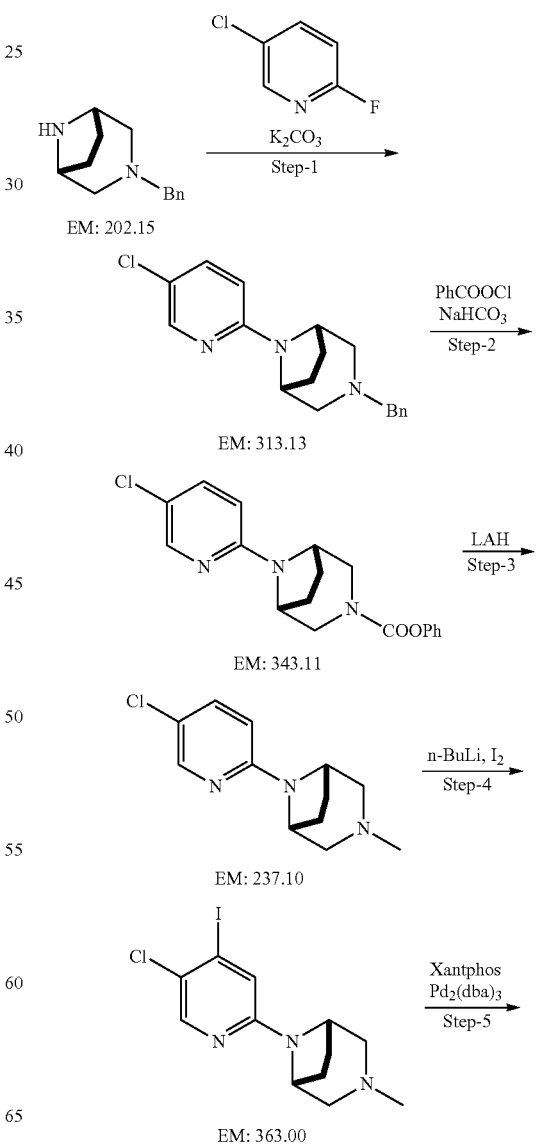

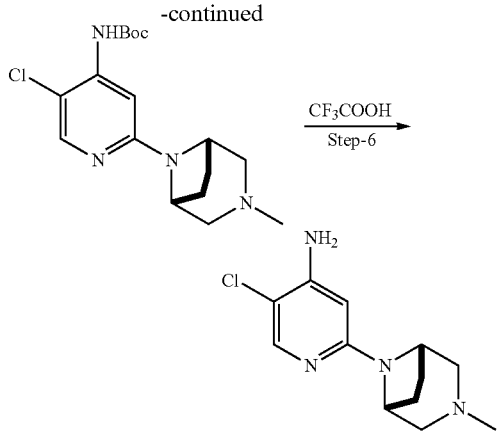

Step 1: To a solution of (1R,5S)-3-benzyl-3,8-diazabicyclo[3.2.1]octane (6 g, 29.7 mmol, 1.0 eq) in DMSO (60 mL) was added K₂CO₃ (12.3 g, 89.1 mmol, 3.0 eq) then 5-chloro-2-fluoropyridine (5.8 g, 44.55 mmol, 1.5 eq) was added at the same temperature and the reaction mixture was heated to 90° C. for 16 h. TLC analysis indicated formation of a less polar spot. Then, the reaction mixture was cooled to RT and quenched with ice cold water (200 mL) and extracted with EtOAc (2×500 mL). The combined organic layer was dried over Na₂SO₄ and concentrated under reduced pressure to give crude product which was purified by column chromatography (silica gel, 100-200 mesh) using 0-10% EtOAc in petroleum ether as an eluent to afford (1R,5S)-3-benzyl-8-(5-chloropyridin-2-yl)-3,8-diazabicyclo[3.2.1]octane (5 g, 53.89%) as a white solid. LC-MS: m/z 313.99 (M+H).

Step 2: A suspension of (1R,5S)-3-benzyl-8-(5-chloropyridin-2-yl)-3,8-diazabicyclo[3.2.1]octane (15 g, 57.25 mmol, 1.0 eq) in DCM (150 mL) was cooled to 0° C. and phenylchloroformate (8 mL, 63.89 mmol, 4.0 eq) and sodium bicarbonate (5.3 g, 63.89 mmol, 4.0 eq) were added, then the reaction mixture was stirred at RT for 16 h. TLC analysis indicated formation of a polar spot and the reaction mixture was concentrated under reduced pressure to give crude compound which was diluted with water (200 mL) and extracted with EtOAc (2×500 mL). The combined organic layer was dried over Na₂SO₄ and concentrated under reduced pressure to give crude compound which was purified by column chromatography (silica gel, 100-200 mesh) using 0-10% EtOAc in petroleum ether as eluent to afford (1R,5S)-phenyl 8-(5-chloropyridin-2-yl)-3,8-diazabicyclo[3.2.1]octane-3-carboxylate (4.3 g, 79.6%) as an off-white solid.

Step 3: To a solution of (1R,5S)-phenyl 8-(5-chloropyridin-2-yl)-3,8-diazabicyclo[3.2.1]octane-3-carboxylate (4 g, 11.66 mmol, 1.0 eq) in THF (150 mL) was added LAH (0.62 g, 11.66 mmol, 1.0 eq) portionwise at 0° C. then the mixture was allowed to warm to RT and stirred for 16 h. TLC analysis indicated formation of a polar spot, the reaction mixture was cooled to 0° C. and water (0.62 mL), 10% NaOH solution (1.9 mL) and water (1.9 mL) was added then the mixture stirred for 30 min. After that, the mixture was filtered through a celite pad and washed with THF (200 mL). The filtrate was dried over Na₂SO₄ and concentrated under reduced pressure to afford crude compound which was purified by column chromatography (silica gel, 100-200 mesh) using 30-100% EtOAc in petroleum ether as an eluent to afford (1R,5S)-8-(5-chloropyridin-2-yl)-3-methyl-3,8-diazabicyclo[3.2.1]octane (2.3 g, 85.5%) as an off-white semi-solid. LC-MS: m/z 237.92 (M+H).

Step 4: A suspension of (1R,5S)-8-(5-chloropyridin-2-yl)-3-methyl-3,8-diazabicyclo[3.2.1]octane (2.5 g, 10.5 mmol, 1.0 eq) in dry THF (20 mL) was cooled to −78° C. then PMDTA (8.78 mL, 42.2 mmol, 4.0 eq) and n-BuLi (16.8 mL, 42.16 mmol, 4.0 eq, 2.5 M in THF) were added and the reaction mixture was stirred at the same temperature for 2 h. Then, iodine solution (5.3 g, 21.0 mmol, 2.0 eq, in THF) was added and the mixture slowly allowed to warm to RT and stirred for 16 h. TLC analysis indicated formation of a less polar spot and the reaction mixture was quenched with hypo solution (100 mL) and extracted with EtOAc (2×500 mL). The combined organic layer was dried over Na₂SO₄ and concentrated under reduced pressure to afford crude compound which was purified by column chromatography (silica gel, 100-200 mesh) using 30-100% EtOAc in petroleum ether as an eluent to afford (1R,5S)-8-(5-chloro-4-iodopyridin-2-yl)-3-methyl-3,8-diazabicyclo[3.2.1]octane (1.2 g, 31.5%) as a brown semi-solid. LC-MS: m/z 364.13 (M+H).

Step 5: A mixture of (1R,5S)-8-(5-chloro-4-iodopyridin-2-yl)-3-methyl-3,8-diazabicyclo[3.2.1]octane (1.0 g, 2.75 mmol, 1.0 eq), tert-butylcarbamate (1.78 g, 3.3 mmol, 1.2 eq) and cesium carbonate (1.78 g, 5.5 mmol, 2.0 eq) in toluene (20 mL) was degassed with argon for 20 min., then Pd₂(dba)₃ (80 mg, 0.13 mmol, 0.05 eq) and xantphos (251 mg, 0.27 mmol, 0.1 eq) were added at RT then the mixture heated to 100° C. for 16 h. TLC analysis indicated formation of a polar spot. Then, the reaction mixture was filtered through celite and washed with EtOAc (200 mL) and the filtrate was concentrated under reduced pressure to crude residue, which was purified by column chromatography (silica gel, 100-200 mesh) using 50-100% EtOAc in petroleum ether to give tert-butyl (5-chloro-2-((1R,5S)-3-methyl-3,8-diazabicyclo[3.2.1]octan-8-yl)pyridin-4-yl)carbamate (0.9 g, 90%) as a gummy brown liquid. LC-MS: m/z 353.32 (M+H).

Step 6: To a stirred solution of tert-butyl (5-chloro-2-((1R,5S)-3-methyl-3,8-diazabicyclo[3.2.1]octan-8-yl)pyridin-4-yl)carbamate (0.9 g, 2.55 mmol, 1.0 eq) in DCM (20 mL) was added TFA (2.54 mL, 30.6 mmol, 12.0 eq) at 0° C. dropwise and the reaction mixture was stirred at RT for 16 h. TLC analysis indicated formation of a polar spot and the mixture was concentrated under reduced pressure to crude residue, which was basified with methanolic ammonia solution and concentrated under reduced pressure to crude compound. The crude compound was purified by column chromatography (neutral alumina) using 0-5% MeOH in DCM as an eluent to afford 5-chloro-2-((1R,5S)-3-methyl-3,8-diazabicyclo[3.2.1]octan-8-yl)pyridin-4-amine (410 mg, 64%) as an off-white solid. LC-MS: m/z 253.1 (M+H).

Synthesis of (S)-5-chloro-2-(2-methyl-4-(oxetan-3-yl)piperazin-1-yl)pyridin-4-amine

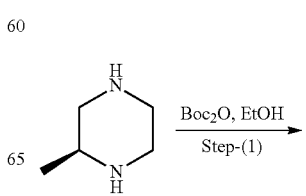

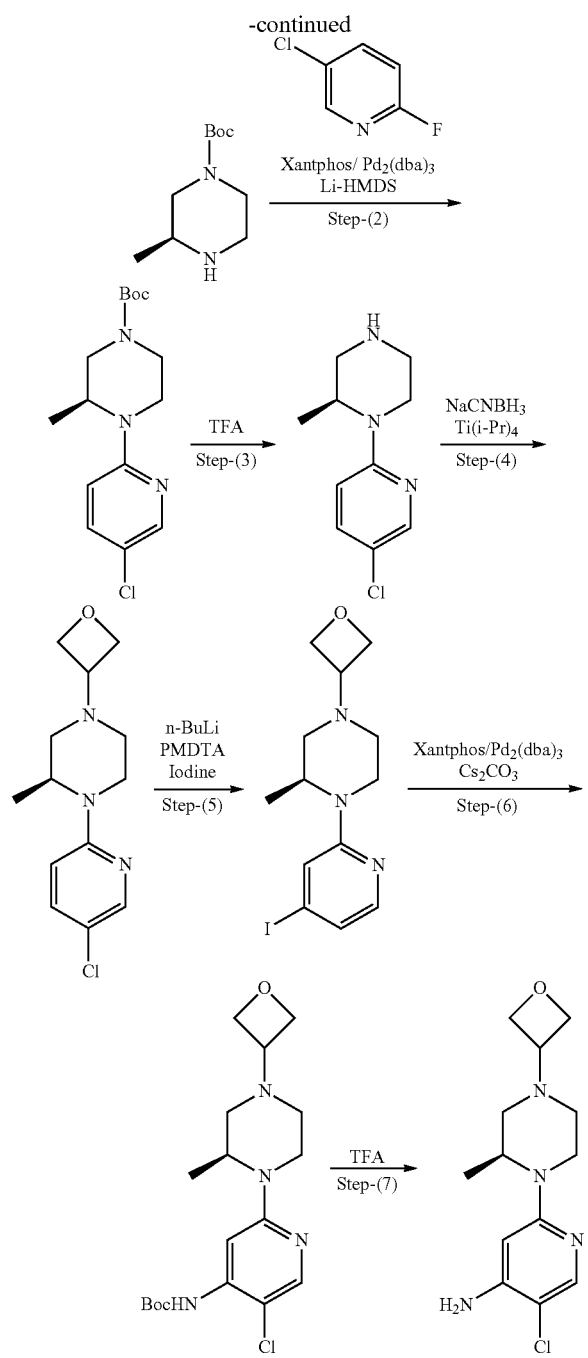

Step 1: To a solution of (S)-2-methylpiperazine (10 g, 100 mmol, 1 eq) in EtOH (200 mL) was added DIPEA (43.58 mL, 250 mmol, 2.5 eq) and Boc$_2$O (21.8 mL, 100 mmol, 1 eq) at RT, then the reaction mixture was continued for 16 h. TLC analysis indicated formation of a less polar spot. The reaction mixture was concentrated to crude compound, which was diluted with water and extracted with EtOAc (3×100 mL). The combined organic layer was dried over Na$_2$SO$_4$ then concentrated to give (S)-tert-butyl 3-methylpiperazine-1-carboxylate (18 g, 90%) as a colorless oil.

Step 2: To stirred (S)-tert-butyl 3-methylpiperazine-1-carboxylate (18 g, 90 mmol, 1 eq) was added 5-chloro-2-fluoropyridine (23.58 g, 180 mmol, 2 eq), xantphos (1.56 g, 2.7 mmol, 0.03 eq), Pd$_2$(dba)$_3$ (2.47 g, 2.7 mmol, 0.03 eq) and Li-HMDS (450 mL, 450 mmol, 5 eq) at RT under an argon atmosphere, then the reaction mixture was heated to 90° C. for 16 h. TLC analysis indicated formation of a less polar spot. The reaction mixture was cooled to RT then filtered through a celite pad, which was washed with EtOAc (3 times). The filtrate was diluted with water and extracted with EtOAc (3×100 mL). The combined organic layer was dried over Na$_2$SO$_4$ then concentrated to crude compound. The crude compound was purified by column chromatography (silica gel, 100-200 mesh) using 0-10% EtOAc in petroleum ether as eluent to afford (S)-tert-butyl 4-(5-chloropyridin-2-yl)-3-methylpiperazine-1-carboxylate (24 g, 85.74%) as a brown oil. LC-MS: m/z 312.17 (M+H).

Step 3: To a stirred solution of (S)-tert-butyl 4-(5-chloropyridin-2-yl)-3-methylpiperazine-1-carboxylate (24 g, 77.17 mmol, 1 eq) in DCM (250 mL) was added TFA (58.64 mL, 771.70 mmol, 10 eq) at 0° C. then the mixture allowed to warm to RT and stirred for 16 h. TLC analysis indicated formation of a polar spot. The reaction mixture was concentrated to crude residue, which was basified with aqueous NaHCO$_3$ solution then extracted with EtOAc (3×100 mL). The combined organic layer was dried over Na$_2$SO$_4$ then concentrated to crude compound. The crude compound was purified by column chromatography (silica gel, 100-200 mesh) using 0-2% MeOH in DCM as eluent to afford (S)-1-(5-chloropyridin-2-yl)-2-methylpiperazine (14 g, 85.99%) as a brown oil. LC-MS: m/z 212.12 (M+H).

Step 4: To a stirred solution of (S)-1-(5-chloropyridin-2-yl)-2-methylpiperazine (4 g, 18.95 mmol, 1 eq) in MeOH (60 mL) was added oxetan-3-one (1.66 mL, 28.43 mmol, 1.5 eq) and Ti(i-OPr)$_4$ (8.4 mL, 28.43 mmol, 1.5 eq) at RT under an argon atmosphere and stirring continued for 2 h, after which NaCNBH$_3$ (2.39 g, 37.91 mmol, 2 eq) was added at RT, and stirring continued for 2 h. TLC analysis indicated formation of a less polar spot. The reaction mixture was diluted with water and filtered through a celite pad and the filtrate was extracted with EtOAc (3×90 mL). The combined organic layer was dried over Na$_2$SO$_4$ then concentrated to crude compound. The crude compound was purified by column chromatography (silica gel, 100-200 mesh) using 0-30% EtOAc in petroleum ether as eluent to afford (S)-1-(5-chloropyridin-2-yl)-2-methyl-4-(oxetan-3-yl)piperazine (2.8 g, 55%) as a brown oil. LC-MS: m/z 268.15 (M+H).

Step 5: To a stirred solution of (S)-1-(5-chloropyridin-2-yl)-2-methyl-4-(oxetan-3-yl)piperazine (2.8 g, 10.48 mmol, 1 eq) in THF (60 mL) was added PMDTA (4.8 mL, 23.07 mmol, 2.2 eq) and n-BuLi (9.2 mL, 23.07 mmol, 2.2 eq, 2.5 M in THF) at −78° C. under an argon atmosphere then the reaction mixture was continued for 2 h and a solution of I$_2$ (5.32 g, 20.97 mmol, 2 eq, in THF) was added at −78° C., and after that, the mixture slowly allowed to warm to RT and stirred for 16 h. TLC analysis indicated formation of a less polar spot. The reaction mixture was quenched in an aqueous solution of sodium thiosulphate then extracted with EtOAc (3×80 mL). The combined organic layer was dried over Na$_2$SO$_4$ then concentrated under reduced pressure to give crude (S)-1-(4-iodopyridin-2-yl)-2-methyl-4-(oxetan-3-yl)piperazine (5 g, crude) as a brown oil. LC-MS: m/z 394.07 (M+H).

Step 6: To a stirred solution of (S)-1-(4-iodopyridin-2-yl)-2-methyl-4-(oxetan-3-yl)piperazine (5 g, 12.72 mmol, 1 eq) in toluene (80 mL) was added Cs$_2$CO$_3$ (8.2 g, 25.44 mmol, 2 eq) and NH$_2$Boc (1.77 g, 15.26 mmol, 1.2 eq) at RT then the reaction mixture was degassed with argon for 5 min. Then, xantphos (220 mg, 0.38 mmol, 0.03 eq) and Pd$_2$(dba)$_3$ (350 mg, 0.38 mmol, 0.03 eq) were added at RT, and after that, the reaction mixture was heated to 90° C. for 16 h. TLC analysis indicated formation of a polar spot. The reaction mixture was filtered through a celite pad then the filtrate was concentrated to crude compound. The crude compound was purified by column chromatography (silica gel, 100-200 mesh) using 0-1% MeOH in DCM as eluent to afford (S)-tert-butyl (5-chloro-2-(2-methyl-4-(oxetan-3-yl)piperazin-1-yl)pyridin-4-yl)carbamate (3.5 g, 87%, per two steps) as a brown oil. LC-MS: m/z 383.23 (M+H).

Step 7: To a stirred solution of (S)-tert-butyl (5-chloro-2-(2-methyl-4-(oxetan-3-yl)piperazin-1-yl)pyridin-4-yl)carbamate (3.5 g, 9.16 mmol, 1 eq) in DCM (30 mL) was added TFA (6.9 mL, 91.62 mmol, 10 eq) at RT and stirring continued for 16 h. TLC analysis indicated formation of a polar spot. The reaction mixture was concentrated to crude, which was basified by aqueous NaHCO₃ solution then extracted with EtOAc (3×60 mL). The combined organic layer was dried over Na₂SO₄ then concentrated under reduced pressure to crude compound. The crude compound was purified by column chromatography (silica gel, 100-200 mesh) using 0-2% MeOH in DCM as eluent to afford (S)-5-chloro-2-(2-methyl-4-(oxetan-3-yl)piperazin-1-yl)pyridin-4-amine (1.5 g 58%) as a brown oil. LC-MS: m/z 283.0 (M+H).

Synthesis of (S)-5-chloro-2-(2-methyl-4-((1-methylcyclopropyl)methyl)piperazin-1-yl)pyridin-4-amine

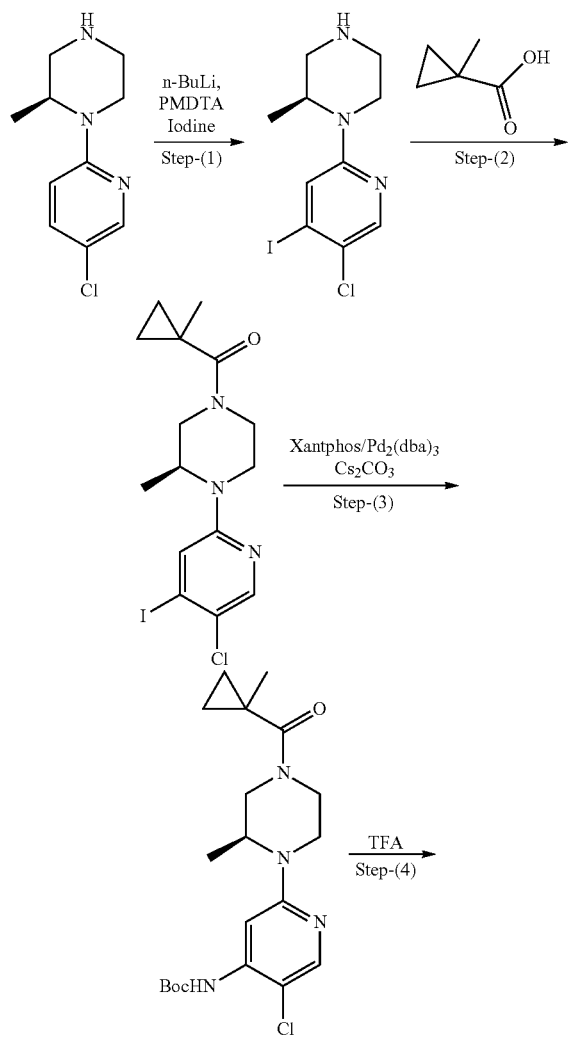

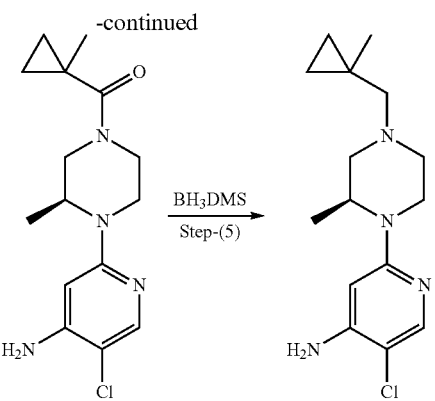

Step 1: To a stirred solution of (S)-1-(5-chloropyridin-2-yl)-2-methylpiperazine (10 g, 47.3 mmol, 1 eq) in THF (40 mL) was added NaH (1.36 g, 56.8 mmol, 1.2 eq) at 0° C. for 30 mins, then the mixture was cooled to −78° C. and PMDTA (41.0 mL, 189.5 mmol, 4 eq) and n-BuLi (75.8 mL, 189.5 mmol, 4 eq, 2.5 M in THF) were added at −78° C. under an argon atmosphere. The reaction mixture was continued for 2 h and a solution of I₂ (24.0 g, 94.7 mmol, 2 eq) in THF (100 mL) was added at −78° C., and after that, the mixture slowly allowed to warm to RT and stirred for 16 h. TLC analysis indicated formation of a less polar spot. The reaction mixture was quenched in an aqueous solution of sodium thiosulphate then extracted with EtOAc (2×200 mL). The combined organic layer was dried over Na₂SO₄ then concentrated under reduced pressure to give crude (S)-1-(5-chloro-4-iodopyridin-2-yl)-2-methylpiperazine (8 g, crude) as a brown oil. LC-MS: m/z 338.24 (M+H).

Step 2: To a stirred solution of (S)-1-(5-chloro-4-iodopyridin-2-yl)-2-methylpiperazine (8 g, 23.8 mmol, 1 eq) in DCM:DMF (40:40 mL) and 1-methylcyclopropanecarboxylic acid (2.38 g, 23.8 mol, 1 eq) was added EDC.HCl (6.8 g, 35.7 mmol, 1.5 eq) and HOBt (4.82 g, 35.7 mmol, 1.5 eq) at 0° C. under an argon atmosphere followed by DiPEA (12.2 mL, 71.4 mmol, 3 eq) and the mixture allowed to warm to RT and stirred for 16 h. TLC analysis indicated formation of a less polar spot. The reaction mixture was diluted with water (500 mL) and extracted with EtOAc (2×200 mL). The organic layer was washed with water (2×200 mL), dried over Na₂SO₄ and concentrated under reduced pressure to give crude product. The crude product was purified by column chromatography (silica gel, 100-200 mesh) using 5-10% EtOAc in petroleum ether as an eluent to afford (S)-(4-(5-chloro-4-iodopyridin-2-yl)-3-methylpiperazin-1-yl)(1-methylcyclopropyl)methanone (3 g, 43.08%) as a pale yellow colored liquid. LC-MS: m/z 419.84 (M+H).

Step 3: To a stirred solution of (S)-(4-(5-chloro-4-iodopyridin-2-yl)-3-methylpiperazin-1-yl)(1-methylcyclopropyl)methanone (3 g, 7.15 mmol, 1 eq) in toluene (30 mL) was added Cs₂CO₃ (4.65 g, 14.31 mmol, 2 eq) and NH₂Boc (1 g, 8.59 mmol, 1.2 eq) at RT then the reaction mixture was degassed with argon for 5 min. Then, xantphos (240 mg, 0.42 mmol, 0.06 eq) and Pd₂(dba)₃ (190 mg, 0.21 mmol, 0.03 eq) were added at RT, and after that, the reaction mixture was heated to 90° C. for 16 h. TLC analysis indicated formation of a polar spot. The reaction mixture was filtered through a celite pad then the filtrate was concentrated to crude compound. The crude compound was purified by column chromatography (silica gel, 100-200 mesh) using 0-30% EtOAc in petroleum ether as eluent to afford (S)-tert-butyl (5-chloro-2-(2-methyl-4-(1-methylcyclopropanecarbonyl)piperazin-1-yl)pyridin-4-yl)carbamate (2.5 g, 87%) as a brown oil. LC-MS: m/z 408.96 (M+H).

Step 4: To a stirred solution of (S)-tert-butyl (5-chloro-2-(2-methyl-4-(1-methylcyclopropanecarbonyl)piperazin-1-yl)pyridin-4-yl)carbamate (3.5 g, 8.55 mmol, 1 eq) in DCM (30 mL) was added TFA (6.5 mL, 85.52 mmol, 10 eq) at RT and stirring continued for 16 h. TLC analysis indicated formation of a polar spot. The reaction mixture was concentrated to crude, which was basified by aqueous NaHCO₃ solution then extracted with EtOAc (3×60 mL). The combined organic layer was dried over Na₂SO₄ then concentrated under reduced pressure to afford (S)-(4-(4-amino-5-chloropyridin-2-yl)-3-methylpiperazin-1-yl)(1-methylcyclopropyl)methanone (2.2 g, 58%) as an off-white solid. LC-MS: m/z 308.92 (M+H).

Step 5: To a stirred solution of (S)-(4-(4-amino-5-chloropyridin-2-yl)-3-methylpiperazin-1-yl)(1-methylcyclopropyl)methanone (2.2 g, 7.0 mmol, 1 eq) in THF (25 mL) was added BH₃DMS (3.54 mL, 35.48 mmol, 10 eq) at 0° C.-RT and stirring continued for 16 h. TLC analysis indicated formation of a less polar spot. The reaction mixture was cooled to 0° C., quenched with methanol, and stirred at rt for another 16 h. TLC analysis indicated formation of a less polar spot. The mixture was concentrated to crude, then extracted with EtOAc (2×100 mL). The combined organic layer was dried over Na₂SO₄ then concentrated under reduced pressure. The crude compound was purified by column chromatography (silica gel, 100-200 mesh) using 0-20% EtOAc in petroleum ether as eluent to afford (S)-5-chloro-2-(2-methyl-4-((1-methylcyclopropyl)methyl)piperazin-1-yl)pyridin-4-amine (1.1 g, 87%) as an off-white solid. LC-MS: m/z 295.19 (M+H).

Synthesis of 2-chloro-5-morpholinoaniline

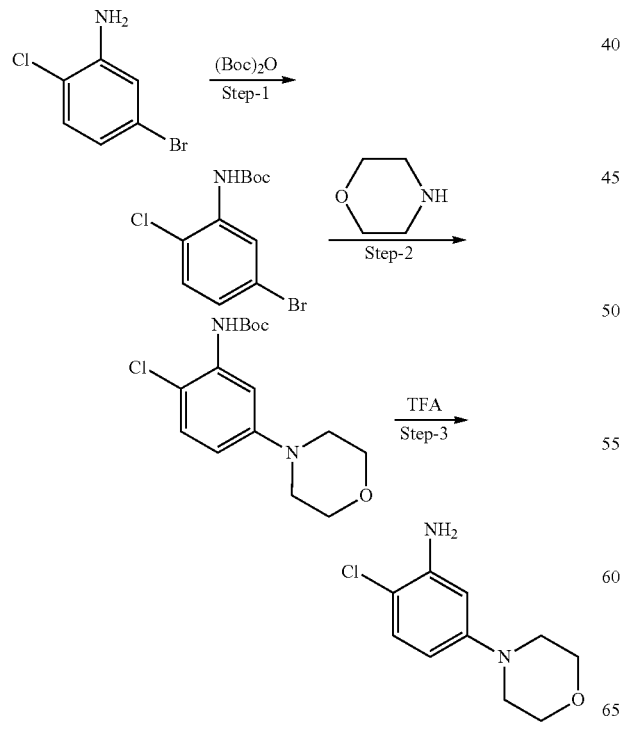

Step 1: A solution of 5-bromo-2-chloroaniline (1 g, 4.84 mmol, 1 eq), TEA (2.03 mL, 14.53 mmol, 3 eq) in DCM (6.3 mL) was cooled to 0° C. under an argon atmosphere, then Boc-anhydride (1.33 mL, 5.80 mmol, 1.2 eq) was added in a dropwise fashion at 0° C. and then DIMAP (0.590 g, 4.84 mmol, 1 eq) was added. Then, the reaction was allowed to warm to RT and stirred for 16 h. TLC analysis indicated formation of a non-polar spot. After 16 h, the reaction mixture was quenched with water (10 mL) and extracted with DCM (2×20 mL). The combined organic layer was washed with brine and dried over Na₂SO₄ which was concentrated under reduced pressure to give crude product. The crude product was purified by column chromatography (silica gel, 100-200 mesh) using 1-2% EtOAc in petroleum ether as an eluent to afford tert-butyl (5-bromo-2-chlorophenyl)carbamate (0.9 g, 61.22%) as a bright white powder.

Step 2: To a solution of tert-butyl (5-bromo-2-chlorophenyl)carbamate (9 g, 29.51 mmol, 1 eq) and morpholine (5.06 mL, 58.65 mmol, 1.99 eq) in toluene (135 mL) was added a Cs₂CO₃ (11.97 g, 36.83 mmol, 1.24 eq) and the mixture degassed for 30 min using argon. After 30 min, BINAP (1.81 g, 2.90 mmol, 0.1 eq) & Pd(OAc)₂ (0.663 mg, 0.985 mmol, 0.1 eq) were added and the mixture again degassed for 5 min and heated to 110° C. in a sealed tube for 16 h. TLC analysis indicated formation of a polar spot. After 16 h, the reaction mixture was cooled to RT and filtered through a celite bed. The celite bed was washed with EtOAc (2×30 mL), and the filtrate was concentrated under reduced pressure to give residue which was purified via column chromatography (silica gel, 100-200 mesh) using 10-25% EtOAc in petroleum ether as an eluent to afford tert-butyl (2-chloro-5-morpholinophenyl)carbamate (4.4 g, 47.82%) as a yellow liquid. LC-MS: m/z 313.26 (M+H).

Step 3: To a solution of tert-butyl (2-chloro-5-morpholinophenyl)carbamate (4.4 g, 14.09 mmol, 1 eq) in DCM (44 mL) at 0° C. under an argon atmosphere, trifluoroacetic acid (8.8 mL, 115 mmol, 8.15 meq) was added dropwise at 0° C. Then, the reaction mixture was allowed to warm to RT and stirred for 16 h. TLC analysis indicated formation of a polar spot. After 16 h, the reaction mixture was basified to pH 8-9 using saturated NaHCO₃ solution (100 mL) and extracted with DCM (3×50 mL). The combined organic layer was dried over Na₂SO₄ and concentrated under reduced pressure to give residue. The residue was washed with n-pentane (2×10 mL) which afforded 2-chloro-5-morpholinoaniline (1.6 g, 53.69%) as an off-white solid. LC-MS: m/z 213.13 (M+H).

Synthesis of 2-chloro-5-(4-methylpiperazin-1-yl)aniline

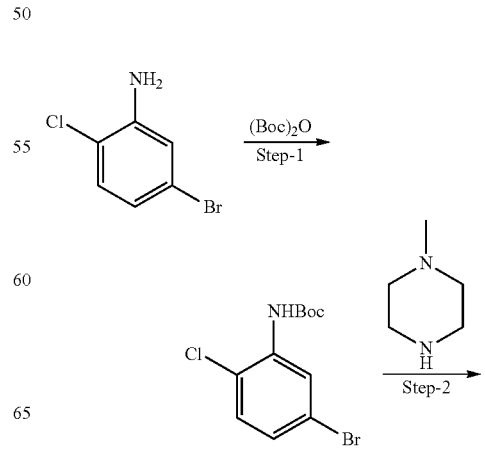

-continued

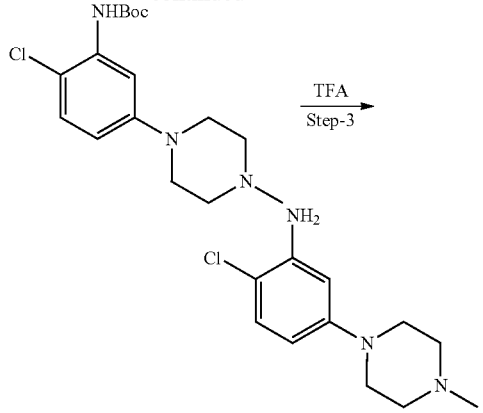

Step 1: A solution of 5-bromo-2-chloroaniline (1 g, 4.84 mmol, 1 eq) and TEA (2.03 mL, 14.53 mmol, 3 eq) in DCM (6.3 mL) was cooled to 0° C. under an argon atmosphere, followed by an addition of Boc-anhydride (1.33 mL, 5.80 mmol, 1.2 eq) in a dropwise fashion at 0° C. and then DMAP (0.590 g, 4.84 mmol, 1 eq). Then, the reaction was allowed to warm to RT and stirred for 16 h. TLC analysis indicated formation of a non-polar spot. After 16 h, the reaction mixture was quenched with water (10 mL) and extracted with DCM (2×20 mL). The combined organic layer was washed with brine and dried over $Na_2SO_4$ then concentrated under reduced pressure to give crude product. The crude product was purified by column chromatography (silica gel, 100-200 mesh) using 1-2% EtOAc in petroleum ether as an eluent to afford tert-butyl (5-bromo-2-chlorophenyl)carbamate (0.9 g, 61.22%) as a bright white powder.

Step 2: To a solution of tert-butyl (5-bromo-2-chlorophenyl)carbamate (1 g, 3.26 mmol, 1 eq) and N-methyl piperazine (0.722 mL, 6.52 mmol, 2 eq) in toluene (25 mL) was added $Cs_2CO_3$ (1.32 g, 4.05 mmol, 1.24 eq) and the mixture degassed for 30 min using argon. After 30 min, BINAP (0.2 g, 0.32 mmol, 0.1 eq) and Pd(OAc)$_2$ (88.1 mg, 0.391 mmol, 0.1 eq) were added and the mixture again degassed for 5 min then heated to 110° C. in a sealed tube for 16 h. TLC analysis indicated formation of a polar spot. After 16 h, the reaction mixture was cooled to RT and filtered through a celite bed. The celite bed was washed with EtOAc (2×10 mL), the filtrate was concentrated under reduced pressure to give residue and the residue was purified via column chromatography (silica gel, 100-200 mesh) using 80-100% EtOAc in petroleum ether as an eluent to afford tert-butyl (2-chloro-5-(4-methylpiperazin-1-yl)phenyl)carbamate (0.3 g, 28.57%) as a colorless sticky mass.

Step 3: To a solution of tert-butyl (2-chloro-5-(4-methylpiperazin-1-yl)phenyl)carbamate (0.4 g, 1.23 mmol, 1 eq) in DCM (4 mL) at 0° C. under an argon atmosphere, trifluoroacetic acid (3 mL, 39.21 mmol, 31.87 eq) was added dropwise at 0° C. Then, the reaction mixture was allowed to warm to RT and stirred for 16 h. TLC analysis indicated formation of a polar spot. After 16 h, the reaction mixture was basified to pH 8-9 using saturated $NaHCO_3$ solution (50 mL) and extracted with DCM (3×10 mL). The combined organic layer was dried over $Na_2SO_4$ and concentrated under reduced pressure to give residue. The residue was purified by column chromatography (silica gel, 100-200 mesh) using 2-5% MeOH in DCM as an eluent to afford 5-(4-methylpiperazin-1-yl)aniline (120 mg, 43.47%) as an off-white solid. LC-MS: m/z 226.29 (M+H).

Synthesis of 2-chloro-4-fluoro-5-morpholinoaniline

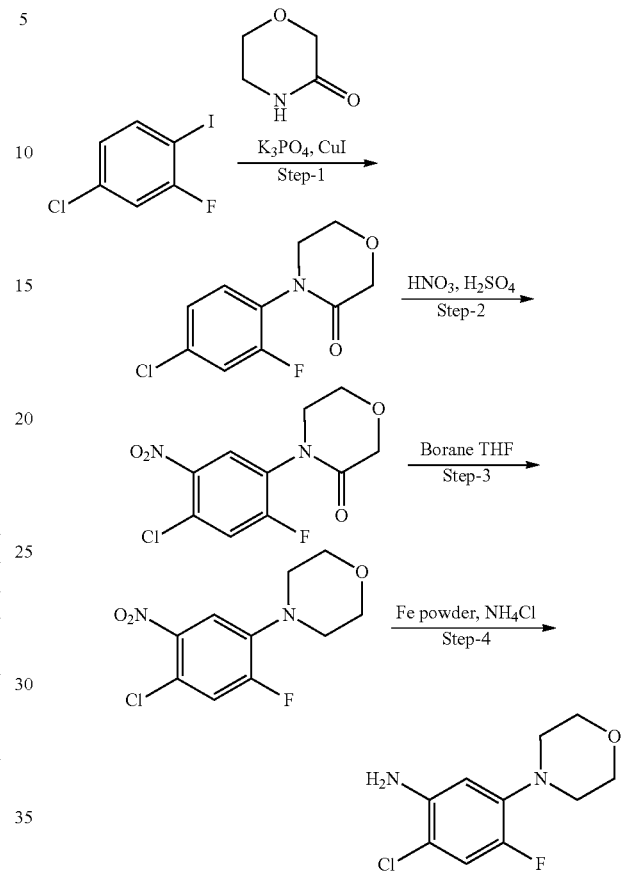

Step 1: To a solution of 4-chloro-2-fluoro-1-iodobenzene (4 g, 15.6 mmol, 1 eq) in 1,4 dioxane (40 mL) was added morpholin-3-one (3.15 g, 31.25 mmol, 2 eq) followed by addition of (1R,2R)-cyclopropane 1,2-diamine (0.26 g, 2.34 mmol, 0.15 eq), $K_3PO_4$ (6.62 g, 31.25 mmol, 2 eq) and CuI (0.089 g, 0.46 mmol, 0.03 eq). Then, the mixture was degassed with argon for 20 mins in a sealed tube at RT and heated to 120° C. for 16 h. Then, the reaction mixture was cooled to RT, filtered through a celite bed, washed with EtOAc (100 mL) and concentrated under reduced pressure to give crude product. The crude product was purified by CombiFlash column chromatography using 0-18% EtOAc in petroleum ether as an eluent to afford 4-(4-chloro-2-fluorophenyl)morpholin-3-one (2.5 g, 71.4%) as an off-white solid. LC-MS: m/z 230.02 (M+H).

Step 2: To a solution of 4-(4-chloro-2-fluorophenyl)morpholin-3-one (2.5 g, 10.9 mmol, 1.0 eq) in concentrated $H_2SO_4$ (50 mL) was added fuming nitric acid (0.36 mL, 12.0 mmol, 1.1 eq) dropwise at 0° C. over 30 min. Then, powdered dry ice was added and the mixture extracted with EtOAc (2×100 mL). The combined organic layer was dried over $Na_2SO_4$ and concentrated under reduced pressure to give crude product which was washed with n-pentane and ether to afford 4-(4-chloro-2-fluoro-5-nitrophenyl)morpholin-3-one (1.7 g, 58.6%) as an off-white solid.

Step 3: To a solution of 4-(4-chloro-2-fluoro-5-nitrophenyl)morpholin-3-one (1.7 g, 6.2 mmol, 1 eq), in dry THF (40 mL) was added Borane THF (17.3 mL, 17.3 mmol, 2.8 eq, 1M in THF) at 0° C.-rt for 3 h. TLC analysis indicated formation of a nonpolar spot. The reaction mixture was slowly quenched with methanol at 0° C. and concentrated under reduced pressure to give residue which was washed with pentane and gave 4-(4-chloro-2-fluoro-5-nitrophenyl) morpholine (1.1 g, 68.3% yield) as a pale yellow solid. LC-MS: m/z 260.94 (M+H).

Step 4: To a solution of 4-(4-chloro-2-fluoro-5-nitrophenyl)morpholine (1.1 g, 4.23 mmol, 1 eq) in EtOH:$H_2O$ (16:4 mL) was added iron powder (0.93 g, 16.92 mmol, 4.0 eq) and $NH_4Cl$ (0.89 g, 16.92 mmol, 4.0 eq) at RT then the mixture heated at 75° C. over 1 h. TLC analysis indicated formation of a polar spot. Then, the reaction mixture was cooled to RT and filtered through a celite bed, concentrated under reduced pressure, extracted in EtOAc (3×50 mL), and washed with water (2×50 mL) and brine (2×50 mL). The combined organic layer was dried over $Na_2SO_4$ and concentrated under reduced pressure to give crude product. The crude compound was purified by washing with n-pentane to give 2-chloro-4-fluoro-5-morpholinoaniline (0.8 g, 82.4%) as a brown colored solid. LC-MS: m/z 231.04 (M+H).

Table 1 contains a list of exemplary compounds of Formula I synthesized with the abovementioned methods.

Example 2: Biological Assays

Compounds of the present application displayed inhibition of the interaction between BCL6-BTB domain and SMRT/NCOR2 in the following assays:

BCL6-BTB—SMRT Peptide Inhibition Fluorescence Polarization (FP) Screen

This assay was used to determine whether compounds inhibit the interaction between the BTB domain of BCL6 and a peptide derived from the BCL6 binding domain (BBD) of the SMRT/NCOR2 corepressor protein Compounds were dissolved in 100% DMSO at 10 mM, assayed fresh, and then stored at −20° C. for repeat studies and future work. The reaction mixture was made up of 1.25 μM of the 25 kd BCL6-BTB domain (Thioredoxin-His6-STag-TEV-biotinylation-thrombin-BCL6 amino acids 1-129) plus 20 nM of the peptide probe (Ac-GSL-VATVKEAGRSIHEIPA, SEQ ID NO:1) with 16aa from the SMRT BBD (1414-1429) with a Bodipy-TMR fluorescent label on the lysine. The assay buffer was 10 mM HEPES pH 7.4, 150 mM NaCl, 0.05% Tween-20, 3 mM EDTA, and had a final DMSO concentration of 5%. 20 μl of this assay mixture was added to each well of the 384 well plates with the exception of the control wells that contained no protein (for setting the minimum FP value). Compounds were directly sprayed using an HP D300 Digital Dispenser from 10 mM DMSO stocks onto black 384 well plates (greiner bio-one #781900) in a concentration range from 1 μM to 500 μM (10 points in duplicate). The assay was equilibrated for 1 hour prior to reading the FP values (Ex 540 nm/Em 580 nm) with a Perkin Elmer Envision plate reader. The results were curve fitted and $IC_{50}$ values were calculated using the BioAssay software from CambridgeSoft. Representative compounds display IC50<1 uM in this assay (NB: lower limit of this assay was 1 uM).

Surface Plasmon Resonance (SPR) Assay

SPR studies were performed using a Biacore™ T200 instrument (GE Health Sciences Inc.). The BCL6 BTB protein used in the FP assay was biotinylated using the site specific biotinylating enzyme BirA, and then cleaved with TEV protease to produce the BCL6 BTB domain (biotin-thrombin-BCL6 amino acids 1-129; 17 kd) that was used in SPR. This protein was stably captured (1000RU) to strepta-vidin coupled SA chips (BR-1005-31, GE Health Sciences Inc.) according to the manufacture's protocol. Compounds were dissolved in 100% DMSO at 10 mM and 2-fold serial dilutions were performed in 100% DMSO. For SPR analysis the serially titrated compounds were diluted 1/20 into buffer (10 mM HEPES pH 7.4, 150 mM NaCl, 0.05% Tween-20, 3 mM EDTA) giving a final concentration of 5% DMSO. The Biacore flow rate was set at 100 μl/min. For KD determinations, single cycle kinetic analysis was performed with an on time of 60 seconds, and an off time of 300 seconds. Curve fitting and KD calculations were performed with the Biacore T200 Evaluation software (GE Health Sciences Inc).

Cell-Based Luciferase Assay:

A BCL6 reporter construct containing three copies of the consensus BCL6 binding site, the TK promoter, and the firefly luciferase gene was stably expressed in SuDHL4 cells after lentivirus infection and selection with Blasticidin. SuDHL4-3×BCL6-TK-Luc cells were seeded into a Viewplate 384-well assay dish at 15,000 cells/well in 25 medium (Alpha-MEM high glucose containing 10% FBS, 25 mM HEPES, 200 mM GlutaMAX, 100 g/mL Normocin, and 50 mg/mL Gentamycin, Invitrogen). A HP D300 digital dispenser was used to dose cells with DMSO or test compounds across a 10-point range of concentrations (high dose of 10 μM), and cultures were grown in a humidified 5% $CO_2$ incubator at 37° C. After two days, plates were removed from the incubator and equilibrated to room temperature. An equal volume of neolite reporter gene assay reagent was added to each well, and samples were processed according to the manufacturer's instructions (Perkin Elmer). The luminescent signal was measured using an Envision plate reader equipped with a US-Luminescence detector.

Tumor Cell Growth Inhibition Assay:

Karpas422 cells were seeded into a 96-well plate at 2,000 cells/well in 150 μl medium (Alpha-MEM containing 10% FBS, 100 mg/mL Normocin, and 50 mg/mL Gentamycin, Invitrogen). A HP D300 digital dispenser was used to dose cells with DMSO or test compounds across a 10-point range of concentrations (high dose of 5 μM), and cultures were grown in a humidified 5% $CO_2$ incubator at 37° C. After six days, plates were removed from incubator and equilibrated to room temperature. An equal volume of ATPlite assay reagent was added to each well, and samples were processed according to the manufacturer's instructions (Perkin Elmer). The luminescent signal was measured using an Envision plate reader equipped with a US-Luminescence detector.

Table 2 contains data on the biochemical activity, cell-based luciferase and tumor growth inhibition assays for the compounds.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Examples of Compounds of Formula I

| No | Structure | IUPAC Chemical Name |
|---|---|---|
| I-1 | 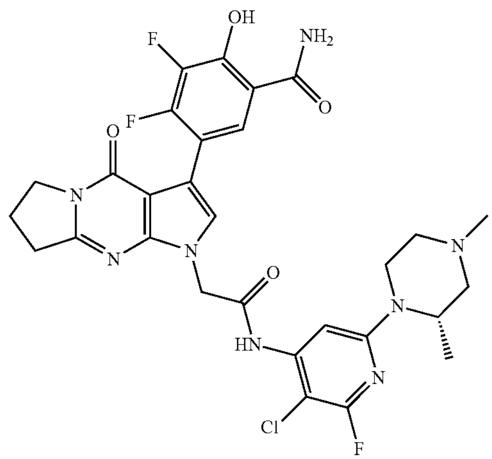 [SMILES: C[C@H]1CN(C)CCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |
| I-2 | 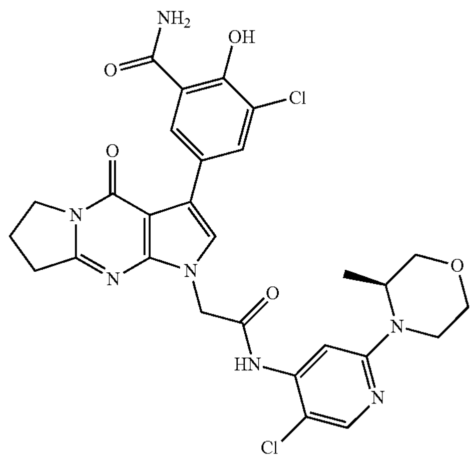 [SMILES: C[C@H]1COCCN1c1cc(NC(=O)Cn2cc(-c3cc(Cl)c(O)c(C(N)=O)c3)c3c(=O)n4c(nc32)CCC4)c(Cl)cn1] | (S)-3-chloro-5-(1-(2-((5-chloro-2-(3-methyl-morpholino)pyridin-4-yl)amino)-2-oxoethyl)-4-oxo-4,6,7,8-tetrahydro-1H-dipyrrolo[1,2-a:2',3'-d]pyrimidin-3-yl)-2-hydroxy-benzamide |
| I-3 | 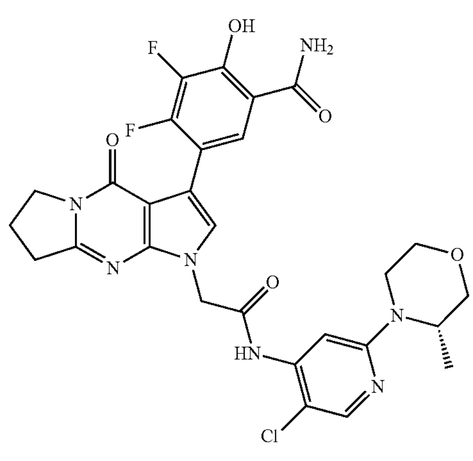 [SMILES: C[C@H]1COCCN1c1cc(NC(=O)Cn2cc(-c3cc(C(N)=O)c(O)c(F)c3F)c3c(=O)n4c(nc32)CCC4)c(Cl)cn1] | (S)-5-(1-(2-((5-chloro-2-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |

TABLE 1-continued

Examples of Compounds of Formula I

| No | Structure | IUPAC Chemical Name |
|---|---|---|
| I-4 | 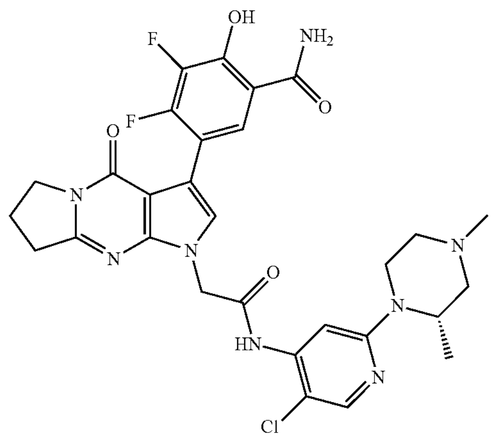 [SMILES: C[C@H]1CN(C)CCN1c1cc(NC(=O)Cn2cc(-c3cc(C(N)=O)c(O)c(F)c3F)c3c(=O)n4c(nc32)CCC4)c(Cl)cn1] | (S)-5-(1-(2-((5-chloro-2-(2,4-dimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-5 | 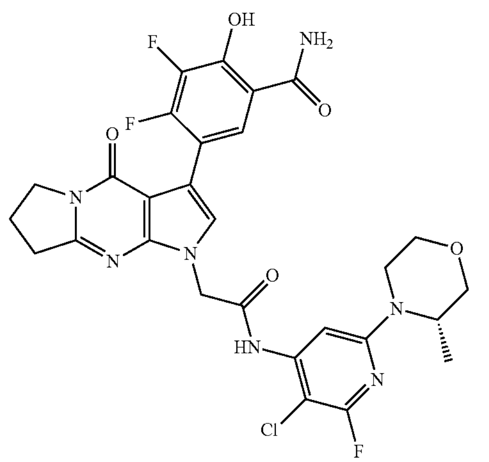 [SMILES: C[C@H]1COCCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-2-fluoro-6-(3-methyl-morpholino)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |
| I-6 | 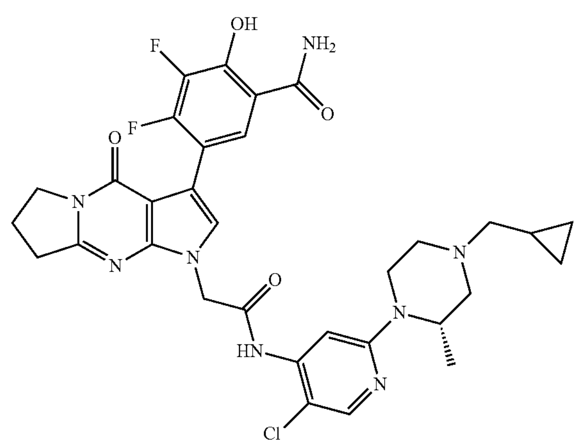 [SMILES: C[C@H]1CN(CC2CC2)CCN1c1cc(NC(=O)Cn2cc(-c3cc(C(N)=O)c(O)c(F)c3F)c3c(=O)n4c(nc32)CCC4)c(Cl)cn1] | (S)-5-(1-(2-((5-chloro-2-(4-(cyclopropylmethyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |

TABLE 1-continued

Examples of Compounds of Formula I

| No | Structure | IUPAC Chemical Name |
|---|---|---|
| I-7 | 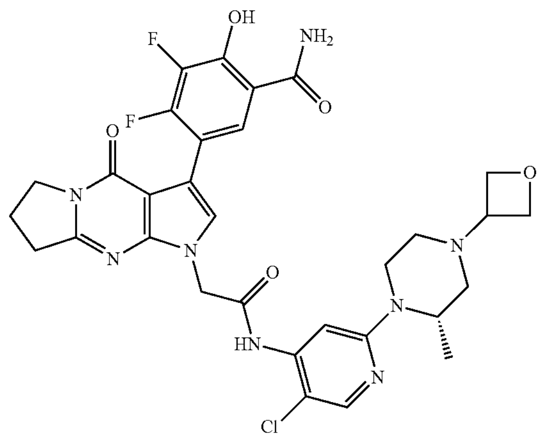 | (S)-5-(1-(2-((5-chloro-2-(2-methyl-4-(oxetan-3-yl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-8 | 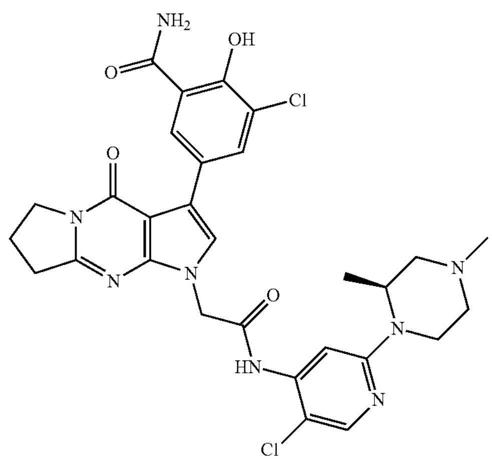 [SMILES: C[C@H]1CN(C)CCN1c1cc(NC(=O)Cn2cc(-c3cc(Cl)c(O)c(C(N)=O)c3)c3c(=O)n4c(nc32)CCC4)c(Cl)cn1] | (S)-3-chloro-5-(1-(2-((5-chloro-2-(2,4-dimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-2-hydroxybenzamide |
| I-9 | 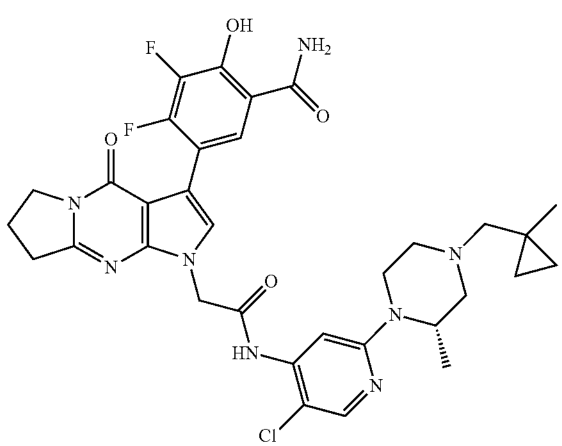 [SMILES: C[C@H]1CN(CC2(C)CC2)CCN1c1cc(NC(=O)Cn2cc(-c3cc(C(N)=O)c(O)c(F)c3F)c3c(=O)n4c(nc32)CCC4)c(Cl)cn1] | (S)-5-(1-(2-((5-chloro-2-(2-methyl-4-((1-methylcyclopropyl)methyl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-10 | 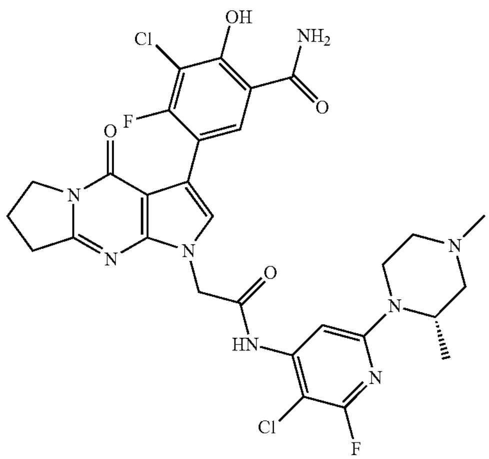 [SMILES: C[C@H]1CN(C)CCN1c1cc(NC(=O)Cn2cc(-c3cc(C(N)=O)c(O)c(Cl)c3F)c3c(=O)n4c(nc32)CCC4)c(Cl)c(F)n1] | (S)-3-chloro-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-benzamide |
| I-11 | 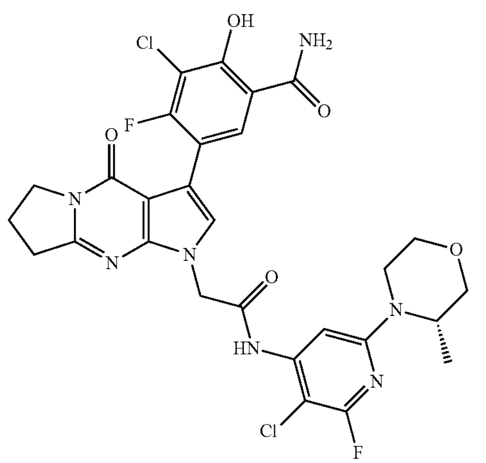 [SMILES: C[C@H]1COCCN1c1cc(NC(=O)Cn2cc(-c3cc(C(N)=O)c(O)c(Cl)c3F)c3c(=O)n4c(nc32)CCC4)c(Cl)c(F)n1] | (S)-3-chloro-5-(1-(2-((3-chloro-2-fluoro-6-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxybenzamide |
| I-12 | 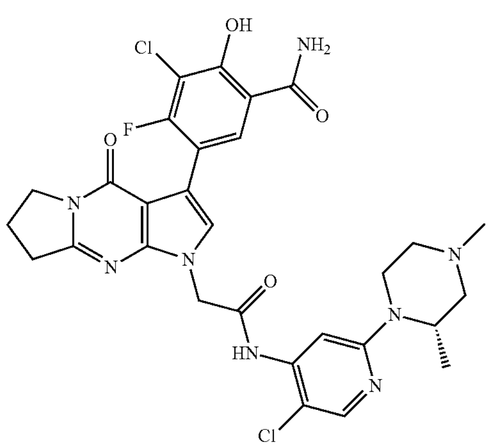 [SMILES: C[C@H]1CN(C)CCN1c1cc(NC(=O)Cn2cc(-c3cc(C(N)=O)c(O)c(Cl)c3F)c3c(=O)n4c(nc32)CCC4)c(Cl)cn1] | (S)-3-chloro-5-(1-(2-((5-chloro-2-(2,4-dimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-benzamide |

TABLE 1-continued

Examples of Compounds of Formula I

| No | Structure | IUPAC Chemical Name |
|---|---|---|
| I-13 | 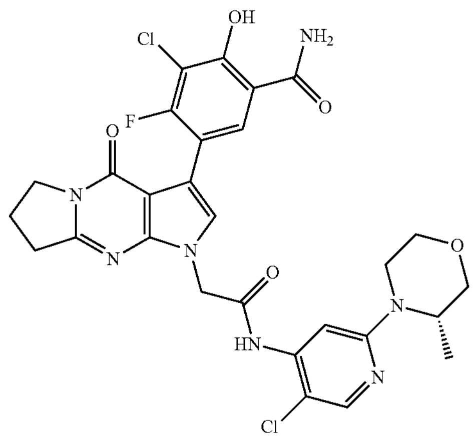 [SMILES: C[C@H]1COCCN1c1cc(NC(=O)Cn2cc(-c3cc(C(N)=O)c(O)c(Cl)c3F)c3c(=O)n4c(nc32)CCC4)c(Cl)cn1] | (S)-3-chloro-5-(1-(2-((5-chloro-2-(3-methyl-morpholino)pyridin-4-yl)amino)-2-oxoethyl)-4-oxo-4,6,7,8-tetra-hydro-1H-dipyrrolo[1,2-a:2',3'-d]pyrimidin-3-yl)-4-fluoro-2-hydroxybenzamide |
| I-14 | 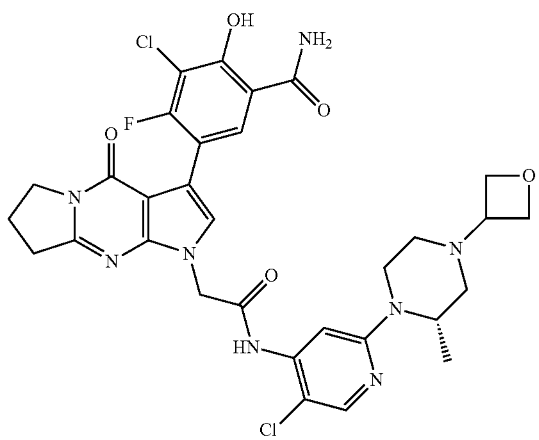 [SMILES: C[C@H]1CN(C2COC2)CCN1c1cc(NC(=O)Cn2cc(-c3cc(C(N)=O)c(O)c(Cl)c3F)c3c(=O)n4c(nc32)CCC4)c(Cl)cn1] | (S)-3-chloro-5-(1-(2-((5-chloro-2-(2-methyl-4-(oxetan-3-yl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-benzamide |
| I-15 | 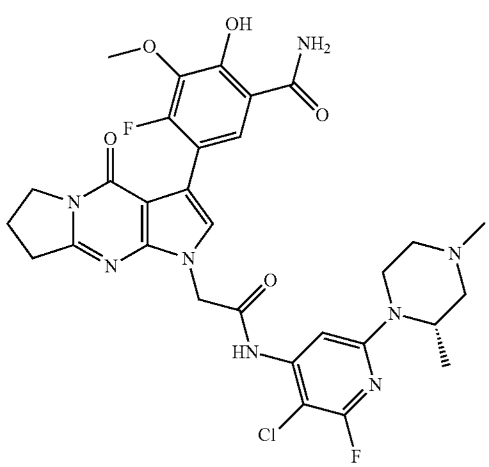 [SMILES: COc1c(O)c(C(N)=O)cc(-c2cn(CC(=O)Nc3cc(N4CCN(C)C[C@@H]4C)nc(F)c3Cl)c3nc4n(c(=O)c23)CCC4)c1F] | (S)-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-3-methoxybenzamide |

TABLE 1-continued

Examples of Compounds of Formula I

| No | Structure | IUPAC Chemical Name |
|---|---|---|
| I-16 | 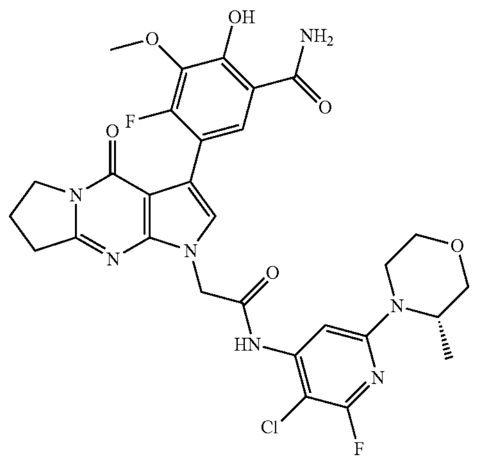 [SMILES: COc1c(O)c(C(N)=O)cc(-c2cn(CC(=O)Nc3cc(N4CCOC[C@@H]4C)nc(F)c3Cl)c3nc4n(c(=O)c23)CCC4)c1F] | (S)-5-(1-(2-((3-chloro-2-fluoro-6-(3-methyl-morpholino)pyridin-4-yl)amino)-2oxoethyl)-4-oxo-4,6,7,8-tetra-hydro-1H-dipyrrolo[1,2-a:2',3'-d]pyrimidin-3-yl)-4-fluoro-2-hydroxy-3-methoxybenzamide |
| I-17 | 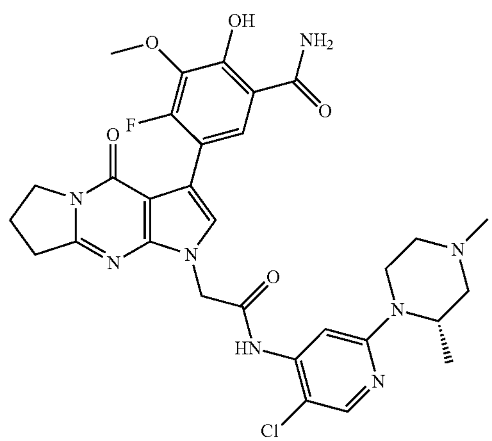 [SMILES: COc1c(O)c(C(N)=O)cc(-c2cn(CC(=O)Nc3cc(N4CCN(C)C[C@@H]4C)ncc3Cl)c3nc4n(c(=O)c23)CCC4)c1F] | (S)-5-(1-(2-((5-chloro-2-(2,4-dimethyl-piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-3-methoxybenzamide |
| I-18 | 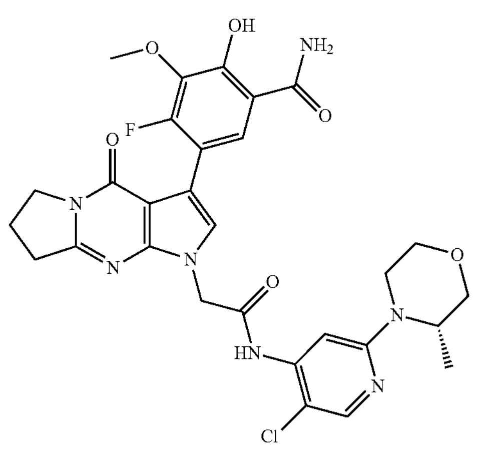 [SMILES: COc1c(O)c(C(N)=O)cc(-c2cn(CC(=O)Nc3cc(N4CCOC[C@@H]4C)ncc3Cl)c3nc4n(c(=O)c23)CCC4)c1F] | (S)-5-(1-(2-((5-chloro-2-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-3-methoxybenzamide |

TABLE 1-continued

Examples of Compounds of Formula I

| No | Structure | IUPAC Chemical Name |
|---|---|---|
| I-19 | 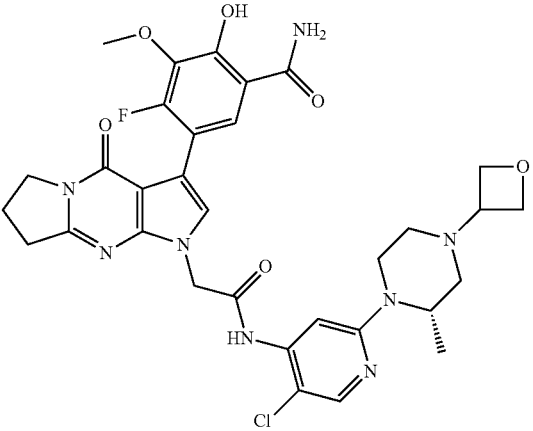 [SMILES: COc1c(O)c(C(N)=O)cc(-c2cn(CC(=O)Nc3cc(N4CCN(C5COC5)C[C@@H]4C)ncc3Cl)c3nc4n(c(=O)c23)CCC4)c1F] | (S)-5-(1-(2-((5-chloro-2-(2-methyl-4-(oxetan-3-yl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-3-methoxybenzamide |
| I-20 | 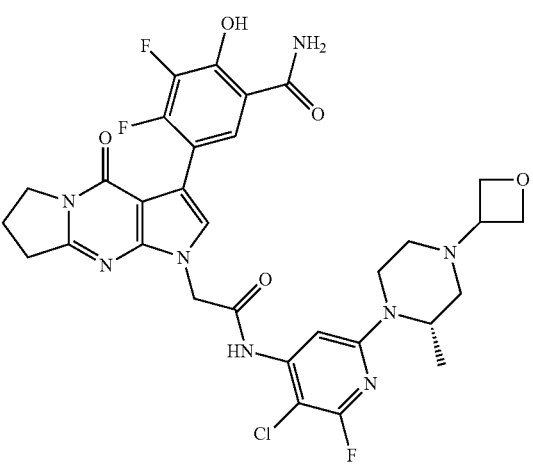 | (S)-5-(1-(2-((3-chloro-2-fluoro-6-(2-methyl-4-(oxetan-3-yl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-21 | 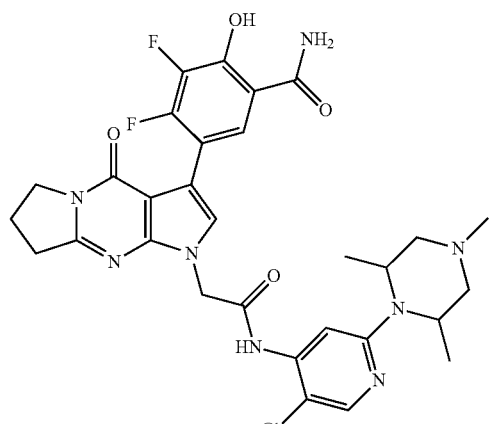 | 5-(1-(2-((5-chloro-2-(2,4,6-trimethyl-piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-22 | 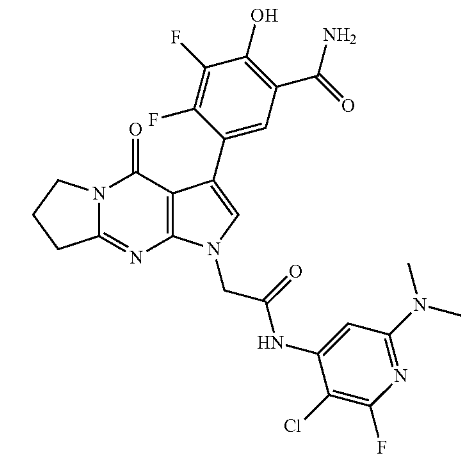 [SMILES: CN(C)c1cc(NC(=O)Cn2cc(-c3cc(C(N)=O)c(O)c(F)c3F)c3c(=O)n4c(nc32)CCC4)c(Cl)c(F)n1] | 5-(1-(2-((3-chloro-6-(dimethylamino)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-23 | 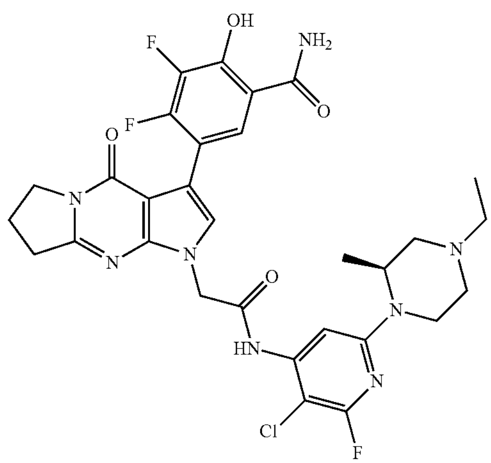 [SMILES: CCN1CCN(c2cc(NC(=O)Cn3cc(-c4cc(C(N)=O)c(O)c(F)c4F)c4c(=O)n5c(nc43)CCC5)c(Cl)c(F)n2)[C@@H](C)C1] | (S)-5-(1-(2-((3-chloro-6-(4-ethyl-2-methyl-piperazin-1-yl)-2-fluoro-pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-24 | 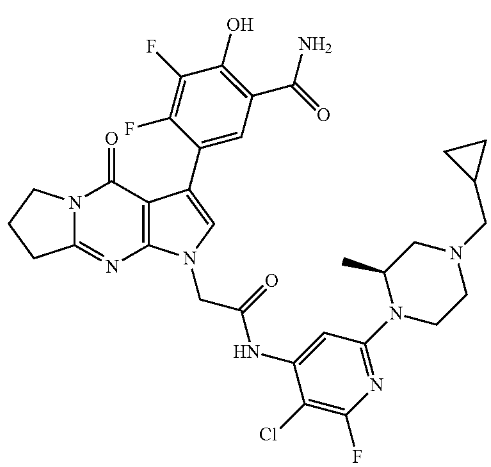 [SMILES: C[C@H]1CN(CC2CC2)CCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-6-(4-(cyclopropylmethyl)-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |

TABLE 1-continued

Examples of Compounds of Formula I

| No | Structure | IUPAC Chemical Name |
| --- | --- | --- |
| I-25 | 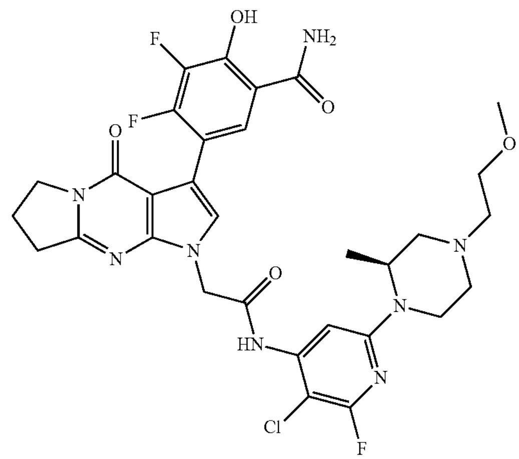 | (S)-5-(1-(2-((3-chloro-2-fluoro-6-(4-(2-methoxyethyl)-2-methyl-piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |
| I-26 | 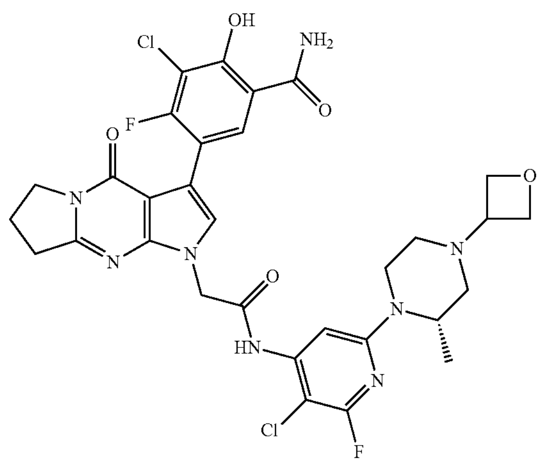 [SMILES: C[C@H]1CN(C2COC2)CCN1c1cc(NC(=O)Cn2cc(-c3cc(C(N)=O)c(O)c(Cl)c3F)c3c(=O)n4c(nc32)CCC4)c(Cl)c(F)n1] | (S)-3-chloro-5-(1-(2-((3-chloro-2-fluoro-6-(2-methyl-4-(oxetan-3-yl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-benzamide |
| I-27 | 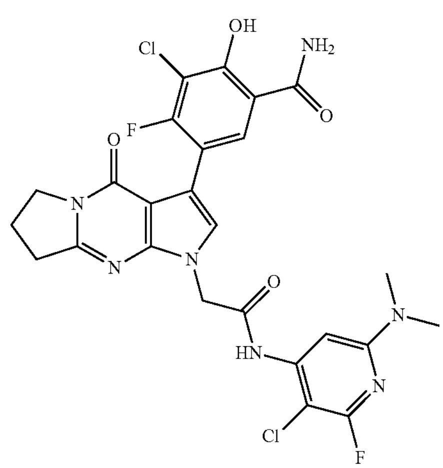 [SMILES: CN(C)c1cc(NC(=O)Cn2cc(-c3cc(C(N)=O)c(O)c(Cl)c3F)c3c(=O)n4c(nc32)CCC4)c(Cl)c(F)n1] | 3-chloro-5-(1-(2-((3-chloro-6-(dimethyl-amino)-2-fluoro-pyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxy-benzamide |

TABLE 1-continued

Examples of Compounds of Formula I

| No | Structure | IUPAC Chemical Name |
|---|---|---|
| I-28 | 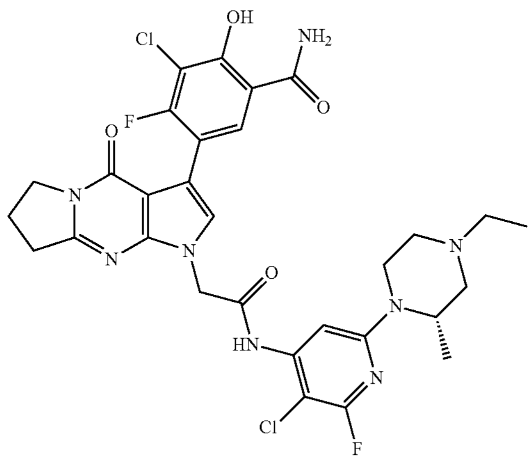 [SMILES: CCN1CCN(c2cc(NC(=O)Cn3cc(-c4cc(C(N)=O)c(O)c(Cl)c4F)c4c(=O)n5c(nc43)CCC5)c(Cl)c(F)n2)[C@@H](C)C1] | (S)-3-chloro-5-(1-(2-((3-chloro-6-(4-ethyl-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxybenzamide |
| I-29 | 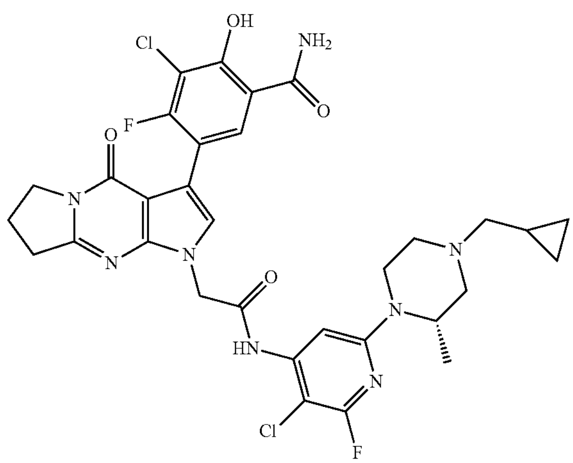 [SMILES: C[C@H]1CN(CC2CC2)CCN1c1cc(NC(=O)Cn2cc(-c3cc(C(N)=O)c(O)c(Cl)c3F)c3c(=O)n4c(nc32)CCC4)c(Cl)c(F)n1] | (S)-3-chloro-5-(1-(2-((3-chloro-6-(4-(cyclopropylmethyl)-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-fluoro-2-hydroxybenzamide |
| I-30 | 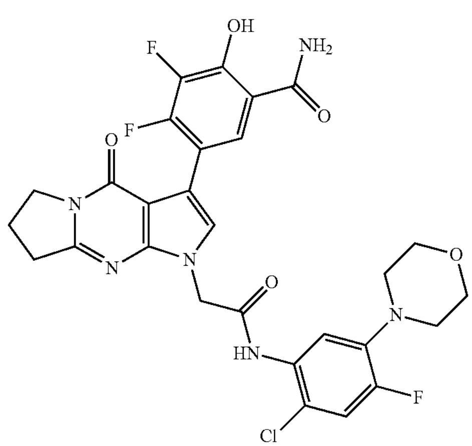 [SMILES: NC(=O)c1cc(-c2cn(CC(=O)Nc3cc(N4CCOCC4)c(F)cc3Cl)c3nc4n(c(=O)c23)CCC4)c(F)c(F)c1O] | 5-(1-(2-((2-chloro-4-fluoro-5-morpholinophenyl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-31 | 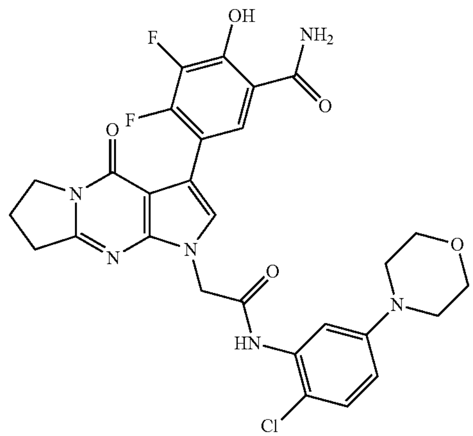 [SMILES: NC(=O)c1cc(-c2cn(CC(=O)Nc3cc(N4CCOCC4)ccc3Cl)c3nc4n(c(=O)c23)CCC4)c(F)c(F)c1O] | 5-(1-(2-((2-chloro-5-morpholinophenyl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-32 | 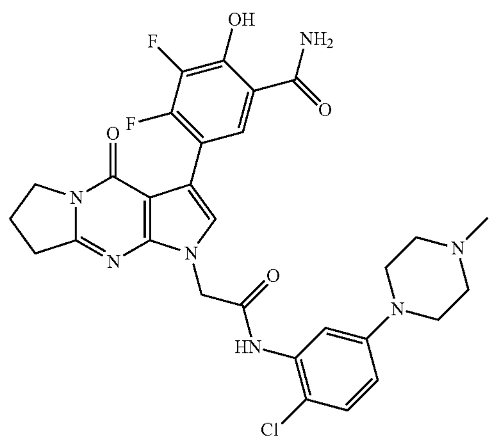 [SMILES: CN1CCN(c2ccc(Cl)c(NC(=O)Cn3cc(-c4cc(C(N)=O)c(O)c(F)c4F)c4c(=O)n5c(nc43)CCC5)c2)CC1] | 5-(1-(2-((2-chloro-5-(4-methylpiperazin-1-yl)phenyl)amino)-2-oxo-ethyl)-4-oxo-4,6,7,8-tetrahydro-1H-dipyrrolo[1,2-a:2',3'-d]pyrimidin-3-yl)-3,4-difluoro-2-hydroxybenzamide |
| I-33 | 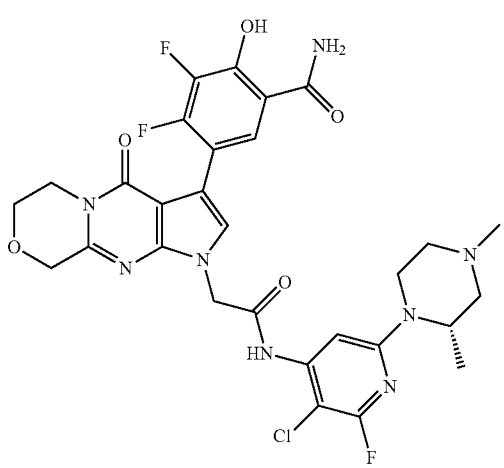 [SMILES: C[C@H]1CN(C)CCN1c1cc(NC(=O)Cn2cc(-c3cc(C(N)=O)c(O)c(F)c3F)c3c(=O)n4c(nc32)COCC4)c(Cl)c(F)n1] | (S)-5-(1-(2-((3-chloro-6-(2,4-dimethylpiperazin-1-yl)-2-fluoropyridin-4-yl)amino)-2-oxoethyl)-4-oxo-4,6,7,9-tetrahydro-1H-pyrrolo[2',3':4,5]pyrimido[2,1-c][1,4]oxazin-3-yl)-3,4-difluoro-2-hydroxybenzamide |

TABLE 1-continued

Examples of Compounds of Formula I

| No | Structure | IUPAC Chemical Name |
|---|---|---|
| I-34 | 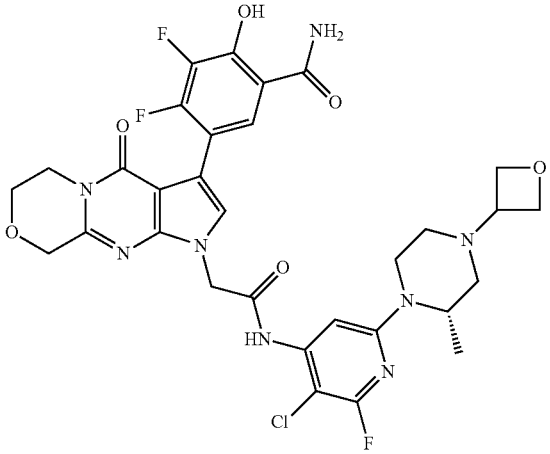 [SMILES: C[C@H]1CN(C2COC2)CCN1c1cc(NC(=O)Cn2cc(-c3cc(C(N)=O)c(O)c(F)c3F)c3c(=O)n4c(nc32)COCC4)c(Cl)c(F)n1] | (S)-5-(1-(2-((3-chloro-2-fluoro-6-(2-methyl-4-(oxetan-3-yl)piperazin-1-yl)pyridin-4-yl)amino)-2-oxoethyl)-4-oxo-4,6,7,9-tetrahydro-1H-pyrrolo[2',3':4,5]pyrimido[2,1-c][1,4]oxazin-3-yl)-3,4-difluoro-2-hydroxybenzamide |
| I-35 | 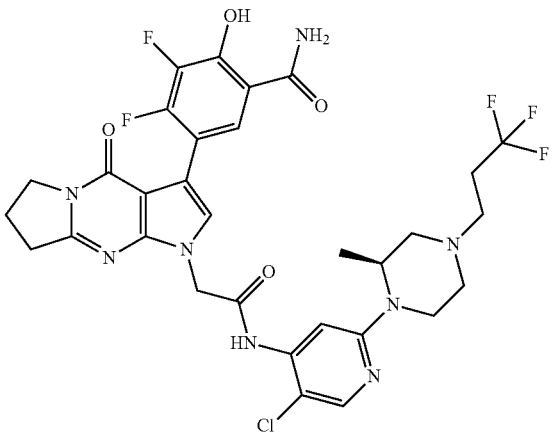 [SMILES: C[C@H]1CN(CCC(F)(F)F)CCN1c1cc(NC(=O)Cn2cc(-c3cc(C(N)=O)c(O)c(F)c3F)c3c(=O)n4c(nc32)CCC4)c(Cl)cn1] | (S)-5-(1-(2-((5-chloro-2-(2-methyl-4-(3,3,3-trifluoropropyl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-36 | 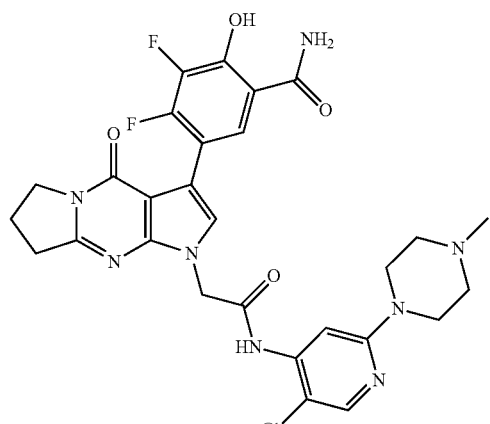 | 5-(1-(2-((5-chloro-2-(4-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-37 | 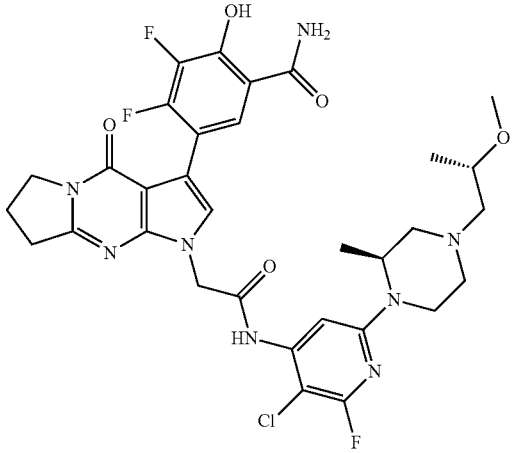 | 5-(1-(2-((3-chloro-2-fluoro-6-((S)-4-((S)-2-methoxypropyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-38 | 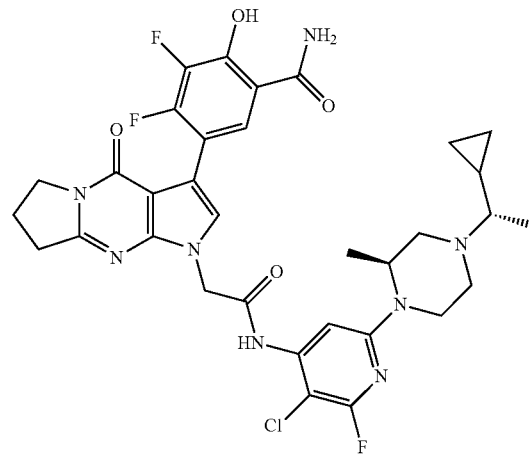 | 5-(1-(2-((3-chloro-6-((S)-4-((S)-1-cyclopropylethyl)-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-39 | 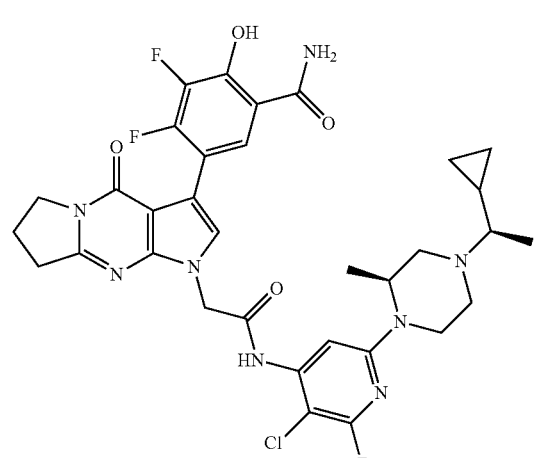 | 5-(1-(2-((3-chloro-6-((S)-4-((R)-1-cyclopropylethyl)-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-40 | 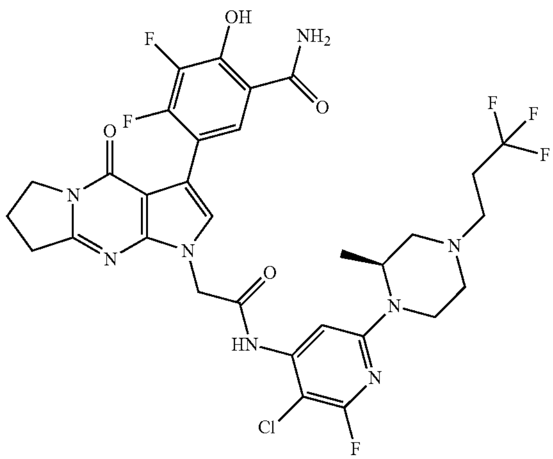 [SMILES: C[C@H]1CN(CCC(F)(F)F)CCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-2-fluoro-6-(2-methyl-4-(3,3,3-trifluoropropyl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |
| I-41 | 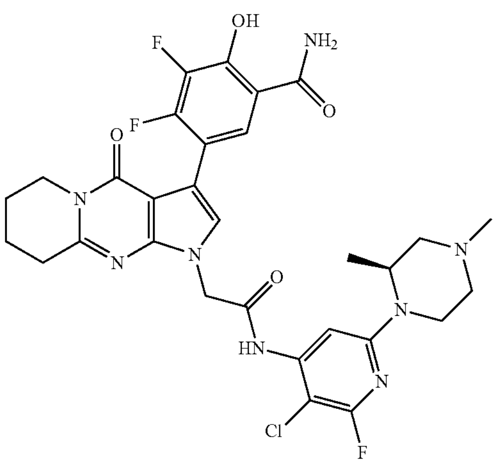 | (S)-5-(1-(2-((3-chloro-6-(2,4-dimethyl-piperazin-1-yl)-2-fluoropyridin-4-yl)amino)-2-oxoethyl)-4-oxo-1,4,6,7,8,9-hexahydropyrido[1,2-a]pyrrolo[2,3-d]pyrimidin-3-yl)-3,4-difluoro-2-hydroxy-benzamide |
| I-42 | 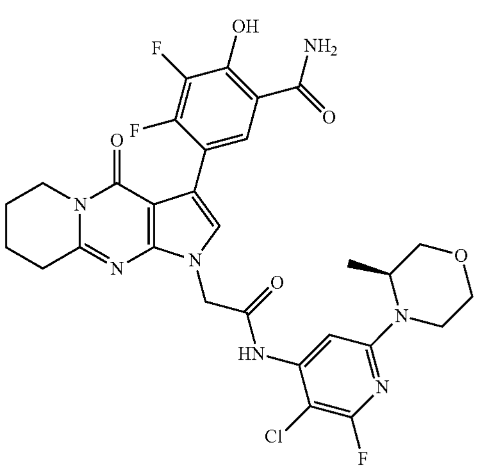 [SMILES: C[C@H]1COCCN1c1cc(NC(=O)Cn2cc(-c3cc(C(N)=O)c(O)c(F)c3F)c3c(=O)n4c(nc32)CCCC4)c(Cl)c(F)n1] | (S)-5-(1-(2-((3-chloro-2-fluoro-6-(3-methyl-morpholino)pyridin-4-yl)amino)-2-oxoethyl)-4-oxo-1,4,6,7,8,9-hexahydropyrido[1,2-a]pyrrolo[2,3-d]pyrimidin-3-yl)-3,4-difluoro-2-hydroxy-benzamide |

TABLE 1-continued

Examples of Compounds of Formula I

| No | Structure | IUPAC Chemical Name |
|---|---|---|
| I-43 | 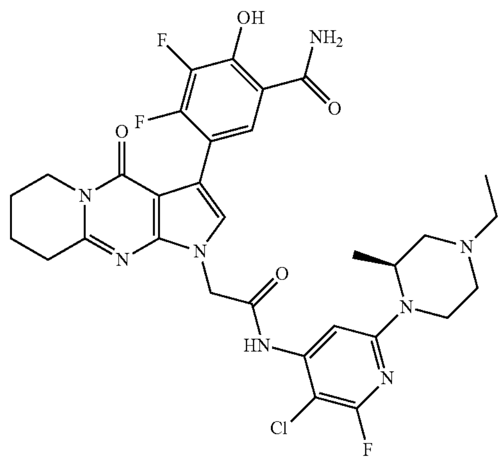 [SMILES: CCN1CCN(c2cc(NC(=O)Cn3cc(-c4cc(C(N)=O)c(O)c(F)c4F)c4c(=O)n5c(nc43)CCCC5)c(Cl)c(F)n2)[C@@H](C)C1] | (S)-5-(1-(2-((3-chloro-6-(4-ethyl-2-methyl-piperazin-1-yl)-2-fluoropyridin-4-yl)amino)-2-oxoethyl)-4-oxo-1,4,6,7,8,9-hexahydropyrido[1,2-a]pyrrolo[2,3-d]pyrimidin-3-yl)-3,4-difluoro-2-hydroxy-benzamide |
| I-44 | 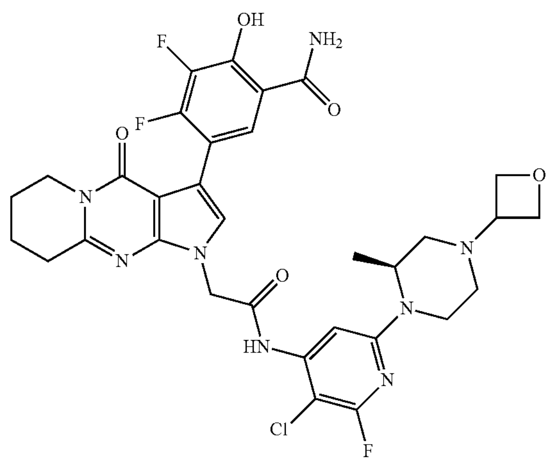 [SMILES: C[C@H]1CN(C2COC2)CCN1c1cc(NC(=O)Cn2cc(-c3cc(C(N)=O)c(O)c(F)c3F)c3c(=O)n4c(nc32)CCCC4)c(Cl)c(F)n1] | (S)-5-(1-(2-((3-chloro-2-fluoro-6-(2-methyl-4-(oxetan-3-yl)piperazin-1-yl)pyridin-4-yl)amino)-2-oxo-ethyl)-4-oxo-1,4,6,7,8,9-hexahydropyrido[1,2-a]pyrrolo[2,3-d]pyrimidin-3-yl)-3,4-difluoro-2-hydroxy-benzamide |
| I-45 | 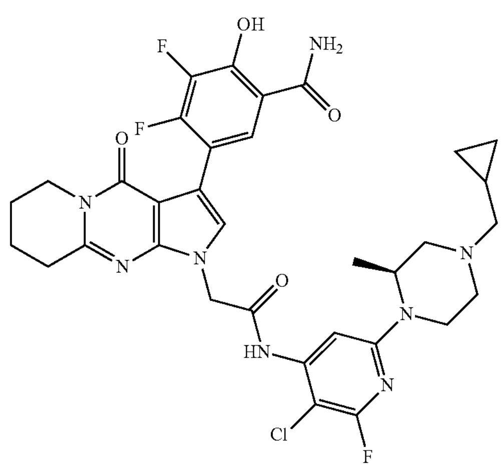 [SMILES: C[C@H]1CN(CC2CC2)CCN1c1cc(NC(=O)Cn2cc(-c3cc(C(N)=O)c(O)c(F)c3F)c3c(=O)n4c(nc32)CCCC4)c(Cl)c(F)n1] | (S)-5-(1-(2-((3-chloro-6-(4-(cyclopropyl-methyl)-2-methyl-piperazin-1-yl)-2-fluoropyridin-4-yl)amino)-2-oxoethyl)-4-oxo-1,4,6,7,8,9-hexahydropyrido[1,2-a]pyrrolo[2,3-d]pyrimidin-3-yl)-3,4-difluoro-2-hydroxy-benzamide |

TABLE 1-continued

Examples of Compounds of Formula I

| No | Structure | IUPAC Chemical Name |
|---|---|---|
| I-46 | 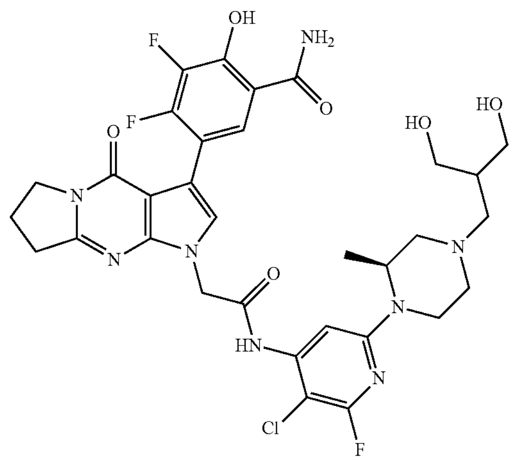 [SMILES: C[C@H]1CN(CC(CO)CO)CCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-2-fluoro-6-(4-(3-hydroxy-2-(hydroxymethyl)propyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-47 | 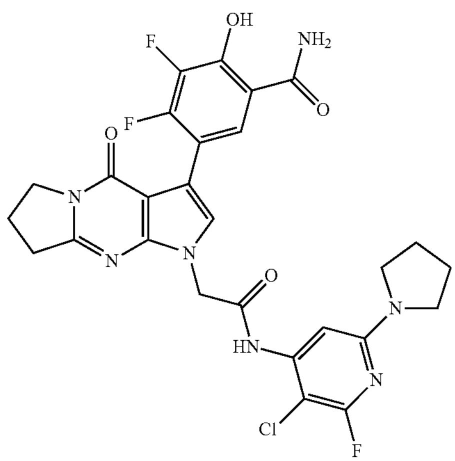 [SMILES: NC(=O)c1cc(-c2cn(CC(=O)Nc3cc(N4CCCC4)nc(F)c3Cl)c3nc4n(c(=O)c23)CCC4)c(F)c(F)c1O] | 5-(1-(2-((3-chloro-2-fluoro-6-(pyrrolidin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-48 | 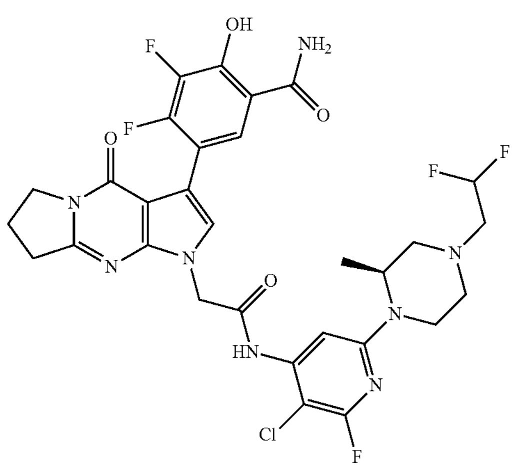 [SMILES: C[C@H]1CN(CC(F)F)CCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-6-(4-(2,2-difluoroethyl)-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-49 | 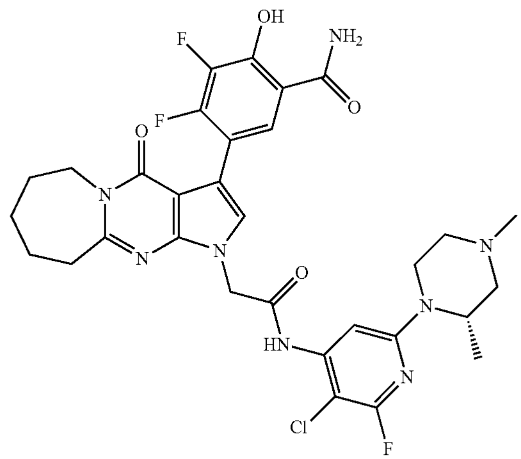 [SMILES: C[C@H]1CN(C)CCN1c1cc(NC(=O)Cn2cc(-c3cc(C(N)=O)c(O)c(F)c3F)c3c(=O)n4c(nc32)CCCCC4)c(Cl)c(F)n1] | (S)-5-(1-(2-((3-chloro-6-(2,4-dimethyl-piperazin-1-yl)-2-fluoropyridin-4-yl)amino)-2-oxoethyl)-4-oxo-4,6,7,8,9,10-hexahydro-1H-pyrrolo[2',3':4,5]pyrimido[1,2-a]azepin-3-yl)-3,4-difluoro-2-hydroxy-benzamide |
| I-50 | 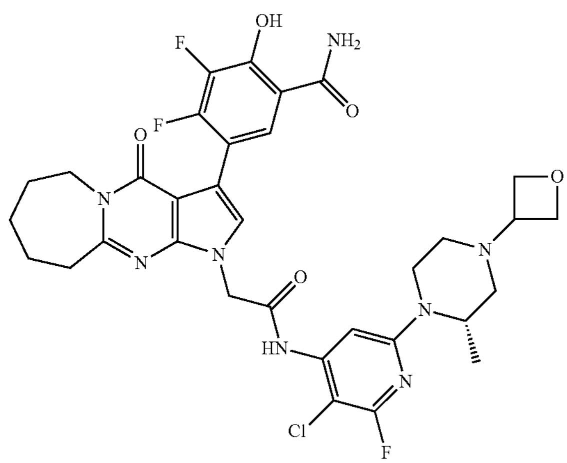 [SMILES: C[C@H]1CN(C2COC2)CCN1c1cc(NC(=O)Cn2cc(-c3cc(C(N)=O)c(O)c(F)c3F)c3c(=O)n4c(nc32)CCCCC4)c(Cl)c(F)n1] | (S)-5-(1-(2-((3-chloro-2-fluoro-6-(2-methyl-4-(oxetan-3-yl)piperazin-1-yl)pyridin-4-yl)amino)-2-oxo-ethyl)-4-oxo-4,6,7,8,9,10-hexahydro-1H-pyrrolo[2',3':4,5]pyrimido[1,2-a]azepin-3-yl)-3,4-difluoro-2-hydroxybenzamide |
| I-51 | 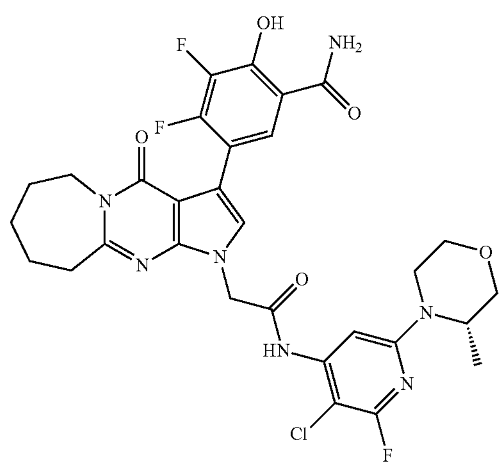 [SMILES: C[C@H]1COCCN1c1cc(NC(=O)Cn2cc(-c3cc(C(N)=O)c(O)c(F)c3F)c3c(=O)n4c(nc32)CCCCC4)c(Cl)c(F)n1] | (S)-5-(1-(2-((3-chloro-2-fluoro-6-(3-methyl-morpholino)pyridin-4-yl)amino)-2-oxoethyl)-4-oxo-4,6,7,8,9,10-hexahydro-1H-pyrrolo[2',3':4,5]pyrimido[1,2-a]azepin-3-yl)-3,4-difluoro-2-hydroxy-benzamide |

TABLE 1-continued

Examples of Compounds of Formula I

| No | Structure | IUPAC Chemical Name |
|---|---|---|
| I-52 | 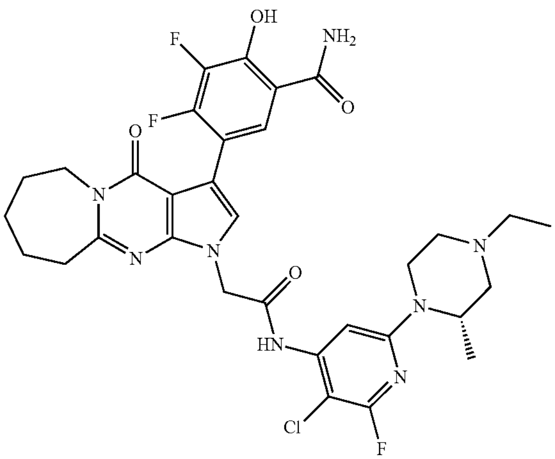 [SMILES: CCN1CCN(c2cc(NC(=O)Cn3cc(-c4cc(C(N)=O)c(O)c(F)c4F)c4c(=O)n5c(nc43)CCCCC5)c(Cl)c(F)n2)[C@@H](C)C1] | (S)-5-(1-(2-((3-chloro-6-(4-ethyl-2-methyl-piperazin-1-yl)-2-fluoropyridin-4-yl)amino)-2-oxoethyl)-4-oxo-4,6,7,8,9,10-hexahydro-1H-pyrrolo[2',3':4,5]pyrimido[1,2-a]azepin-3-yl)-3,4-difluoro-2-hydroxybenzamide |
| I-53 | 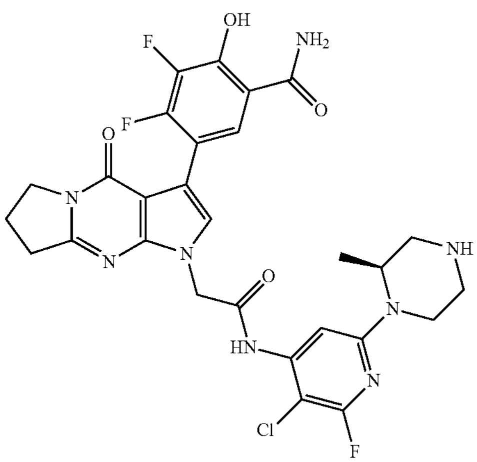 [SMILES: C[C@H]1CNCCN1c1cc(NC(=O)Cn2cc(-c3cc(C(N)=O)c(O)c(F)c3F)c3c(=O)n4c(nc32)CCC4)c(Cl)c(F)n1] | (S)-5-(1-(2-((3-chloro-2-fluoro-6-(2-methyl-piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |
| I-54 | 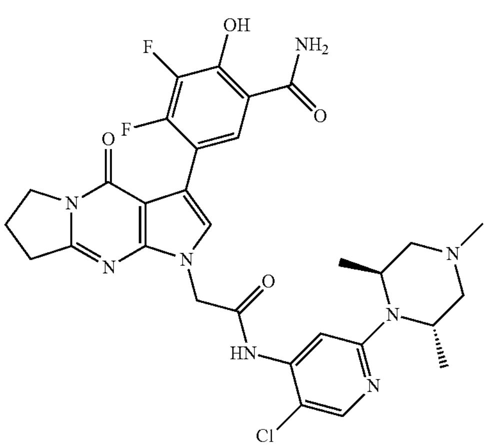 [SMILES: C[C@H]1CN(C)C[C@H](C)N1c1cc(NC(=O)Cn2cc(-c3cc(C(N)=O)c(O)c(F)c3F)c3c(=O)n4c(nc32)CCC4)c(Cl)cn1] | 5-(1-(2-((5-chloro-2-((2S,6S)-2,4,6-trimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-55 | 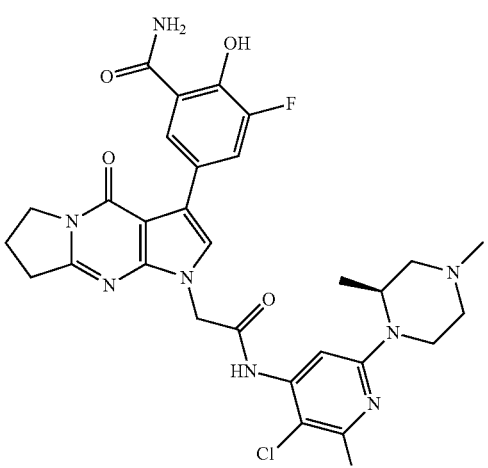 | (S)-5-(1-(2-((3-chloro-6-(2,4-dimethyl-piperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxybenzamide |
| I-56 | 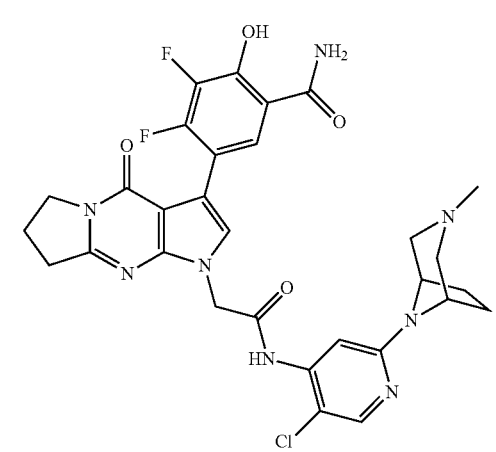 [SMILES: CN1CC2CCC(C1)N2c1cc(NC(=O)Cn2cc(-c3cc(C(N)=O)c(O)c(F)c3F)c3c(=O)n4c(nc32)CCC4)c(Cl)cn1] | 5-(1-(2-((5-chloro-2-((1R,5S)-3-methyl-3,8-diazabicyclo[3.2.1]octan-8-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |
| I-57 | 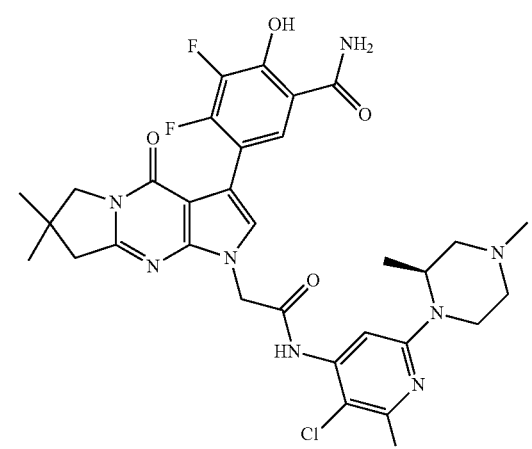 | (S)-5-(1-(2-((3-chloro-6-(2,4-dimethyl-piperazin-1-yl)-2-fluoropyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-3,4-difluoro-2-hydroxy-benzamide |

TABLE 1-continued

Examples of Compounds of Formula I

| No | Structure | IUPAC Chemical Name |
|---|---|---|
| I-58 | 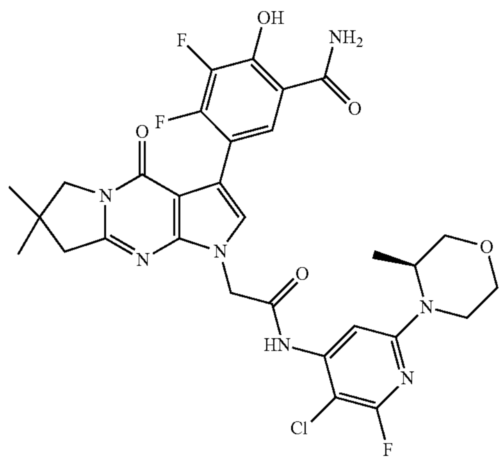 [SMILES: C[C@H]1COCCN1c1cc(NC(=O)Cn2cc(-c3cc(C(N)=O)c(O)c(F)c3F)c3c(=O)n4c(nc32)CC(C)(C)C4)c(Cl)c(F)n1] | (S)-5-(1-(2-((3-chloro-2-fluoro-6-(3-methyl-morpholino)pyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-3,4-difluoro-2-hydroxy-benzamide |
| I-59 | 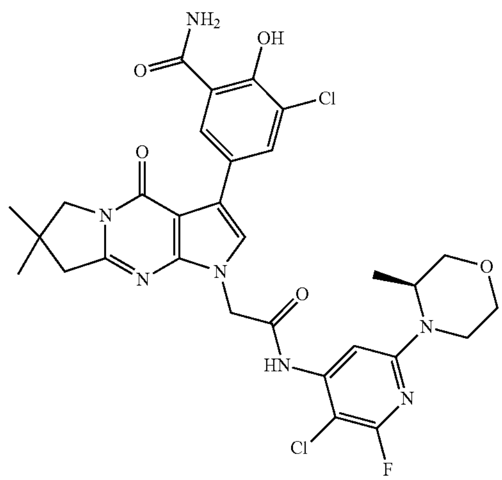 [SMILES: C[C@H]1COCCN1c1cc(NC(=O)Cn2cc(-c3cc(Cl)c(O)c(C(N)=O)c3)c3c(=O)n4c(nc32)CC(C)(C)C4)c(Cl)c(F)n1] | (S)-3-chloro-5-(1-(2-((3-chloro-2-fluoro-6-(3-methylmorpho-lino)pyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-2-hydroxybenzamide |
| I-60 | 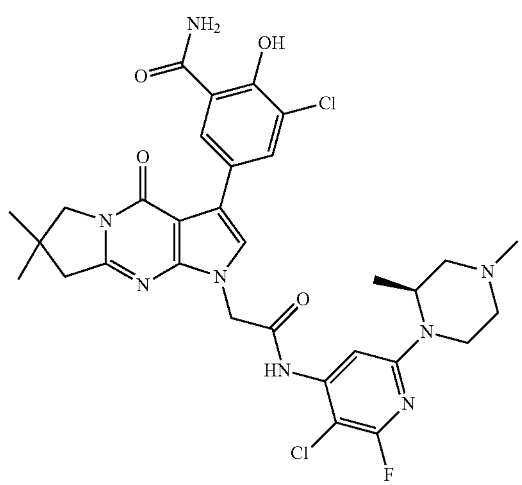 | (S)-3-chloro-5-(1-(2-((3-chloro-6-(2,4-dimethylpiperazin-1-yl)-2-fluoropyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-2-hydroxybenzamide |

TABLE 1-continued

Examples of Compounds of Formula I

| No | Structure | IUPAC Chemical Name |
|---|---|---|
| I-61 | 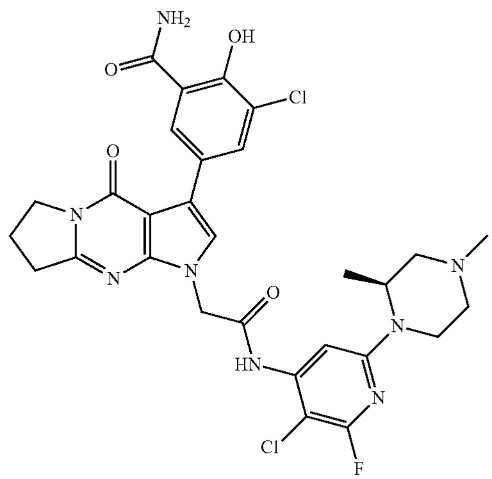 | (S)-3-chloro-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-2-hydroxybenzamide |
| I-62 | 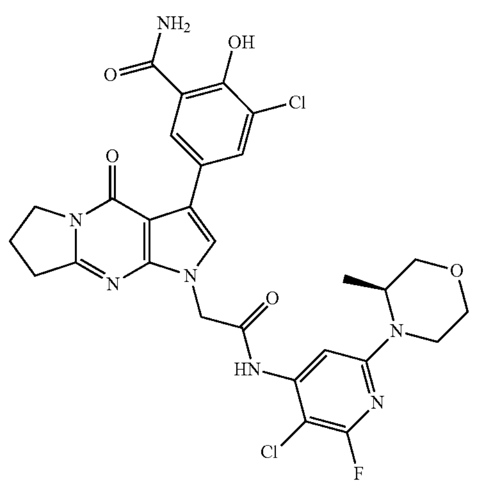 [SMILES: C[C@H]1COCCN1c1cc(NC(=O)Cn2cc(-c3cc(Cl)c(O)c(C(N)=O)c3)c3c(=O)n4c(nc32)CCC4)c(Cl)c(F)n1] | (S)-3-chloro-5-(1-(2-((3-chloro-2-fluoro-6-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-2-hydroxybenzamide |
| I-63 | 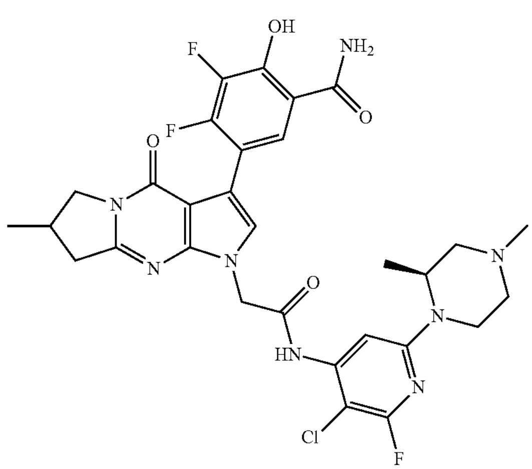 | 5-(1-(2-((3-chloro-6-((S)-2,4-dimethylpiperazin-1-yl)-2-fluoropyridin-4-yl)amino)-2-oxoethyl)-7-methyl-4-oxo-4,6,7,8-tetrahydro-1H-dipyrrolo[1,2-a:2',3'-d]pyrimidin-3-yl)-3,4-difluoro-2-hydroxybenzamide |

TABLE 1-continued

Examples of Compounds of Formula I

| No | Structure | IUPAC Chemical Name |
|---|---|---|
| I-64 | 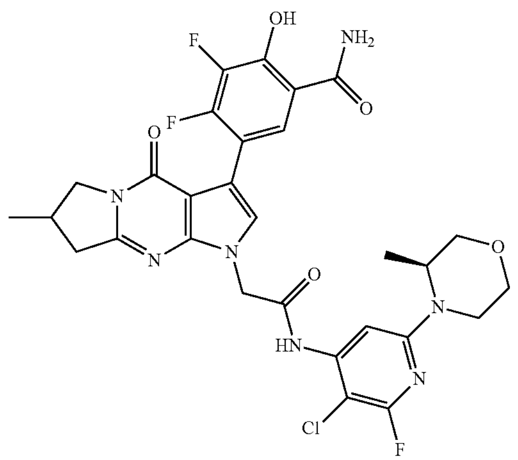 [SMILES: CC1Cc2nc3c(c(-c4cc(C(N)=O)c(O)c(F)c4F)cn3CC(=O)Nc3cc(N4CCOC[C@@H]4C)nc(F)c3Cl)c(=O)n2C1] | 5-(1-(2-((3-chloro-2-fluoro-6-((S)-3-methylmorpholino)pyridin-4-yl)amino)-2-oxoethyl)-7-methyl-4-oxo-4,6,7,8-tetrahydro-1H-dipyrrolo[1,2-a:2',3'-d]pyrimidin-3-yl)-3,4-difluoro-2-hydroxybenzamide |
| I-65 | 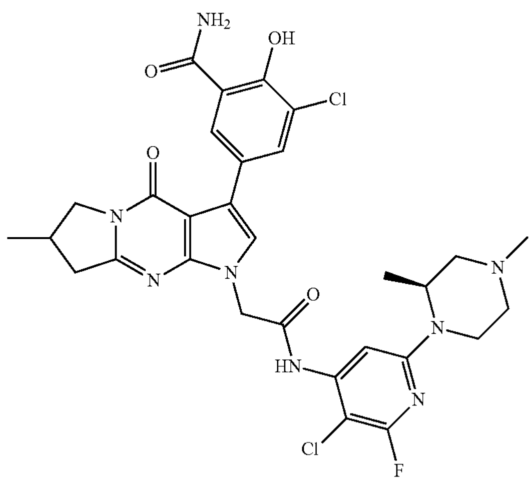 | 3-chloro-5-(1-(2-((3-chloro-6-((S)-2,4-dimethylpiperazin-1-yl)-2-fluoropyridin-4-yl)amino)-2-oxoethyl)-7-methyl-4-oxo-4,6,7,8-tetrahydro-1H-dipyrrolo[1,2-a:2',3'-d]pyrimidin-3-yl)-2-hydroxybenzamide |
| I-66 | 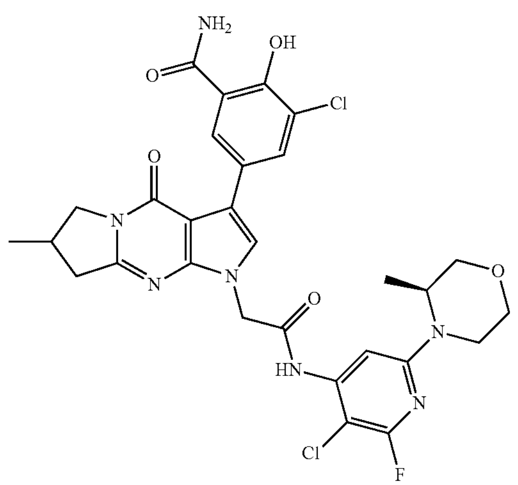 [SMILES: CC1Cc2nc3c(c(-c4cc(Cl)c(O)c(C(N)=O)c4)cn3CC(=O)Nc3cc(N4CCOC[C@@H]4C)nc(F)c3Cl)c(=O)n2C1] | 3-chloro-5-(1-(2-((3-chloro-2-fluoro-6-((S)-3-methylmorpholino)pyridin-4-yl)amino)-2-oxoethyl)-7-methyl-4-oxo-4,6,7,8-tetrahydro-1H-dipyrrolo[1,2-a:2',3'-d]pyrimidin-3-yl)-2-hydroxybenzamide |

TABLE 1-continued

Examples of Compounds of Formula I

| No | Structure | IUPAC Chemical Name |
|---|---|---|
| I-67 | 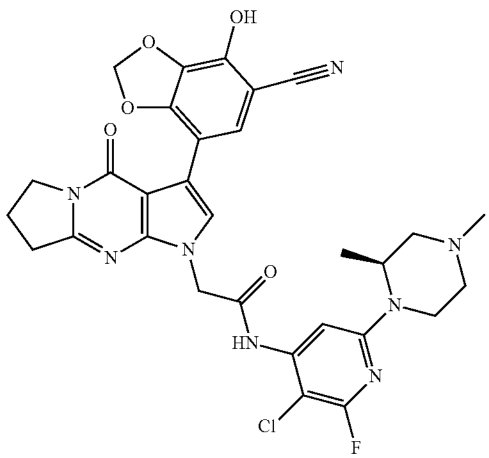 [SMILES: C[C@H]1CN(C)CCN1c1cc(NC(=O)Cn2cc(-c3cc(C#N)c(O)c4c3OCO4)c3c(=O)n4c(nc32)CCC4)c(Cl)c(F)n1] | (S)-N-(3-chloro-6-(2,4-dimethyl-piperazin-1-yl)-2-fluoropyridin-4-yl)-2-(3-(6-cyano-7-hydroxybenzo[d][1,3]dioxol-4-yl)-4-oxo-4,6,7,8-tetrahydro-1H-dipyrrolo[1,2-a:2',3'-d]pyrimidin-1-yl)acetamide |
| I-68 | 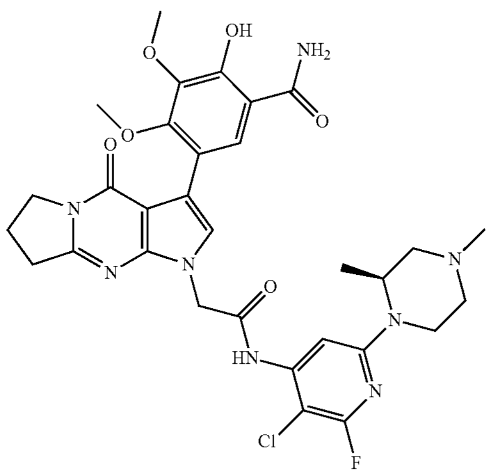 [SMILES: COc1c(-c2cn(CC(=O)Nc3cc(N4CCN(C)C[C@@H]4C)nc(F)c3Cl)c3nc4n(c(=O)c23)CCC4)cc(C(N)=O)c(O)c1OC] | (S)-5-(1-(2-((3-chloro-6-(2,4-dimethylpiperazin-1-yl)-2-fluoro-pyridin-4-yl)amino)-2-oxoethyl)-4-oxo-4,6,7,8-tetrahydro-1H-dipyrrolo[1,2-a:2',3'-d]pyrimidin-3-yl)-2-hydroxy-3,4-dimethoxy-benzamide |
| I-69 | 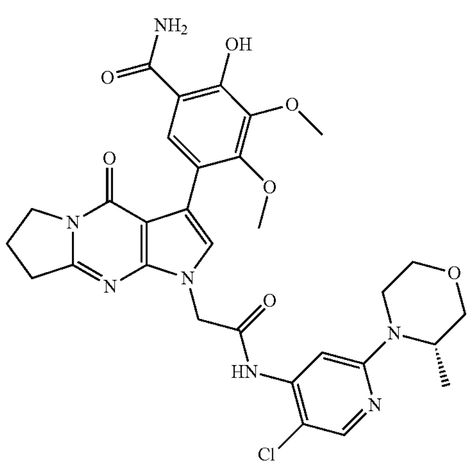 [SMILES: COc1c(-c2cn(CC(=O)Nc3cc(N4CCOC[C@@H]4C)ncc3Cl)c3nc4n(c(=O)c23)CCC4)cc(C(N)=O)c(O)c1OC] | (S)-5-(1-(2-((5-chloro-2-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-2-hydroxy-3,4-dimethoxy-benzamide |

TABLE 1-continued

Examples of Compounds of Formula I

| No | Structure | IUPAC Chemical Name |
|---|---|---|
| I-70 | 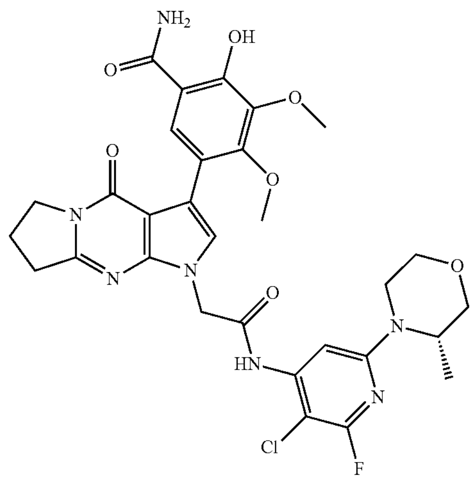 [SMILES: COc1c(-c2cn(CC(=O)Nc3cc(N4CCOC[C@@H]4C)nc(F)c3Cl)c3nc4n(c(=O)c23)CCC4)cc(C(N)=O)c(O)c1OC] | (S)-5-(1-(2-((3-chloro-2-fluoro-6-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-2-hydroxy-3,4-dimethoxybenzamide |
| I-71 | 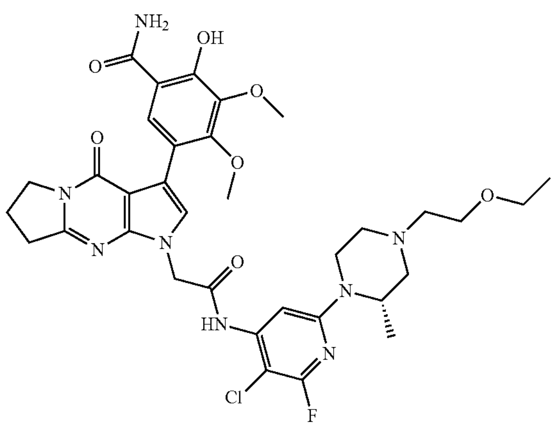 [SMILES: CCOCCN1CCN(c2cc(NC(=O)Cn3cc(-c4cc(C(N)=O)c(O)c(OC)c4OC)c4c(=O)n5c(nc43)CCC5)c(Cl)c(F)n2)[C@@H](C)C1] | (S)-5-(1-(2-((3-chloro-6-(4-(2-ethoxyethyl)-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-2-hydroxy-3,4-dimethoxybenzamide |
| I-72 | 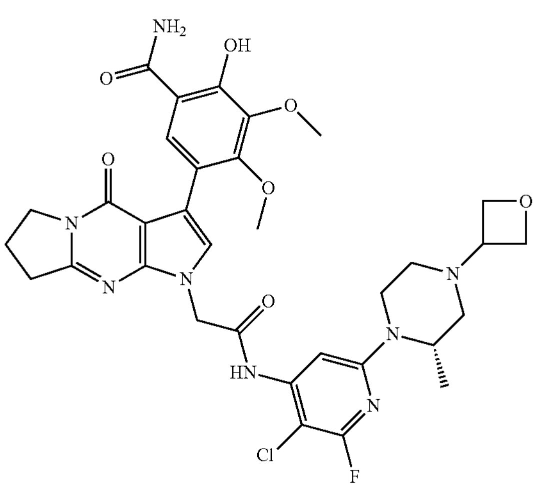 [SMILES: COc1c(-c2cn(CC(=O)Nc3cc(N4CCN(C5COC5)C[C@@H]4C)nc(F)c3Cl)c3nc4n(c(=O)c23)CCC4)cc(C(N)=O)c(O)c1OC] | (S)-5-(1-(2-((3-chloro-2-fluoro-6-(2-methyl-4-(oxetan-3-yl)piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-2-hydroxy-3,4-dimethoxybenzamide |

TABLE 1-continued

Examples of Compounds of Formula I

| No | Structure | IUPAC Chemical Name |
|---|---|---|
| I-73 | 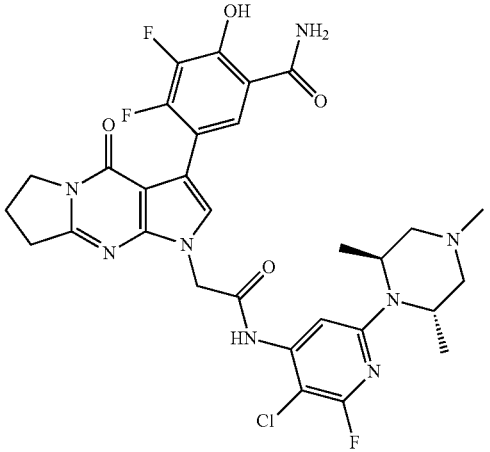 [SMILES: C[C@H]1CN(C)C[C@H](C)N1c1cc(NC(=O)Cn2cc(-c3cc(C(N)=O)c(O)c(F)c3F)c3c(=O)n4c(nc32)CCC4)c(Cl)c(F)n1] | 5-(1-(2-((3-chloro-2-fluoro-6-((2S,6S)-2,4,6-trimethyl-piperazin-1-yl)pyridin-4-yl)amino)-2-oxo-ethyl)-4-oxo-4,6,7,8-tetrahydro-1H-dipyrrolo[1,2-a:2',3'-d]pyrimidin-3-yl)-3,4-difluoro-2-hydroxybenzamide |
| I-74 | 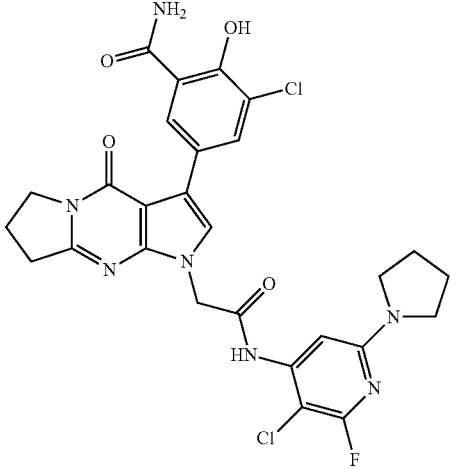 [SMILES: NC(=O)c1cc(-c2cn(CC(=O)Nc3cc(N4CCCC4)nc(F)c3Cl)c3nc4n(c(=O)c23)CCC4)cc(Cl)c1O] | 3-chloro-5-(1-(2-((3-chloro-2-fluoro-6-(pyrrolidin-1-yl)pyridin-4-yl)amino)-2-oxo-ethyl)-4-oxo-4,6,7,8-tetrahydro-1H-dipyrrolo[1,2-a:2',3'-d]pyrimidin-3-yl)-2-hydroxy-benzamide |
| I-75 | 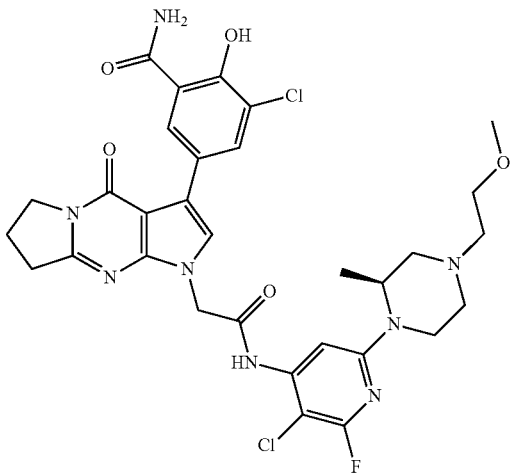 | (S)-3-chloro-5-(1-(2-((3-chloro-2-fluoro-6-(4-(2-methoxyethyl)-2-methylpiperazin-1-yl)pyridin-4-yl)amino)-2-oxoethyl)-4-oxo-4,6,7,8-tetra-hydro-1H-dipyrrolo[1,2-a:2',3'-d]pyrimi-din-3-yl)-2-hydroxy-benzamide |

TABLE 1-continued

Examples of Compounds of Formula I

| No | Structure | IUPAC Chemical Name |
|---|---|---|
| I-76 | 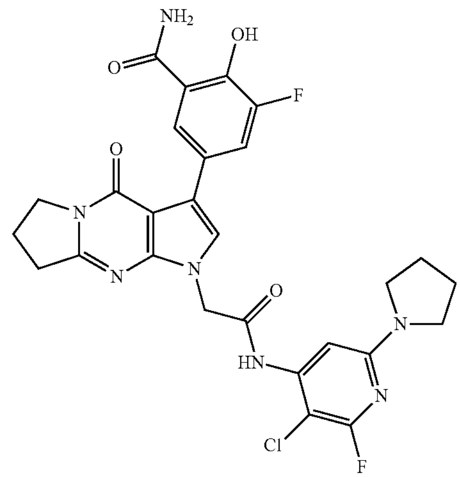 [SMILES: NC(=O)c1cc(-c2cn(CC(=O)Nc3cc(N4CCCC4)nc(F)c3Cl)c3nc4n(c(=O)c23)CCC4)cc(F)c1O] | 5-(1-(2-((3-chloro-2-fluoro-6-(pyrrolidin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxy-benzamide |
| I-77 | 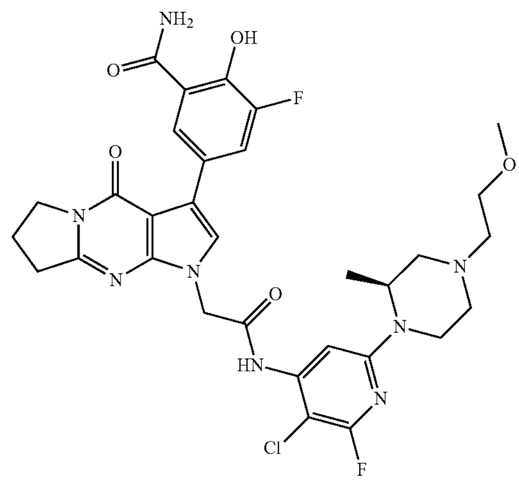 [SMILES: COCCN1CCN(c2cc(NC(=O)Cn3cc(-c4cc(F)c(O)c(C(N)=O)c4)c4c(=O)n5c(nc43)CCC5)c(Cl)c(F)n2)[C@@H](C)C1] | (S)-5-(1-(2-((3-chloro-2-fluoro-6-(4-(2-methoxyethyl)-2-methylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxy-benzamide |
| I-78 | 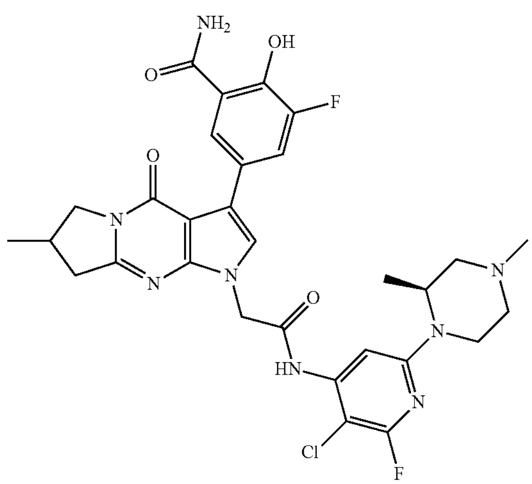 | 5-(1-(2-((3-chloro-6-((S)-2,4-dimethyl-piperazin-1-yl)-2-fluoropyridin-4-yl)amino)-2-oxoethyl)-7-methyl-4-oxo-4,6,7,8-tetrahydro-1H-dipyrrolo[1,2-a:2',3'-d]pyrimidin-3-yl)-3-fluoro-2-hydroxy-benzamide |

TABLE 1-continued

Examples of Compounds of Formula I

| No | Structure | IUPAC Chemical Name |
|---|---|---|
| I-79 | 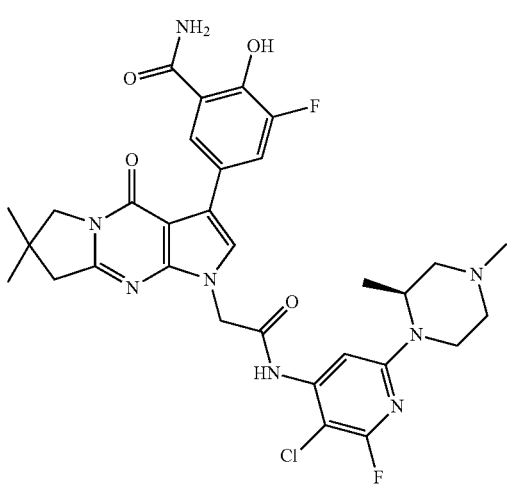 | (S)-5-(1-(2-((3-chloro-6-(2,4-dimethyl-piperazin-1-yl)-2-fluoropyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-3-fluoro-2-hydroxy-benzamide |
| I-80 | 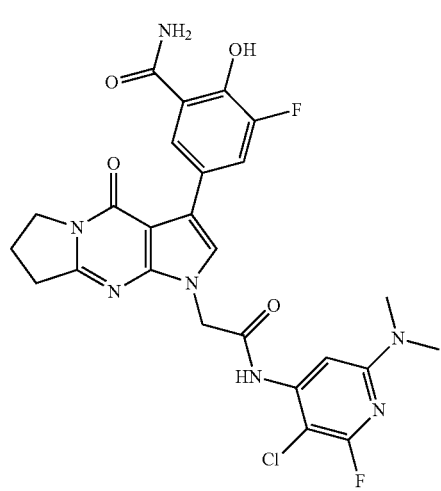 [SMILES: CN(C)c1cc(NC(=O)Cn2cc(-c3cc(F)c(O)c(C(N)=O)c3)c3c(=O)n4c(nc32)CCC4)c(Cl)c(F)n1] | 5-(1-(2-((3-chloro-6-(dimethylamino)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxy-benzamide |
| I-81 | 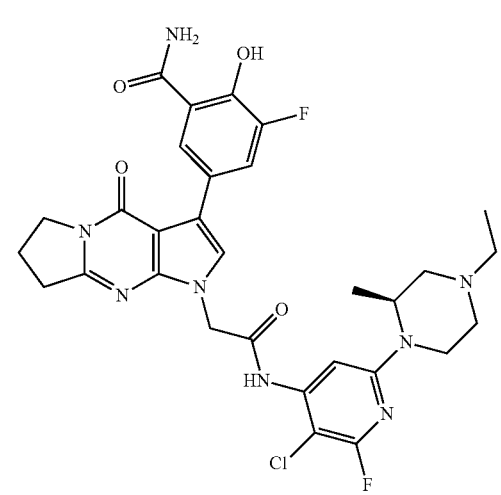 | (S)-5-(1-(2-((3-chloro-6-(4-ethyl-2-methyl-piperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxy-benzamide |

TABLE 1-continued

Examples of Compounds of Formula I

| No | Structure | IUPAC Chemical Name |
|---|---|---|
| I-82 | 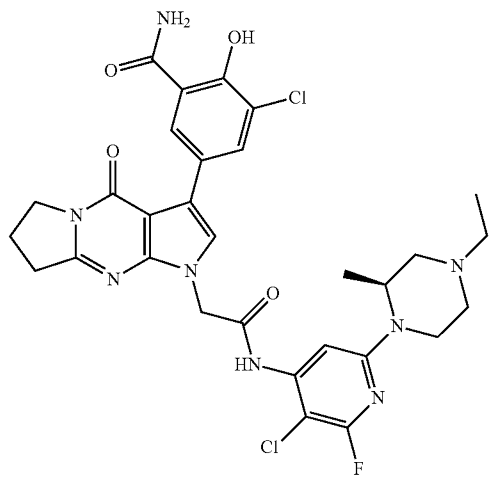 | (S)-3-chloro-5-(1-(2-((3-chloro-6-(4-ethyl-2-methylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-2-hydroxybenzamide |
| I-83 | 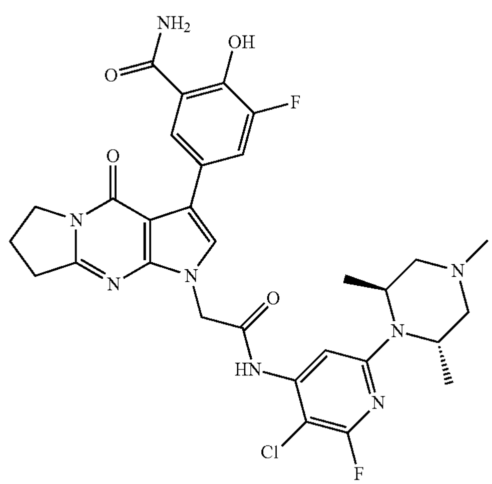 [SMILES: C[C@H]1CN(C)C[C@H](C)N1c1cc(NC(=O)Cn2cc(-c3cc(F)c(O)c(C(N)=O)c3)c3c(=O)n4c(nc32)CCC4)c(Cl)c(F)n1] | 5-(1-(2-((3-chloro-2-fluoro-6-((2S,6S)-2,4,6-trimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxybenzamide |
| I-84 | 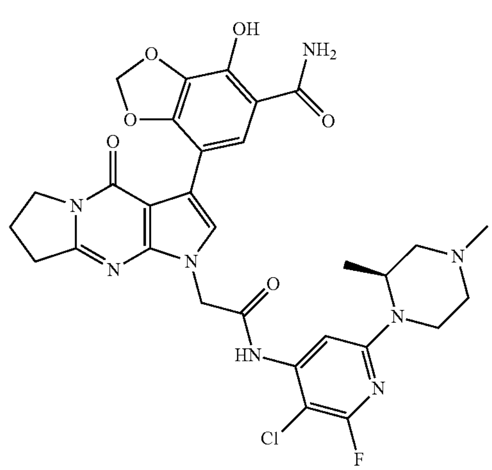 [SMILES: C[C@H]1CN(C)CCN1c1cc(NC(=O)Cn2cc(-c3cc(C(N)=O)c(O)c4c3OCO4)c3c(=O)n4c(nc32)CCC4)c(Cl)c(F)n1] | (S)-7-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-hydroxybenzo[d][1,3]dioxole-5-carboxamide |

TABLE 1-continued

Examples of Compounds of Formula I

| No | Structure | IUPAC Chemical Name |
|---|---|---|
| I-85 | 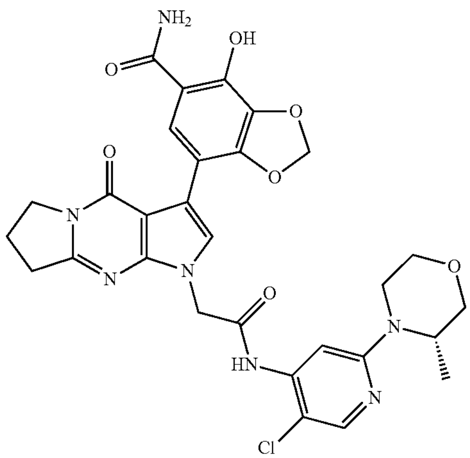 [SMILES: C[C@H]1COCCN1c1cc(NC(=O)Cn2cc(-c3cc(C(N)=O)c(O)c4c3OCO4)c3c(=O)n4c(nc32)CCC4)c(Cl)cn1] | (S)-7-(1-(2-((5-chloro-2-(3-methylmorpholino)pyridin-4-yl)amino)-2-oxoethyl)-4-oxo-4,6,7,8-tetrahydro-1H-dipyrrolo[1,2-a:2',3'-d]pyrimidin-3-yl)-4-hydroxybenzo[d][1,3]dioxole-5-carboxamide |
| I-86 | 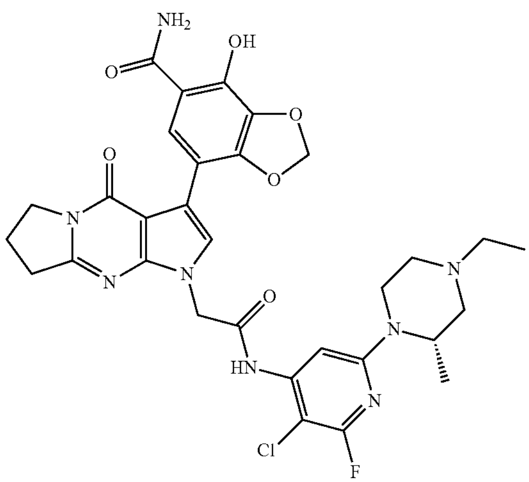 [SMILES: CCN1CCN(c2cc(NC(=O)Cn3cc(-c4cc(C(N)=O)c(O)c5c4OCO5)c4c(=O)n5c(nc43)CCC5)c(Cl)c(F)n2)[C@@H](C)C1] | (S)-7-(1-(2-((3-chloro-6-(4-ethyl-2-methyl-piperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-4-hydroxybenzo[d][1,3]dioxole-5-carboxamide |
| I-87 | 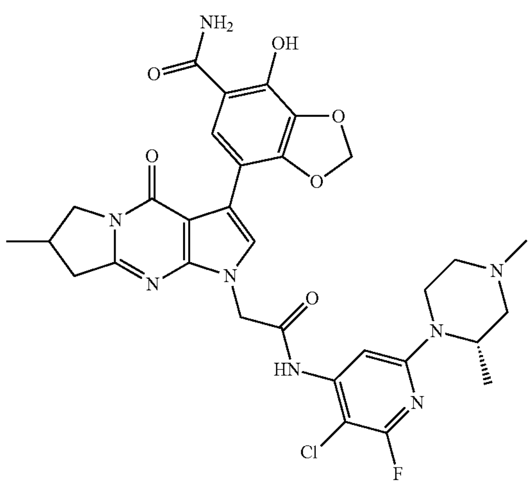 | 7-(1-(2-((3-chloro-6-((S)-2,4-dimethyl-piperazin-1-yl)-2-fluoropyridin-4-yl)amino)-2-oxoethyl)-7-methyl-4-oxo-4,6,7,8-tetrahydro-1H-dipyrrolo[1,2-a:2',3'-d]pyrimidin-3-yl)-4-hydroxybenzo[d][1,3]dioxole-5-carboxamide |

TABLE 1-continued

Examples of Compounds of Formula I

| No | Structure | IUPAC Chemical Name |
|---|---|---|
| I-88 | 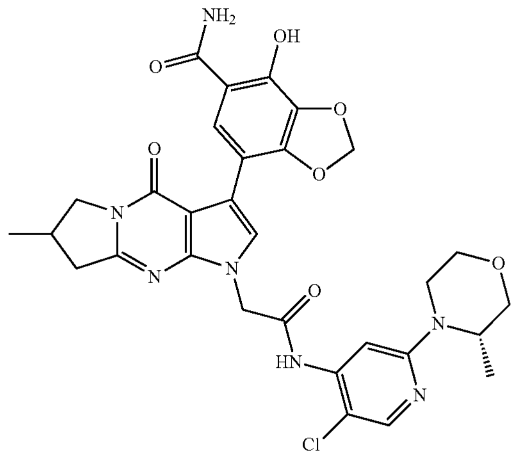 [SMILES: CC1Cc2nc3c(c(-c4cc(C(N)=O)c(O)c5c4OCO5)cn3CC(=O)Nc3cc(N4CCOC[C@@H]4C)ncc3Cl)c(=O)n2C1] | 7-(1-(2-((5-chloro-2-((S)-3-methylmorpholino)pyridin-4-yl)amino)-2-oxoethyl)-7-methyl-4-oxo-4,6,7,8-tetrahydro-1H-dipyrrolo[1,2-a:2',3'-d]pyrimidin-3-yl)-4-hydroxybenzo[d][1,3]dioxole-5-carboxamide |
| I-89 | 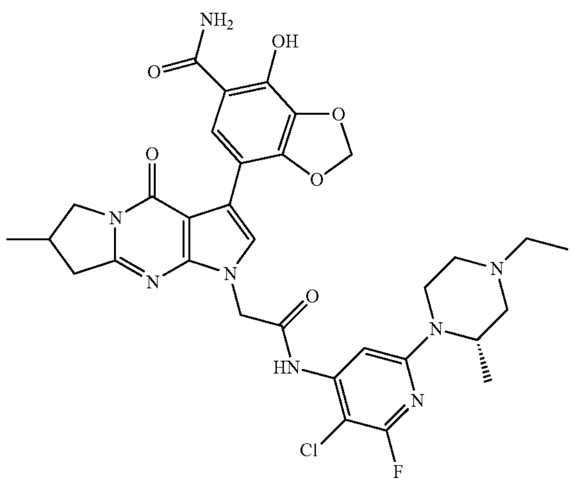 [SMILES: CCN1CCN(c2cc(NC(=O)Cn3cc(-c4cc(C(N)=O)c(O)c5c4OCO5)c4c(=O)n5c(nc43)CC(C)C5)c(Cl)c(F)n2)[C@@H](C)C1] | 7-(1-(2-((3-chloro-6-((S)-4-ethyl-2-methyl-piperazin-1-yl)-2-fluoropyridin-4-yl)amino)-2-oxoethyl)-7-methyl-4-oxo-4,6,7,8-tetrahydro-1H-dipyrrolo[1,2-a:2',3'-d]pyrimidin-3-yl)-4-hydroxybenzo[d][1,3]dioxole-5-carboxamide |
| I-90 | 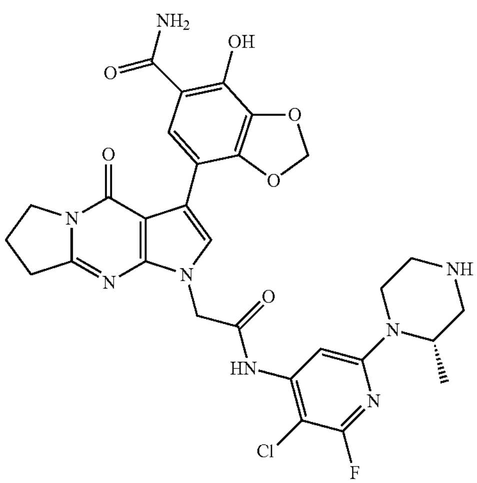 [SMILES: C[C@H]1CNCCN1c1cc(NC(=O)Cn2cc(-c3cc(C(N)=O)c(O)c4c3OCO4)c3c(=O)n4c(nc32)CCC4)c(Cl)c(F)n1] | (S)-7-(1-(2-((3-chloro-2-fluoro-6-(2-methyl-piperazin-1-yl)pyridin-4-yl)amino)-2-oxo-ethyl)-4-oxo-4,6,7,8-tetrahydro-1H-dipyrrolo[1,2-a:2',3'-d]pyrimidin-3-yl)-4-hydroxybenzo[d][1,3]dioxole-5-carboxamide |

TABLE 1-continued

Examples of Compounds of Formula I

| No | Structure | IUPAC Chemical Name |
|---|---|---|
| I-91 | 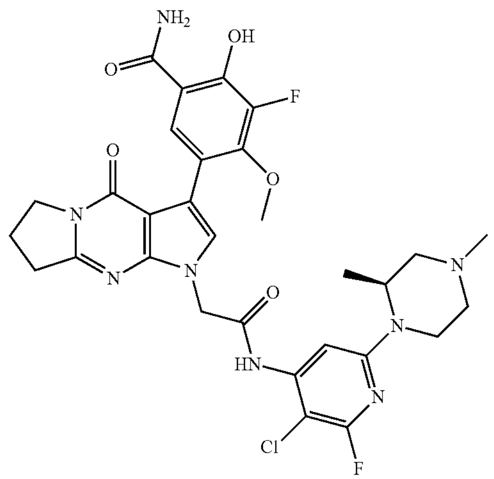 [SMILES: COc1c(-c2cn(CC(=O)Nc3cc(N4CCN(C)C[C@@H]4C)nc(F)c3Cl)c3nc4n(c(=O)c23)CCC4)cc(C(N)=O)c(O)c1F] | (S)-5-(1-(2-((3-chloro-6-(2,4-dimethylpiperazin-1-yl)-2-fluoro-pyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxy-4-methoxy-benzamide |
| I-92 | 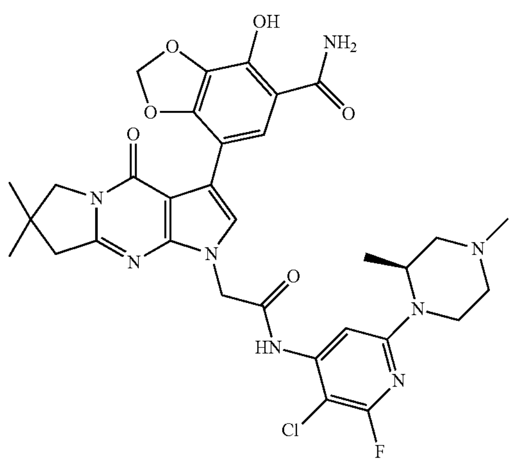 | (S)-7-(1-(2-((3-chloro-6-(2,4-dimethylpiperazin-1-yl)-2-fluoro-pyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-4-hydroxy-benzo[d][1,3]dioxole-5-carboxamide |
| I-93 | 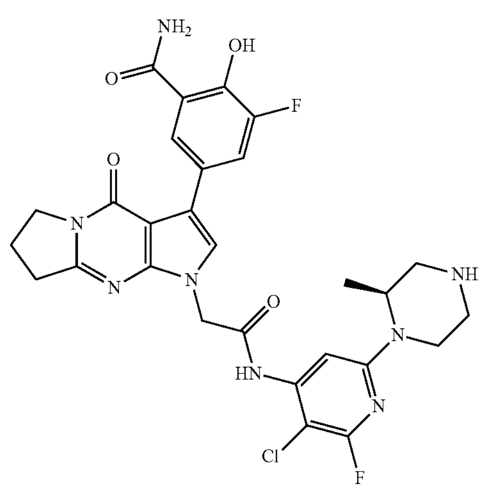 [SMILES: C[C@H]1CNCCN1c1cc(NC(=O)Cn2cc(-c3cc(F)c(O)c(C(N)=O)c3)c3c(=O)n4c(nc32)CCC4)c(Cl)c(F)n1] | (S)-5-(1-(2-((3-chloro-2-fluoro-6-(2-methyl-piperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3-fluoro-2-hydroxy-benzamide |

TABLE 1-continued

Examples of Compounds of Formula I

| No | Structure | IUPAC Chemical Name |
|---|---|---|
| I-94 | 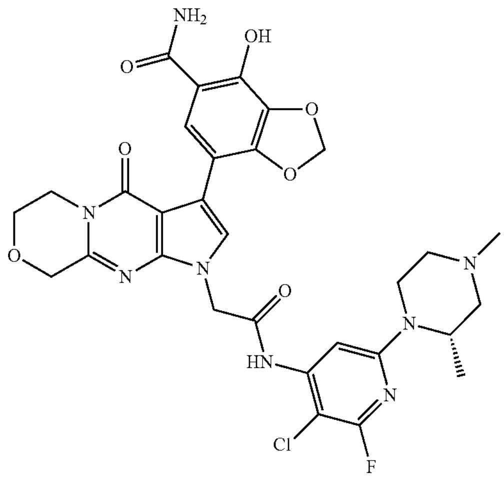 [SMILES: C[C@H]1CN(C)CCN1c1cc(NC(=O)Cn2cc(-c3cc(C(N)=O)c(O)c4c3OCO4)c3c(=O)n4c(nc32)COCC4)c(Cl)c(F)n1] | (S)-7-(1-(2-((3-chloro-6-(2,4-dimethylpiperazin-1-yl)-2-fluoropyridin-4-yl)amino)-2-oxoethyl)-4-oxo-4,6,7,9-tetrahydro-1H-pyrrolo[2',3':4,5]pyrimido[2,1-c][1,4]oxazin-3-yl)-4-hydroxybenzo[d][1,3]dioxole-5-carboxamide |
| I-95 | 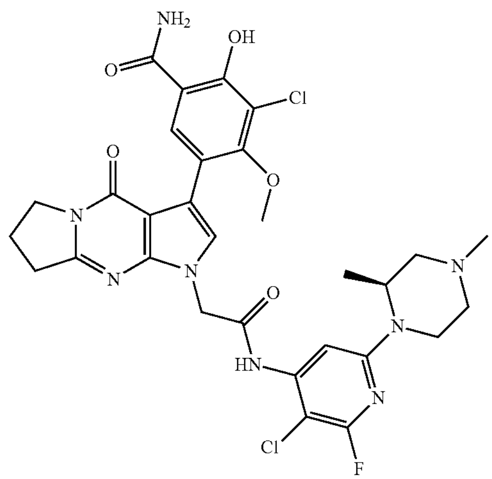 | (S)-3-chloro-5-(1-(2-((3-chloro-6-(2,4-dimethylpiperazin-1-yl)-2-fluoropyridin-4-yl)amino)-2-oxoethyl)-4-oxo-4,6,7,8-tetrahydro-1H-dipyrrolo[1,2-a:2',3'-d]pyrimidin-3-yl)-2-hydroxy-4-methoxybenzamide |
| I-96 | 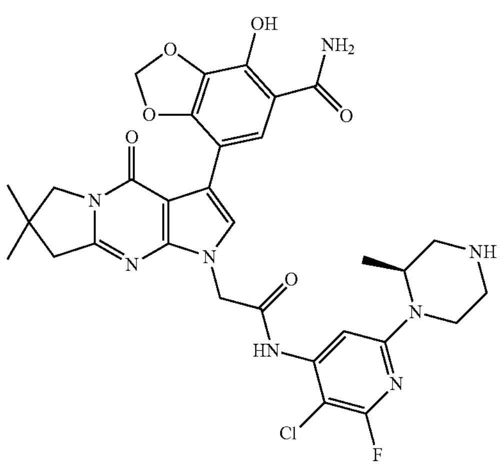 [SMILES: C[C@H]1CNCCN1c1cc(NC(=O)Cn2cc(-c3cc(C(N)=O)c(O)c4c3OCO4)c3c(=O)n4c(nc32)CC(C)(C)C4)c(Cl)c(F)n1] | (S)-7-(1-(2-((3-chloro-2-fluoro-6-(2-methylpiperazin-1-yl)pyridin-4-yl)amino)-2-oxoethyl)-7,7-dimethyl-4-oxo-4,6,7,8-tetrahydro-1H-dipyrrolo[1,2-a:2',3'-d]pyrimidin-3-yl)-4-hydroxybenzo[d][1,3]dioxole-5-carboxamide |

TABLE 1-continued

Examples of Compounds of Formula I

| No | Structure | IUPAC Chemical Name |
|---|---|---|
| I-97 | 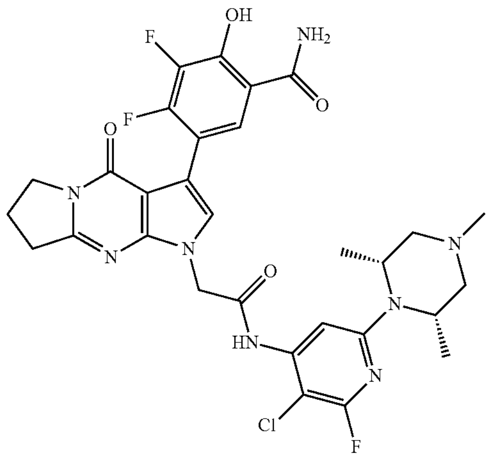 [SMILES: C[C@@H]1CN(C)C[C@H](C)N1c1cc(NC(=O)Cn2cc(-c3cc(C(N)=O)c(O)c(F)c3F)c3c(=O)n4c(nc32)CCC4)c(Cl)c(F)n1] | 5-(1-(2-((3-chloro-2-fluoro-6-((2R,6S)-2,4,6-trimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-3,4-difluoro-2-hydroxy-benzamide |
| I-98 | 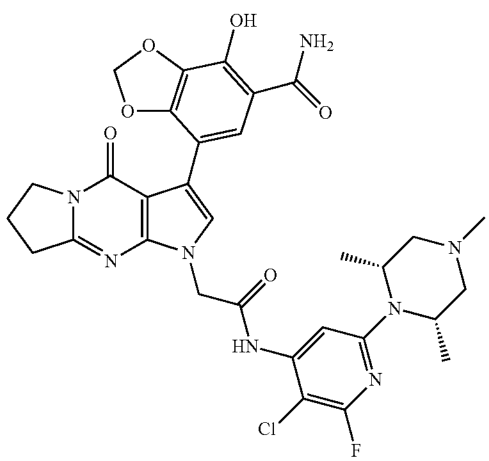 [SMILES: C[C@@H]1CN(C)C[C@H](C)N1c1cc(NC(=O)Cn2cc(-c3cc(C(N)=O)c(O)c4c3OCO4)c3c(=O)n4c(nc32)CCC4)c(Cl)c(F)n1] | 7-(1-(2-((3-chloro-2-fluoro-6-((2R,6S)-2,4,6-trimethylpiperazin-1-yl)pyridin-4-yl)amino)-2-oxoethyl)-4-oxo-4,6,7,8-tetrahydro-1H-dipyrrolo[1,2-a:2',3'-d]pyrimidin-3-yl)-4-hydroxybenzo[d][1,3]dioxole-5-carboxamide |

TABLE 2

Biochemical activity, cell-based luciferase and tumor growth inhibition assays.

| Compound # | SPR $K_d$ (μM) | Luc $IC_{50}$ (μM) | GI Karpas $EC_{50}$ (μM) |
|---|---|---|---|
| I-1 | 0.00585 | 0.0852 | 0.0673 |
| I-2 | 0.00448 | 0.095 | 0.304 |
| I-3 | 0.0252 | 0.708 | 0.502 |
| I-4 | 0.0232 | 0.318 | 0.312 |
| I-5 | 0.0117 | 0.167 | 0.124 |
| I-6 | 0.0259 | 0.306 | 0.997 |
| I-7 | 0.0176 | 0.213 | 0.299 |
| I-8 | 0.00527 | 0.101 | 0.214 |
| I-9 | 0.0568 | 0.743 | 0.692 |
| I-10 | 0.0497 | 0.448 | 0.416 |
| I-11 | 0.112 | 0.988 | 1.9 |
| I-12 | 0.111 | 0.994 | 1.47 |
| I-13 | 0.111 | 1.32 | 1.87 |
| I-14 | 0.0581 | 0.774 | 0.698 |
| I-15 | 0.0341 | 0.374 | 0.649 |
| I-16 | 0.0342 | 0.51 | 0.778 |
| I-17 | 0.0496 | 0.85 | 0.985 |
| I-18 | 0.0343 | 0.818 | 0.688 |
| I-19 | 0.0266 | 0.501 | 0.513 |
| I-20 | 0.00396 | 0.0612 | 0.0576 |
| I-21 | 0.0256 | 0.355 | 0.329 |
| I-22 | 0.0118 | 0.274 | 0.146 |
| I-23 | 0.00797 | 0.0915 | 0.102 |
| I-24 | 0.0123 | 0.152 | 0.134 |
| I-25 | 0.00564 | 0.0787 | 0.0751 |
| I-26 | 0.0302 | 0.585 | 0.549 |
| I-27 | 0.19 | 1.14 | 1.63 |
| I-28 | 0.135 | 1.34 | 0.779 |

TABLE 2-continued

Biochemical activity, cell-based luciferase and tumor growth inhibition assays.

| Compound # | SPR $K_d$ (μM) | Luc $IC_{50}$ (μM) | GI Karpas $EC_{50}$ (μM) |
|---|---|---|---|
| I-29 | 0.24 | 2.15 | 2.59 |
| I-30 | 0.106 | 1.11 | 0.98 |
| I-31 | 0.141 | 6.3 | 2.69 |
| I-32 | 0.261 | 3.58 | 1.34 |
| I-33 | 0.011 | 0.149 | 0.214 |
| I-34 | 0.00724 | 0.155 | 0.177 |
| I-35 | 0.0243 | 0.237 | 0.194 |
| I-36 | 0.0232 | 0.701 | 0.48 |
| I-37 | 0.0144 | 0.109 | 0.113 |
| I-38 | 0.0325 | 0.193 | 0.444 |
| I-39 | 0.0349 | 0.21 | 0.384 |
| I-40 | 0.134 | 0.187 | 0.273 |
| I-41 | 0.0261 | 0.183 | 0.202 |
| I-42 | 0.029 | 0.407 | 0.331 |
| I-43 | 0.0428 | 0.232 | 0.24 |
| I-44 | 0.025 | 0.104 | 0.31 |
| I-45 | 0.0318 | 0.469 | 1.33 |
| I-46 | 0.00313 | 0.935 | 0.487 |
| I-47 | 0.0239 | 0.166 | 0.212 |
| I-48 | 0.0137 | 0.0964 | 0.0646 |
| I-49 | 0.0466 | 0.518 | 0.458 |
| I-50 | 0.043 | 0.395 | 0.475 |
| I-51 | 0.0891 | 3.05 | 0.974 |
| I-52 | 0.0765 | 0.82 | 1.67 |
| I-53 | 0.00583 | 0.504 | 0.646 |
| I-54 | 0.0976 | 5.98 | 2 |
| I-55 | 0.0015 | 0.0135 | 0.0166 |
| I-56 | 0.0387 | 0.684 | 0.586 |
| I-57 | 0.0112 | 0.114 | 0.0621 |
| I-58 | 0.0287 | 0.19 | 0.0962 |
| I-59 | 0.0234 | 0.19 | 0.0488 |
| I-60 | 0.0134 | 0.186 | 0.0972 |
| I-61 | 0.00371 | 0.0417 | 0.0222 |
| I-62 | 0.00717 | 0.0785 | 0.0312 |
| I-63 | 0.0102 | 0.11 | 0.12 |
| I-64 | 0.0274 | 0.38 | 0.174 |
| I-65 | 0.00628 | 0.0468 | 0.0421 |
| I-66 | 0.0159 | 0.186 | 0.0742 |
| I-67 | 0.00672 | 0.541 | 0.874 |
| I-68 | 0.0313 | 3.42 | 1.62 |
| I-69 | 0.294 | 7.97 | 10 |
| I-70 | 0.255 | 3.82 | 4.07 |
| I-71 | 0.181 | 1.64 | 1.37 |
| I-72 | 0.0851 | 1.56 | 0.429 |
| I-73 | 0.0586 | 1.05 | 0.648 |
| I-74 | 0.0148 | 0.148 | 0.21 |
| I-75 | 0.0037 | 0.0367 | 0.0489 |
| I-76 | 0.00302 | 0.0851 | 0.0928 |
| I-77 | 0.00142 | 0.0274 | 0.0207 |
| I-78 | 0.00203 | 0.0307 | 0.021 |
| I-79 | 0.00279 | 0.0352 | 0.0398 |
| I-80 | 0.00383 | 0.0872 | 0.0701 |
| I-81 | 0.00155 | 0.0283 | 0.0313 |
| I-82 | 0.00413 | 0.0631 | 0.0278 |
| I-83 | 0.0112 | 0.465 | 0.109 |
| I-84 | 0.00053 | 0.0083 | 0.00822 |
| I-85 | 0.00161 | 0.0154 | 0.0296 |
| I-86 | 0.00081 | 0.00785 | 0.00688 |
| I-87 | 0.00077 | 0.0106 | 0.00904 |
| I-88 | 0.00214 | 0.0394 | 0.0176 |
| I-89 | 0.00136 | 0.0129 | 0.0111 |
| I-90 | 0.0007 | 0.0235 | 0.022 |
| I-91 | 0.0947 | 1.03 | 1.79 |
| I-92 | 0.00087 | 0.0124 | 0.00922 |
| I-93 | 0.00179 | 0.14 | 0.0839 |
| I-94 | 0.00133 | 0.0283 | 0.0178 |
| I-95 | 0.45 | 0.993 | 0.879 |
| I-96 | 0.00096 | 0.0175 | 0.0142 |
| I-97 | 0.0119 | 0.0635 | 0.0709 |
| I-98 | 0.00096 | 0.00816 | 0.00842 |

The invention claimed is:
1. A compound of formula I, or a pharmaceutically acceptable salt thereof:

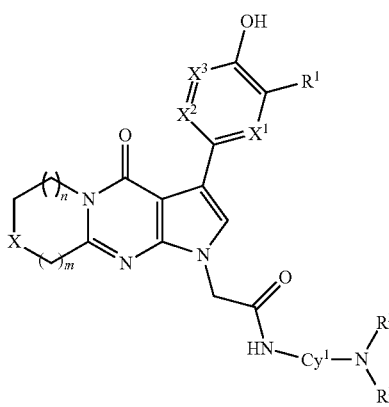

(I)

wherein
X is selected from $CR^4R^5$, O, S, S(O), $SO_2$ and $NR^4$;
$X^1$, $X^2$ and $X^3$ are independently selected from $CR^6$ and N, or
$X^2$ and $X^3$ are linked to form, together with the carbon atoms to which they are attached, a 3-8-membered heterocycloalkyl or heteroaromatic ring, both of which optionally contain one to two additional heteroatoms selected from O, S, S(O), $SO_2$ and $NR^7$;
$Cy^1$ is selected from phenyl and $C_{5-6}$heteroaryl, both of which are unsubstituted or substituted with one to three substituents selected from halo, $C_{1-6}$alkyl and $OC_{1-6}$alkyl;
$R^1$ is selected from $C(O)NR^8R^9$, $C(O)OR^8$, CN and

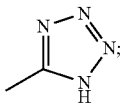

$R^2$ and $R^3$ are independently selected from H, $C_{1-10}$alkyl and $C_{1-6}$alkylene-O—$C_{1-6}$alkyl, or
$R^2$ and $R^3$ are linked to form, together with the nitrogen atom to which they are attached, a 3-10-membered heterocycloalkyl or heteroaromatic ring, both of which optionally contain one to two additional heteroatoms selected from O, S, S(O), $SO_2$, NH and $NR^{10}$, and both of which are unsubstituted or substituted with one to four substituents selected from $R^{11}$;
$R^4$ and $R^5$ are independently selected from H and $C_{1-6}$alkyl;
$R^6$ is selected from H, OH, $OC_{1-6}$alkyl, $C_{1-6}$alkyl and halo;
$R^7$ is selected from H and $C_{1-6}$alkyl;
$R^8$ and $R^9$ are independently selected from H and $C_{1-6}$alkyl;
$R^{10}$ is selected from $C_{1-10}$alkyl, $ZC_{3-10}$cycloalkyl, $ZC_{3-10}$heterocycloalkyl, $ZC_{6-10}$aryl and $ZC_{6-10}$heteroaryl, each of which is unsubstituted or substituted with one to three substituents selected from $C_{1-6}$alkyl, $OC_{1-6}$alkyl, OH and halo;
$R^{11}$ is selected from $C_{1-10}$alkyl, $OC_{1-6}$alkyl, OH, $C_{1-6}$alkylene-O—$C_{1-6}$alkyl, $C_{1-10}$alkylene-OH $C_{1-10}$alkylene $(OH)_2$ and halo;

Z is selected from a direct bond and $C_{1-6}$alkylene;
n and m are independently selected from 0, 1, 2 and 3; and
all alkyl and alkylene groups are optionally fluoro-substituted.

2. The compound of claim 1, wherein X is selected from $CR^4R^5$, O and $NR^4$, and $R^4$ and $R^5$ are independently selected from H and $C_{1-4}$alkyl.

3. The compound of claim 1, wherein $X^1$, $X^2$ and $X^3$ are independently selected from $CR^6$ and N, and $R^6$ is selected from H, OH, $C_{1-4}$alkyl, $OC_{1-4}$alkyl, F and Cl.

4. The compound of claim 1, wherein $X^2$ and $X^3$ are linked to form, together with the carbon atoms to which they are attached, a 4-6-membered heterocycloalkyl ring which optionally contains one or two additional heteroatoms selected from O, S, S(O), $SO_2$ and $NR^7$, and $R^7$ is selected from H and $C_{1-4}$alkyl.

5. The compound of claim 1, wherein $Cy^1$ is selected from phenyl and $C_6$heteroaryl, both of which are unsubstituted or substituted with one to three substituents selected from Cl, F, $C_{1-4}$alkyl and $OC_{1-4}$alkyl.

6. The compound of claim 1, wherein $R^1$ is selected from $C(O)NR^8R^9$ and CN, and $R^8$ and $R^9$ are independently selected from H and $C_{1-4}$alkyl.

7. The compound of claim 1, wherein, $R^2$ and $R^3$ are independently selected from H, $C_{1-6}$alkyl and $C_{1-4}$alkylene-O—$C_{1-4}$alkyl, or wherein $R^2$ and $R^3$ are linked to form, together with the nitrogen atom to which they are attached, a 4-10-membered heterocycloalkyl ring, which optionally contains one to two additional heteroatoms selected from O, S, S(O), $SO_2$, NH and $NR^{10}$, and is unsubstituted or substituted with one to four substituents selected from $R^{11}$.

8. The compound of claim 7, wherein $R^2$ and $R^3$ are linked to form, together with the nitrogen atom to which they are attached a heterocycloalkyl ring selected from:

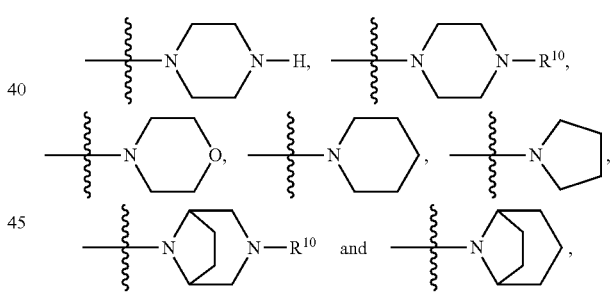

each of which is unsubstituted or substituted with one or two substituents selected from $R^{11}$.

9. The compound of claim 1, wherein $R^{10}$ is selected from $C_{1-6}$alkyl, $ZC_{3-6}$cycloalkyl, $ZC_{3-6}$heterocycloalkyl, Zphenyl and $ZC_{5-6}$heteroaryl, each of which is unsubstituted or substituted with one to three substituents selected from $C_{1-4}$alkyl, $OC_{1-4}$alkyl, OH, Cl and F.

10. The compound of claim 9, wherein $R^{10}$ is selected from $CH_3$, $CH_2CH_3$, $C_{1-4}$alkyleneO$C_{1-4}$alkyl, $C_{1-4}$alkyleneCF$_3$, $C_{1-4}$alkyleneCF$_2$H, $CH_2CH(OCH_3)CH_3$, $CH_2CH(CH_2OH)_2$,

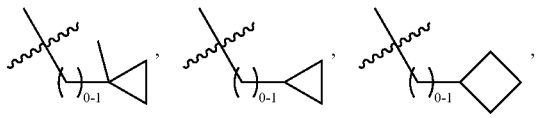

-continued

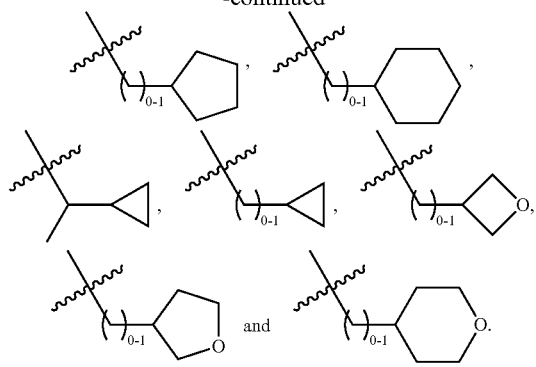

11. The compound of claim 1, wherein $R^{11}$ is selected from $C_{1-6}$alkyl, $OC_{1-6}$alkyl, OH, $C_{1-6}$alkylene-O—$C_{1-6}$alkyl, $C_{1-6}$alkylene-OH $C_{1-6}$alkylene(OH)$_2$, Cl and F.

12. The compound of claim 1, wherein n and m are independently selected from 0, 1 and 2, or both n and m are 1, or n is 0 and m is 1, or m is 0 and n is 1, or n is 2 and m is 1.

13. The compound of claim 1, selected from compound number I-1 to I-98 in Table 1, or a pharmaceutically acceptable salt, solvent and/or prodrug thereof.

14. A pharmaceutical composition comprising one of more compounds of claim 1 and a pharmaceutically acceptable carrier.

* * * * *

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Synthetic construct

<400> SEQUENCE: 1

Gly Ser Leu Val Ala Thr Val Lys Glu Ala Gly Arg Ser Ile His Glu
1               5                   10                  15

Ile Pro Ala